United States Patent [19]

Capon et al.

[11] Patent Number: 5,837,464
[45] Date of Patent: Nov. 17, 1998

[54] COMPOSITIONS AND METHODS FOR DETERMINING ANTI-VIRAL DRUG SUSCEPTIBILITY AND RESISTANCE AND ANTI-VIRAL DRUG SCREENING

[75] Inventors: Daniel Capon, Hillsborough; Christos J. Petropoulos, Half Moon Bay, both of Calif.

[73] Assignee: ViroLogic, Inc., S. San Francisco, Calif.

[21] Appl. No.: 790,963

[22] Filed: Jan. 29, 1997

[51] Int. Cl.⁶ .................................................... C12Q 1/68
[52] U.S. Cl. ........................ 435/6; 435/369; 435/320.1
[58] Field of Search ............................. 435/6, 369, 320.1

[56] References Cited

U.S. PATENT DOCUMENTS

| | | | |
|---|---|---|---|
| 4,952,496 | 8/1990 | Studier et al. | 435/91.41 |
| 5,126,251 | 6/1992 | Moss et al. | 435/69.1 |
| 5,135,855 | 8/1992 | Moss et al. | 435/69.1 |
| 5,354,674 | 10/1994 | Hodgson | 435/172.3 |
| 5,462,873 | 10/1995 | Garfinkel et al. | 435/254.2 |

FOREIGN PATENT DOCUMENTS

| | | |
|---|---|---|
| WO9119798 | 12/1991 | WIPO . |
| WO9207943 | 5/1992 | WIPO . |
| WO9419478 | 9/1994 | WIPO . |
| WO9429438 | 12/1994 | WIPO . |
| WO522622 | 8/1995 | WIPO . |

OTHER PUBLICATIONS

Danos, Olivier and Mulligan, Richard C. "Safe and Efficient Generation of Recombinant Retroviruses with Amphotropic and Ecotropic Host Ranges" *Proc. Natl. Acad. Sci. USA* (Sep. 1988) vol. 85, pp. 6460–6464 (Exhibit 11);.

Fuerst, Thomas R., and Moss, Bernard "Structure and Stability of mRNA Synthesized by Vaccinia Virus–encoded Bacteriophage T7 RNA Polymerase in Mammalian Cells" *J. Mol. Biol.* (1989) vol. 206, pp. 333–348 (Exhibit 12);.

Lieber, Andre, et al., "High Level Gene Expression in Mammalian Cells by a Nuclear 17–Phage RNA Polymerase" *Nucleic Acids Research* (1989) vol. 17, No. 21, pp. 8485–8493 (Exhibit 3);.

Larder, Brendan A., et al., "HIV with Reduced Sensitivity to Zidovudine (AZT) Isolated During Prolonged Therapy-"*Science* (Mar. 31, 1989) vol. 243, pp.1731–1734 (Exhibit 14);.

Andreasson, K.I., et al., "Production of Pro–Opiomelanocortin (POMC) by a Vaccinia Virus Transient Expression System and In Vitro Processing of the Expressed Prohormone by POMC–converting Enzyme" *F.E.B.S* Letters (May 1989) vol. 248, No. 1.2 pp. 43–47 (Exhibit 15);.

Elroy–Stein, Orna, et al., "Cap–Independent Translation of mRNA Conferred by Encephalomyocarditis Virus 5' Sequence Improves the Performance of the Vaccinia Virus/Bacteriophage T7 Hybrid Expression System" *Proc. Natl. Acad. Sci. USA* (Aug. 1989) vol. 86, pp. 6126–6130 (Exhibit 16);.

Larder, Brendan A., and Sharon D.Kemp, "Multiple Mutations in HIV–1 Reverse Transcriptase confer High–Level Resistance ot Zidovudine (AZT)" *Science* (Dec. 1089) vol. 246, pp. 1155–1158 (Exhibit 17);.

Elroy–Stein, Orna and Bernard Moss, "Cytoplasmic Expression System Based on Constructive Synthesis of Bacteriophage T7 RNA Polymerase in Mammalian Cells" *Proc. Natl. Acad. Sci. USA* (Spe. 1990) vol. 87, pp. 6743–6747 (Exhibit 18);.

Page, Kathleen A., et al., "Construction and Use of a Human Immunodeficiency Virus Vector for Analysis of Virus Infectivity" *Journal of Virology* (Nov. 1990) vol. 64, No. 11, pp. 5270–5276 (Exhibit 19);.

Moss, B et al., "New Mammalian Expression Vectors" *Nature* (Nov. 1990) vol. 348, pp. 91–92 (Exhibit 20);.

Deng, Hong, et al., "High–Efficiency Protein Synthesis from T7 RNA Polymerase Transcripts in 3T3 Fibroblasts" *GENE* (1991)pp. 193–201 (Exhibit 21);.

Goldman, Mark E., et al., "L–696,229 Specifically Inhibits Human Immunodeficiency Virus Type 1 Reverse Transcriptase and Possesses Antiviral Activity In Vitro" *Antimicrobial Agents and Chemotherapy* (May 1992) vol. 36, No. 5, pp. 1019–1023 (Exhibit 22);.

Saari, Walfred, S., et al. "2–Pyridinone Derivatives: A New Class of Nonnucleoside, HIV–1 Spedivid Reverse Transcriptase Inhibitors" *Journal of Medicinal Chemistry* (1991) vol. 34, No. 9, pp. 2922–2925 (Exhibit 23);.

(List continued on next page.)

*Primary Examiner*—James Ketter
*Attorney, Agent, or Firm*—John P. White; Cooper & Dunham LLP

[57] ABSTRACT

This invention provides a method for determining susceptibility for an anti-viral drug comprising: (a) introducing a resistance test vector comprising a patient-derived segment and an indicator gene into a host cell; (b) culturing the host cell from (a); (c) measuring expression of the indicator gene in a target host cell; and (d) comparing the expression of the indicator gene from (c) with the expression of the indicator gene measured when steps (a)–(c) are carried out in the absence of the anti-viral drug, wherein a test concentration of the anti-viral drug is present at steps (a)–(c); at steps (b)–(c); or at step (c). This invention also provides a method for determining anti-viral drug resistance in a patient comprising: (a) determining anti-viral drug susceptibility in the patient at a first time using the susceptibility test described above, wherein the patient-derived segment is obtained from the patient at about said time; (b) determining anti-viral drug susceptibility of the same patient at a later time; and (c) comparing the anti-viral drug susceptibilities determined in step (a) and (b), wherein a decrease in anti-viral drug susceptibility at the later time compared to the first time indicates development or progression of anti-viral drug resistance in the patient. This invention also provides a method for evaluating the biological effectiveness of a candidate anti-viral drug compound. Compositions including resistance test vectors comprising a patient-derived segment and an indicator gene and host cells transformed with the resistance test vectors are provided.

83 Claims, 23 Drawing Sheets

OTHER PUBLICATIONS

Landau, Nathaniel, R., et al., "Pseudotyping with Human T–Cell Leukemia Virus Type I Broadens the Human Immunodeficiency Virus Host Range" *Journal of Medicinal Chemistry* (1991) vol. 34, No. 9, pp 2922–2925 (Exhibit 23);.

Goldman, Mark E., et al., "Pyridinone Derivatives: Specific Human Immunodeficiency Virus Type 1 Reverse Transcriptase Inhibitors with Antiviral Activity" *Proc. Natl. Acad. Sci. USA* (Aug. 1991) vol. 88, pp. 6863–6867 (Exhibit 25);.

Nunberg, Jack H., et al., "Viral Resistance to Human Immunodeficiency Virus Type–1 Specific Pyridinone Reverse Transcriptase Inhibitors" *Journal of Virology* (Sep. 1991) vol. 65, No. 9, pp. 4887–4892 (Exhibit 26);.

St. Clair, M.H., et al. "Resistance to ddI and Sensitivity to AZT Induced by a Mutation in HIV–1 Reverse transcriptase" *Science* (Sep. 27, 1991) vol. 253, pp. 1557–1559 (Exhibit 27);.

Huang, Mingjun and Summers, Jesse "Infection Initiated by the RNA Pregenome of a DNA Virus" *Journal of Virology* (Oct. 1991) vol. 65, No. 10, pp. 5435–5439 (Exhibit 28);.

Larder, Brendan, A., et al., "Zidovudine–Resistant Human Immunodeficiency Virus Selected by Passage in Cell Culture" *Journal of Virology* (Oct. 1991) vol. 65, No. 10, pp. 5232–5236 (Exhibit 29);.

Homberger, F.R., et al. "Detection of Rodent Coronaviruses in Tissues and Cell Cultures by Using Polymerase Chain Reaction" *J. Clin. Microbiol.* (Dec. 1991) vol. 29:2789–2793 (Exhibit 30);.

Sardana, Vinod, V., et al., "Functional Analysis of HIV–1 Reverse Transcriptase Amino Acids Involved in Resistance to Multiple Nonnucleoside Inhibitors" *Journal of Biological Chemistry* (1992) vol. 267, No. 25, pp. 17526–17530 (Exhibit 31);.

Yang, Xian–Cheng, et al., "Cell–Specific Posttranslational Events Affect Functional Expression at the Plasma Membrane but not Tetrodotoxin Sensitivity of the Rat Brain IIA Sodium Channel α–Subunit Expressed in Mammalian Cells" *The Journal of Neuroscience* (Jan. 1992) vol. 12(1), pp. 268–277 (Exhibit 32);.

Richman, Douglas D. "Antiretroviral Drug Resistance: Mechanisms, Pathogenesis, Clinical Significance" pp. 1–13 (Exhibit 33);.

Condra, Jon H., et al., "Identification of the Human Immunodeficiency Virus Reverse Transcriptase Residues That Contribute to the Activity of Diverse Nonnucleoside Inhibitors" Antimicrobial *Agents and Chemotherapy* (Jul. 1992) vol. 36, No. 7, pp. 1441–1446 (Exhibit 34);.

Trono, Didier, "Partial Reverse Transcripts in Virions from Human Immunodeficiency and Murine Leukemia Viruses" *Journal of Virology*(Aug. 1992) vol. 66, No. 8, pp. 4893–4900 (Exhibit 35);.

Lori, Franco, et al., "Viral DNA Carried by Human Immunodeficiency Virus Type 1 Virions" *Journal of Virology* (Aug. 1992) vol. 66, No. 8, pp. 5067–5074 (Exhibit 36);.

Larder, Brendan A., "3'–Azido–3'–Deoxythymidine Resistance Suppressed by a Mutation Conferring Human Immunodeficiency Virus Type 1 Resistance to Nonnucleoside Reverse Transcriptase Inhibitors" *Antimicrobial Agents and Chemotherapy* (Dec. 1992) vol. 36, No. 12, pp. 2664–2669 (Exhibit 37);.

Gu, Zhengxian, et al., "Novel Mutation in the Human Immunodeficiency Virus Type 1 Reverse Transcriptase Gene That Encodes Cross–Resistance to 2",3'–Dideoxyinosine and 2', 3'–Dideoxycytidine" *Journal of Virology* (Dec. 1992) vol. 66, No. 12, pp. 7128–7135 (Exhibit 38);.

Baltimore, David, "The Treaure Under the Right Stone" *Reverse Transcriptase* (1993) pp. 1–3 (Exhibit 39);.

Larder, Brendan A., "Inhibitors of HIV Reverse Transcriptase as Antiviral Agents and Drug Resistance" Chapter 11 *Reverse Transcriptase* pp. 205–222 Cold Spring Harbor Laboratory Press (1993)(Exhibit 40);.

Gao, Xiang , and Huang, Leaf, "Cytoplasmic Expression of a Reporter Gene by Co–Delivery of T7 RNA Polymerase and T7 Promoter Sequence with Cationic Liposomes" *Nucleic acids Research* (1993) vol. 21, No. 12, pp. 267–2872 (Exhibit 41);.

Gottesman, Michael M., and Pastan, Ira, "Biochemistry of Multidrug Resistance Mediated by the Multidrug Transporter" *Annu. Rev. Biochem.* (1993) vol. 62, pp. 385–427;.

Le Grice, Stuart F.J., "Human Immunodeficiency Virus Reverse Transcriptase" *Reverse Transcriptace* (1993) pp. 163–191 (Exhibit 43);.

Telesnitsky, Alice and Goff, Stephen P., "Strong–stop Strand transfer during Reverse Transcription" *Reverse Transcriptase* (1993) pp. 49–83 (Exhibit 44);.

Wlodawer, Alexander and Erickson, John W., "Structure–Based Inhibitors of HIV–1 1 Protease" *Annu. Rev. Biochem.* (1993) vol. 62, pp. 543–585 (Exhibit 45);.

Richman, Douglas D., "HIV Drug Resistance" *Annu. Rev. Pharmacol. Toxicol.* (1993) vol. 32, pp. 149–164 (Exhibit 46);

Sandig, Volker, et al., "A Phage T7 Class–III Promoter Functions as a Polymerase II Promoter in Mammalian Cells" *GENE* (1993) pp. 255–259 (Exhibit 47);.

Lieber, Andre, et al., "A Mutant T7 Phage Promoter is Specifically Transcribed by T7–RNA Polymerase in Mammalian Cells" *Eur. J. Biochem.* (1993) vol. 217, pp. 387–394 (Exhibit 48);.

Chattopadhyay, Sisir K., et al., "Genomes of Murine Leukemia Viruses Isolated from Wild Mice" *Journal of Virology* (Sep. 1981) vol. 39, No. 3, pp. 777–791 (Exhibit 49);.

Richman, Douglas D., "Minireview, Resistance of Clinical Isolates of Human Immunodeficiency Virus to Antiretroviral Agents" *Antimicrobial Agents and Chemotherapy* (June 1993) vol. 37, No. 6, pp. 1207–1213 (Exhibit 50);.

Richardson, Jennifer H., et al., "Packaging of Human Immunodeficiency Virus Type 1 RNA Requires cis–Acting Sequences Outside the 5' Leader Region" *Journal of Virology* (July 1993) vol. 67, No. 7, pp. 3997–4005 (Exhibit 51);.

Byrnes, Vera W., et al., "Comprehensive Mutant Enzyme and Viral Variant Assessment of Human Immunodeficiency Virus Type 1 Reverse Transcriptase Resistance to Non-nucleoside Inhibitors" *Antimicrobial Agents and Chemotherapy* (Aug. 1993) vol. 37, No. 8, pp. 1576–1579 (Exhibit 52);.

Emini, Emillo A., et al., "HIV–1 Error Revealed" *Nature* (Aug. 19, 1993) vol. 364, pp. 679 (Exhibit 53);.

Balzarini, Jan et al., "Treatment of Human Immunodeficiency Virus Type 1 (HIV–1)–Infected Cells with Combinations of HIV–1–Specific Inhibitors Results in a Different Resistance Pattern Than Does Treatment with Single–Drug Therapy" *Journal of Virology* (Sep. 1993) vol. 67, No. 9, pp. 5353–5359 (Exhibit 54);.

Larder, Brendan A., et al., "Convergent Combination Therapy can Select Viable Multidrug Multidrug–Resistant HIV–1 In Vitro" *Nature* (Sep. 30, 1993) vol. 365, pp. 451–453 (Exhibit 55);.

Sag, Michael S., et al., "A short–Term Clinical Evaluation of L–697,661, A Non–Nucleoside Inhibitor of HIV–1 Reverse Transcriptase" *The New England Journal of Medicine* (Oct. 7, 1993) vol. 329, No. 15, pp. 1065–1072 (Exhibit 56);

Boyer, Paul L. et al., "Mutational Analysis of the Fingers and Palm Subdomains of Human Immunodeficiency Virus Type–1 (HIV–1) Reverse Transcriptase" *J. Mol. Biology* (1994) vol. 243, pp. 472–483 (Exhibit 57);

Deng, Hong, and Wolff, Jon A., "Self–Amplifying Expression from the T7 Promoter in 3T3 Mouse Fibroblasts" *GENE* (1994) pp. 245–249 (Exhibit 58);.

Richman, Douglas D., "Resistance, Drug Failure, and Disease Progression" *AIDS research and Human Retroviruses* (1994) vol. 10, No. 8, pp. 901–905 (Exhibit 59);.

Ansari–Lari, M. Ali and Gibbs, Richard A., "Analysis of HIV Type 1 Reverse Transcriptase Expression in a Human Cell Line" *AIDS Research and Human Retroviruses* (1994) vol. 10, No. 9, pp. 1117–1124 (Exhibit 60);.

Mirochnitchenki, Oleg, et al., "Production of Single–Stranded DNA in Mammalian Cells by Means of a Bacterial Retron" *The Journal of Biological Chemistry* (Jan. 1994) vol. 269, No. 4, pp. 2380–2383 (Exhibit 61);.

Katz, Richard A., and Skalka, Anna Marie "The Retroviral Enzymes" *Annu. Rev. Biochem.* (1994) vol. 63, pp. 133–173 (Exhibit 62);.

Chen, Xiaozhuo, et al., "A Self–Initiating Eukaryotic Transient Gene Expression System Based on Cotransfection of Bacteriophase T7 RNA Polymerase and DNA Vectors Containing a T7 Autogene" *Nucleic Acids Research* (1994) vol. 22, No. 11, pp. 2114–2120 (Exhibit 63);.

Kellam, Paul, et al., "Zidovudine Treatment Results in the Selection of Human Immunodeficiency Virus Type 1 Variants Whose Genotypes Confer Increasing Levels of Drug Resistance" *Journal of General Virology* (1994) vol. 75, pp. 341–351 (Exhibit 64);.

Kellam, Paul, and Larder, Brendan A,. "Recombinant Virus Assay: a Rapid, Phenotypic Assay for Assissment of Drug Susceptibility of Human Immunodeficiency Virus Type 1 Isolates" *Antimicrobial Agents and Chemotherapy* (1994) vol. 38, No. 1, pp. 23–30 (Exhibit 65);.

El–Farrash, Mohamed A., et al., "Generation and Characterization of a Human Immunodeficiency Virus Type 1 (HIV–1) Mutant Resistant to an HIV–1 Protease Inhibitor" *Journal of Virology* (Jan. 1994) vol. 68, No. 1, pp. 233–239 (Exhibit 66);.

Chen, Benjamin K., et al., "Distinct Modes of Human Immunodeficiency Virus Type 1 Proviral Latency Revealed by Superinfection of Nonproductively Infected Cell Lines with Recombinant Luciferase–Encoded Viruses" *Journal of Virology* (Feb. 1994) vol. 68, No. 2, pp. 654–660 (Exhibit 67);.

Richman, Douglas D., et al., "Nevirapine Resistance Mutations of Human Immunodeficiency Virus Type 1 Selected During Therapy" *Journal of Virology* (Mar. 1994) vol. 68, pp. 1660–1666 (Exhibit 68);.

Ho, David D., et al., "Characterization of Human Immunodeficiency Virus Type 1 Variants with Increased Resistance to a $C_2$–Symmetric Protease Inhibitor" *Journal of Virology* (Mar. 1994) vol. 68, No. 3, pp. 2016–2020 (Exhibit 69);.

Boyer, Paul L. et al., "Sensitivity of Wild–Type Human Immunodeficiency Virus Type 1 Reverse Transcriptase to Dideoxynucleotides Depends on Template Length; The Sensitivity of Drug–Resistant Mutants Does Not" *P.N.A.S. USE* (May 1994) vol. 91, pp. 4882–4886 (Exhibit 70);,.

Brynes, Vera W., et al."Susceptibilities of Human Immunodeficiency Virus Type 1 Enzyme and Viral Variants Expressing Multiple Resistance–Engendering Amino Acid Substitutions to Reverse Transcriptase Inhibitors" *Antimicrobial Agents and Chemotherapy* (Jun. 1994) vol. 38, No. 6, pp. 1404–1407 (Exhibit 71);.

Parolin, Cristina, et al., "Analysis in Human Immunodeficiency Virus Type 1 Vectors of cis–Acting Sequences That Affect Gene Transfer into Human Lymphocytes" *Journal of Virology* (Jun. 1994) vol. 68, No. 6, pp. 3888–3895 (Exhibit 72);.

Carroll, Richard, et al., "A Human Immunodeficiency Virus Type 1 (HIV–1)–Based Retroviral Vectory System Utilizing Stable HIV–1 Packaging Cell Lines" *Journal of Virology* (Sep. 1994) vol. 68, No. 9, pp. 6047–6051 (Exhibit 73);.

Richman, douglas D., "Drug Resistance in Viruses" *Trends in Microbiology* (Oct. 10, 1994) vol. 2, No. 10, pp. 401–408 (Exhibit 74);.

Zhang, Hui, et al., "Intravirion Reverse Transcripts in the Peripheral Blood Plasma ofHuman Immunodeficiency Virus Type 1–Infected Individuals" *Journal of Virology* (Nov. 1994) vol. 68, No. 11, pp. 7591–7597 (Exhibit 75);.

Kalderon, Daniel, et al., "A Short Amino Acid Sequence Able to Specify Nuclear Location" *Cell* (Dec. 1984 — Part 2) vol. 39, pp. 499–509 (Exhibit 76);.

Ho. David D. "Time to Hit HIV, Early and Hard" *The New England Journal of Medicine* (1995) vol. 333, No. 7, pp. 450–451 (Exhibit 77);.

Wyatt, Linda S., et al., "Replication–Deficient Vaccinia Virus Encoding Bacteriophage T7 RNA Polymerase for Transient Gene Expression in Mammalian Cells" *Virology* (1995) vol. 210, pp. 202–205 (Exhibit 78);.

Ward, George A., et al., "Stringent Chemical and Thermal Regulation of Recombinant Gene Expression by Vaccinia Virus Vectors in Mammalian Cells" *Proc. Natl. Acad. Sci.USA* (1995) pp. 6773–6777 (Exhibit 79);.

Wei, Xiping, et al., "Viral Dynamics in Human Immunodeficiency Virus Type 1 Infection" *Nature* (Jan. 1995) vol. 373, pp. 117–122 (Exhibit 80);.

Richman, Douglas D., "Drug Resistance in Relation to Pathogenesis" *AIDS* (1995) vol. 9 (Suppl A) pp. S49–S53 (Exhibit 81);.

Volberding, Paul, "The Need for Additional Options in the Treatment of Human Immunodeficiency Virus Infection" *The Journal of Infectious Diseases* (1995) vol. 17 (Suppl 2) pp. S150–S154 (Exhibit 82);.

Coffin, John M. "HIV Population Dynamics in Vivo: Implications for Genetic Variation, Pathogenesis, and Therapy" *Science* (Jan. 27, 1995) vol. 267, pp. 483–489 (Exhibit 83);.

Kim Baek and Loeb Lawrence, A "Human Immunodeficiency Virus Reverse Transcriptase Substitutes for DNA Polymerase in *Esherichia Coli*" *P.N.A.S.* I vol. 92, pp. 684–688 (Exhibit 84);.

Wain–Hobson, Simon "Virological Mayhem" *Nature* (Jan. 1995) vol. 373, p. 102 (Exhibit 85);.

Ho, david D., et al., "Rapid Turnover of Plasma Virions and CD4 Lymphocytes in HIV–1 Infection" *Nature* (Jan. 1995) pp. 123–126 (Exhibit 86);.

D'Aquila, Richard T., et al., "Zidovudine Resistance and HIV–1 Disease Progression During Antiretroviral Therapy" *Annals of Internal Medicine* (Mar. 15, 1995) vol. 122, No. 6, pp. 401–408 (Exhibit 87);.

Condra, John H., et al., "In Vivo Emergence of HIV–1 Variants Resistant to Multiple Protease Inhibitors" *Nature* (Apr. 6, 1995) vol. 374, pp. 569–571 (Exhibit 88);.

Boyer, Paul L., and Hughes, Stephen H., "Analysis of Mutations at Position 184 in Reverse Transcriptase of Human Immunodeficiency Virus Type 1" *Antimicrobial Agents and Chemotherapy* (Jul. 1995) vol. 39, No. 7, pp. 1624–1628 (Exhibit 89);.

He, Jianglin, and Landau, Nathaniel R., "Use of a Novel Human Immunodeficiency Virus Type 1 Reporter Virus Expressing Human Placental Alkaline Phosphatase To Detect an Alternative Viral Receptor" *Journal of Virology* (Jul. 1995) vol. 69, No. 7, pp. 4587–4592 (Exhibit 90);.

Kim, Baek and Loeb, Lawrence A., "A Screen in *Escherchia coli* for Nucleoside Analogs That Target Human Immunodeficiency Virus (HIV) Reverse Transcriptase: Coexpression of HIV Reverse Transcriptase and Herpes Simplex Virus Thymidine Kinase" *Journal of Virology* (Oct. 1995) vol. 69, No. 10, pp. 6563–6566 (Exhibit 91);.

Saunders, J., and Cameron, J.M., "Recent Development in the Design of Antiviral Agents" *Med. Res. Rev.* (Nov. 1995) vol. 15:497–531 (Exhibit 92);.

Young, Steven D., et al., "L–743,726 (DMP–266): a Novel, Highly Potent Nonnucleoside Inhibitor of the Human Immunodeficiency Virus Type 1 Reverse Transcriptase" *Antimicrobial Agents and Chemotherapy* (Dec. 1995) vol. 39, No. 12, pp. 2602–2605 (Exhibit 93);.

Goldman, Mark E., et al., "A Nonnucleoside Reverse Transcriptase Inhibitor Active on Human Immunodeficiency Virus Type 1 Isolates Resistant to Related Inhibitors" *Antimicrobial Agents and Chemotherapy* (May 1993) vol 37, No. 5, pp. 947–949 (Exhibit 94);

Fang, Guowei, et al., "Molecular Cloning of Full–Length HIV–1 Genomes Directly from Plasma Viral RNA" *Journal of Acquired Immune Deficiency Syndromes and Human Retrovirology* (1996) vol. 12, No. 4, pp. 352–357 (Exhibit 95);.

Heid, Christian A., et al., "Real Time Quantitative PCR" *Genome Research* (1996) pp. 986–994 (Exhibit 96);.

Romeyn, Mary, "Report from the 3rd Conference of Retroviruses and Opportunistic Infections" *BETA* (Mar. 1996) (Exhibit 97);.

Schapiro, Jonathan, M., "Causes of Long Term Efficacy and/or Drug Failure in Protease (PR) Inhibitor Monotherapy" *ICA Abstracts* (Exhibit 98):.

Mamtora, gargi, et al., "HIV–1 Genechiptm and Dideoxynucleotide Sequence Analysis of HIV–1 Genomes Present in Plasma Samples from Patients of ACTG 143 Study" *ICA Abstracts* (Exhibit 99);.

Garrett, Miyada, C., et al., "Sequencing HIV Isolates Using the Genechiptm HIV PRT Assay" *ICA Abstracts* (Exhibit 100);.

Gingeras, Thomas R., et al. "Detection of Rifampin Conferring Mutations and Mycobacteria Speciation Using Myco Genechiptm" *ICA Abstracts* (Exhibit 101);.

Fischl, Margaret A., "Treatment of HIV Infection" *Section II–Management of HIV Infections and Their Complications*, Chapter 8, pp. 141–160, (Exhibit 102);.

Saag, Michael S. "AIDS Testing Now and in the Future" *Section I–The Virus: Its Transmission and Infection*, Chapter 4, pp. 65–88, 1994 (Exhibit 103) and ;.

Richman, Douglas, D., "Antiviral Drug Resistance: Issues and Challenges" *Antiviral Drug Resistance,* Introductory Chapter, pp. 1–19 (Exhibit 104).

Japour, Anthony J., "Standardized Peripheral Blood Mononuclear Cell Culture Assay for Determination of Drug Susceptibilities of Clinical Human Immunodeficiency Virus Type 1 isolates" *Antimicrobial Agents and Chemotherapy* (May 1993) vol. 37, pp. 1095–1101. (Exhibit 2).

Pauwels, Rudi, et al. "Rapid and Automated Tetrazolium–based Colorimetric Assay for the Detection of anti–HIV Compounds" *Journal of Virological Methods* (1988) vol. 20, pp. 309–321. (Exhibit 3).

Kellam, Paul and Larder, Brendan A. "Recombinant Virus Assay: a Rapid, Phenotypic Assay for Assessment of Drug Susceptibility of Human Immunodeficiency Virus Type 1 Isolates" *Antimicrobial Agents and Chemotherapy* (May 1993) vol. 38, pp. 23–30. (Exhibit C).

Kellam, P, et al. 1994, Antimicrobial Agents and Chemotherapy, vol. 38, pp. 23–30.

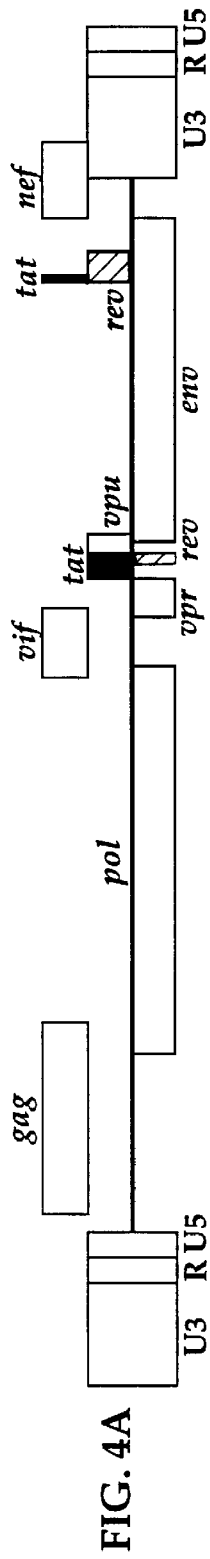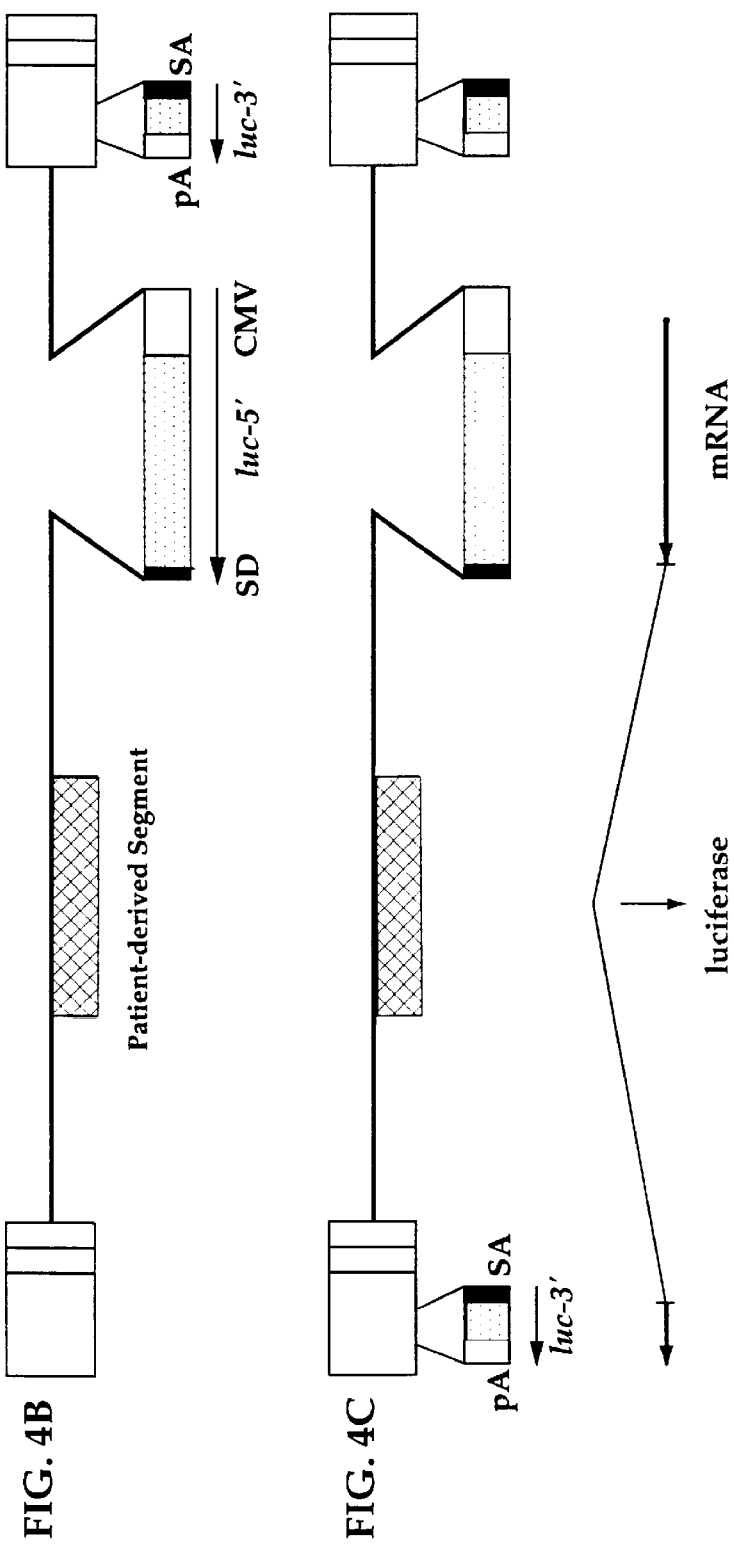
FIG. 4A
FIG. 4B
FIG. 4C

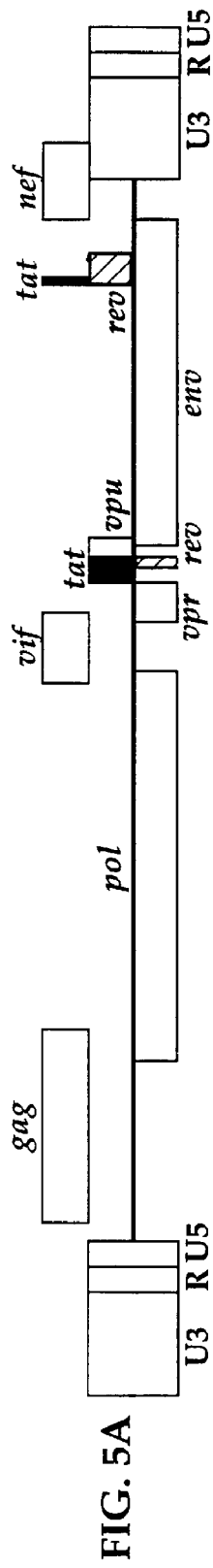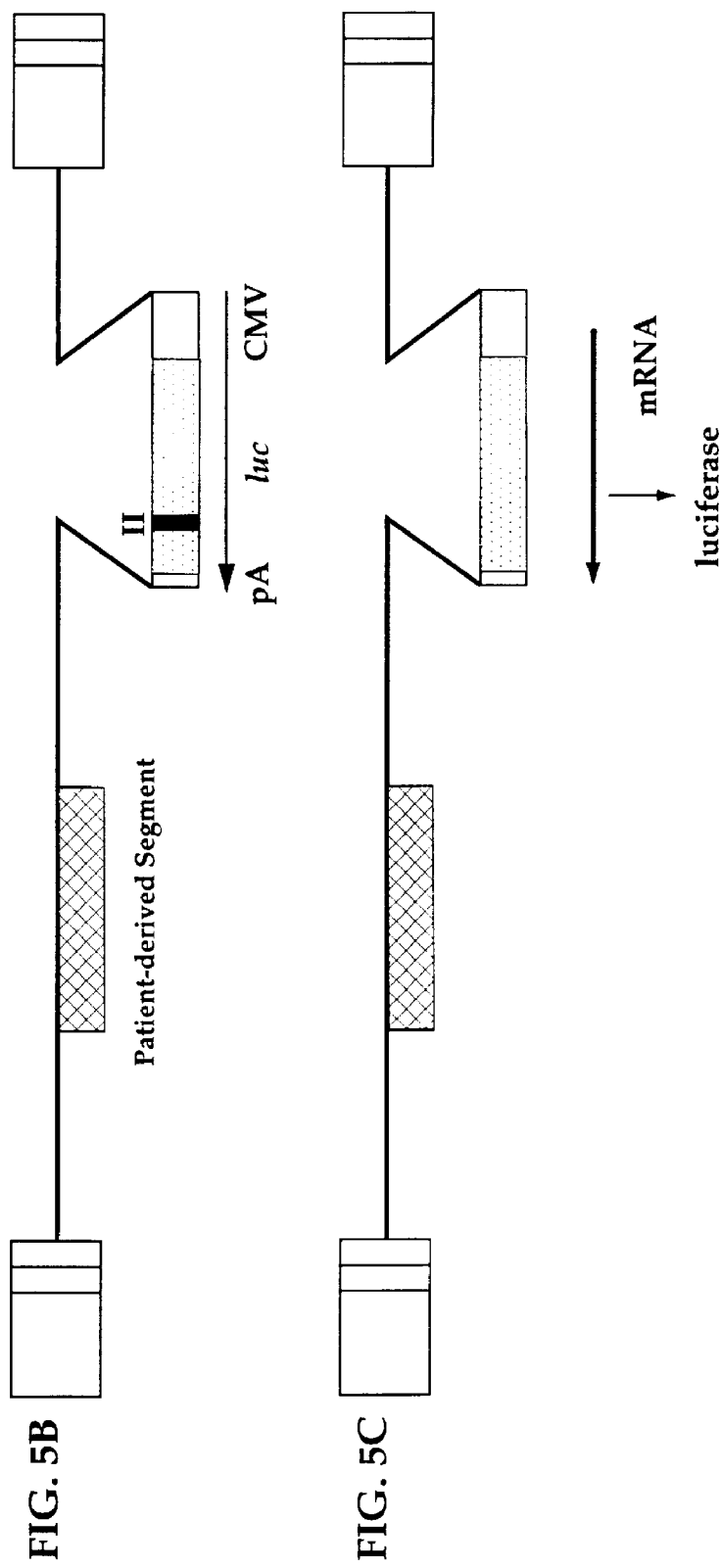
FIG. 5A
FIG. 5B
FIG. 5C

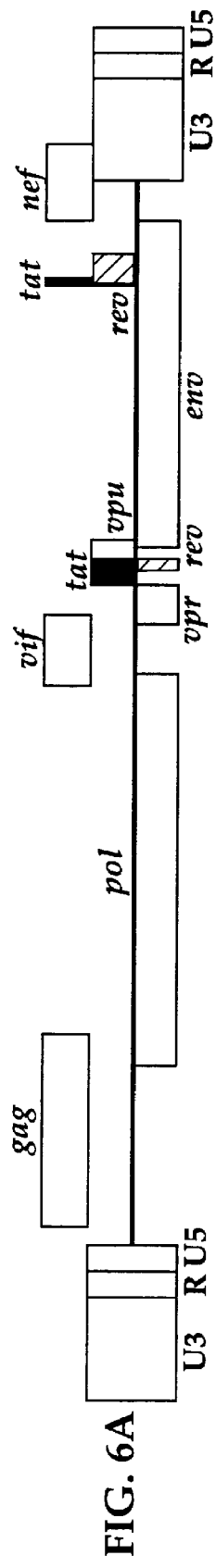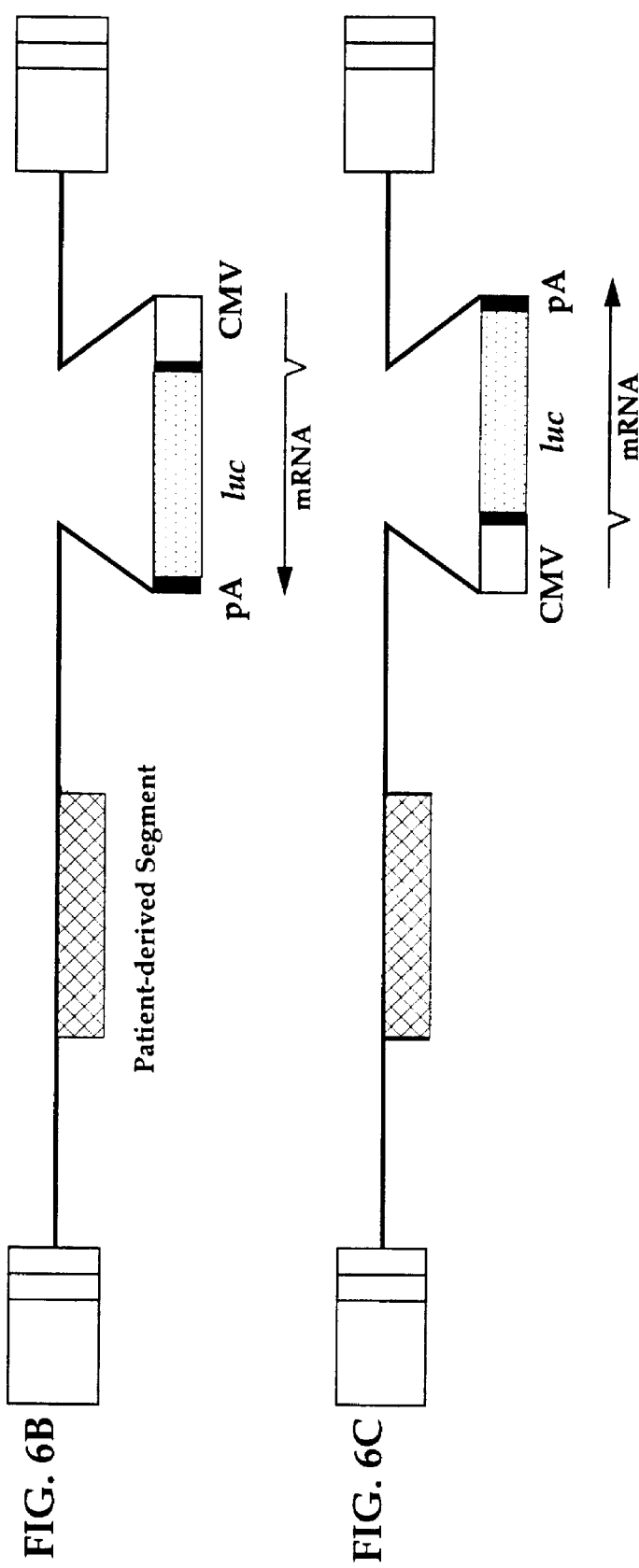
FIG. 6A
FIG. 6B
FIG. 6C

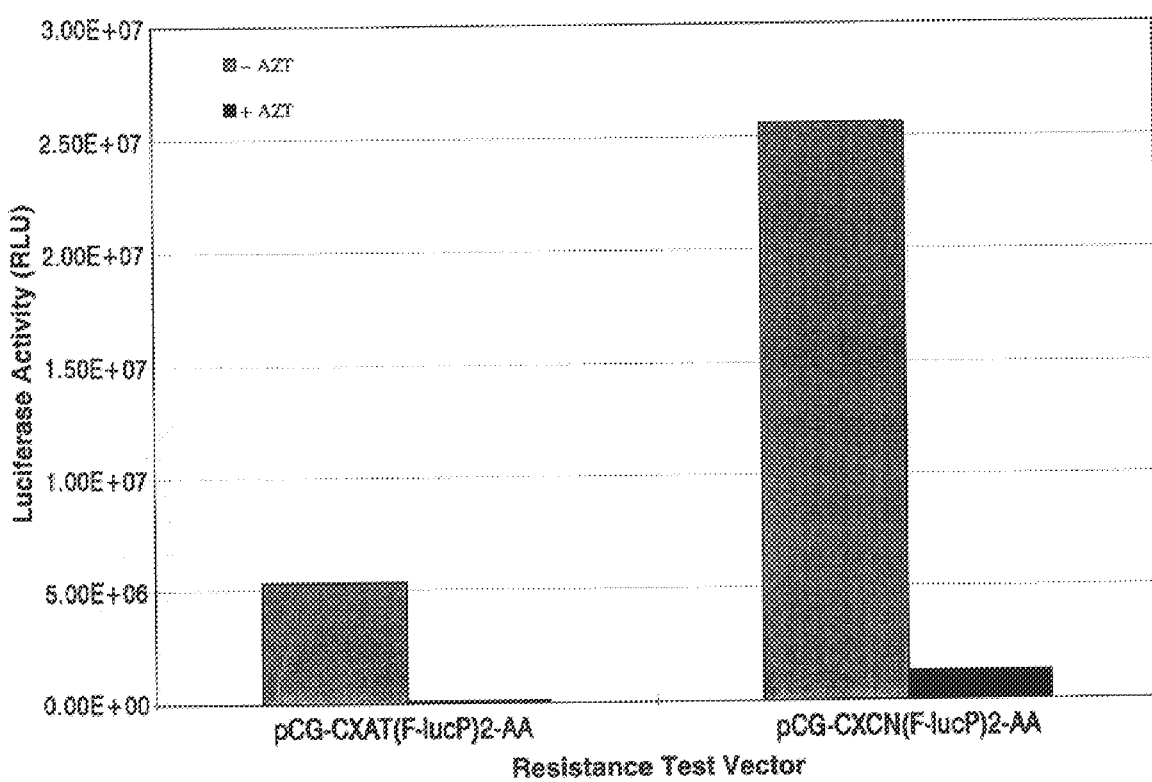

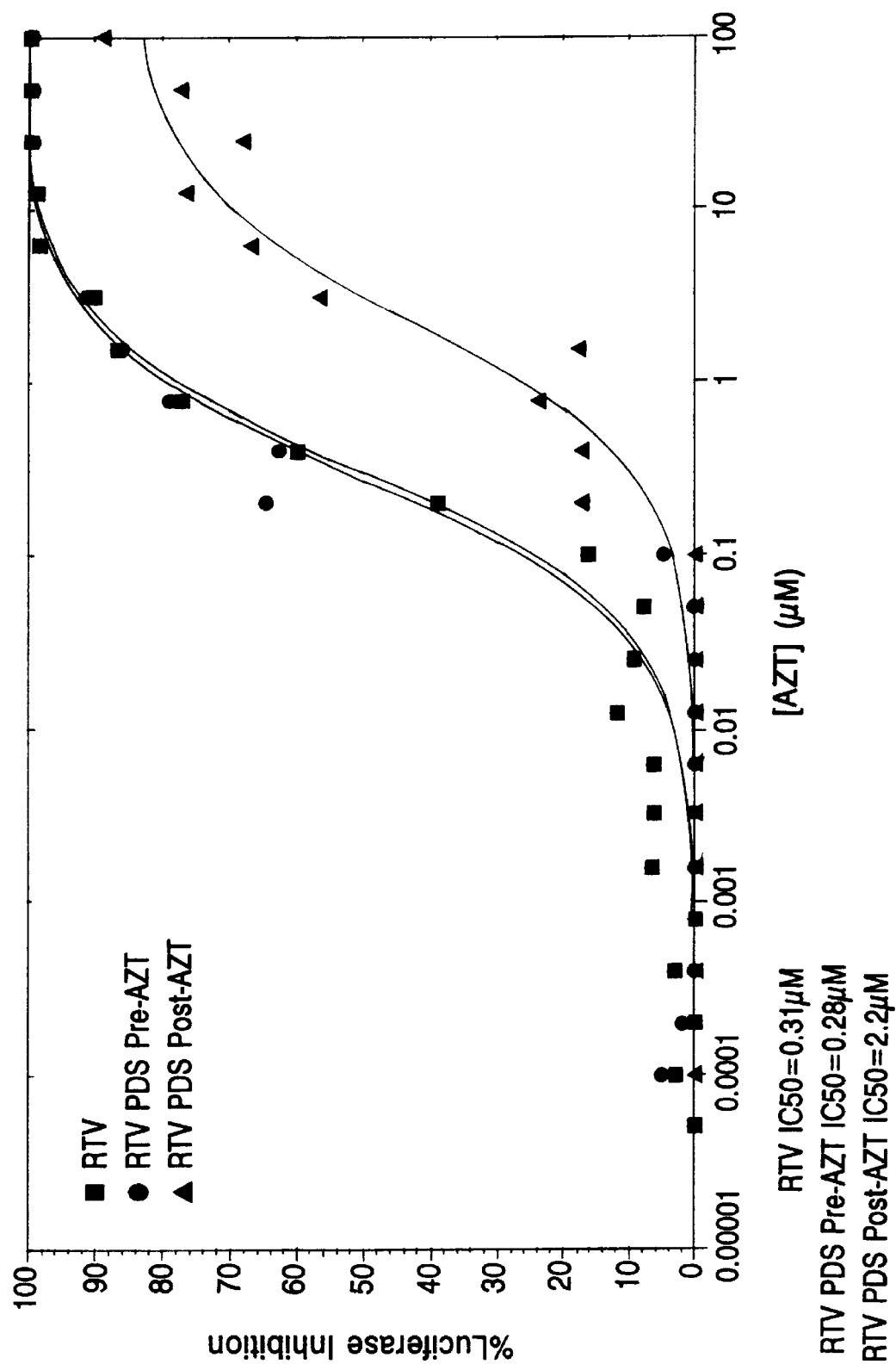

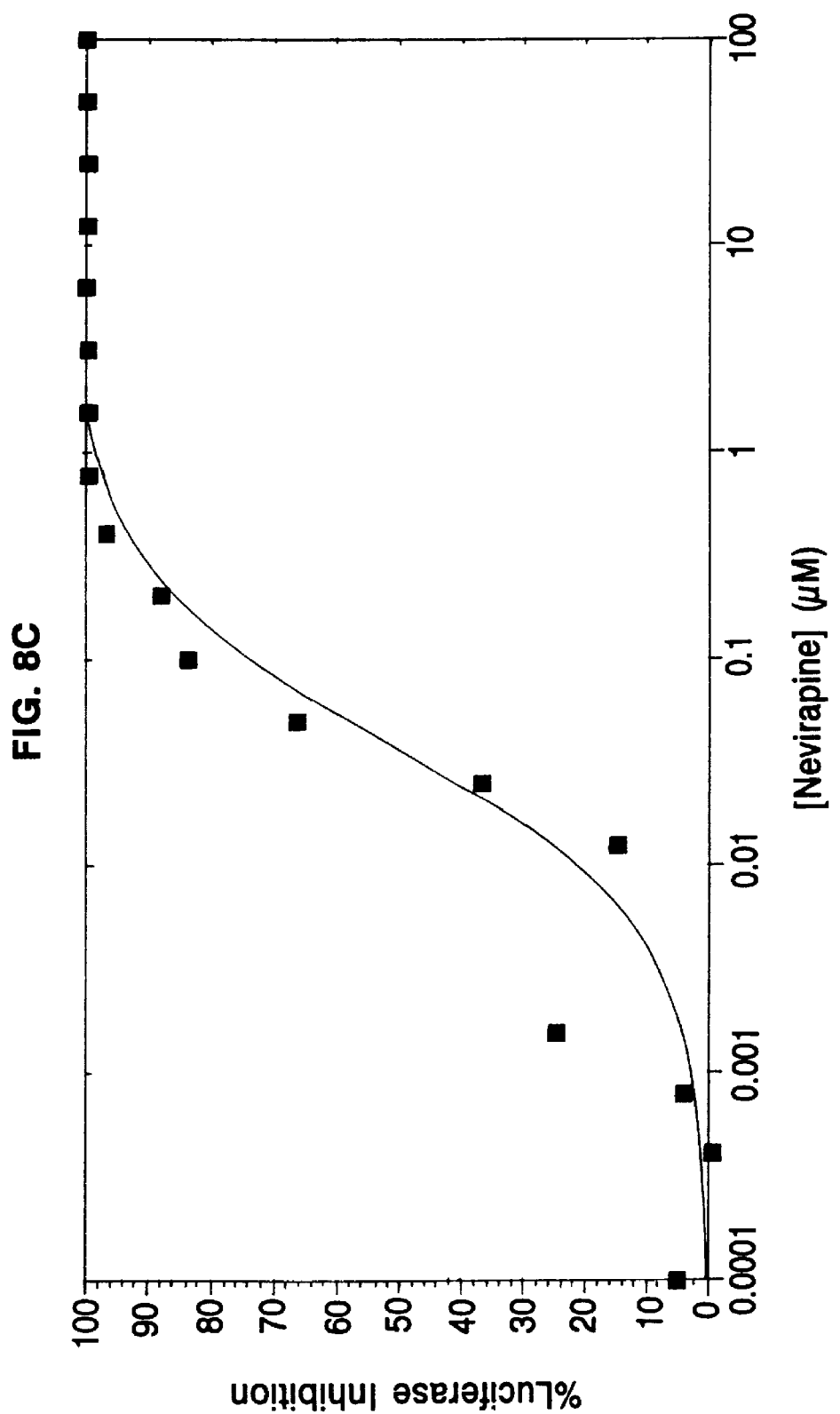

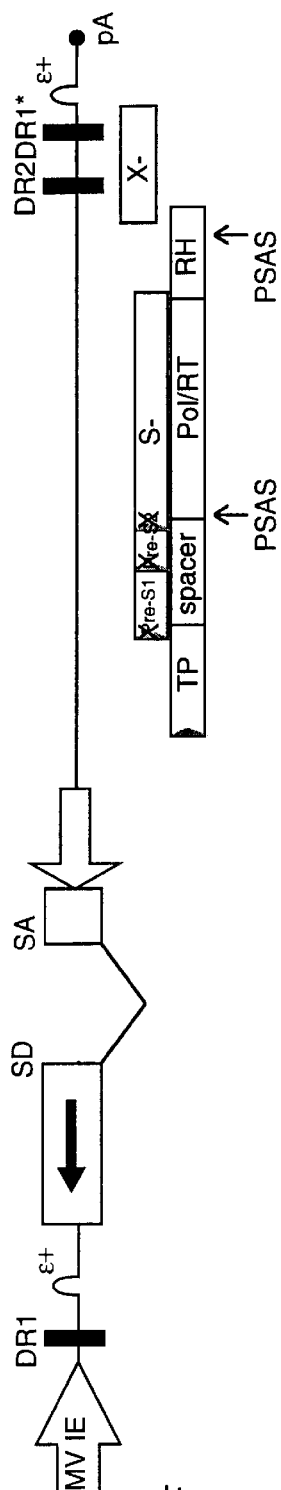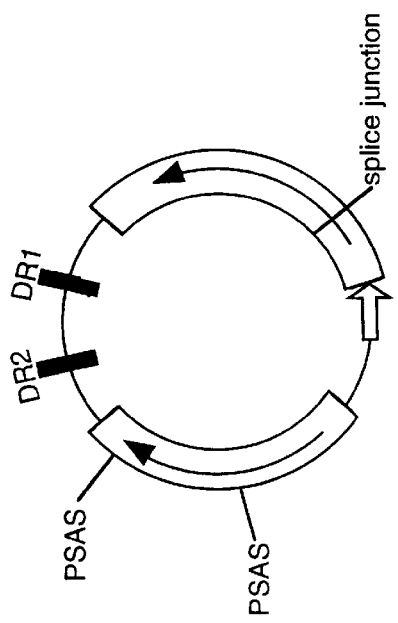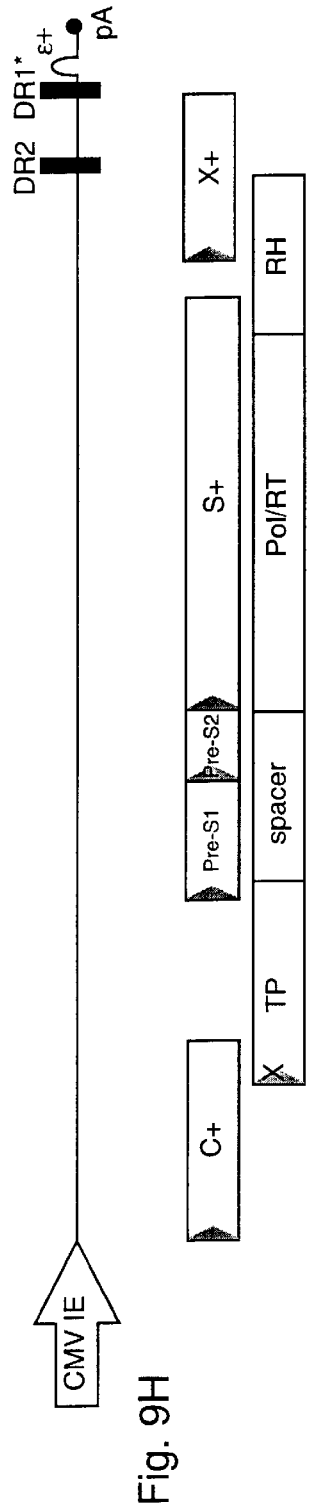
Fig. 9F
Fig. 9G
Fig. 9H

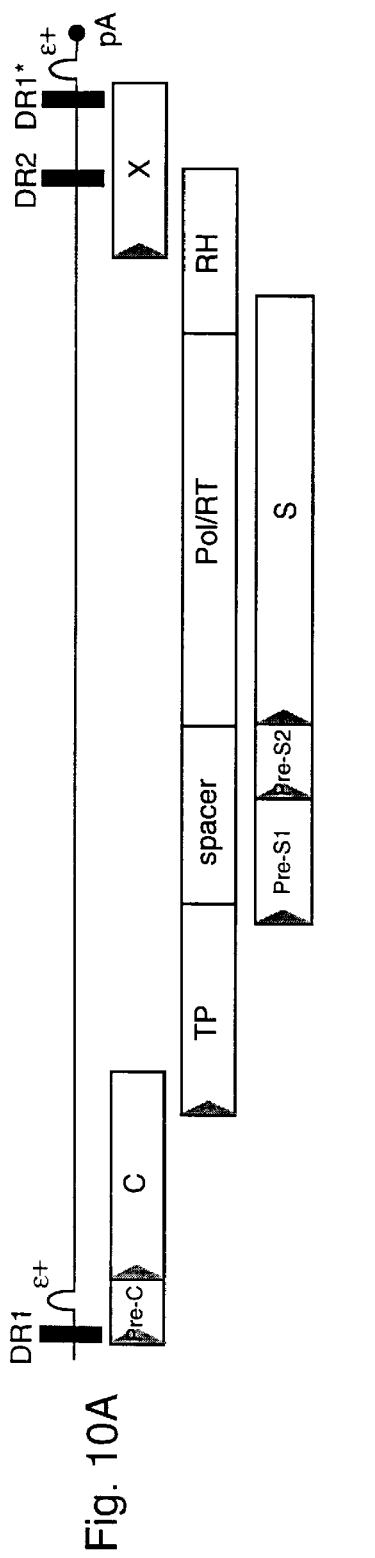
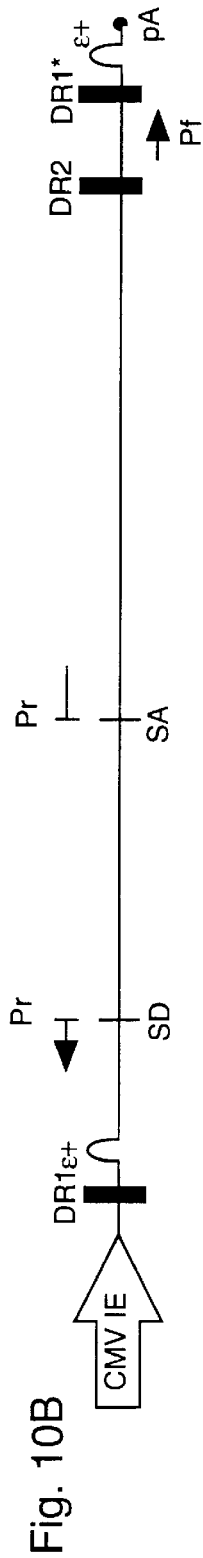
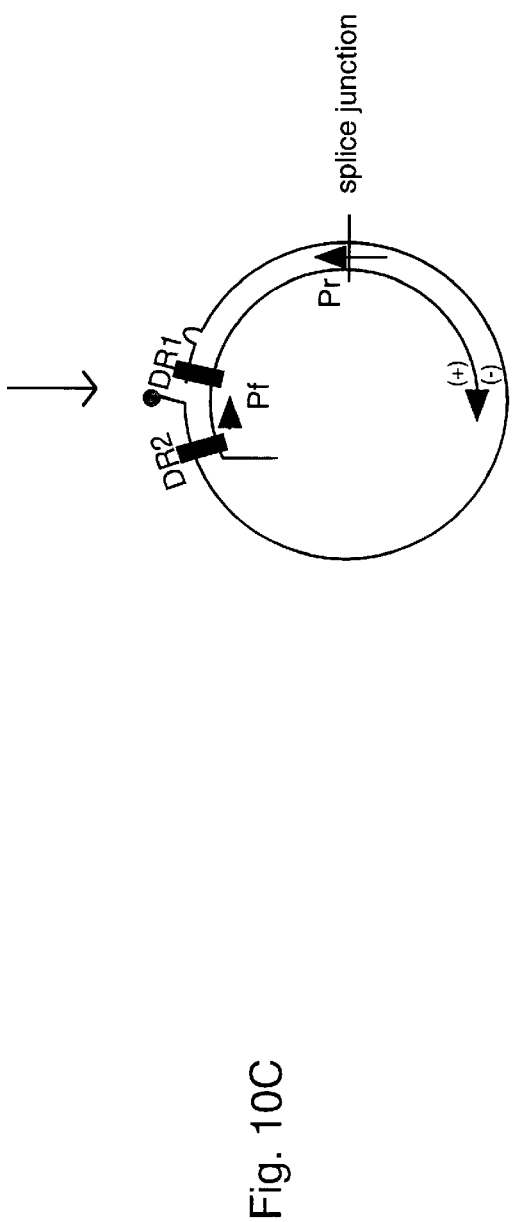
Fig. 10A
Fig. 10B
Fig. 10C

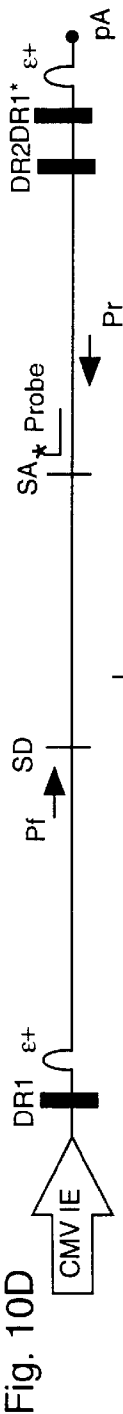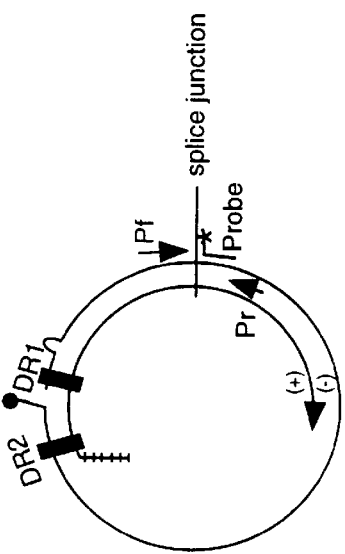
Fig. 10D  Fig. 10E  Fig. 10F  Fig. 10G

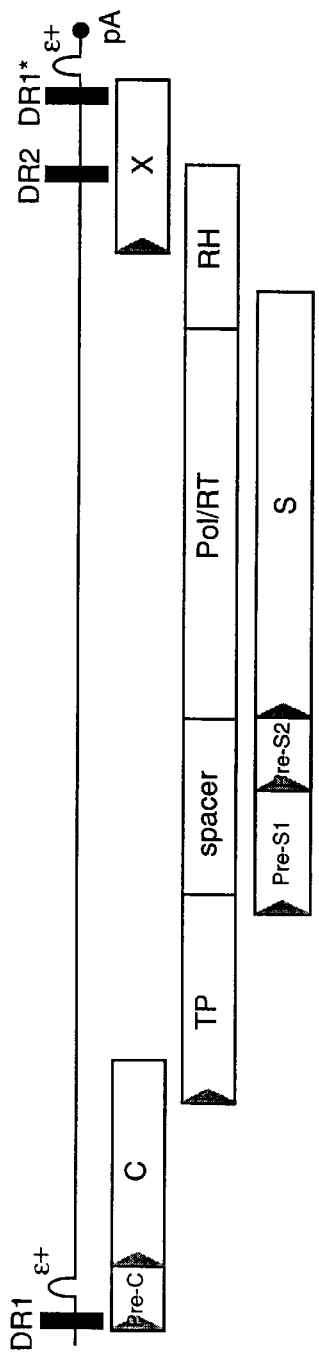
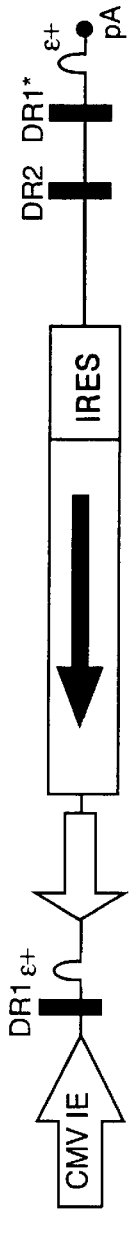
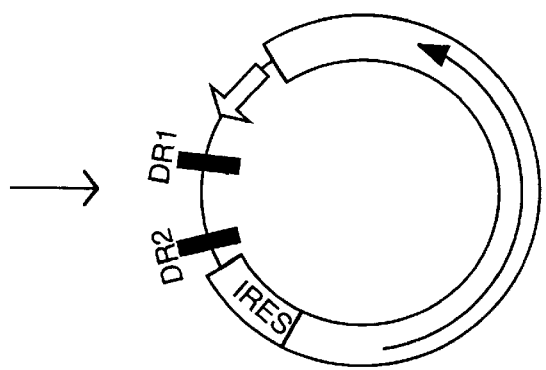
FIG. 11A
Fig. 11B
Fig. 11C

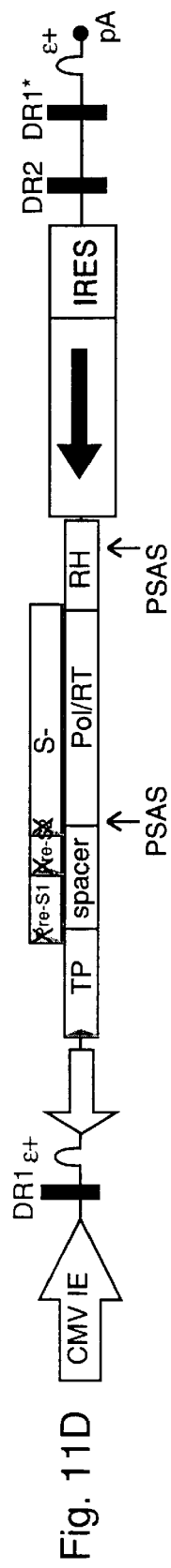
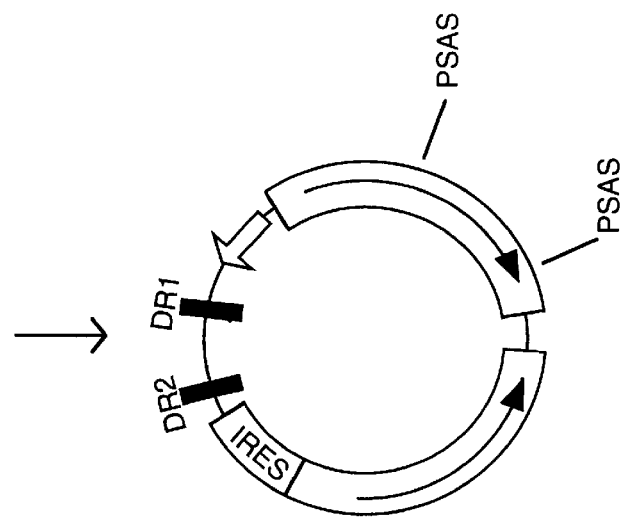
Fig. 11D
Fig. 11E

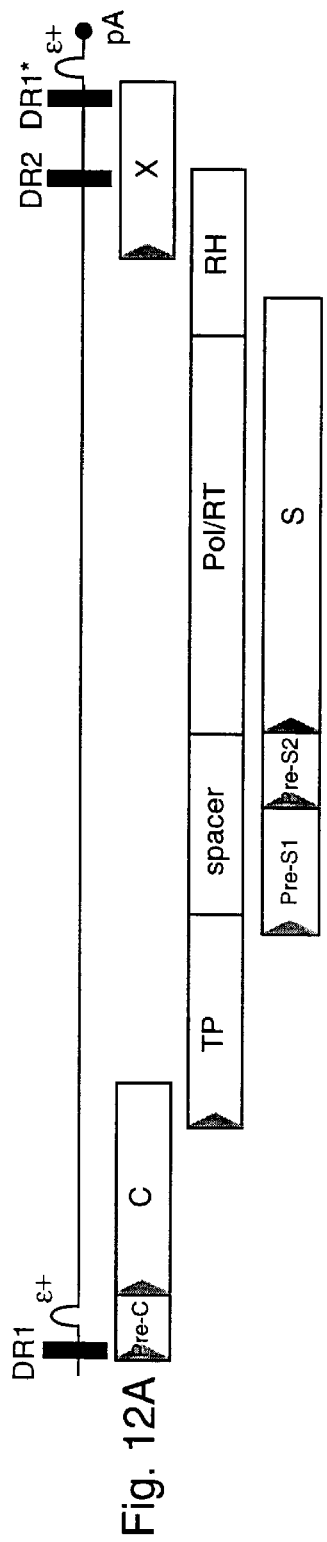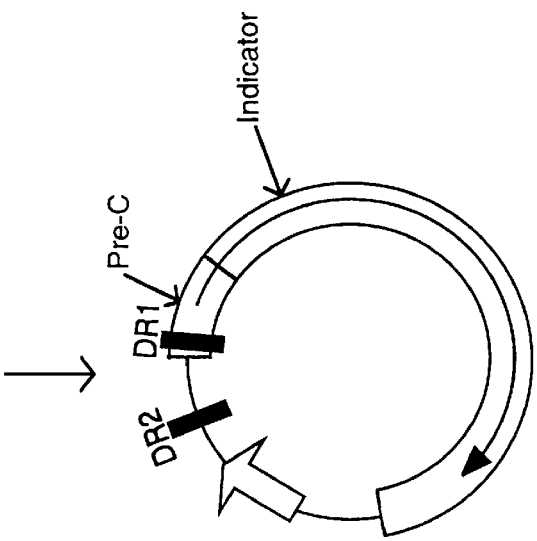
Fig. 12A
Fig. 12B
Fig. 12C

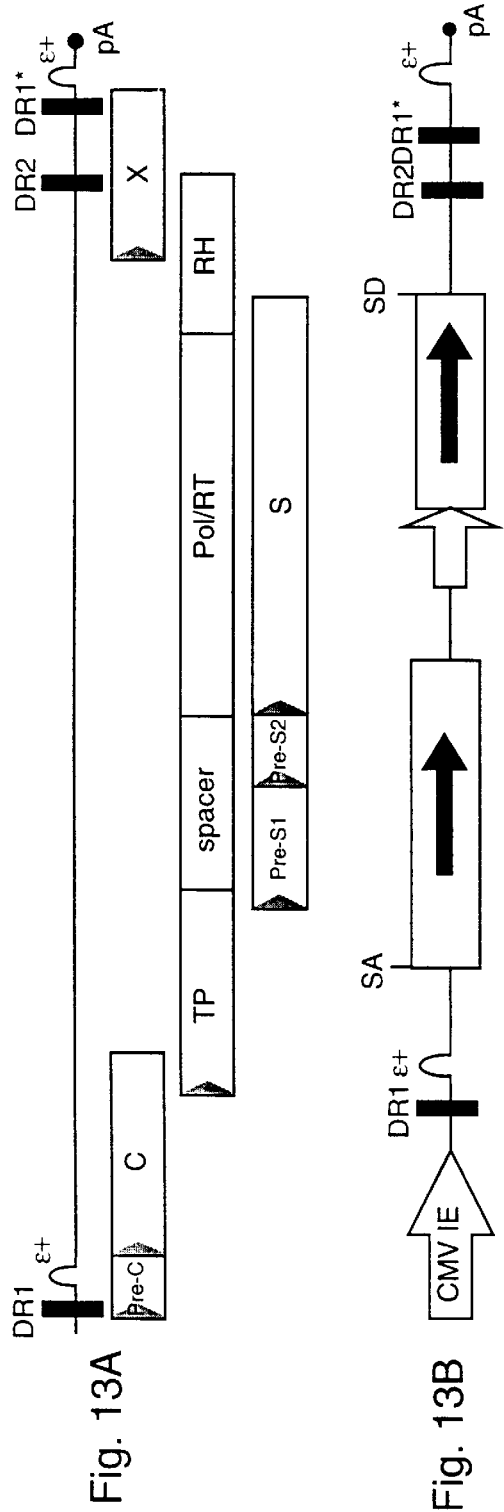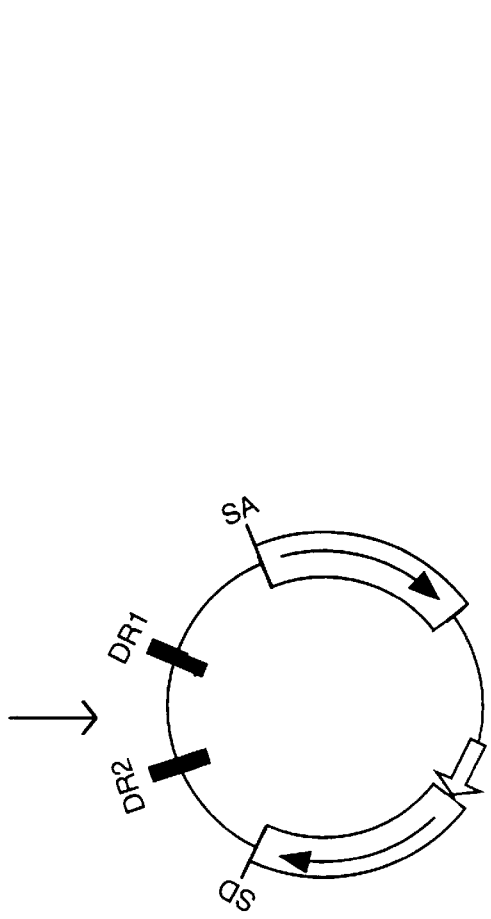
Fig. 13A
Fig. 13B
Fig. 13C

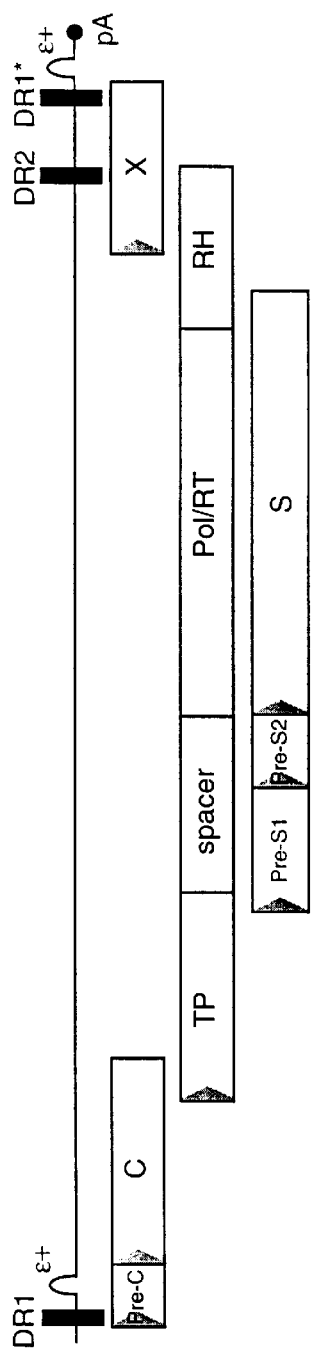
Fig. 14A
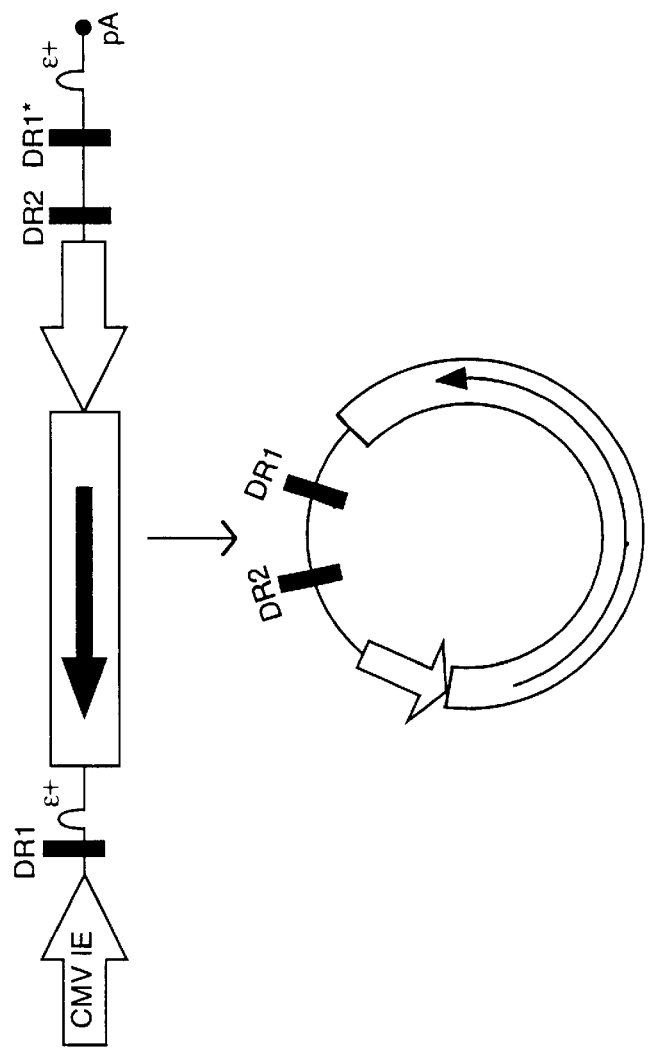
Fig. 14B
Fig. 14C

COMPOSITIONS AND METHODS FOR DETERMINING ANTI-VIRAL DRUG SUSCEPTIBILITY AND RESISTANCE AND ANTI-VIRAL DRUG SCREENING

This application claims the benefit of U.S. Provisional Application No. 60/010,715, filed Jan. 29, 1996, the content of which is incorporated herein by reference.

TECHNICAL FIELD

This invention relates to anti-viral drug susceptibility and resistance tests to be used in identifying effective drug regimens for the treatment of viral infections. The invention further relates to novel vectors, host cells and compositions for carrying out these novel anti-viral drug susceptibility and resistance tests. This invention also relates to the screening of candidate drugs for their capacity to inhibit selected viral sequences and/or viral proteins. More particularly, the invention relates to the use of recombinant DNA technology to first construct a resistance test vector comprising a patient-derived segment and an indicator gene, then introducing the resistance test vector into a host cell, and determining the expression or inhibition of the indicator gene product in a target host cell in the presence of an anti-viral drug. This invention is also related to the means and methods of identifying anti-viral drugs which have distinct patterns of resistance when compared with existing anti-viral drugs. This invention also relates to methods and compositions for the identification and assessment of the biological effectiveness of potential therapeutic compounds. This invention is more particularly related to drug susceptibility and resistance tests useful in providing an optimal therapeutic regimen for the treatment of various viral diseases, including for example, HIV/AIDS and hepatitis.

BACKGROUND OF THE INVENTION

Viral Drug Resistance

The use of anti-viral compounds for chemotherapy and chemoprophylaxis of viral diseases is a relatively new development in the field of infectious diseases, particularly when compared with the more than 50 years of experience with antibacterial antibiotics. The design of anti-viral compounds is not straightforward because viruses present a number of unique problems. Viruses must replicate intracellularly and often employ host cell enzymes, macromolecules, and organelles for the synthesis of virus particles. Therefore, safe and effective anti-viral compounds must be able to discriminate with a high degree of efficiency between cellular and virus-specific functions. In addition, because of the nature of virus replication, evaluation of the in vitro sensitivity of virus isolates to anti-viral compounds must be carried out in a complex culture system consisting of living cells (e.g. tissue culture). The results from such assay systems vary widely according to the type of tissue culture cells which are employed and the conditions of assay. Despite these complexities nine drugs have been approved for AIDS therapy, five reverse transcriptase inhibitors AZT, ddI, ddC, d4T, 3TC, one non-nucleoside reverse transcriptase inhibitor, nevirapine and three protease inhibitors saquinavir, ritonavir and indinovir and several additional anti-viral drug candidates have been recently developed such as nelfinavir, delaviridine, VX-478 and 1592.

Viral drug resistance is a substantial problem given the high rate of viral replication and mutation frequencies. Drug resistant mutants were first recognized for poxviruses with thiosemicarbazone (Appleyard and Way (1966) *Brit. J. Exptl. Pathol.* 47, 144–51), for poliovirus with guanidine (Melnick et al. (1961) *Science* 134, 557), for influenza A virus with amantadine (Oxford et al. (1970) *Nature* 226, 82–83; Cochran et al. (1965) *Ann. NY Acad Sci* 130, 423–429) and for herpes simplex virus with iododeoxyuridine (Jawetz et al. (1970) *Ann. NY Acad Sci* 173, 282–291). Approximately 75 HIV drug resistance mutations to various anti-viral agents have been identified to date (Mellors et al. (1995) *Intnl. Antiviral News*, supplement and Condra, J. H. et al. (1996) *J Virol.* 70, 8270–8276).

The small and efficient genomes of viruses have lent themselves to the intensive investigation of the molecular genetics, structure and replicative cycles of most important human viral pathogens. As a consequence, the sites and mechanisms have been characterized for both the activity of and resistance to anti-viral drugs more precisely than have those for any other class of drugs. (Richman (1994) *Trends Microbiol.* 2, 401–407). The likelihood that resistant mutants will emerge is a function of at least four factors: 1) the viral mutation frequency; 2) the intrinsic mutability of the viral target site with respect to a specific anti-viral; 3) the selective pressure of the anti-viral drug; and, 4) the magnitude and rate of virus replication. With regard to the first factor, for single stranded RNA viruses, whose genome replication lacks a proofreading mechanism, the mutation frequencies are approximately $3 \times 10^{-5}$ per base-pair per replicative cycle (Holland et al. (1992) *Curr. Topics Microbiol Immunol.* 176, 1–20; Mansky et al. (1995) *J Virol.* 69, 5087–94; Coffin (1995) *Science* 267, 483–489). Thus, a single 10 kilobase genome, like that of human immunodeficiency virus (HIV), would be expected to contain on average one mutation for every three progeny viral genomes. As to the second factor, the intrinsic mutability of the viral target site in response to a specific anti-viral agent can significantly affect the likelihood of resistant mutants. For example, zidovudine (AZT) selects for mutations in the reverse transcriptase of HIV more readily in vitro and in vivo than does the other approved thymidine analog d4T (stavudine).

One, perhaps inevitable consequence of the action of an anti-viral drug is that it confers sufficient selective pressure on virus replication to select for drug-resistant mutants (Herrmann et al. (1977) *Ann NY Acad Sci* 284, 632–7). With respect to the third factor, with increasing drug exposure, the selective pressure on the replicating virus population increases to promote the more rapid emergence of drug resistant mutants. For example, higher doses of AZT tend to select for drug resistant virus more rapidly than do lower doses (Richman et al. (1990) *J. AIDS.* 3, 743–6). This selective pressure for resistant mutants increases the likelihood of such mutants arising as long as significant levels of virus replication are sustained.

The fourth factor, the magnitude and rate of replication of the virus population, has major consequences on the likelihood of emergence of resistant mutants. Many virus infections are characterized by high levels of virus replication with high rates of virus turnover. This is especially true of chronic infections with HIV as well as hepatitis B and C viruses. The likelihood of emergence of AZT resistance increases in HIV-infected patients with diminishing CD4 lymphocyte counts which are associated with increasing levels of HIV replication (Ibid).

Higher levels of virus increase the probability of preexisting mutants. It has been shown that the emergence of a resistant population results from the survival and selective proliferation of a previously existing subpopulation that randomly emerges in the absence of selective pressure. All viruses have a baseline mutation rate. With calculations of approximately $10^{10}$ new virions being generated daily during HIV infection (Ho et al. (1995) *Nature* 373, 123–126), a mutation rate of $10^{-4}$ to $10^{-5}$ per nucleotide guarantees the preexistence of almost any mutation at any time point during HIV infection. Evidence is accumulating that drug resistant mutants do in fact exist in subpopulations of HIV infected individuals (Najera et al. (1994) *AIDS Res Hum Retroviruses* 10, 1479–88; Najera et al. (1995) *J Virol.* 69, 23–31). The preexistence of drug resistant picornavirus mutants at a rate of approximately $10^{-5}$ is also well documented (Ahmad et al. (1987) *Antiviral Res.* 8, 27–39).

Human Immunodeficiency Virus (HIV)

Acquired immune deficiency syndrome (AIDS) is a fatal human disease, generally considered to be one of the more serious diseases to ever affect humankind. Globally, the numbers of human immunodeficiency virus (HIV) infected individuals and of AIDS cases increase relentlessly and efforts to curb the course of the pandemic, some believe, are of limited effectiveness. Two types of HIV are now recognized: HIV-1 and HIV-2. By Dec. 31, 1994 a total of 1,025,073 AIDS cases had been reported to the World Health Organization. This is only a portion of the total cases, and WHO estimates that as of late 1994, allowing for underdiagnosis, underreporting and delays in reporting, and based on the estimated number of HIV infections, there have been over 4.5 million cumulative AIDS cases worldwide (Mertens et al. (1995) *AIDS* 9 (Suppl A), S259–S272). Since HIV began its spread in North America, Europe and sub-Saharan Africa, over 19.5 million men, women and children are estimated to have been infected (Ibid). One of the distinguishing features of the AIDS pandemic has been its global spread within the last 20 years, with about 190 countries reporting AIDS cases today. The projections of HIV infection worldwide by the WHO are staggering. The projected cumulative total of adult AIDS cases by the year 2000 is nearly 10 million. By the year 2000, the cumulative number of HIV-related deaths in adults is predicted to rise to more than 8 million from the current total of around 3 million.

HIV-1 and HIV-2 are enveloped retroviruses with a diploid genome having two identical RNA molecules. The molecular organization of HIV is (5') U3-R-U5-gag-pol-env-U3-R-U5 (3') as shown in FIG. 1*a*. The U3, R, and U5 sequences form the long terminal repeats (LTR) which are the regulatory elements that promote the expression of the viral genes and sometimes nearby cellular genes in infected hosts. The internal regions of the viral RNA code for the structural proteins: gag (p55, p17, p24 and p7 core proteins), pol (p10 protease, p66 and p51 reverse transcriptase and p32 integrase) and env (gp120 and gp41 envelope glycoproteins). Gag codes for a polyprotein precursor that is cleaved by a viral protease into three or four structural proteins; pol codes for reverse transcriptase (RT) and the viral protease and integrase; env codes for the transmembrane and outer glycoprotein of the virus. The gag and pol genes are expressed as a genomic RNA while the env gene is expressed as a spliced subgenomic RNA. In addition to the env gene there are other HIV genes produced by spliced subgenomic RNAs that contribute to the replication and biologic activities of the virus. These genes include: tat which encodes a protein that activates the expression of viral and some cellular genes; rev which encodes a protein that promotes the expression of unspliced or single-spliced viral mRNAs; nef which encodes a myristylated protein that appears to modulate viral production under certain conditions; vif which encodes a protein that affects the ability of virus particles to infect target cells but does not appear to affect viral expression or transmission by cell-to-cell contact; vpr which encodes a virion-associated protein; and vpu which encodes a protein that appears to promote the extracellular release of viral particles.

No disease better exemplifies the problem of viral drug resistance than AIDS. Drug resistant HIV isolates have been identified for nucleoside and non-nucleoside reverse transcriptase inhibitors and for protease inhibitors. The emergence of HIV isolates resistant to AZT is not surprising since AZT and other reverse transcriptase inhibitors only reduce virus replication by about 90%. High rates of virus replication in the presence of the selective pressure of drug treatment provide ideal conditions for the emergence of drug-resistant mutants. Patients at later stages of infection who have higher levels of virus replication develop resistant virus with AZT treatment more quickly than those at early stages of infection (Richman et al. (1990) *J AIDS* 3, 743–6). The initial description of the emergence of resistance to AZT identified progressive and stepwise reductions in drug susceptibility (Larder et al. (1989) *Science* 243, 1731–1734). This was explained by the recognition of multiple mutations in the gene for reverse transcriptase that contributed to reduced susceptibility (Larder et al. (1989) *Science* 246, 1155–1158). These mutations had an additive or even synergistic contribution to the phenotype of reduced susceptibility (Kellam et al. (1992) *Proc. Natl. Acad. Sci.* 89, 1934–1938). The cumulative acquisition of such mutations resulted in progressive decreases in susceptibility. Similar effects have been seen with non-nucleoside reverse transcriptase inhibitors (Nunberg et al. (1991) *J Virol* 65, 4887–4892; Sardanna et al. (1992) *J Biol Chem* 267, 17526–17530). Studies of protease inhibitors have found that the selection of HIV strains with reduced drug susceptibility occurs within weeks (Ho et al. (1994) *J Virol* 68, 2016–2020; Kaplan et al. (1994) *Proc. Natl. Acad. Sci.* 91, 5597–5601). While recent studies have shown protease inhibitors to be more powerful than reverse transcriptase inhibitors, nevertheless resistance has developed. (Condra et al., Id. and Report 3rd Conference on Retroviruses and Opportunistic Infections, March 1996). Subtherapeutic drug levels, whether caused by reduced dosing, drug interactions, malabsorption or reduced bioavailability due to other factors, or self-imposed drug holidays, all permit increased viral replication and increased opportunity for mutation and resistance. (Id.)

The selective pressure of drug treatment permits the outgrowth of preexisting mutants. With continuing viral replication in the absence of completely suppressive antiviral drug activity, the cumulative acquisition of multiple mutations can occur over time, as has been described for AZT and protease inhibitors of HIV. Indeed viral mutants multiply resistant to different drugs have been observed (Larder et al. (1989) *Science* 243, 1731–1734; Larder et al. (1989) *Science* 246, 1155–1158; Condra et al. (1995) *Nature* 374, 569–71). With the inevitable emergence of resistance in many viral infections, as with HIV for example, strategies must be designed to optimize treatment in the face of resistant virus populations. Ascertaining the contribution of drug resistance to drug failure is a difficult problem because patients who are more likely to develop drug resistance are more likely to have other confounding factors that will predispose them to a poor prognosis (Richman (1994) *AIDS Res Hum Retroviruses* 10, 901–905). In addition patients contain mixtures of viruses with different susceptibilities.

Hepatitis B (HBV)

HBV is a causative agent for acute and chronic hepatitis, which strikes about 200 million patients worldwide. Zuckerman A. J. *Trans. R. Soc. Trop. Med. Hygiene* (1982) 76, 711–718. HBV infection acquired in adult life is often clinically inapparent, and most acutely infected adults recover completely from the disease and clear the virus. Rarely, however, the acute liver disease may be so severe that the patient dies of fulminant hepatitis. A small fraction, perhaps 5 to 10%, of acutely infected adults, becomes persistently infected by the virus and develops chronic liver disease of varying severity. Neonatally transmitted HBV infection, however, is rarely cleared, and more than 90% of such children become chronically infected. Because HBV is commonly spread from infected mother to newborn infant in highly populated areas of Africa and Asia, several hundred million people throughout the world are persistently infected by HBV for most of their lives and suffer varying degrees of chronic liver disease, which greatly increases their risk of developing cirrhosis and hepatocellular carcinoma (HCC). Indeed, the risk of HCC is increased 100-fold in patients with chronic hepatitis, and the lifetime risk of HCC in males infected at birth approaches 40%. Beasley RP et al., *Lancet* (1981) 2, 1129–1133. Accordingly, a large fraction of the world's population suffers from and dies of these late complications of HBV infection. The development of anti-HBV drugs has been long awaited, but has been hampered by the extremely narrow host range of HBV: HBV replicates mainly in human and chimpanzee livers and not in experimental animals or in cultured cells. Tiollais, P et al. *Nature* (London) (1985) 317, 489–495.

Hepatitis B virus is a DNA virus with a compact genomic structure; despite its small, circular, 3200 base pairs, HBV DNA codes for four sets of viral products and has a complex, multiparticle structure. HBV achieves its genomic economy by relying on an efficient strategy of encoding proteins from four overlapping genes: S, C, P, and X. HBV is one of a family of animal viruses, hepadnaviruses, and is classified as hepadnavirus type 1. Similar viruses infect certain species of woodchucks, ground and tree squirrels, and Pekin ducks. All hepadnaviruses, including HBV, share the following characteristics: 1) three distinctive morphological forms exist, 2) all members have proteins that are functional and structural counterparts to the envelope and nucleocapsid antigens of HBV, 3) they replicate within the liver but can also exist in extrahepatic sites, 4) they contain an endogenous DNA polymerase with both RNA- and DNA-dependent DNA polymerase activities, 5) their genomes are partially double stranded circular DNA molecules, 6) they are associated with acute and chronic hepatitis and hepatocellular carcinoma and 7) replication of their genome goes through an RNA intermediate which is reverse transcribed into DNA using the virus's endogenous RNA-dependent DNA polymerase activity in a manner analogous to that seen in retroviruses. In the nucleus of infected liver cells, the partially double stranded DNA is converted to a covalently closed circular double stranded DNA (cccDNA) by the DNA-dependent DNA polymerase. Transcription of the viral DNA is accomplished by a host RNA polymerase and gives rise to several RNA transcripts that differ in their initiation sites but all terminate at a common polyadenylation signal. The longest of these RNAs acts as the pregenome for the virus as well as the message for the some of the viral proteins. Viral proteins are translated from the pregenomic RNAs, and the proteins and RNA pregenome are packaged into virions and secreted from the hepatocyte. Although HBV is difficult to cultivate in vitro, several cells have been successfully transfected with HBV DNA resulting in the in vitro production of HBV particles.

There are three particulate forms of HBV: non-infectious 22 nm particles, which appear as either spherical or long filamentous forms, and 42 nm double-shelled spherical particles which represent the intact infectious hepatitis B virion. The envelope protein, HBsAg, is the product of the S gene of HBV and is found on the outer surface of the virion and on the smaller spherical and tubular structures. Upstream of the S gene open reading frame are the pre-S gene open reading frames, pre-S1 and pre-S2, which code for the pre-S gene products, including receptors on the HBV surface for polymerized human serum albumin and the attachment sites for hepatocyte receptors. The intact 42 nm virion can be disrupted by mild detergents and the 27 nm nucleocapsid core particle isolated. The core is composed of two nucleocapsid proteins coded for by the C gene. The C gene has two initiation codons defining a core and a precore region. The major antigen expressed on the surface of the nucleocapsid core is coded for by the core region and is referred to as hepatitis B core antigen (HBcAg). Hepatitis B e antigen (HBeAg) is produced from the same C gene by initiation at the precore ATG.

Also packaged within the nucleocapsid core is a DNA polymerase, which directs replication and repair of HBV DNA. The DNA polymerase is coded for by the P gene, the third and largest of the HBV genes. The enzyme has both DNA-dependent DNA polymerase and RNA-dependent reverse transcriptase activities and is also required for efficient encapsidation of the pregenomic RNA. The fourth gene, X, codes for a small, non-particle-associated protein which has been shown to be capable of transactivating the transcription of both viral and cellular genes.

Although HBV replication is fairly well understood, early steps in HBV infection have not been well defined. Cellular receptors or attachment sites on the virions cannot be studied without appropriate tissue culture assays. In an effort to address this problem, certain cell lines have been developed, human hepatoblastoma cells Huh (HB 611) (Ueda, K. et al., *Virology* (1989) 169, 213–216) and HepG2 cells (Galle, P. R. and Theilmann, L. *Arzneim-Forsch. Drug Res.* (1990) 40, 1380–1382) for evaluation of anti-HBV drugs.

Recently, attention has focused on molecular variants of HBV. Variation occurs throughout the HBV genome, and clinical isolates of HBV that do not express viral proteins have been attributed to mutation in individual or even multiple gene locations. For example, variants have been described which lack nucleocapsid proteins, envelope proteins, or both. Two mutants have attracted attention. The first is found in certain patients with severe chronic HBV infection. These patients were found to be infected with an HBV mutant that contained an alteration in the precore region rendering the virus incapable of encoding HBeAg. The most commonly encountered mutation in such patients is a single base substitution, from G to A, which occurs in the second to last codon of the pre-C gene at nucleotide 1896. This substitution results in the replacement of the TGG tryptophan codon by a stop codon (TAG), which prevents the translation of HBeAg. Patients with such precore mutants that are unable to secrete HBeAg tend to have severe liver disease that progresses rapidly to cirrhosis and that does not respond readily to anti-viral therapy.

The second category of HBV mutants consists of escape mutants, in which a single amino acid substitution, from glycine to arginine, occurs at position 145 of the immunodominant a determinant common to all subtypes of HBsAg. This change in HBsAg leads to a critical conformational change that results in a loss of neutralizing activity by anti-HBs antibody.

Presently Available Viral Resistance Assays

The definition of viral drug susceptibility is generally understood to be the concentration of the anti-viral agent at which a given percentage of viral replication is inhibited (e.g. the $IC_{50}$ for an anti-viral agent is the concentration at which 50% of virus replication is inhibited). Thus, a decrease in viral drug susceptibility is the hallmark that an anti-viral has selected for mutant virus that is resistant to that anti-viral drug. Viral drug resistance is generally defined as a decrease in viral drug susceptibility in a given patient over time. In the clinical context, viral drug resistance is evidenced by the anti-viral drug being less effective or no longer being clinically effective in a patient.

At present the tools available to the researcher and clinician to assess anti-viral drug susceptibility and resistance are inadequate. The classical test for determining the resistance and sensitivity of HIV to an anti-viral agent is complex, time-consuming, expensive, and is hazardous in that it requires the culture of pathogenic virus from each and every patient (Barre-Sinoussi et al (1983) *Science* 220, 868–871; Popovic et al. (1984) *Science* 224, 497–500). In this procedure, the patient's peripheral blood mononuclear cells (PBMC) are first cultured to establish a viral stock of known multiplicity of infection (moi), and the viral stock thereby produced is used to infect a target indicator cell line. The resulting burst of viral replication is then typically measured in the presence and absence of an anti-viral agent by determining the production of viral antigens in the cell culture. Such tests can be performed reliably only in the hands of expert investigators, and may take two to three months to carry out at a cost of thousands of dollars per patient for each agent tested. Furthermore, as viral stocks of sufficient moi cannot be established from the PBMC of some HIV patients, the classical test for HIV resistance cannot be performed on all HIV-infected individuals. More significantly, in the course of generating the viral stock by passage of the virus in culture, the characteristics of the viruses themselves can change and may therefore obscure the true nature of the patient's virus. Thus, the application of the classical test has been limited to gathering information about trends in clinical trials and has not been available for a prospective analysis which could be used to custom tailor anti-viral therapy for a given patient. Notwithstanding these limitations, the classical test has two important qualities: it is specific for the agent under evaluation, and it provides information on the phenotype of the patient's own virus, that is, the concentration of the drug which inhibits 50% of viral replication ($IC_{50}$).

A number of attempts have been made to improve upon the classical test, but each of these has serious shortcomings. The first type of these tests can be described as nonspecific in that they do not determine the characteristics of a patient's own virus at all, but rather provide an independent measure of the course of the infection. Among these tests are those which measure the patient's $CD4^+$ T cell count, the hallmark of HIV disease progression (Goedert et al. (1987) *JAMA* 257, 331–334), those which measure viral antigen levels (e.g., p24 core antigen (Allain et al. (1987) *N. Engl. J. Med.* 317, 1114–1121)), and those which measure viral RNA and DNA levels (e.g., quantitative polymerase chain reaction and branched DNA assays (Piatak et al. (1993) *Science* 259, 1749–1754; Urdea (1993) *Clin. Chem.* 39, 725–726)). The primary disadvantage of such nonspecific tests is that they do not provide any information on viral drug resistance per se, but rather attempt to infer this information from the apparent course of the patient's disease. In addition, many factors other than viral drug resistance can affect the level of the parameter under consideration. In other words, $CD4^+$ T cell counts, p24 antigen levels and HIV viral RNA levels can vary for reasons other than drug resistance during the course of disease.

Another modified classical test amplifies the viral gene that is the target of the anti-viral agent. In this test the viral gene from a given patient is amplified and then recombined into a biologically active proviral clone of HIV. This proviral clone is transfected into human cells to generate a viral stock of known moi which can then be used to infect a target indicator cell line. In the manner of the classical test, one then determines the production of viral antigens in the presence or absence of the anti-viral agent. One such assay described by Kellam and Larder (1994) *Antimicrobial Agents and Chemo*. 38, 23–30, involves PCR amplification of reverse transcriptase coding sequences from a patient, which is then introduced into a proviral DNA clone by homologous recombination to reconstitute the complete viral genome including the reverse transcriptase gene which was deleted. The resulting recombinant virus produced from such clones is then cultured in T-cell lines, and the drug sensitivity is tested in the HeLa $CD4^+$ plaque reduction assay. However, this class of test still requires the culturing of virus to determine drug resistance, and is thus difficult, lengthy and costly and requires the laboratory investigator to handle hazardous viral cultures. Furthermore, given the attendant variation of the virus itself during the culture process, the results may be correspondingly inaccurate.

A second class of test attempts to provide specific information on the genotype of the patient's HIV, with the ultimate goal of correlating this genotypic information with the virus' drug resistant phenotype. Indeed, specific amino acid substitutions within viral genes such as reverse transcriptase and protease genes have been shown to correspond to specific levels of viral resistance to reverse transcriptase and protease inhibitors, respectively (Larder et al. (1994) *J. Gen Virol.* 75, 951–957). A major shortcoming associated with such an analysis is that it is indirect and can be obfuscated by secondary mutations which have been shown to add to or counter the effects of the first mutation. It is the complex interplay of all amino acid residues within a given viral polypeptide which ultimately determines the gene product's activity in the presence or absence of an inhibitor. Thus, a database of vast and impractical proportions would be necessary to interpret the status of drug resistance or sensitivity of a given genotype, given the number of potential amino acid changes in the HIV genome.

A third class of test, a recently developed bacterial-based assay makes use of a molecularly cloned viral gene (specifically, the reverse transcriptase gene) which has been inserted into a bacterial expression vector. Upon transformation of special strains of *E. coli* which are deficient in the bacterial DNA polymerase I, the cloned reverse transcriptase gene can rescue the growth of the bacteria under selected growth conditions. In making *E. coli* dependent upon reverse transcriptase for their growth, one can ascertain the effects of certain reverse transcriptase inhibitors on the activity of the viral gene (PCT Application No. WO 95/22622). A major shortcoming with this approach, however, is that the inhibitor may be transported across the cell membrane and metabolized differently by the bacteria than it is by a human cell, and as a result the concentration of the true metabolic inhibitor of the reverse transcriptase may be grossly different in the bacterium than it would be in a relevant human cell target of infection, or the true inhibitor may be absent altogether. Indeed, nucleoside metabolism is known to differ markedly between human and bacterial cells. Another significant shortcoming of this approach is that the assay measures DNA-dependent DNA polymerase activity of reverse transcriptase but not the RNA-dependent DNA polymerase, strand transfer or RNAse H activities of the reverse transcriptase. Thus, an anti-viral compound which acts, at least in part, on these other activities would not have its full inhibitory activity in this assay. Yet another difficulty with this approach is that it is a growth-based test; thus if an inhibitor (eg., a nucleoside analog) also blocks bacterial growth for reasons other than its effects on reverse transcriptase, it can not be adequately tested in this system.

Viral Vectors

Viral vectors and particularly retroviral vectors have been used for modifying mammalian cells because of the high efficiency with which retroviral vectors infect target cells and integrate into the target cell genome. Because of their ability to insert into the genome of mammalian cells much attention has focused on retroviral vectors for use in gene therapy. Details on retroviral vectors and their use can be found in patents and patent publications including European Patent Application EPA 0 178 220, U.S. Pat. No. 4,405,712, PCT Application WO 92/07943, U.S. Pat. No. 4,980,289, U.S. Pat. No. 5,439,809 and PCT Application WO 89/11539. The teachings of these patents and publications are incorporated herein by reference.

One consequence of the emphasis on retroviral vector technology has been the development of packaging cell lines. A major problem with the use of retroviruses is the possibility of the spread of replication-competent retrovirus. There is thus a need for producing helper vectors which could not be processed into virions. As a result packaging defective vectors and packaging cell lines were developed. Details on packaging-defective vectors and packaging cell lines can be found in patents and patent publications, including U.S. Pat. No. 5,124,263, European Patent Application Pub. No. 0386 882, PCT Application No. WO 91/19798, PCT Application No. WO 88/08454, PCT Application No. WO 93/03143, U.S. Pat. No. 4,650,764, U.S. Pat. No. 4,861,719 and U.S. Pat. No. 5,278,056, the disclosures of which are incorporated herein by reference.

It is an object of this invention to provide a drug susceptibility and resistance test capable of showing whether a viral population in a patient is resistant to a given prescribed drug. Another object of this invention is to provide a test that will enable the physician to substitute one or more drugs in a therapeutic regimen for a patient that has become resistant to a given drug or drugs after a previous course of therapy. Yet another object of this invention is to provide a test that will enable selection of an effective drug regimen for the treatment of virus infections. Yet another object of this invention is to provide a safe, standardized, affordable, rapid, precise and reliable assay of drug susceptibility and resistance for clinical and research application. Still another object of this invention is to provide a test and methods for evaluating the biological effectiveness of candidate drug compounds which act on specific viral genes and/or viral proteins particularly with respect to viral drug resistance and cross resistance. It is also an object of this invention to provide the means and compositions for evaluating viral drug resistance and susceptibility. This and other objects of this invention will be apparent from the specification as a whole.

SUMMARY OF THE INVENTION

Objects of the present invention are accomplished by a novel test for determining susceptibility for an anti-viral drug comprising: (a) introducing a resistance test vector comprising a patient-derived segment and an indicator gene into a host cell; (b) culturing the host cell from step (a) (c) measuring expression of the indicator gene in a target host cell; and (d) comparing the expression of the indicator gene from step (c) with the expression of the indicator gene measured when steps (a)–(c) are carried out in the absence of the anti-viral drug, wherein a test concentration of the anti-viral drug is present at steps (a)–(c); at steps (b)–(c); or at step (c).

This invention also provides a method for determining anti-viral drug resistance in a patient comprising: (a) developing a standard curve of drug susceptibility for an anti-viral drug; (b) determining anti-viral drug susceptibility in the patient using the susceptibility test described above; and (c) comparing the anti-viral drug susceptibility in step (b) with the standard curve determined in step (a), wherein a decrease in anti-viral susceptibility indicates development of anti-viral drug resistance in the patient.

This invention further provides a method for determining anti-viral drug resistance in a patient comprising: (a) determining anti-viral drug susceptibility in the patient at a first time according to the above method, wherein the patient-derived segment is obtained from the patient at said time; (b) determining anti-viral drug susceptibility of the same patient at a later time; and (c) comparing the anti-viral drug susceptibilities determined in step (a) and (b), wherein a decrease in anti-viral drug susceptibility at the later time compared to the first time indicates the development or progression of anti-viral drug resistance in the patient.

The assay of this invention enables a physician to assess whether a viral gene encoding a viral protein or a functional viral sequence, each of which may be the target of an anti-viral agent, has mutated to render the drug less effective. More particularly, the novel assay of this invention enables one to determine whether a virus has become resistant to a particular anti-viral drug. Furthermore, this invention enables a physician to assess drug susceptibility and resistance of combination therapy. In addition the assay enables one to alter a therapeutic regimen prospectively by testing particular drug(s) or combinations of drugs and determining whether these drugs, alone or in combination, inhibit one or more viral gene(s) and/or viral protein(s). This invention provides significant advantages over presently available assays by providing a safer, more affordable, more reliable, more rapid and more effective drug susceptibility and resistance assay to assess the therapeutic efficacy of particular anti-viral drug(s) or combinations of drugs enabling a physician to optimize treatment. The assay of this invention has the significant advantage of enabling the evaluation of resistance and susceptibility at all stages of drug development: 1) during preclinical evaluation of candidate compounds; 2) during clinical evaluation of new drugs; 3) during patient therapy enabling design of an effective therapeutic regimen to overcome the problem of drug resistance; and 4) as part of epidemiologic surveillance, evaluating the prevalence of resistance during the use of approved and experimental drugs.

The present invention is directed to the methods and compositions of assessing drug susceptibility and resistance, including: a) the assay method of determining the susceptibility and resistance of a patient-derived segment to an anti-viral drug; b) compositions including resistance test vectors comprising a patient-derived segment and an indicator gene; and c) host cells containing the resistance test vectors. This invention is further directed to the compositions and methods of constructing the vectors and host cells which are used in the drug susceptibility and resistance assay of this invention.

In one aspect of the invention there is provided a method for determining susceptibility for an anti-HIV drug comprising: (a) introducing a resistance test vector comprising a patient-derived segment and an indicator gene into a host cell; (b) culturing the host cell from step (a); (c) measuring expression of the indicator gene in a target host cell; and (d) comparing the expression of the indicator gene from step (c) with the expression of the indicator gene measured when steps (a)–(c) are carried out in the absence of the anti-HIV drug, wherein a test concentration of the anti-HIV drug is present at steps (a)–(c); at steps (b)–(c) or at step (c).

In one aspect of the invention there is provided a method for determining susceptibility for an anti-HIV drug comprising: (a) introducing a resistance test vector comprising a patient-derived segment and an indicator gene into a host cell; (b) culturing the host cell from step (a); (c) measuring an indicator in a target host cell wherein said indicator is a DNA or RNA structure; and (d) comparing the measurement of the indicator from step (c) with the measurement of the indicator when steps (a)–(c) are carried out in the absence of the anti-HIV drug, wherein a test concentration of the anti-HIV drug is present at steps (a)–(c); at steps (b)–(c); or at step (c).

In one aspect of the invention there is provided a method for determining susceptibility for an anti-HBV drug comprising: (a) introducing a resistance test vector comprising a patient-derived segment and an indicator gene into a host cell; (b) culturing the host cell from step (a); (c) measuring expression of the indicator gene in a target host cell; and (d) comparing the expression of the indicator gene from step (c) with the expression of the indicator gene measured when steps (a)–(c) are carried out in the absence of the anti-HBV drug, wherein a test concentration of the anti-HBV drug is present at steps (a)–(c); at steps (b)–(c) or at step (c).

In one aspect of the invention there is provided a method for determining susceptibility for an anti-HBV drug comprising: (a) introducing a resistance test vector comprising a patient-derived segment and an indicator gene into a host cell; (b) culturing the host cell from step (a); (c) measuring an indicator in a target host cell wherein said indicator is a DNA or RNA structure; and (d) comparing the measurement of the indicator from step (c) with the measurement of the indicator when steps (a)–(c) are carried out in the absence of the anti-HBV drug, wherein a test concentration of the anti-HBV drug is present at steps (a)–(c); at steps (b)–(c); or at step (c).

This invention also provides a method for determining anti-HIV drug resistance in a patient comprising:(a) developing a standard curve of drug susceptibility for an anti-HIV drug; (b) determining anti-HIV drug susceptibility in the patient using the susceptibility test described above; and (c) comparing the anti-HIV drug susceptibility in step (b) with the standard curve determined in step (a), wherein a decrease in anti-HIV susceptibility indicates development of anti-HIV drug resistance in the patient.

This invention also provides a method for determining anti-HBV drug resistance in a patient comprising:(a) developing a standard curve of drug susceptibility for an anti-HBV drug; (b) determining anti-HBV drug susceptibility in the patient using the susceptibility test described above; and (c) comparing the anti-HBV drug susceptibility in step (b) with the standard curve determined in step (a), wherein a decrease in anti-HBV susceptibility indicates development of anti-HBV drug resistance in the patient.

This invention also provides a method for evaluating the biological effectiveness of a candidate anti-viral drug compound comprising: (a) introducing a resistance test vector comprising a patient-derived segment and an indicator gene into a host cell; (b) culturing the host cell from step (a); (c) measuring expression of the indicator gene in a target host cell; and (d) comparing the expression of the indicator gene from step (c) with the expression of the indicator gene measured when steps (a)–(c) are carried out in the absence of the candidate anti-viral drug compound, wherein a test concentration of the candidate anti-viral drug compound is present at steps (a)–(c); at steps (b)–(c); or at step (c).

This invention also provides a method for evaluating the biological effectiveness of a candidate anti-viral drug compound comprising: (a) introducing a resistance test vector comprising a patient-derived segment and an indicator gene into a host cell; (b) culturing the host cell from step (a); (c) measuring an indicator in a target host cell wherein said indicator is a DNA or RNA structure; and (d) comparing the measurement of the indicator from step (c) with the measurement of the indicator when steps (a)–(c) are carried out in the absence of the candidate anti-viral drug compound, wherein a test concentration of the candidate anti-viral drug compound is present at steps (a)–(c); at steps (b)–(c); or at step (c).

The resistance test vector comprising the patient-derived viral segment(s) (e.g. HIV, HBV, etc.) and the indicator gene may additionally include one or more non-patient-derived segments. In one embodiment the resistance test vector is constructed from a genomic viral vector which may include a deletion in one or more genes. For example, in the case of HIV, env is deleted in a resistance test vector which otherwise preserves the mRNA expression and processing characteristics of the complete virus. Alternatively, the resistance test vector is constructed from a subgenomic viral vector which may include only one or a few viral genes which are typically the target of the anti-viral drug. For example in the case of HBV, one or more of the HBV genes encoding certain structural and enzymatic functions necessary for HBV DNA replication and virus particle formation (i.e. C, S and X genes) may be deleted from a resistance test vector which otherwise preserves mRNA expression and processing characteristics of the complete virus. The resistance test vector further comprises either the native enhancer/promoter of the particular virus or a foreign enhancer/promoter for the expression of the anti-viral target genes.

The expression of the indicator gene in the resistance test vector in the target cell is ultimately dependent upon the action of the patient-derived segment sequences. The indicator gene may be functional or non-functional. In the case of a non-functional indicator gene, the indicator gene is not efficiently expressed in a host cell transfected by the resistance test vector until it is converted into a functional indicator gene through the action of one or more of the patient-derived segment products. In one embodiment, the indicator gene is rendered non-functional through use of a permuted promoter, i.e. a promoter that, although in the same transcriptional orientation as the indicator gene, follows rather than precedes the coding sequence of the indicator gene. In addition, the orientation of the non-functional indicator gene is opposite to that of the viral promoters or LTRs. Thus the coding sequence of the non-functional indicator gene can neither be transcribed by the permuted promoter nor by the viral promoters. In the case of HIV, the indicator gene is rearranged as a consequence of reverse transcription so that the permuted promoter now precedes the indicator gene sequence, which as a result can be functionally expressed. In the case of HBV, the indicator gene is rearranged as a consequence of circularization of the genome during HBV replication. In a second embodiment, the indicator gene is rendered non-functional through use of a permuted coding region, i.e. an indicator gene coding region in which the 5' portion of the coding region follows rather than precedes the 3' portion of the coding region. In this configuration, no mRNA is expressed which can give rise to a functional indicator gene product. In the case of HIV, the indicator gene is rearranged as a consequence of reverse transcription so that the 5' coding region of the indicator gene now precedes the 3' coding region, and as a result the indicator gene can be functionally expressed. In the case of HBV, the indicator gene is rearranged as a result of circularization of the genome during HBV replication. In a third embodiment, the indicator gene is rendered non-functional through use of an inverted intron, i.e. an intron inserted into the coding sequence of the indicator gene with a transcriptional orientation opposite to that of the indicator gene. In addition, the indicator gene itself contains a functional promoter with the entire transcriptional unit oriented opposite to the viral promoters. Thus the non-functional indicator gene is in the wrong orientation to be transcribed by the viral LTRs in the case of HIV or the HBV enhancer-promoter and it cannot be functionally transcribed by its own promoter, as the inverted intron cannot be properly excised by splicing. However, in the case of retroviruses and hepadnaviruses, and HIV and HBV specifically, transcription by the viral promoters result in the formation of mRNA in which removal of the inverted intron can occur by splicing. In retroviruses, as a consequence of reverse transcription of the resulting spliced transcript and the integration of the resulting provirus into the host cell chromosome, the indicator gene can now be functionally transcribed by its own promoter. In HBV, as a consequence of reverse transcription of the resulting spliced transcript and circularization of the genomic DNA in the host cell, the indicator gene can now be functionally transcribed by its own promoter.

Resistance test vectors comprising a non-functional indicator gene can be used to carry out resistance tests in either a particle-based or non-particle-based assay. The particle based assay is based on resistance test vector viral particles, which are replication defective, being produced by the resistance test vector host cells. The trans-acting factors necessary for production of the resistance test vector viral particles are provided by the packaging expression vectors which are transfected into the packaging host cell. In contrast the non-particle based resistance test is performed by transfection of a single host cell with a resistance test vector in the absence of packaging expression vectors.

In the case of the functional indicator gene, the functional indicator gene is efficiently expressed in a first host cell transfected by the resistance test vector (referred to herein as a resistance test vector host cell). Thus, the function of the indicator gene in the resistance test vector host cell is not dependent on the patient-derived segment. However, the capacity of the indicator gene to be expressed in a second host cell (referred to herein as a target host cell) is dependent on the production of functional resistance test vector viral particles in the resistance test vector host cell. Thus, the activity of the indicator gene in the target host cells is dependent on the activity of the patient-derived segments.

In another aspect this invention is directed to anti-viral drug susceptibility and resistance tests for HIV/AIDS or HBV. Particular resistance test vectors of the invention for use in the HIV/AIDS anti-viral drug susceptibility and resistance test are identified as well as resistance test vector host cells. In yet another aspect this invention is directed to anti-viral drug susceptibility and resistance tests for hepatitis. Similarly in the case of HBV, particular resistance test vectors (also referred to herein as resistance test vector systems) of the invention for use in the HBV anti-viral drug susceptibility and resistance test are identified as well as resistance test vector host cells.

In yet another aspect this invention provides for the identification and assessment of the biological effectiveness of potential therapeutic anti-viral compounds for the treatment of viral diseases. In still another aspect the invention is directed to a host cell transfected with one or more vectors to assess drug susceptibility. In another aspect, the invention is directed to a novel resistance test vector comprising a patient-derived viral gene(s) and an indicator gene.

BRIEF DESCRIPTION OF THE DRAWINGS

FIG. 1. B. Generalized diagrammatic representation of the HIV genomic viral vector which contains the following elements in a 5' to 3' orientation: 1) an HIV-LTR U3 region, 2) an HIV-LTR R region, 3) an HIV-LTR U5 region, 4) the coding regions of the HIV gag-pol, vif, vpr, tat, rev, vpu, deleted env, and nef genes, and 5) a 3' HIV-LTR.

FIG. 1. C. Generalized diagrammatic representation of the HIV genomic viral vector which contains the following elements in a 5' to 3' orientation: 1) a CMV IE enhancer-promoter, 2) an HIV-LTR R region, 3) an HIV-LTR U5 region, 4) the coding regions of the HIV gag-pol, vif, vpr, tat, rev, vpu, deleted env, and nef genes, and 5) a 3' HIV-LTR.

FIG. 1. D. Generalized diagrammatic representation of the HIV subgenomic viral vector which contains the following elements in a 5' to 3' orientation: 1) an HIV-LTR U3 region, 2) an HIV-LTR R region, 3) an HIV-LTR U5 region, 4) the coding region of the HIV gag-pol gene, and 5) a 3' HIV-LTR.

FIG. 1. E. Generalized diagrammatic representation of the HIV subgenomic viral vector which contains the following elements in a 5' to 3' orientation: 1) a CMV IE enhancer-promoter, 2) an HIV-LTR R region, 3) an HIV-LTR U5 region, 4) the coding region of the HIV gag-pol gene, and 5) a 3' HIV-LTR.

FIG. 2. B. Diagrammatic representation of the resistance test vector comprising a nonfunctional indicator gene comprising a permuted promoter having the following elements in a 5' to 3' orientation: 1) an HIV-LTR U3 region (pLG-lucPP-HS and pLG-lucPP-PB) or a CMV IE enhancer-promoter (pCG-lucPP-HS and pCG-lucPP-PB), 2) an HIV-LTR R region, 3) an HIV-LTR U5 region containing an inserted T7 phage RNA polymerase promoter (herein referred to as T7 promoter) with a transcriptional orientation opposite to that of the LTRs, 4) the coding regions of the HIV gag-pol, vif, vpr, tat, rev, vpu, deleted env, and nef genes, 5) a patient-derived segment(s) inserted into the patient sequence acceptor sites, 6) an indicator gene cassette inserted into the deleted env gene, and 7) a 3' HIV-LTR.

FIG. 2. C. Diagrammatic representation showing the conversion of the non-functional indicator gene (permuted promoter) in the resistance test vector, described in 2(a), to a functional indicator gene by reverse transcriptase. The conversion to a functional indicator gene results from the repositioning of the T7 promoter relative to the indicator gene coding region.

FIG. 2. D. Diagrammatic representation of the resistance test vector, based on the genomic indicator gene viral vector pCG(NF-lucP)1-PP/T7, comprising a nonfunctional indicator gene comprising a permuted promoter having the following elements in a 5' to 3' orientation: (1) a CMV IE enhancer-promoter, (2) an HIV-LTR R region, (3) an HIV-LTR U5 region into which has been inserted a T7 promoter with a transcriptional orientation opposite to that of the CMV promoter, (4) the coding regions of HIV gag-pol, vif, vpr, tat, rev, vpu, deleted env, and nef genes, (5) a patient-derived segment(s) inserted into the patient sequence acceptor sites, (6) a luciferase indicator gene cassette inserted into the deleted env gene, (7) 3' HIV LTR U3 and R regions, (8) the SV40 polyadenylation signal region, and (9) the SV40 origin of replication region.

FIG. 2. E. Diagrammatic representation showing the conversion of the non-functional indicator gene (permuted promoter) in the resistance test vector, pCG(NF-lucP)1-PP/T7 described in 2(d), to a functional indicator gene by reverse transcriptase. The conversion to a functional indicator gene results from the repositioning of the T7 promoter relative to the indicator gene coding region.

FIG. 3. B. Diagrammatic representation of the packaging expression vector pLTR-HIV3' which provides the vif, vpr, tat, rev, vpu and nef genes, each of which is expressed as a spliced subgenomic mRNA transcribed from the HIV LTR U3 region.

FIG. 3. C. Diagrammatic representation of the packaging expression vector pCMV-HIV3' which provides the vif, vpr, tat, rev, vpu and nef genes, each of which is expressed as a spliced subgenomic mRNA transcribed from the CMV IE enhancer-promoter.

FIG. 3. D. Diagrammatic representation of the packaging expression vector pVL-env4070A [pCXAS(4070A env) ] which provides the amphotrophic MLV env gene product, by transcription from the CMV IE enhancer-promoter.

FIG. 4. A. Diagrammatic representation of the DNA genomic structure of HIV-1.

FIG. 4. B. A generalized diagrammatic representation of the resistance test vectors comprising a nonfunctional indicator gene comprising a permuted coding region containing the following elements in a 5' to 3' orientation: 1) an HIV-LTR U3 region (pLG-lucPC-HS and pLG-lucPC-PB) or a first CMV IE enhancer-promoter (pCG-lucPC-HS and pCG-lucPC-PB), 2) the HIV-LTR R and U5 regions, 3) the coding regions of the HIV gag-pol, vif, vpr, tat, rev, vpu, deleted env, and nef genes, 4) a patient-derived segment(s) inserted into the patient sequence acceptor sites, 5) a first indicator gene cassette containing the 5' coding region of the luciferase gene, inserted into the deleted env gene, 6) a second indicator gene cassette containing the 3' coding region of the luciferase gene, inserted into a deleted 3' HIV-LTR U3 region, and 7) a 3' HIV-LTR R and U5 region.

FIG. 4. C. Diagrammatic representation showing the conversion of the non-functional indicator gene (permuted coding region) in the resistance test vector, described in 4(a), to a functional indicator gene by reverse transcriptase. Following reverse transcription and strand transfer, the luciferase 3' coding region is copied from the 3' LTR to the 5' LTR, permitting the transcription of mRNA which can be spliced to generate a functional luciferase coding region.

FIG. 5. A. Diagrammatic representation of the DNA genomic structure of HIV-1.

FIG. 5. B. A generalized diagrammatic representation of the resistance test vectors comprising a nonfunctional indicator gene comprising an inverted intron containing the following elements in a 5' to 3' orientation: 1) an HIV-LTR U3 region (pLG-lucII-HS and pLG-lucII-PB) or a first CMV IE enhancer-promoter (pCG-lucII-HS and pCG-lucII-PB), 2) the HIV-LTR R and U5 regions, 3) the coding regions of the HIV gag-pol, vif, vpr, tat, rev, vpu, deleted env, and nef genes, 4) patient-derived segment(s) inserted into the patient sequence acceptor site, 5) an indicator gene cassette inserted into the deleted env gene, and 5) a 3' HIV-LTR.

FIG. 5. C. Diagrammatic representation showing the conversion of the non-functional indicator gene (inverted intron) in the resistance test vector, described in 5(a), to a functional indicator gene by reverse transcriptase. The overall transcriptional orientation of the indicator gene cassette is opposite to that of the first CMV enhancer-promoter and viral LTRs, while the orientation of the artificial intron is the same as the latter elements. Transcription of the indicator gene by the second CMV enhancer-promoter does not lead to the production of functional transcripts as the inverted intron cannot be spliced in this orientation. Transcription of the indicator gene by the 5' viral LTR or the first CMV IE enhancer-promoter, however, leads to the removal of the inverted intron by RNA splicing, although the indicator gene is still not functionally expressed as the resulting transcript has an antisense orientation. Following the reverse transcription of this transcript and integration of the resultant proviral DNA, the indicator gene can be functionally transcribed by the second CMV enhancer-promoter as the inverted intron has been previously removed.

FIG. 6. A. Diagrammatic representation of the DNA genomic structure of HIV-1 is shown above (a) and (b).

FIG. 6. B. A generalized diagrammatic representation of the resistant test vectors comprising a functional indicator gene having the following elements in a 5' to 3' orientation: 1) an HIV-LTR U3 region (pLG-luc-HS-1 and pLG-luc-PB-1) or a first CMV IE enhancer-promoter (pCG-luc-HS-1 and pCG-luc-PB-1), 2) the HIV-LTR R and U5 regions, 3) the coding region of the HIV gag-pol, vif, vpr, tat, rev, vpu, deleted env, and nef genes, 4) a functional indicator gene cassette inserted into the deleted env gene, with a transcriptional orientation opposite to the viral LTRs and 5) a 3' HIV-LTR.

FIG. 6. C. A generalized diagrammatic representation of the resistance test vectors comprising a functional indicator gene cassette (pLG-luc-HS-2, pLG-luc-PB-2, pCG-luc-HS-2 and pCG-luc-PB-2) in which the transcriptional orientation of the indicator gene cassette is the same as the viral LTRs.

FIG. 7. B. Diagrammatic representation of the resistance test vector, based on the genomic indicator gene viral vector pCG-CXCN(F-lucP)2AA, comprising a functional indicator gene having the following elements in a 5' to 3' orientation: (1) a CMV IE enhancer-promoter region, (2) HIV LTR "R" and "U5" regions, (3) the coding regions of the HIV gag-pol, vif, vpr, 5' tat exon, 5' rev exon, vpu, deleted env, 3' tat exon, 3' rev exon, and nef genes, (4) "test" patient-derived segment(s) inserted into the patient sequence acceptor sites (ApaI, AgeI), (5) a functional indicator gene cassette (CXCN(lucP)) inserted into the deleted env gene, (6) HIV LTR "U3" and "R" regions, (7) the SV40 polyadenylation signal sequence region, and (8) the SV40 origin of replication region.

FIG. 7. C. Diagramatic representation of the predicted integrated proviral structure of the resistance test vector, pCG-CXCN(F-lucP)2-AA, and the transcription of the functional indicator gene cassette in the target host cell.

FIG. 7. D. Diagrammatic representation of the resistance test vector, based on the genomic indicator gene viral vector pCG-CXAT(F-lucP)2-AA, comprising a functional indicator gene having the following elements in a 5' to 3' orientation: (1) a CMV IE enhancer-promoter region, (2) HIV LTR "BR" and "U5" regions, (3) the coding regions of the HIV gag-pol, vif, vpr, 5' tat exon, 5' rev exon, vpu, deleted env, 3' tat exon, 3' rev exon, and nef genes, (4) "test" patient-derived segment(s) inserted into the patient sequence acceptor sites (ApaI, AgeI), (5) the functional indicator gene cassette (CXAT(lucP)) inserted into the deleted env gene, (6) HIV LTR "U3" and "R" regions, (7) the SV40 polyadenylation signal sequence region, and (8) the SV40 origin of replication region.

FIG. 7. E. Diagrammatic representation of the predicted integrated proviral structure of the resistance test vector, pCG-CXAT(F-lucP)2-AA, and the transcription of the functional indicator gene cassette in the target host cell.

FIG. 8. B. Drug susceptibility and resistance test performed with the resistance test vector, pCG-CXCN(F-lucP) 2-AA containing pre-AZT treatment and post-AZT treatment "test" patient-derived segments. The resistance test vectors are derived from the genomic indicator gene viral vector, pCG-CXCN(F-lucP)2-AA. Data are presented as percent inhibition of luciferase gene activity in target host cells vs. AZT concentration ($log_{10}$). pCG-CXCN(F-lucP)2-AA is plotted as solid boxes. pCG-CXCN(F-lucP)2-AA containing patient-derived segments prior to AZT treatment is plotted as solid circles and post-AZT treatment as solid triangles.

FIG. 8. C. Drug susceptibility and resistance test performed with the resistance test vector, pCG-CXCN(F-lucP) 2-AA containing the reverse transcriptase segment derived from the biologically active proviral clone, pNL4-3. Data are presented as percent inhibition of luciferase gene activity in target host cells vs. nevirapine concentration ($log_{10}$) and is plotted as solid boxes.

FIG. 8. D. Drug susceptibility and resistance test performed with the resistance test vector, pCG-CXCN(F-lucP) 2-AA containing the protease segment derived from the biologically active proviral clone, pNL4-3. Data are presented as percent inhibition of luciferase gene activity in target host cells vs. indinavir concentration ($log_{10}$) and is plotted as solid boxes.

FIG. 9. B. A generalized diagrammatic representation of the subgenomic indicator gene viral vector, pCS-HBV (NF-IG)II-(PSAS−), a component of the resistance test vector system, comprising an indicator gene cassette and an inverted intron containing the following elements in a 5' to 3' orientation: (1) the CMV IE enhancer-promoter region, (2) the 5' region of the HBV genome and the DR1 and 5' ε (the pre-C ORF translation initiation codon is eliminated), (3) a non-functional indicator gene cassette in which the indicator gene ORF contains an inverted intron, (4) the region of the HBV genome containing DR2, DR1*, the 3' ε, and the 3' HBV polyadenylation (pA) signal region.

FIG. 9. C. Diagrammatic representation of the covalently closed circular DNA (cccDNA) form of the subgenomic indicator gene viral vector, pCS-HBV(F-IG)II(PSAS−), containing a functional indicator gene cassette assembled as a result of HBV viral replication.

FIG. 9. D. Diagrammatic representation of one example of a packaging vector, pPK-CPX, a component of the resistance test vector system comprising a patient-derived segment containing the following elements in a 5' to 3' orientation: (1) the CMV IE enhancer-promoter region, (2) the region of the HBV genome spanning from the C ORF translation initiation codon to the 3' pA signal and including the C, P, S, and X genes. The C gene of the packaging vector, pPK-CPX, is modified such that it does not contain the pre-C ORF sequences and does not express the S proteins (as shown by the X at the translation initiation sites).

FIG. 9. E. Diagrammatic representation of an additional packaging vector, pPK-S, providing the S gene proteins, that is cotransfected with the resistance test vector system comprising the indicator gene viral vector, pCS-HBV(NF-IG)II-(PSAS−), and the packaging plasmid, pPK-CPX.

FIG. 9. F. A generalized diagrammatic representation of the resistance test vector, pCS-HBV(NF-IG)II-(PSAS+), comprising a non-functional indicator gene with an inverted intron containing the following elements in a 5' to 3' orientation: (1) the CMV IE enhancer-promoter region, (2) the 5' region of the HBV genome and the DR1 and 5' ε (the pre-C ORF translation initiation codon is eliminated), (3) indicator gene cassette (containing an inverted intron) within the region of the HBV genome which contains a patient-derived P gene segment, (4) the region of the HBV genome containing DR2, DR1*, the 3' ε, and the 3' HBV pA signal region.

FIG. 9. G. Diagrammatic representation of the covalently closed circular DNA (cccDNA) form of the resistance test vector, pCS-HBV(F-IG)II-(PSAS+), containing a functional indicator gene cassette and a patient-derived P gene segment assembled as a result of HBV viral replication.

FIG. 9. H. Diagrammatic representation of a packaging vector, pPK-CSX, providing the C, S and X gene proteins, that is cotransfected with the resistance test vector, pCS-HBV(NF-IG)II-(PSAS+).

FIG. 10 A. Diagrammatic representation of the RNA pregenomic structure of HBV.

FIG. 10. B. Diagrammatic representation of an HBV indicator gene viral vector containing a non-functional indicator gene cassette. Primer binding sites for the amplification of a target DNA sequence are shown. The location and orientation of the forward primer (Pf) and reverse primer (Pr) binding sites do not constitute a functional amplification unit in the linear form of the vector that is used to transfect packaging host cells. The Pr binding site is designed to span the junction sequence that is generated by splicing of the pregenomic RNA.

FIG. 10. C. Diagrammatic representation of the rc-DNA form of the indicator gene viral vector described in 10B. Primer binding sites for the amplification of a target DNA sequence are shown. The location and orientation of the Pf and Pr primer binding sites constitute a functional amplification unit in the plus strand DNA component of the rc-DNA form and the plus and minus strand DNA components of the cccDNA form of the vector that is generated by HBV DNA replication within the virus particles produced in packaging host cells. The Pr binding site is assembled by the splicing of the pregenomic RNA.

FIG. 10. D. Diagrammatic representation of an HBV indicator gene viral vector containing a non-functional indicator gene cassette. Primer binding sites for the amplification of a target DNA sequence are shown. The location and orientation of the Pf and Pr binding sites constitute a functional amplification unit in the linear form of the vector that is used to transfect packaging host cells, but the Pf binding site is not adjacent to the binding site of the exonuclease detection probe (probe) in the unspliced linear form of the vector. This arrangement of Pf, Pr, and probe binding sites does not constitute an efficient exonuclease detection unit.

FIG. 10. E. Diagrammatic representation of the rc-DNA form of the indicator gene viral vector described in 10D. Primer binding sites for the amplification of a target DNA sequence are shown. The location and orientation of the Pf and Pr primer binding sites constitute a functional amplification unit in the rc-DNA and cccDNA forms of the vector that are generated by HBV DNA replication in packaging host cells. The location of the Pf binding site is brought immediately adjacent to the binding site of the exonuclease detection probe (probe) in the rc-DNA and cccDNA forms of the vector. This arrangement of Pf, Pr, and probe binding sites constitute an efficient exonuclease detection unit.

FIG. 10. F. Diagrammatic representation of an HBV indicator gene viral vector. Primer binding sites for the amplification of a target DNA sequence are shown. The location and orientation of the forward primer (Pf) and reverse primer (Pr) binding sites do not constitute a functional amplification unit in the linear form of the vector that is used to transfect packaging host cells.

FIG. 10. G. Diagrammatic representation of the rc-DNA form of the indicator gene viral vector described in 10F. Primer binding sites for the amplification of a target DNA sequence are shown. The location and orientation of the Pf and Pr primer binding sites constitute a functional amplification unit in the plus strand DNA component of the rc-DNA form and the plus and minus strand DNA components of the cccDNA form of the vector that is generated by HBV DNA replication within the virus particles produced in packaging host cells.

FIG. 11 A. Diagrammatic representation of the RNA pregenomic structure of HBV.

FIG. 11. B. A generalized diagrammatic representation of the subgenomic indicator gene viral vector, pCS-HBV (NF-IG)PP-(PSAS−), a component of the resistance test vector system comprising a non-functional indicator gene with a permuted promoter containing the following elements in a 5' to 3' orientation: (1) the CMV IE enhancer promoter region, (2) the 5' region of the HBV genome and the DR1 and 5' $\epsilon$ (the pre-C ORF translation initiation codon is eliminated), (3) a non-functional indicator gene cassette assembled such that the promoter region is positioned 3', i.e. downstream, of the indicator gene ORF, (4) the 3' region of the HBV genome containing DR2, DR1*, the 3' $\epsilon$, and the 3' HBV pA signal region (the pre-C ORF translation initiation codon is eliminated). The packaging vector, pPK-CPX, a component of the resistance test vector system comprising a patient-derived P gene segment is shown in FIG. 9D and the S packaging vector, pPK-S, is shown in FIG. 9E.

FIG. 11. C. Diagrammatic representation of the covalently closed circular DNA (cccDNA) form of the subgenomic indicator gene viral vector, pCS-HBV(F-IG) PP(PSAS−), containing a functional indicator gene cassette assembled as a result of HBV viral replication.

FIG. 11. D. A generalized diagrammatic representation of the resistance test vector, pCS-HBV(NF-IG) PP(PSAS+), comprising a non-functional indicator gene with a permuted promoter containing the following elements in a 5' to 3' orientation: (1) the CMV IE enhancer-promoter region, (2) the 5' region of the HBV genome and the DR1 and 5' copy of $\epsilon$ (the pre-C ORF translation initiation codon is eliminated) (3) an enhancer-promoter region (permuted promoter), (4) the P gene containing the patient-derived segment (5) the indicator gene ORF (6) an internal ribosome entry site (IRES), and (7) the 3' region of the HBV genome containing DR2, DR1*, the 3' $\epsilon$, and the 3' HBV pA signal region (the pre-C ORF translation initiation codon is eliminated). The packaging vector, pPK-CSX, providing the C, S and X genes is cotransfected with the resistance test vector, pCS-HBV(NF-IG)PP(PSAS+), and is shown in FIG. 9H.

FIG. 11. E. Diagrammatic representation of the covalently closed circular DNA (cccDNA) form of the resistance test vector, pCS-HBV(F-IG)PP(PSAS+), containing a functional indicator gene cassette and a patient-derived P gene segment assembled as a result of HBV viral replication.

FIG. 12. B. A generalized diagrammatic representation of the subgenomic indicator gene viral vector, pCS-HBV (NF-IG)PPTIS-(PSAS−), a component of the resistance test vector system comprising a non-functional indicator gene with a permuted promoter and translation initiation site containing the following elements in a 5' to 3' orientation: (1) the CMV IE enhancer-promoter region, (2) the 5' region of the HBV genome including the DR1 and 5' $\epsilon$ (the pre-C ORF translation initiation codon is eliminated), (3) an indicator gene ORF lacking a translation initiation site, (4) an enhancer-promoter region (permuted promoter) (5) the 3' region of the HBV genome containing DR2, pre-C ORF translation initiation codon, DR1*, the 3' $\epsilon$, and the 3' HBV pA signal region. The packaging vector, pPK-CPX, a component of the resistance test vector system comprising a patient-derived segment is shown in FIG. 9D and the S packaging vector, pPK-S, is shown in FIG. 9E.

FIG. 12. C. Diagrammatic representation of the covalently closed circular DNA (cccDNA) form of the subgenomic indicator gene viral vector, pCS-HBV(F-IG) PPTIS(PSAS−), containing a functional indicator gene cassette assembled as a result of HBV viral replication.

FIG. 12. D. A generalized diagrammatic representation of the resistance test vector, pCS-HBV(NF-IG) PPTIS (PSAS+), comprising a non-functional indicator gene with a permuted promoter containing the following elements in a 5' to 3' orientation: (1) the CMV IE enhancer-promoter region, (2) the 5' region of the HBV genome including the DR1 and 5' $\epsilon$ (the pre-C ORF translation initiation codon is eliminated), (3) an indicator gene ORF lacking a translation initiation site, (4) the P gene containing the patient-derived segment, (5) an enhancer-promoter region (permuted promoter) (6) the 3' region of the HBV genome containing DR2, pre-C ORF translation initiation codon, DR1*, the 3' $\epsilon$, and the 3' HBV pA signal region. The packaging vector, pPK-CSX, providing the C, S and X genes is cotransfected with the resistance test vector, pCS-HBV(NF-IG)PPTIS (PSAS+), and is shown in FIG. 9H.

FIG. 12. E. Diagrammatic representation of the covalently closed circular DNA (cccDNA) form of the resistance test vector, pCS-HBV(F-IG)PPTIS(PSAS+) containing a functional indicator gene cassette and a patient-derived P gene segment assembled as a result of HBV viral replication.

FIG. 13. B. A generalized diagrammatic representation of the subgenomic indicator gene viral vector, pCS-HBV (NF-IG)PCR-(PSAS−), a component of the resistance test vector system comprising a non-functional indicator gene with a permuted coding region containing the following elements in a 5' to 3' orientation: (1) the CMV IE enhancer-promoter region, (2) the 5' region of the HBV genome including the DR1 and 5' ε (the pre-C ORF translation initiation codon is eliminated), (3) a non-functional indicator gene cassette assembled such that the promoter region and a 5' portion of the coding region are positioned 3', i.e. downstream, of the remaining 3' portion of the coding region, (4) the 3' region of the HBV genome containing DR2, DR1*, the 3' ε, and the 3' HBV pA signal region (the pre-C ORF translation initiation codon is eliminated). The packaging vector, pPK-CPX, a component of the resistance test vector system comprising a patient-derived P gene segment is shown in FIG. 9D and the S packaging vector, pPK-S, is shown in FIG. 9E.

FIG. 13. C. Diagrammatic representation of the covalently closed circular DNA (cccDNA) form of the subgenomic indicator gene viral vector, pCS-HBV(F-IG)PCR(PSAS−), containing a functional indicator gene cassette assembled as a result of HBV viral replication.

FIG. 13. D. A generalized diagrammatic representation of the resistance test vector, pCS-HBV(NF-IG)PCR(PSAS+), comprising a non-functional indicator gene with a permuted coding region containing the following elements in a 5' to 3' orientation: (1) the CMV IE enhancer-promoter region, (2) the 5' region of the HBV genome including the DR1 and 5' ε (the pre-C ORF translation initiation codon is eliminated), (3) the 3' portion of the indicator gene ORF beginning with a splice acceptor sequence in the reverse orientation, (4) the P gene containing the patient-derived segment, (5) an enhancer-promoter region, (6) the 5' portion of the indicator gene ORF ending in a splice donor sequence in the reverse orientation, (7) the 3' region of the HBV genome containing DR2, DR1*, the 3' ε, and the 3' HBV pA signal region (the pre-C ORF translation initiation codon is eliminated). The packaging vector, pPK-CSX, providing the C, S and X genes is cotransfected with the resistance test vector, pCS-HBV (NF-IG)PCR(PSAS+), and is shown in FIG. 9H.

FIG. 13. E. Diagrammatic representation of the covalently closed circular DNA (cccDNA) form of the resistance test vector, pCS-HBV(F-IG)PCR(PSAS+), containing a functional indicator gene cassette and a patient-derived P gene segment assembled as a result of HBV viral replication.

FIG. 14. B. A generalized diagrammatic representation of the subgenomic indicator gene viral vector component, pCS-HBV(F-IG)(PSAS−), a component of the resistance test vector system comprising a functional indicator gene cassette containing the following elements in a 5' to 3' orientation: (1) the CMV IE enhancer-promoter region, (2) the 5' region of the HBV genome including the DR1 and 5' ε (the pre-C ORF translation initiation codon is eliminated), (3) a functional indicator gene cassette, (4) the 3' region of the HBV genome containing DR2, DR1*, the 3' ε, and the 3' HBV pA signal region (the pre-C ORF translation initia-
tion codon is eliminated). The packaging vector, pPK-CPX, a component of the resistance test vector system comprising a patient-derived P gene segment is shown in FIG. 9D and the S packaging vector, pPK-S, is shown in FIG. 9E.

FIG. 14. C. Diagrammatic representation of the covalently closed circular DNA (cccDNA) form of the subgenomic indicator gene viral vector, pCS-HBV(F-IG) (PSAS−), containing a functional indicator gene.

FIG. 14. D. A generalized diagrammatic representation of the resistance test vector, pCS-HBV(F-IG) (PSAS+), comprising a functional indicator gene containing the following elements in a 5' to 3' orientation: (1) the CMV IE enhancer promoter region, (2) the 5' region of the HBV genome including the DR1 and 5' ε (the pre-C ORF translation initiation codon is eliminated), (3) a functional indicator gene cassette, (4) the P gene containing the patient-derived segment, (5) the 3' region of the HBV genome containing DR2, DR1*, the 3' ε, and the 3' HBV pA signal region (the pre-C ORF translation initiation codon is eliminated). The packaging vector, pPK-CSX, providing the C, S and X genes, that is cotransfected with the resistance test vector, pCS-HBV(F-IG)(PSAS+), and is shown in FIG. 9H.

FIG. 14. E. Diagrammatic representation of the covalently closed circular DNA (cccDNA) form of the resistance test vector, pCS-HBV(F-IG)(PSAS+) containing a functional indicator gene.

DETAILED DESCRIPTION OF THE INVENTION

Figure 1A:
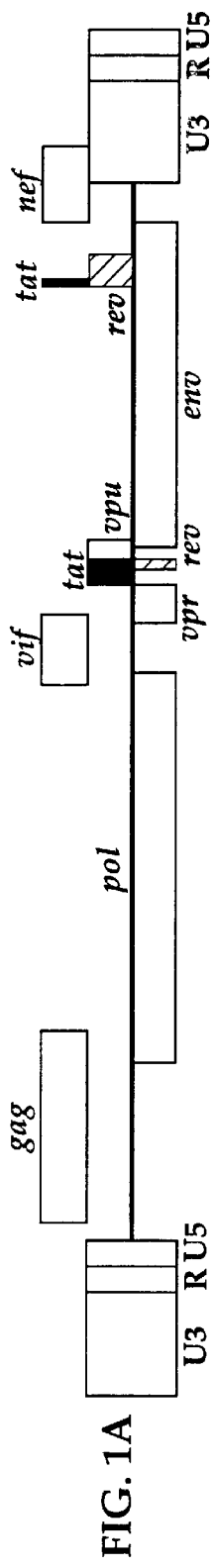
FIG. 1. A. Diagrammatic representation of the DNA genomic structure of HIV-1. Viral proteins are encoded in each of the three reading frames by the gag, pol, vif, vpr, tat, rev, vpu, env and nef genes. The RNA is transcribed from viral DNA and processed by viral and cellular enzymes, giving rise to both genomic viral RNA and mRNA. The U3, R and U5 elements of the viral long terminal repeat (LTR) are indicated.
Figure 1B:
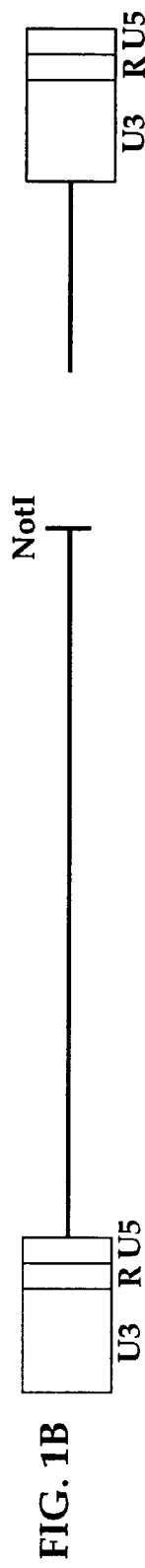
Figure 1C:
Figure 1D:
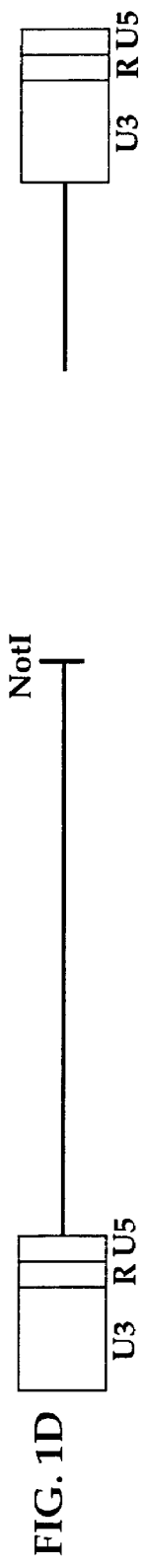
Figure 1E:

In order that the invention described herein may be more fully understood, the following description is set forth.

The present invention provides a novel drug susceptibility and resistance assay comprising the steps of: (a) introducing a resistance test vector comprising a patient-derived segment and an indicator gene into a host cell; (b) culturing the host cell from step (a); (c) measuring expression of the indicator gene in a target host cell; and (d) comparing the expression of the indicator gene from step (c) with the expression of the indicator gene measured when steps (a)–(c) are carried out in the absence of the anti-viral drug, wherein a test concentration of the anti-viral drug is present at steps (a)–(c); at steps (b)–(c); or at step (c).

In one aspect of the invention there is provided a method for determining susceptibility for an anti-viral drug comprising: (a) introducing a resistance test vector comprising a patient-derived segment and an indicator gene into a host cell; (b) culturing the host cell from step (a) (c) measuring an indicator in a target host cell wherein said indicator is a DNA or RNA structure; and (d) comparing the measurement of the indicator from step (c) with the measurement of the indicator when steps (a)–(c) are carried out in the absence of the anti-viral drug, wherein a test concentration of the anti-viral drug is present at steps (a)–(c); at steps (b)–(c); or at step (c).

This invention also provides a method for determining anti-viral drug resistance in a patient comprising: (a) developing a standard curve of drug susceptibility for an anti-viral drug; (b) determining anti-viral drug susceptibility in the patient using either of the susceptibility tests described above; and (c) comparing the anti-viral drug susceptibility in step (b) with the standard curve determined in step (a), wherein a decrease in anti-viral susceptibility indicates development of anti-viral drug resistance in the patient.

This invention also provides a method for determining anti-viral drug resistance in a patient comprising: (a) determining anti-viral drug susceptibility in the patient at a first time according to either of the above methods, wherein the patient-derived segment is obtained from the patient at about said time; (b) determining anti-viral drug susceptibility of the same patient at a later time; and (c) comparing the anti-viral drug susceptibilities determined in step (a) and (b), wherein a decrease in anti-viral drug susceptibility at the later time compared to the first time indicates development or progression of anti-viral drug resistance in the patient.

The assay of this invention can be used for any viral disease where anti-viral drug susceptibility and resistance is a concern including, for example, HIV, herpes simplex virus, cytomegalovirus virus, varicella zoster virus, other human herpes (HIV) viruses, influenza A virus, respiratory syncytial virus, hepatitis A, B and C viruses, rhinovirus, and human papilloma virus. The foregoing are representative of certain viruses for which there is presently available anti-viral chemotherapy, and represent the viral families retroviridae, herpesviridae, orthomyxoviridae, pneumovirus and hepadnaviridae. The assay of this invention would be used with other viral infections arising from infections due to other viruses within these families as well as viral infections arising from viruses in other viral families. In addition, the drug susceptibility and resistance test of this invention is useful for screening for compounds to treat viral diseases for which there is no currently available therapy.

The structure, life cycle and genetic elements of the viruses which could be tested in the drug susceptibility and resistance test of this invention would be known to one of ordinary skill in the art. It is useful to the practice of this invention, for example, to understand the life cycle of a retrovirus, as well as the viral genes required for retrovirus rescue and infectivity. Retrovirally infected cells shed a membrane virus containing a diploid RNA genome. The virus, studded with an envelope glycoprotein (which serves to determine the host range of infectivity), attaches to a cellular receptor in the plasma membrane of the cell to be infected. After receptor binding, the virus is internalized and uncoated as it passes through the cytoplasm of the host cell. Either on its way to the nucleus or in the nucleus, the reverse transcriptase molecules resident in the viral core drive the synthesis of the double-stranded DNA provirus, a synthesis that is primed by the binding of a tRNA molecule to the genomic viral RNA. The double-stranded DNA provirus is subsequently integrated in the genome of the host cell, where it can serve as a transcriptional template for both mRNAs encoding viral proteins and virion genomic RNA, which will be packaged into viral core particles. On their way out of the infected cell, core particles move through the cytoplasm, attach to the inside of the plasma membrane of the newly infected cell, and bud, taking with them tracts of membrane containing the virally encoded envelope glycoprotein gene product. This cycle of infection—reverse transcription, transcription, translation, virion assembly, and budding—repeats itself over and over again as infection spreads.

The viral RNA and, as a result, the proviral DNA encode several cis-acting elements that are vital to the successful completion of the viral lifecycle. The virion RNA carries the viral promoter at its 3' end. Replicative acrobatics place the viral promoter at the 5' end of the proviral genome as the genome is reverse transcribed. Just 3' to the 5' retroviral LTR lies the viral packaging site. The retroviral lifecycle requires the presence of virally encoded transacting factors. The viral-RNA-dependent DNA polymerase (pol)—reverse transcriptase is also contained within the viral core and is vital to the viral life cycle in that it is responsible for the conversion of the genomic RNA to the integrative intermediate proviral DNA. The viral envelope glycoprotein, env, is required for viral attachment to the uninfected cell and for viral spread. There are also transcriptional trans-activating factors, so called transactivators, that can serve to modulate the level of transcription of the integrated parental provirus. Typically, replication-competent (non-defective) viruses are self-contained in that they encode all of these trans-acting factors. Their defective counterparts are not self-contained.

In the case of a DNA virus, such as a hepadnavirus, understanding the life cycle and viral genes required for infection is useful to the practice of this invention. The process of HBV entry has not been well defined. Replication of HBV uses an RNA intermediate template. In the infected cell the first step in replication is the conversion of the asymmetric relaxed circle DNA (rc-DNA) to covalently closed circle DNA (cccDNA). This process, which occurs within the nucleus of infected liver cells, involves completion of the DNA positive-strand synthesis and ligation of the DNA ends. In the second step, the cccDNA is transcribed by the host RNA polymerase to generate a 3.5 kB RNA template (the pregenome). This pregenome is complexed with protein in the viral core. The third step involves the synthesis of the first negativesense DNA strand by copying the pregenomic RNA using the virally encoded P protein reverse transcriptase. The P protein also serves as the minus strand DNA primer. Finally, the synthesis of the second positive-sense DNA strand occurs by copying the first DNA strand, using the P protein DNA polymerase activity and an oligomer of viral RNA as primer. The pregenome also transcribes mRNA for the major structural core proteins.

The following flow chart illustrates certain of the various vectors and host cells which may be used in this invention. It is not intended to be all inclusive.

Vectors

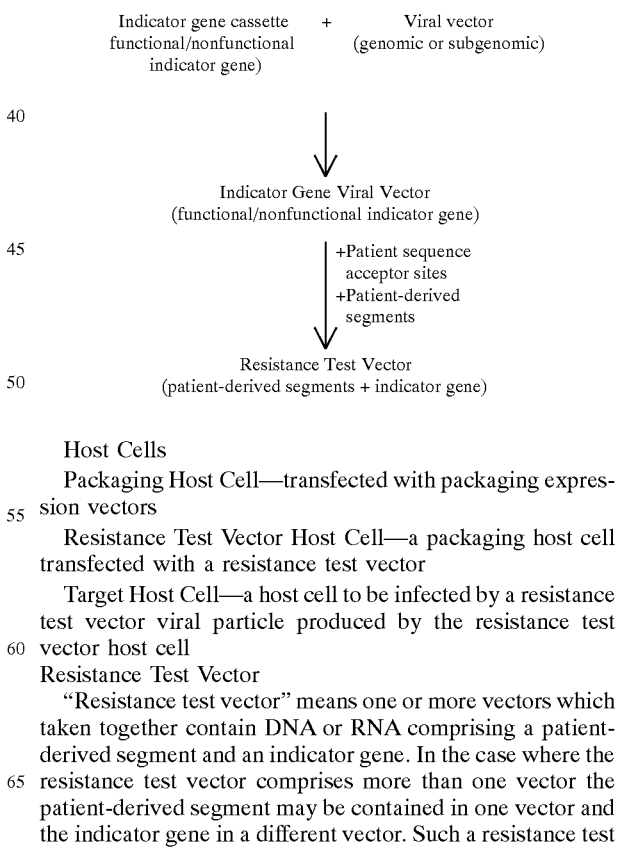

Host Cells

Packaging Host Cell—transfected with packaging expression vectors

Resistance Test Vector Host Cell—a packaging host cell transfected with a resistance test vector Target Host Cell—a host cell to be infected by a resistance test vector viral particle produced by the resistance test vector host cell Resistance Test Vector "Resistance test vector" means one or more vectors which taken together contain DNA or RNA comprising a patient-derived segment and an indicator gene. In the case where the resistance test vector comprises more than one vector the patient-derived segment may be contained in one vector and the indicator gene in a different vector. Such a resistance test vector comprising more than one vector is referred to herein as a resistance test vector system for purposes of clarity but is nevertheless understood to be a resistance test vector. The DNA or RNA of a resistance test vector may thus be contained in one or more DNA or RNA molecules. In one embodiment, the resistance test vector is made by insertion of a patient-derived segment into an indicator gene viral vector. In another embodiment, the resistance test vector is made by insertion of a patient-derived segment into a packaging vector while the indicator gene is contained in a second vector, for example an indicator gene viral vector. As used herein, "patient-derived segment" refers to one or more viral segments obtained directly from a patient using various means, for example, molecular cloning or polymerase chain reaction (PCR) amplification of a population of patient-derived segments using viral DNA or complementary DNA (cDNA) prepared from viral RNA, present in the cells (e.g. peripheral blood mononuclear cells, PBMC), serum or other bodily fluids of infected patients. When a viral segment is "obtained directly" from a patient it is obtained without passage of the virus through culture, or if the virus is cultured, then by a minimum number of passages to essentially eliminate the selection of mutations in culture. The term "viral segment" refers to any functional viral sequence or viral gene encoding a gene product (e.g., a protein) that is the target of an anti-viral drug. The term "functional viral sequence" as used herein refers to any nucleic acid sequence (DNA or RNA) with functional activity such as enhancers, promoters, polyadenylation sites, sites of action of transacting factors, such as tar and RRE, packaging sequences, integration sequences, or splicing sequences. If a drug were to target more than one functional viral sequence or viral gene product then patient-derived segments corresponding to each said viral gene would be inserted in the resistance test vector. In the case of combination therapy where two or more anti-virals targeting two different functional viral sequences or viral gene products are being evaluated, patient-derived segments corresponding to each functional viral sequence or viral gene product would be inserted in the resistance test vector. The patient-derived segments are inserted into unique restriction sites or specified locations, called patient sequence acceptor sites, in the indicator gene viral vector or for example, a packaging vector depending on the particular construction being used as described herein.

As used herein, "patient-derived segment" encompasses segments derived from human and various animal species. Such species include, but are not limited to chimpanzees, horses, cattles, cats and dogs.

Patient-derived segments can also be incorporated into resistance test vectors using any of several alternative cloning techniques. For example, cloning via the introduction of class II restriction sites into both the plasmid backbone and the patient-derived segments or by uracil DNA glycosylase primer cloning (refs).

The patient-derived segment may be obtained by any method of molecular cloning or gene amplification, or modifications thereof, by introducing patient sequence acceptor sites, as described below, at the ends of the patient-derived segment to be introduced into the resistance test vector. For example, in a gene amplification method such as PCR, restriction sites corresponding to the patient-sequence acceptor sites can be incorporated at the ends of the primers used in the PCR reaction. Similarly, in a molecular cloning method such as cDNA cloning, said restriction sites can be incorporated at the ends of the primers used for first or second strand cDNA synthesis, or in a method such as primer-repair of DNA, whether cloned or uncloned DNA, said restriction sites can be incorporated into the primers used for the repair reaction. The patient sequence acceptor sites and primers are designed to improve the representation of patient-derived segments. Sets of resistance test vectors having designed patient sequence acceptor sites provide representation of patient-derived segments that would be underrepresented in one resistance test vector alone.

Resistance test vectors are prepared by modifying an indicator gene viral vector (described below) by introducing patient sequence acceptor sites, amplifying or cloning patient-derived segments and inserting the amplified or cloned sequences precisely into indicator gene viral vectors at the patient sequence acceptor sites. The resistance test vectors are constructed from indicator gene viral vectors which are in turn derived from genomic viral vectors or subgenomic viral vectors and an indicator gene cassette, each of which is described below. Resistance test vectors are then introduced into a host cell. Alternatively, a resistance test vector (also referred to as a resistance test vector system) is prepared by introducing patient sequence acceptor sites into a packaging vector, amplifying or cloning patient-derived segments and inserting the amplified or cloned sequences precisely into the packaging vector at the patient sequence acceptor sites and co-transfecting this packaging vector with an indicator gene viral vector.

In one preferred embodiment, the resistance test vector may be introduced into packaging host cells together with packaging expression vectors, as defined below, to produce resistance test vector viral particles that are used in drug resistance and susceptibility tests that are referred to herein as a "particle-based test." In an alternative preferred embodiment, the resistance test vector may be introduced into a host cell in the absence of packaging expression vectors to carry out a drug resistance and susceptibility test that is referred to herein as a "non-particle-based test." As used herein a "packaging expression vector" provides the factors, such as packaging proteins (e.g. structural proteins such as core and envelope polypeptides), transacting factors, or genes required by replication-defective retrovirus or hepadnavirus. In such a situation, a replication-competent viral genome is enfeebled in a manner such that it cannot replicate on its own. This means that, although the packaging expression vector can produce the trans-acting or missing genes required to rescue a defective viral genome present in a cell containing the enfeebled genome, the enfeebled genome cannot rescue itself.

Indicator or Indicator Gene

"Indicator or indicator gene" refers to a nucleic acid encoding a protein, DNA or RNA structure that either directly or through a reaction gives rise to a measurable or noticeable aspect, e.g. a color or light of a measurable wavelength or in the case of DNA or RNA used as an indicator a change or generation of a specific DNA or RNA structure. Preferred examples of an indicator gene is the *E. coli* lacZ gene which encodes beta-galactosidase, the luc gene which encodes luciferase either from, for example, *Photonis pyralis* (the firefly) or *Renilla reniformis* (the sea pansy), the *E. coli* phoA gene which encodes alkaline phosphatase, green fluorescent protein and the bacterial CAT gene which encodes chloramphenicol acetyltransferase. Additional preferred examples of an indicator gene are secreted proteins or cell surface proteins that are readily measured by assay, such as radioimmunoassay (RIA), or fluorescent activated cell sorting (FACS), including, for example, growth factors, cytokines and cell surface antigens (e.g. growth hormone, Il-2 or CD4, respectively). "Indicator gene" is understood to also include a selection gene, also referred to as a selectable marker. Examples of suitable selectable markers for mammalian cells are dihydrofolate reductase (DHFR), thymidine kinase, hygromycin, neomycin, zeocin or E. coli gpt. In the case of the foregoing examples of indicator genes, the indicator gene and the patient-derived segment are discrete, i.e. distinct and separate genes. In some cases a patient-derived segment may also be used as an indicator gene. In one such embodiment in which the patient-derived segment corresponds to more than one viral gene which is the target of an anti-viral, one of said viral genes may also serve as the indicator gene. For example, a viral protease gene may serve as an indicator gene by virtue of its ability to cleave a chromogenic substrate or its ability to activate an inactive zymogen which in turn cleaves a chromogenic substrate, giving rise in each case to a color reaction. In all of the above examples of indicator genes, the indicator gene may be either "functional" or "non-functional" but in each case the expression of the indicator gene in the target cell is ultimately dependent upon the action of the patient-derived segment.

Functional Indicator Gene

In the case of a "functional indicator gene" the indicator gene may be capable of being expressed in a "packaging host cell/resistance test vector host cell" as defined below, independent of the patient-derived segment, however the functional indicator gene could not be expressed in the target host cell, as defined below, without the production of functional resistance test vector particles and their effective infection of the target host cell. In one embodiment of a functional indicator gene, the indicator gene cassette, comprising control elements and a gene encoding an indicator protein, is inserted into the indicator gene viral vector with the same or opposite transcriptional orientation as the native or foreign enhancer/promoter of the viral vector. One example of a functional indicator gene in the case of HIV or HBV, places the indicator gene and its promoter (a CMV IE enhancer/promoter) in the same or opposite transcriptional orientation as the HIV-LTR or HBV enhancer-promoter, respectively, or the CMV IE enhancer/promoter associated with the viral vector.

Non-Functional Indicator Gene

Alternatively the indicator gene, may be "non-functional" in that the indicator gene is not efficiently expressed in a packaging host cell transfected with the resistance test vector, which is then referred to a resistance test vector host cell, until it is converted into a functional indicator gene through the action of one or more of the patient-derived segment products. An indicator gene is rendered non-functional through genetic manipulation according to this invention.

1. Permuted Promoter In one embodiment an indicator gene is rendered non-functional due to the location of the promoter, in that, although the promoter is in the same transcriptional orientation as the indicator gene, it follows rather than precedes the indicator gene coding sequence. This misplaced promoter is referred to as a "permuted promoter." In addition to the permuted promoter the orientation of the non-functional indicator gene is opposite to that of the native or foreign promoter/enhancer of the viral vector. Thus the coding sequence of the non-functional indicator gene can neither be transcribed by the permuted promoter nor by the viral promoters. The non-functional indicator gene and its permuted promoter is rendered functional by the action of one or more of the viral proteins. One example of a non-functional indicator gene with a permuted promoter in the case of HIV, places a T7 phage RNA polymerase promoter (herein referred to as T7 promoter) promoter in the 5' LTR in the same transcriptional orientation as the indicator gene. The indicator gene cannot be transcribed by the T7 promoter as the indicator gene cassette is positioned upstream of the T7 promoter. The non-functional indicator gene in the resistance test vector is converted into a functional indicator gene by reverse transcriptase upon infection of the target cells, resulting from the repositioning of the T7 promoter, by copying from the 5' LTR to the 3' LTR, relative to the indicator gene coding region. Following the integration of the repaired indicator gene into the target cell chromosome by HIV integrase, a nuclear T7 RNA polymerase expressed by the target cell transcribes the indicator gene. One example of a non-functional indicator gene with a permuted promoter in the case of HBV, places an enhancer-promoter region downstream or 3' of the indicator gene both having the same transcriptional orientation. The indicator gene cannot be transcribed by the enhancer-promoter as the indicator gene cassette is positioned upstream. The non-functional indicator gene in the resistance test vector is converted into a functional indicator gene by reverse transcription and circularization of the HBV indicator gene viral vector by the repositioning of the enhancer-promoter upstream relative to the indicator gene coding region.

A permuted promoter may be any eukaryotic or prokaryotic promoter which can be transcribed in the target host cell. Preferably the promoter will be small in size to enable insertion in the viral genome without disturbing viral replication. More preferably, a promoter that is small in size and is capable of transcription by a single subunit RNA polymerase introduced into the target host cell, such as a bacteriophage promoter, will be used. Examples of such bacteriophage promoters and their cognate RNA polymerases include those of phages T7, T3 and Sp6. A nuclear localization sequence (NLS) may be attached to the RNA polymerase to localize expression of the RNA polymerase to the nucleus where they may be needed to transcribed the repaired indicator gene. Such an NLS may be obtained from any nuclear-transported protein such as the SV40 T antigen. If a phage RNA polymerase is employed, an internal ribosome entry site (IRES) such as the EMC virus 5' untranslated region (UTR) may be added in front of the indicator gene, for translation of the transcripts which are generally uncapped. In the case of HIV, the permuted promoter itself can be introduced at any position within the 5' LTR that is copied to the 3' LTR during reverse transcription so long as LTR function is not disrupted, preferably within the U5 and R portions of the LTR, and most preferably outside of functionally important and highly conserved regions of U5 and R. In the case of HBV, the permuted promoter can be placed at any position that does not disrupt the cis acting elements that are necessary for HBV DNA replication. Blocking sequences may be added at the ends of the resistance test vector should there be inappropriate expression of the non-functional indicator gene due to transfection artifacts (DNA concatenation). In the HIV example of the permuted T7 promoter given above, such a blocking sequence may consist of a T7 transcriptional terminator, positioned to block readthrough transcription resulting from DNA concatenation, but not transcription resulting from repositioning of the permuted T7 promoter from the 5' LTR to the 3' LTR during reverse transcription.

2. Permuted Coding Region In a second embodiment, an indicator gene is rendered non-functional due to the relative location of the 5' and 3' coding regions of the indicator gene, in that, the 3' coding region precedes rather than follows the 5' coding region. This misplaced coding region is referred to as a "permuted coding region." The orientation of the non-functional indicator gene may be the same or opposite to that of the native or foreign promoter/enhancer of the viral vector, as mRNA coding for a functional indicator gene will be produced in the event of either orientation. The non-functional indicator gene and its permuted coding region is rendered functional by the action of one or more of the patient-derived segment products. A second example of a non-functional indicator gene with a permuted coding region in the case of HIV, places a 5' indicator gene coding region with an associated promoter in the 3' LTR U3 region and a 3' indicator gene coding region in an upstream location of the HIV genome, with each coding region having the same transcriptional orientation as the viral LTRs. In both examples, the 5' and 3' coding regions may also have associated splice donor and acceptor sequences, respectively, which may be heterologous or artificial splicing signals. The indicator gene cannot be functionally transcribed either by the associated promoter or viral promoters, as the permuted coding region prevents the formation of functionally spliced transcripts. The non-functional indicator gene in the resistance test vector is converted into a functional indicator gene by reverse transcriptase upon infection of the target cells, resulting from the repositioning of the 5' and 3' indicator gene coding regions relative to one another, by copying of the 3' LTR to the 5' LTR. Following transcription by the promoter associated with the 5' coding region, RNA splicing can join the 5' and 3' coding regions to produce a functional indicator gene product. One example of a non-functional indicator gene with a permuted coding region in the case of HBV, places a 3' indicator gene coding region upstream or 5' of the enhancer-promoter and the 5' coding region of the indicator gene. The transcriptional orientation of the indicator gene 5' and 3' coding regions are identical to one another, and the same as that of the indicator gene viral vector. However, as the indicator gene 5' and 3' coding regions are permuted in the resistance test vectors (i.e., the 5' coding region is downstream of the 3' coding region), no mRNA is transcribed which can be spliced to generate a functional indicator gene coding region. Following reverse transcription and circularization of the indicator gene viral vector, the indicator gene 3' coding region is positioned downstream or 3' to the enhancer-promoter and 5' coding regions thus permitting the transcription of mRNA which can be spliced to generate a functional indicator gene coding region.

3. Inverted Intron In a third embodiment, the indicator gene is rendered non-functional through use of an "inverted intron," i.e. an intron inserted into the coding sequence of the indicator gene with a transcriptional orientation opposite to that of the indicator gene. The overall transcriptional orientation of the indicator gene cassette including its own, linked promoter, is opposite to that of the viral control elements, while the orientation of the artificial intron is the same as the viral control elements. Transcription of the indicator gene by its own linked promoter does not lead to the production of functional transcripts as the inverted intron cannot be spliced in this orientation. Transcription of the indicator gene by the viral control elements does, however, lead to the removal of the inverted intron by RNA splicing, although the indicator gene is still not functionally expressed as the resulting transcript has an antisense orientation. Following the reverse transcription of this transcript and integration of the resultant retroviral DNA, or the circularization of hepadnavirus DNA, the indicator gene can be functionally transcribed using its own linked promoter as the inverted intron has been previously removed. In this case, the indicator gene itself may contain its own functional promoter with the entire transcriptional unit oriented opposite to the viral control elements. Thus the non-functional indicator gene is in the wrong orientation to be transcribed by the viral control elements and it cannot be functionally transcribed by its own promoter, as the inverted intron cannot be properly excised by splicing. However, in the case of a retrovirus and HIV specifically and hepadnaviruses, and HBV specifically, transcription by the viral promoters (HIV LTR or HBV enhancer-promoter) results in the removal of the inverted intron by splicing. As a consequence of reverse transcription of the resulting spliced transcript and the integration of the resulting provirus into the host cell chromosome or circularization of the HBV vector, the indicator gene can now be functionally transcribed by its own promoter. The inverted intron, consisting of a splice donor and acceptor site to remove the intron, is preferably located in the coding region of the indicator gene in order to disrupt translation of the indicator gene. The splice donor and acceptor may be any splice donor and acceptor. A preferred splice donor-receptor is the CMV IE splice donor and the splice acceptor of the second exon of the human alpha globin gene ("intron A").

Indicator Gene Viral Vector—Construction

As used herein, "indicator gene viral vector" refers to a vector(s) comprising an indicator gene and its control elements and one or more viral genes. The indicator gene viral vector is assembled from an indicator gene cassette and a "viral vector," defined below. The indicator gene viral vector may additionally include an enhancer, splicing signals, polyadenylation sequences, transcriptional terminators, or other regulatory sequences. Additionally the indicator gene viral vector may be functional or nonfunctional. In the event that the viral segments which are the target of the anti-viral drug are not included in the indicator gene viral vector they are provided in a second vector. An "indicator gene cassette" comprises an indicator gene and control elements. "Viral vector" refers to a vector comprising some or all of the following: viral genes encoding a gene product, control sequences, viral packaging sequences, and in the case of a retrovirus, integration sequences. The viral vector may additionally include one or more viral segments one or more of which may be the target of an anti-viral drug. Two examples of a viral vector which contain viral genes are referred to herein as an "genomic viral vector" and a "subgenomic viral vector." A "genomic viral vector" is a vector which may comprise a deletion of a one or more viral genes to render the virus replication incompetent, but which otherwise preserves the mRNA expression and processing characteristics of the complete virus. In one embodiment for an HIV drug susceptibility and resistance test, the genomic viral vector comprises the HIV gag-pol, vif, vpr, tat, rev, vpu, and nef genes (some, most or all of env may be deleted). A "subgenomic viral vector" refers to a vector comprising the coding region of one or more viral genes which may encode the proteins that are the target(s) of the anti-viral drug. In the case of HIV, a preferred embodiment is a subgenomic viral vector comprising the HIV gag-pol gene. In the case of HBV a preferred embodiment is a subgenomic viral vector comprising the HBV P gene. In the case of HIV, two examples of proviral clones used for viral vector construction are: HXB2 (Fisher et al., (1986) *Nature*, 320, 367–371) and NL4-3, (Adachi et al., (1986) *J. Virol.*, 59, 284–291). In the case of HBV, a large number of full length genomic sequences have been characterized and could be used for construction of HBV viral vectors: GenBank Nos. M54923, M38636, J02203 and X59795. The viral coding genes may be under the control of a native enhancer/promoter or a foreign viral or cellular enhancer/promoter. A preferred embodiment for an HIV drug susceptibility and resistance test, is to place the genomic or subgenomic viral coding regions under the control of the native enhancer/promoter of the HIV-LTR U3 region or the CMV immediate-early (IE) enhancer/promoter. A preferred embodiment for an HBV drug susceptibility and resistance test, is to place the genomic or subgenomic viral coding regions under the control of the CMV immediate-early (IE) enhancer/promoter. In the case of an indicator gene viral vector that contains one or more viral genes which are the targets or encode proteins which are the targets of an anti-viral drug(s) then said vector contains the patient sequence acceptor sites. The patient-derived segments are inserted in the patient sequence acceptor site in the indicator gene viral vector which is then referred to as the resistance test vector, as described above.

"Patient sequence acceptor sites" are sites in a vector for insertion of patient-derived segments and said sites may be: 1) unique restriction sites introduced by site-directed mutagenesis into a vector; 2) naturally occurring unique restriction sites in the vector; or 3) selected sites into which a patient-derived segment may be inserted using alternative cloning methods (e.g. UDG cloning). In one embodiment the patient sequence acceptor site is introduced into the indicator gene viral vector. The patient sequence acceptor sites are preferably located within or near the coding region of the viral protein which is the target of the anti-viral drug. The viral sequences used for the introduction of patient sequence acceptor sites are preferably chosen so that no change, or a conservative change, is made in the amino acid coding sequence found at that position. Preferably the patient sequence acceptor sites are located within a relatively conserved region of the viral genome to facilitate introduction of the patient-derived segments. Alternatively, the patient sequence acceptor sites are located between functionally important genes or regulatory sequences. Patient-sequence acceptor sites may be located at or near regions in the viral genome that are relatively conserved to permit priming by the primer used to introduce the corresponding restriction site into the patient-derived segment. To improve the representation of patient-derived segments further, such primers may be designed as degenerate pools to accommodate viral sequence heterogeneity, or may incorporate residues such as deoxyinosine (I) which have multiple base-pairing capabilities. Sets of resistance test vectors having patient sequence acceptor sites that define the same or overlapping restriction site intervals may be used together in the drug resistance and susceptibility tests to provide representation of patient-derived segments that contain internal restriction sites identical to a given patient sequence acceptor site, and would thus be underrepresented in either resistance test vector alone.

Host Cells

The resistance test vector is introduced into a host cell. Suitable host cells are mammalian cells. Preferred host cells are derived from human tissues and cells which are the principle targets of viral infection. In the case of HIV these include human cells such as human T cells, monocytes, macrophage, dendritic cells, Langerhans cells, hematopoeitic stem cells or precursor cells, and other cells. In the case of HBV, suitable host cells include hepatoma cell lines (HepG2, Huh7), primary human hepatocytes, mammalian cells which can be infected by pseudotyped HBV, and other cells. Human derived host cells will assure that the anti-viral drug will enter the cell efficiently and be converted by the cellular enzymatic machinery into the metabolically relevant form of the anti-viral inhibitor. Host cells are referred to herein as a "packaging host cells," "resistance test vector host cells," or "target host cells." A "packaging host cell" refers to a host cell that provides the transacting factors and viral packaging proteins required by the replication defective viral vectors used herein, such as the resistance test vectors, to produce resistance test vector viral particles. The packaging proteins may be provided for by the expression of viral genes contained within the resistance test vector itself, a packaging expression vector(s), or both. A packaging host cell is a host cell which is transfected with one or more packaging expression vectors and when transfected with a resistance test vector is then referred to herein as a "resistance test vector host cell" and is sometimes referred to as a packaging host cell/resistance test vector host cell. Preferred host cells for use as packaging host cells for HIV include 293 human embryonic kidney cells (293, Graham, F. L. et al., J. Gen Virol. 36: 59, 1977), BOSC23 (Pear et al., Proc. Natl. Acad. Sci. 90, 8392, 1993), tsa54 and tsa201 cell lines (Heinzel et al., J.Virol. 62, 3738,1988), for HBV HepG2 (Galle and Theilmann, L. Arzheim.-Forschy Drug Res. (1990) 40, 1380–1382), and Huh7 (Ueda, K et al. Virology (1989) 169, 213–216). A "target host cell" refers to a cell to be infected by resistance test vector viral particles produced by the resistance test vector host cell in which expression or inhibition of the indicator gene takes place. Preferred host cells for use as target host cells include human T cell leukemia cell lines including Jurkat (ATCC T1B-152), H9 (ATCC HTB-176), CEM (ATCC CCL-119), HUT78 (ATCC T1B-161), and derivatives thereof.

Drug Susceptibility and Resistance Tests

The drug susceptibility and resistance tests of this invention may be carried out in one or more host cells. Viral drug susceptibility is determined as the concentration of the anti-viral agent at which a given percentage of indicator gene expression is inhibited (e.g. the $IC_{50}$ for an anti-viral agent is the concentration at which 50% of indicator gene expression is inhibited). A standard curve for drug susceptibility of a given anti-viral drug can be developed for a viral segment that is either a standard laboratory viral segment or from a drug-naive patient (i.e. a patient who has not received any anti-viral drug) using the method of this invention. Correspondingly, viral drug resistance is a decrease in viral drug susceptibility for a given patient either by comparing the drug susceptibility to such a given standard or by making sequential measurement in the same patient over time, as determined by increased inhibition of indicator gene expression (i.e. decreased indicator gene expression).

In the first type of drug susceptibility and resistance test, resistance test vector viral particles are produced by a first host cell (the resistance test vector host cell) that is prepared by transfecting a packaging host cell with the resistance test vector and packaging expression vector(s). The resistance test vector viral particles are then used to infect a second host cell (the target host cell) in which the expression of the indicator gene is measured. Such a two cell system comprising a packaging host cell which is transfected with a resistance test vector, which is then referred to as a resistance test vector host cell, and a target cell are used in the case of either a functional or non-functional indicator gene. Functional indicator genes are efficiently expressed upon transfection of the packaging host cell and would require infection of a target host cell with resistance test vector host cell supernatant to carry out the test of this invention. Non-functional indicator genes with a permuted promoter, a permuted coding region, or an inverted intron are not efficiently expressed upon transfection of the packaging host cell and thus the infection of the target host cell can be achieved either by co-cultivation by the resistance test vector host cell and the target host cell or through infection of the target host cell using the resistance test vector host cell supernatant. In the second type of drug susceptibility and resistance test, a single host cell (the resistance test vector host cell) also serves as a target host cell. The packaging host cells are transfected and produce resistance test vector viral particles and some of the packaging host cells also become the target of infection by the resistance test vector particles. Drug susceptibility and resistance tests employing a single host cell type are possible with viral resistance test vectors comprising a non-functional indicator gene with a permuted promoter, a permuted coding region, or an inverted intron. Such indicator genes are not efficiently expressed upon transfection of a first cell, but are only efficiently expressed upon infection of a second cell, and thus provide an opportunity to measure the effect of the anti-viral agent under evaluation. In the case of a drug susceptibility and resistance test using a resistance test vector comprising a functional indicator gene, neither the co-cultivation procedure nor the resistance and susceptibility test using a single cell type can be used for the infection of target cells. A resistance test vector comprising a functional indicator gene requires a two cell system using filtered supernatants from the resistance test vector host cells to infect the target host cell.

In one embodiment of the invention in the case of HIV, a particle-based resistance tests are carried out with resistance test vectors derived from genomic viral vectors, i.e., pLG-lucPP-HS, pCG-lucPP-HS, pLG-lucPP-PB, pCG-lucPP-PB, pLG-lucPC-HS, pCG-lucPC-HS, pLG-lucPC-PB, pCG-lucPC-PB, pLG-lucII-HS, pCG-lucII-HS, pLG-lucII-PB, pCG-lucII-PB, and pCG-CXCN(F-lucP)2-AA which are cotransfected with the packaging expression vector pVL-env4070A (also referred to as pCXAS-4070Aenv). Alternatively, a particle-based resistance test may be carried out with resistance test vectors derived from subgenomic viral vectors, i.e., pLS-lucPP-HS, pCS-lucPP-HS, pLS-lucPP-PB, pCS-luc-PP-PB, pLS-lucPC-HS, pCS-lucPC-HS, pLS-lucPC-PB, pCS-luc-PC-PB, pLS-lucII-HS, pCS-lucII-HS, pLS-lucII-PB, and pCS-luc-II-PB) which are cotransfected with the packaging expression vector pVL-env4070 and either PLTR-HIV3' or pCMV-HIV3'. In another embodiment of the invention in the case of HIV, non-particle-based resistance tests are carried out using each of the above described resistance test vectors by transfection of selected host cells in the absence of packaging expression vectors.

In the case of the particle-based susceptibility and resistance test, resistance test vector viral particles are produced by a first host cell (the resistance test vector host cell) that is prepared by transfecting a packaging host cell with the resistance test vector and packaging expression vector(s). The resistance test vector viral particles are then used to infect a second host cell (the target host cell) in which the expression of the indicator gene is measured. In a second type of particle-based susceptibility and resistance test, a single host cell type (the resistance test vector host cell) serves both purposes: some of the packaging host cells in a given culture are transfected and produce resistance test vector viral particles and some of the host cells in the same culture are the target of infection by the resistance test vector particles thus produced. Resistance tests employing a single host cell type are possible with resistance test vectors comprising a non-functional indicator gene with a permuted promoter since such indicator genes are efficiently expressed upon infection of a permissive host cell, they are not efficiently expressed upon transfection of the same host cell type, and thus provide an opportunity to measure the effect of the anti-viral agent under evaluation. For similar reasons, resistance tests employing two cell types may be carried out by co-cultivating the two cell types as an alternative to infecting the second cell type with viral particles obtained from the supernatants of the first cell type.

In the case of the non-particle-based susceptibility and resistance test, resistance tests are performed by transfection of a single host cell with the resistance test vector in the absence of packaging expression vectors. Non-particle based resistance tests are carried out using the resistance test vectors comprising non-functional indicator genes with either permuted promoters, permuted coding regions or inverted introns. These non-particle based resistance tests are performed by transfection of a single host cell type with each resistance test vector in the absence of packaging expression vectors. Although the non-functional indicator genes contained within these resistance test vectors are not efficiently expressed upon transfection of the host cells, there is detectable indicator gene expression resulting from non-viral particle-based reverse transcription. Reverse transcription and strand transfer results in the conversion of the permuted, non-functional indicator gene to a non-permuted, functional indicator gene. As reverse transcription is completely dependent upon the expression of the pol gene contained within each resistance test vector, anti-viral agents may be tested for their ability to inhibit the pol gene products encoded by the patient-derived segments contained within the resistance test vectors. In the case of HIV, reverse transcription and strand transfer results in the conversion of the non-functional indicator gene to a functional indicator gene. As reverse transcription is completely dependent upon the expression of the patient-derived segment contained within each resistance test vector, anti-viral agents may be tested for their ability to inhibit the gene products encoded by the patient-derived segments contained within the resistance test vectors.

The packaging host cells are transfected with the resistance test vector and the appropriate packaging expression vector(s) to produce resistance test vector host cells. Individual anti-viral agents, including the reverse transcriptase inhibitors AZT, ddI, ddC, d4T and 3TC, and the protease inhibitors saquinavir, ritonavir and indinavir, as well as combinations thereof, are added to individual plates of packaging host cells at the time of their transfection, at an appropriate range of concentrations. Twenty-four to 48 hours after transfection, target host cells are infected by co-cultivation with resistance test vector host cells or with resistance test vector viral particles obtained from filtered supernatants of resistance test vector host cells. Each anti-viral agent, or combination thereof, is added to the target host cells prior to or at the time of infection to achieve the same final concentration of the given agent, or agents, present during the transfection.

Determination of the expression or inhibition of the indicator gene in the target host cells infected by co-cultivation or with filtered viral supernatants is made by assay of indicator gene expression, for example in the case where the indicator gene is the firefly luc gene, by measuring luciferase activity. The reduction in luciferase activity observed for target host cells infected with a given preparation of resistance test vector viral particles in the presence of a given antiviral agent, or agents, as compared to a control run in the absence of the antiviral agent, generally relates to the log of the concentration of the antiviral agent as a sigmoidal curve. This inhibition curve is used to calculate the apparent inhibitory concentration (IC) of that agent, or combination of agents, for the viral target product encoded by the patient-derived segments present in the resistance test vector.

In the case of a one cell susceptibility and resistance test, host cells are transfected with the resistance test vector and the appropriate packaging expression vector(s) to produce resistance test vector host cells. Individual antiviral agents, or combinations thereof, are added to individual plates of transfected cells at the time of their transfection, at an appropriate range of concentrations. Twenty-four to 72 hours after transfection, cells are collected and assayed for firefly luciferase activity. As transfected cells in the culture do not efficiently express the indicator gene, transfected cells in the culture, as well superinfected cells in the culture, can serve as target host cells for indicator gene expression. The reduction in luciferase activity observed for cells transfected in the presence of a given antiviral agent, or agents as compared to a control run in the absence of the antiviral agent(s), generally relates to the log of the concentration of the antiviral agent as a sigmoidal curve. This inhibition curve is used to calculate the apparent inhibitory concentration (IC) of an agent, or combination of agents, for the viral target product encoded by the patient-derived segments present in the resistance test vector.

Antiviral Drugs/Drug Candidates

The antiviral drugs being added to the test system are added at selected times depending upon the target of the antiviral drug. For example, in the case of HIV protease inhibitors, including saquinavir, ritonavir, indinavir, and nelfinavir, they are added to individual plates of packaging host cells at the time of their transfection with a resistance test vector, at an appropriate range of concentrations. HIV protease inhibitors are also added to the target host cells at the time of infection to achieve the same final concentration added during transfections. HIV reverse transcriptase inhibitors, including AZT, ddI, ddC, d4T, 3TC and nevaripine, are added to individual plates of target host cells at the time of infection by the resistance test vector viral particles, at a test concentration. Alternatively, the antiviral drugs may be present throughout the assay. The test concentration is selected from a range of concentrations which is typically between about 0.1nM and about 100 $\mu$M and more specifically for each of the following drugs: AZT, from about 1nM to about 5 $\mu$M; ddI, from about 1nM to about 25 $\mu$M; 3TC, from about 1nM to about 50 $\mu$M; d4T, from about 1nM to about 25 $\mu$M; and, nevaripine, from about 1nM to about 100 $\mu$M.

In another embodiment of this invention, a candidate antiviral compound is tested in the drug susceptibility and resistance test of this invention. The candidate antiviral compound is added to the test system at an appropriate concentration and at selected times depending upon the protein target of the candidate anti-viral. Alternatively, more than one candidate antiviral compound may be tested or a candidate antiviral compound may be tested in combination with an approved antiviral drug such as AZT, ddI, ddC, d4T, 3TC, saquinavir or a compound which is undergoing clinical trials such as ritonavir, or indinovir. The effectiveness of the candidate antiviral will be evaluated by measuring the expression or inhibition of the indicator gene. In another aspect of this embodiment, the drug susceptibility and resistance test may be used to screen for viral mutants. Following the identification of resistant mutants to either known anti-virals or candidate anti-virals the resistant mutants are isolated and the DNA is analyzed. A library of viral resistant mutants can thus be assembled enabling the screening of candidate anti-virals, alone or in combination. This will enable one of ordinary skill to identify effective anti-virals and design effective therapeutic regimens.

General Materials and Methods

Most of the techniques used to construct vectors, and transfect and infect cells, are widely practiced in the art, and most practitioners are familiar with the standard resource materials which describe specific conditions and procedures. However, for convenience, the following paragraphs may serve as a guideline.

"Plasmids" and "vectors" are designated by a lower case p followed by letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

Construction of the vectors of the invention employs standard ligation and restriction techniques which are well understood in the art (see Ausubel et al., (1987) Current Protocols in Molecular Biology, Wiley—Interscience or Maniatis et al., (1992) in Molecular Cloning: A laboratory Manual, Cold Spring Harbor Laboratory, N.Y.). Isolated plasmids, DNA sequences, or synthesized oligonucleotides are cleaved, tailored, and relegated in the form desired. The sequences of all DNA constructs incorporating synthetic DNA were confirmed by DNA sequence analysis (Sanger et al. (1977) *Proc. Natl. Acad. Sci.* 74, 5463–5467).

"Digestion" of DNA refers to catalytic cleavage of the DNA with a restriction enzyme that acts only at certain sequences, restriction sites, in the DNA. The various restriction enzymes used herein are commercially available and their reaction conditions, cofactors and other requirements are known to the ordinarily skilled artisan. For analytical purposes, typically 1 $\mu$g of plasmid or DNA fragment is used with about 2 units of enzyme in about 20 $\mu$l of buffer solution. Alternatively, an excess of restriction enzyme is used to insure complete digestion of the DNA substrate. Incubation times of about one hour to two hours at about 37° C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in *Methods of Enzymology* 65:499–560 (1980).

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 minutes at 20° C. in 50 mM Tris (ph7.6) 50 mM NaCl, 6 mM MgCl$_2$, 6 mM DTT and 5–10 $\mu$M dNTPs. The Klenow fragment fills in at 5' sticky ends but chews back protruding 3' single strands, even though the four dNTPs are present. If desired, selective repair can be performed by supplying only one of the dNTPs, or with selected dNTPs, within the limitations dictated by the nature of the sticky ends. After treatment with Klenow, the mixture is extracted with phenol/chloroform and ethanol precipitated. Treatment under appropriate conditions with S1 nuclease or Bal-31 results in hydrolysis of any single-stranded portion.

Ligations are performed in 15–50 $\mu$l volumes under the following standard conditions and temperatures: 20 mM Tris-Cl pH 7.5, 10 mM MgCl$_2$, 10 mM DTT, 33 mg/ml BSA, 10 mM–50 mM NaCl, and either 40 $\mu$M ATP, 0.01–0.02 (Weiss) units T4 DNA ligase at 0° C. (for "sticky end" ligation) or 1mM ATP, 0.3–0.6 (Weiss) units T4 DNA ligase at 14° C. (for "blunt end" ligation). Intermolecular "sticky end" ligations are usually performed at 33–100 $\mu$g/ml total DNA concentrations (5–100 mM total end concentration). Intermolecular blunt end ligations (usually employing a 10–30 fold molar excess of linkers) are performed at 1 $\mu$M total ends concentration.

"Transient expression" refers to unamplified expression within about one day to two weeks of transfection. The optimal time for transient expression of a particular desired heterologous protein may vary depending on several factors including, for example, any transacting factors which may be employed, translational control mechanisms and the host cell. Transient expression occurs when the particular plasmid that has been transfected functions, i.e., is transcribed and translated. During this time the plasmid DNA which has entered the cell is transferred to the nucleus. The DNA is in a nonintegrated state, free within the nucleus. Transcription of the plasmid taken up by the cell occurs during this period. Following transfection the plasmid DNA may become degraded or diluted by cell division. Random integration within the cell chromatin occurs.

In general, vectors containing promoters and control sequences which are derived from species compatible with the host cell are used with the particular host cell. Promoters suitable for use with prokaryotic hosts illustratively include the beta-lactamase and lactose promoter systems, alkaline phosphatase, the tryptophan (trp) promoter system and hybrid promoters such as tac promoter. However, other functional bacterial promoters are suitable. In addition to prokaryotes, eukaryotic microbes such as yeast cultures may also be used. *Saccharomyces cerevisiae*, or common baker's yeast is the most commonly used eukaryotic microorganism, although a number of other strains are commonly available. Promoters controlling transcription from vectors in mammalian host cells may be obtained from various sources, for example, the genomes of viruses such as: polyoma, simian virus 40 (SV40), adenovirus, retroviruses, hepatitis B virus and preferably cytomegalovirus, or from heterologous mammalian promoters, e.g. b-actin promoter. The early and late promoters of the SV 40 virus are conveniently obtained as an SV40 restriction fragment which also contains the SV40 viral origin of replication. The immediate early promoter of the human cytomegalovirus is conveniently obtained as a HindIII E restriction fragment. Of course, promoters from the host cell or related species also are useful herein.

The vectors used herein may contain a selection gene, also termed a selectable marker. A selection gene encodes a protein, necessary for the survival or growth of a host cell transformed with the vector. Examples of suitable selectable markers for mammalian cells include the dihydrofolate reductase gene (DHFR), the ornithine decarboxylase gene, the multi-drug resistance gene (mdr), the adenosine deaminase gene, and the glutamine synthase gene. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. The second category is referred to as dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin (Southern and Berg (1982) *J. Molec. Appl. Genet.* 1, 327), mycophenolic acid (Mulligan and Berg (1980) *Science* 209, 1422), or hygromycin (Sugden et al. (1985) *Mol. Cell. Biol.* 5, 410–413). The three examples given above employ bacterial genes under eukaryotic control to convey resistance to the appropriate drug neomycin (G418 or genticin), xgpt (mycophenolic acid) or hygromycin, respectively.

"Transfection" means introducing DNA into a host cell so that the DNA is expressed, whether functionally expressed or otherwise; the DNA may also replicate either as an extrachromosomal element or by chromosomal integration. Unless otherwise provided, the method used herein for transformation of the host cells is the calcium phosphate co-precipitation method of Graham and van der Eb (1973) *Virology* 52, 456–457. Alternative methods for transfection are electroporation, the DEAE-dextran method, lipofection and biolistics (Kriegler (1990) Gene Transfer and Expression: A Laboratory Manual, Stockton Press).

Host cells may be transfected with the expression vectors of the present invention and cultured in conventional nutrient media modified as is appropriate for inducing promoters, selecting transformants or amplifying genes. Host cells are cultured in F12: DMEM (Gibco) 50:50 with added glutamine and without antibiotics. The culture conditions, such as temperature, pH and the like, are those previously used with the host cell selected for expression, and will be apparent to the ordinarily skilled artisan.

The following examples merely illustrate the best mode now known for practicing the invention, but should not be construed to limit the invention. All literature references are expressly incorporated by reference.

EXAMPLE 1

HIV Drug Susceptibility And Resistance Test Using Resistance Test Vectors Comprising Patient-derived Segment(s) And A Non-Functional Indicator Gene With A Permuted Promoter.

Indicator Gene Viral Vector—Construction

Indicator gene viral vectors containing a non-functional indicator gene with a permuted promoter were designed using both HIV genomic and subgenomic viral vectors comprising viral genes which are the target(s) of anti-viral drugs. The indicator gene viral vectors pLG-lucPP and pCG-lucPP are based on the genomic viral vectors pLG and pCG; each bears a deletion in the HIV env gene. Resistance test vectors derived from the genomic indicator gene viral vectors, pLG-lucPP and pCG-lucPP, contain a patient sequence acceptor site for insertion of the patient-derived segment and are used in conjunction with a packaging expression vector encoding the amphotrophic MLV 4070A env gene product. The indicator gene viral vectors pLS-lucPP and pCS-lucPP are based on the subgenomic viral vectors pLS and pCS; each encodes the HIV gag-pol gene only. Resistance test vectors derived from the subgenomic indicator gene viral vectors, pLS-lucPP and pCS-lucPP, contain a sequence acceptor site for insertion of patient-derived segment and are used in conjunction with a first packaging expression vector encoding the HIV vif, vpr, tat, rev, vpu and nef genes and a second packaging vector encoding the amphotrophic MLV 4070A env gene product.

HIV Viral Vectors—Genomic and Subqenomic

HIV viral vectors were designed using the sequences of the biologically active proviral clone, HXB2 (Fisher et al.

(1986) *Nature* 320, 367–371). Two types of viral vector were designed: genomic viral vectors with deletions in a single gene such as env, but which otherwise preserve the mRNA expression and processing characteristics of the complete virus, and subgenomic viral vectors which may include only one or a few genes that are typically the specific targets of susceptibility and resistance testing, such as gag-pol, or which may lack viral genes altogether. Both types of vectors have a unique restriction site within the viral genome for the insertion of an indicator gene cassette as well as patient sequence acceptor sites, i.e. additional unique restriction sites near or within the anti-viral target gene (eg., pol) to permit the insertion of patient-derived HIV sequences. In addition, both types of vector were designed to incorporate either the native enhancer-promoter of the HIV-LTR U3 region, or a foreign enhancer-promoter from the CMV immediate-early (IE) region. Standard methods are employed for the construction of plasmid DNAs (Ausubel et al. (1987) Current Protocols in Molecular Biology, Wiley-Interscience). The sequences of all DNA constructs incorporating synthetic DNA are confirmed by DNA sequence analysis (Sanger et al. (1977) *Proc. Natl. Acad. Sci.* 74, 5463–5467).

HIV sequences are obtained from plasmid pBS-HIV (Page et al. (1990) *J. Virol.* 64, 5270–5276) which contains the HXB2 proviral DNA sequence on an HpaI to XbaI restriction fragment inserted into the polylinker of the pBluescript KS (+) plasmid cloning vector (Stratagene, San Diego, Calif.). As this proviral clone contains uncharacterized, flanking human DNA from the site of proviral integration, two steps of site-directed mutagenesis are employed to remove such sequences using plasmid pBS-HIV as a template. In step one, human sequences adjacent to the 5' LTR are removed using oligonucleotide 1 which contains the following sequences in a 5' to 3' direction: 1) a sequence complementary to the first 18 nucleotides of the integrated provirus, within the left U3 region, 2) a six nucleotide SmaI site, and 3) an 18 nucleotide sequence complementary to the region in pBluescript KS (+) just beyond the polylinker and phage T3 promoter. In step two, human sequences adjacent to the 5' LTR are removed using oligonucleotide 2 which contains the following sequences (5' to 3'): 1) an 18 nucleotide sequence complementary to the region in pBluescript KS (+) just beyond the PvuI site, within the LacZ gene, 2) a six nucleotide XbaI site, and 3) a sequence complementary to the last 18 nucleotides of the integrated provirus, within the right U5 region. The resulting plasmid is called pBS-HXB2.

Genomic and subgenomic viral vectors employing the HIV-LTR U3 region as an enhancer-promoter for the expression of anti-viral target genes (FIG. 1) are each derived from plasmid pBS-HXB2 by a single step of site-directed mutagenesis. The genomic viral vector pLG, which is deleted for the env gene, is prepared using oligonucleotide 3 which contains the following sequences (5' to 3'): 1) an 18 nucleotide sequence complementary to positions 7626 to 7643 of HXB2 within the env gene (all coordinates for HXB2 are by reference to GenBank, accession number K03455), 2) an 8 nucleotide NotI site, and 3) an 18 nucleotide sequence complementary to positions 6384 to 6401 of HXB2 within the env gene. The subgenomic viral vector pLS, which is deleted for the env, tat, rev, vif, vpr and vpu genes, is prepared using oligonucleotide 4 which contains the following sequences (5' to 3'): 1) an 18 nucleotide sequence complementary to positions 7626 to 7643 of HXB2 within the env gene, 2) an 8 nucleotide NotI site, and 3) an 18 nucleotide sequence complementary to positions 5109 to 5126 of HXB2 within the vif gene.

Genomic and subgenomic viral vectors which employ the CMV IE region as an enhancer-promoter for the expression of anti-viral target genes are derived from plasmids pLG and pLS, and are called pCG and pCS, respectively (FIG. 1). The genomic viral vector pCG is prepared in two steps. In the first step, an intermediate plasmid is prepared from two DNA fragments: 1) a vector fragment 11.2 kB prepared from digesting plasmid pLG with SmaI and treating the vector with alkaline phosphatase, and 2) a DNA fragment of 0.9 kB containing the CMV IE enhancer-promoter prepared by digesting plasmid pVL-1 (described below) with SmaI. Plasmids containing the CMV IE region in the same transcriptional orientation as the viral LTRs are identified by restriction mapping. In the second step, plasmid pCG is prepared from this intermediate plasmid by site-directed mutagenesis to join the CMV IE enhancer-promoter to the 5'-LTR R region at a position permitting transcription initiation to occur at the beginning of the R region, using oligonucleotide 5 which contains the following sequences (5' to 3'): 1) an 18 nucleotide sequence complementary to positions 455 to 472 of HXB2 at the beginning of the R region, and 2) an 18 nucleotide sequence complementary to positions −18 to −1 of the CMV IE enhancer-promoter (coordinates referenced to Boshart et al. (1985) *Cell* 41, 521–530). The subgenomic viral vector pCS is derived from plasmid pCG and is prepared from two DNA fragments: 1) a vector DNA of 9.1 kB prepared by digesting plasmid pLS with SmaI and ClaI, and 2) a DNA fragment of 1.3 kB prepared by digesting plasmid pCG with SmaI and ClaI.

Genomic Indicator Gene Viral Vector—Permuted Promoter

The indicator gene viral vectors pLG-lucPP and pCG-lucPP, and resistance test vectors derived therefrom, contain the following elements in a 5' to 3' orientation (FIG. 2B): 1) an HIV-LTR U3 region (pLG-lucPP) or a CMV IE enhancer-promoter (pCG-lucPP), 2) an HIV-LTR R region, 3) an HIV-LTR U5 region containing an inserted T7 promoter with a transcriptional orientation opposite to that of the LTRs, 4) the coding regions of the HIV gag-pol, vif, vpr, tat, rev, vpu, deleted env, and nef genes, 5) an indicator gene cassette inserted into the deleted env gene, and 6) a 3' HIV-LTR. The same indicator gene cassette is inserted in pLG-lucPP and pCG-lucPP and contains the following elements: 1) an EMC 5'-UTR region which permits internal ribosome entry, 2) the complete coding region of the luciferase (luc) gene, and 3) a T7 transcriptional terminator. The indicator gene has a transcriptional orientation opposite to the HIV-LTR or CMV IE enhancer-promoter and therefore cannot be functionally transcribed by these elements. The indicator gene also cannot be transcribed by the T7 promoter as the indicator gene cassette is positioned upstream of the T7 promoter. Following reverse transcription and strand transfer, the T7 promoter is copied from the 5' LTR to the 3' LTR, permitting functional transcription of the indicator gene from the newly created T7 promoter by T7 RNA polymerase (FIG. 2C).

Plasmid plucPP, which contains the indicator gene cassette, is prepared in three steps. In the first step, plasmid pVL-EMC/T7 which contains a cassette flanked by unique NotI sites comprising the EMC 5'-UTR element and T7 transcriptional terminator, is prepared from two DNA fragments: 1) a vector DNA of 3.0 kB prepared by digesting plasmid pVL (described below) with NotI and treating the vector with alkaline phosphatase, and 2) a DNA fragment of 0.8 kB containing the EMC 5' UTR and T7 terminator prepared by PCR using plasmid pTM1 (Moss et al. (1990) *Nature* 348, 91–92) as a template and oligonucleotides 6 and 7 as primers, followed by digestion with NotI. Oligonucleotides 6 and 7 each incorporate a NotI restriction site. In the second step, plasmid pVL-luc, which contains the coding region of the firefly luciferase gene inserted into the mammalian expression vector pVL-1 (described below), is prepared from two DNA fragments: a vector DNA of 4.1 kB prepared by digesting plasmid pVL-1 with NruI and BglII, and 2) a DNA fragment of 1.7 kB containing the complete luciferase coding region, prepared by PCR using plasmid pGEM-luc (Promega, Madison, Wis.) as a template and oligonucleotides 8 and 9 as primers followed by digestion with NruI and BglII. Oligonucleotides 8 and 9 incorporate NruI and NcoI, and BglII and XhoI restriction sites, respectively. In the third step, plasmid plucPP, which contains the coding region of the luciferase gene inserted between the EMC 5'-UTR element and T7 transcriptional terminator, is prepared from two DNA fragments: 1) a vector DNA of 3.8 kB prepared by digesting plasmid pVL-EMC/T7 with NcoI and SalI, and 2) a DNA fragment of 1.7 kB containing the complete luciferase coding region, prepared by digesting plasmid pVL-luc with NcoI and XhoI.

Plasmid pLG-lucPP is prepared in two steps. In the first step, plasmid pLG-T7 is prepared by inserting a phage T7 promoter into the upstream HIV-LTR U5 region in plasmid pLG by site-directed mutagenesis using oligonucleotide 10 which contains the following sequences (5' to 3'): 1) an 18 nucleotide sequence complementary to positions 552 to 569 of HXB2 within the U5 region, 2) a 20 nucleotide sequence complementary to the T7 promoter, and 3) an 18 nucleotide sequence complementary to positions 534 to 551 of HXB2 within the U5 region. In the second step, plasmid pLG-lucPP is prepared from two DNA fragments: 1) a vector DNA of 11.2 kB prepared by digesting plasmid pLG-T7 with NotI and treating the resulting vector with alkaline phosphatase, and 2) a DNA fragment of 2.5 kB containing the luciferase indicator gene cassette prepared by digesting plasmid plucPP with NotI. Clones corresponding to pLG-lucPP, which contain the indicator gene cassette inserted into the viral vector with a transcriptional orientation opposite to that of the viral LTRs, are identified by restriction mapping.

Plasmid pCG-lucPP is prepared in two steps. In the first step, plasmid pCG-T7 is prepared by inserting a phage T7 promoter into the upstream HIV-LTR U5 region in plasmid pCG by site-directed mutagenesis using oligonucleotide 10. In the second step, plasmid pCG-lucPP is prepared from two DNA fragments: 1) a vector DNA of 11.7 kB prepared by digesting plasmid pCG-T7 with NotI and treating the resulting vector with alkaline phosphatase, and 2) a DNA fragment of 2.5 kB containing the luciferase indicator gene cassette prepared by digesting plasmid plucPP with NotI. Clones corresponding to pCG-lucPP, which contain the indicator gene cassette inserted into the viral vector with a transcriptional orientation opposite to that of the CMV IE enhancer-promoter and viral LTRs, are identified by restriction mapping.

Genomic Indicator Gene Viral Vector—Permuted Promoter Alternative Construction

The genomic indicator gene viral vector pCG-(NF-lucP) 1-PPT7 contains the following elements in a 5' to 3' orientation (FIG. 2D): 1) a CMV IE enhancer-promoter, 2) an HIV-LTR R region, 3) an HIV-LTR U5 region into which the T7 promoter with a transcriptional orientation opposite to that of the CMV promoter was inserted, 4) the coding regions of HIV gag-pol, vif, vpr, tat, rev, vpu, deleted env, and nef genes, 5) a luciferase indicator gene cassette inserted into the deleted env gene, 6) 3' HIV LTR U3 and R regions, 7) the SV40 polyadenylation signal sequence, and 8) the SV40 origin of replication region. The same indicator gene cassette is inserted in pCG-(NF-lucP)1 and contains the following elements: 1) an EMCV 5'-UTR region which permits internal ribosome entry, 2) the complete coding region of the luciferase (luc) gene, and 3) a T7 transcriptional terminator. The indicator gene has a transcriptional orientation opposite to the CMV IE enhancer-promoter and thus cannot be functionally transcribed by these elements. The indicator gene also cannot be transcribed by the T7 promoter as the indicator gene cassette is positioned upstream of the T7 promoter. Following reverse transcription and strand transfer, the T7 promoter is copied from the 5' LTR to the 3' LTR, permitting functional transcription from the newly created T7 promoter by T7 RNA polymerase.

The genomic indicator gene viral vector pCG-(NF-lucP) 1-PP/T7 is prepared from two DNA fragments: 1) a 9.7 kB vector fragment prepared by digesting pCG-(NF-lucP)1, described below, with NotI and AgeI, and 2) a 3.7 kB fragment containing the CMV IE enhancer-promoter, the HIV-LTR R region, the U5 region containing the T7 promoter, and the 5' portion of the gag-pol coding region, prepared by digesting pBS.NR.T7 with NotI and AgeI. Plasmids containing the proper elements are identified by restriction enzyme digestion.

The viral vector pCG-(NF-lucP)1 contains the following elements in a 5' to 3' orientation: 1) a CMV IE enhancer-promoter, 2) an HIV-LTR R and U5 regions, 3) the coding regions of HIV gag-pol, vif, vpr, tat, rev, vpu, deleted env, and nef genes, 4) a luciferase indicator gene cassette lacking a promoter was inserted into the deleted env gene, 5) 3' HIV LTR U3 and R regions, 6) the SV40 polyadenylation signal sequence, and 7) the SV40 origin of replication region. The indicator gene cassette contains the following elements: 1) an EMCV 5'-UTR region which permits internal ribosome entry, 2) the complete coding region of the luciferase gene, and 3) a T7 transcriptional terminator. The indicator gene has a transcriptional orientation opposite to the CMV IE enhancer-promoter and thus cannot be functionally transcribed by these elements.

pCG-(NF-lucP)1 was constructed from two DNA fragments: 1) an 11.1 kB vector fragment prepared by digesting plasmid pCG-CXAT (F-lucP)1 with BsmBI and treating the vector with alkaline phosphatase, and 2) a 2.3 kB fragment containing the luciferase indicator gene cassette prepared by digesting the expression vector pT7X(lucP), described below, with SgrAI. Plasmids containing the luciferase gene cassette inserted into the viral vector in a transcriptional orientation opposite to that of the viral transcription units were identified by restriction enzyme digestion. pCG-CXAT (F-lucP)1 was generated as described in Example 6 below.

The luciferase indicator gene cassette plasmid, pT7X (lucP) contains the following elements in a 5' to 3' orientation: 1) a T7 promoter, 2) an SgrAI restriction site, 3) an EMCV 5'-UTR region which permits internal ribosome entry, 4) the complete coding region of the luciferase gene, inserted within the multiple cloning site region of pT7X, 5) a T7 transcriptional terminator, 6) an SgrAI restriction site. pT7X(lucP) was constructed from two DNA fragments: 1) a 2.7 kB vector fragment prepared by digesting pT7X, described below, with BglII and XbaI, and 2) a 1.6 kB fragment containing the complete luciferase coding region, prepared by digesting pCXCN(F-lucP) with BglII and XbaI. Plasmids containing the luciferase gene were identified by restriction enzyme digestion.

The pT7X expression vector contains the following elements in a 5' to 3' orientation: 1) a T7 promoter, 2) an SgrAI restriction site, 3) an EMCV 5'-UTR region which permits internal ribosome entry, 4) multiple cloning sites with recognition sequences for restriction enzymes NcoI, BglII, NheI, XhoI, MluI, KpnI, and XbaI, 5) a T7 transcriptional terminator, 6) an SgrAI restriction site. pT7X was constructed from three DNA fragments: 1) a 2.0 kB vector fragment prepared by digesting pSP70 (Promega Corp.) with AatII and BspMI, 2) a 160 bp synthetic fragment containing the 3' portion of the EMCV 5' UTR, the multiple cloning sites, and the T7 terminator, prepared by phosphorylating oligonucleotides p8B (99) and p8C (100) with T4 polynucleotide kinase and ATP, then annealing and ligating them with oligonucleotides p8A (101) and p8D (102), and 3) a 560 bp fragment containing the T7 promoter and the 5' portion of the EMCV 5' UTR, prepared by digesting plasmid pCITE 1 (Novagen) with EcoRI, phosphorylating oligonucleotide p8AR− (103) with T4 polynucleotide kinase and ATP, then annealing with oligonucleotide p8AR+ (104) and ligating them to the EcoR1 digested pCITE 1 plasmid, followed by digestion with DsaI and isolation by gel electrophoresis. The 160 bp fragment contains the following elements in a 5' to 3' orientation: 1) a DsaI compatible cohesive end, 2) sequences identical to bases 1389 to 1428 of pTM1, 3) multiple cloning sites with recognition sequences for restriction enzymes NcoI, BglII, NheI, XhoI, MluI, KpnI, and XbaI, 4) a T7 transcriptional terminator, 5) recognition sites for restriction enzymes SgrAI and AscI and 6) a cohesive end compatible with the BspMI cohesive end from pSP70. The oligonucleotide pair p8AR+ (104) and p8AR− (103) contain the following elements, 1) an AatII compatible cohesive end, 2) a NotI restriction site, 3) a T7 promoter, 4) an SgrAI site, and 5) an EcoRI compatible cohesive which does not regenerate an EcoRI cleavage site when ligated to a compatible EcoRI cohesive end. Plasmids containing the proper elements were identified by restriction enzyme digestion, and the sequences of the synthetically generated portions confirmed by DNA sequencing.

Plasmid pBS.NR.T7 contains the following elements in a 5' to 3' orientation: 1) a CMV IE enhancer-promoter, 2) an HIV-LTR R region, 3) an HIV-LTR U5 region containing a T7 promoter with a transcriptional orientation opposite to that of the CMV promoter, and 4) the coding regions of HIV gag-pol. pBS.NR.T7 is constructed in two steps.

In the first step plasmid pBS.NR is constructed from two fragments: 1) a 2.9 kB vector fragment prepared from pBluescriptII KS+ by digestion with EcoRI and NotI, and 2) a 6.0 kB fragment containing the CMV IE enhancer-promoter, the HIV-LTR R and U5 regions, and the coding regions of HIV gag-pol prepared by digesting plasmid pCG-RTV1 with NotI and EcoRI. Plasmids containing the inserted fragment are identified by restriction digestion.

In the second step, single stranded DNA from plasmid pBS.NR is isolated and used as template in site-directed mutagenesis to insert the T7 promoter into the U5 region, using oligonucleotide MT7P (105) as the primer. Oligonucleotide MT7P (105) contains the following sequences in a 5' to 3' orientation: 1) 18 bases identical to bases 112 to 129 of the pNL4-3 isolate of HIV, 2) a 20 base pair sequence containing the inverted T7 promoter, and 3) 18 bases identical to positions 150 to 167 of the pNL4-3 isolate of HIV. This places the inverted T7 promoter in the middle of a 26 bp portion of the HIV-LTR U5 region that is not essential for infectivity (Vicenzi et al. (1994) *J. Virol.* 68, 7879–7890). Plasmids containing the inverted T7 promoter within the U5 region are identified by restriction digestion, and the sequence confirmed by DNA sequencing.

Subgenomic Indicator Gene Viral Vector—Permuted Promoter

The indicator gene viral vectors pLS-lucPP and pCS-lucPP, and resistance test vectors derived therefrom, contain the following elements in a 5' to 3' orientation (FIG. 2B): 1) an HIV-LTR U3 region (pLS-lucPP) or a CMV IE enhancer-promoter (pCS-lucPP), 2) an HIV-LTR R region, 3) an HIV-LTR U5 region containing an inserted T7 promoter with a transcriptional orientation opposite to that of the LTRs, 4) the coding region of the HIV gag-pol gene, 5) the indicator gene cassette, 6) an RRE element from the HIV env gene containing a viral packaging sequence, and 7) a 3' HIV-LTR. The indicator gene cassette of pLS-lucPP and pCS-lucPP is the same as in pLG-lucPP and pCG-lucPP. As for the latter vectors, the indicator genes of pLS-lucPP and pCS-lucPP cannot be functionally transcribed until reverse transcription and strand transfer results in the copying of the T7 promoter from the 5' LTR to the 3' LTR (FIG. 2C).

Plasmid pLS-lucPP is prepared in two steps. In the first step, plasmid pLS-T7, which contains a phage T7 promoter inserted into the upstream HIV-LTR U5 region of plasmid pLS, is prepared from two DNA fragments: 1) a vector DNA of 9.1 kB prepared by digesting plasmid pLS with SmaI and ClaI, and 2) a DNA fragment of 0.8 containing the HIV-LTR with an R5 region containing an inserted T7 promoter, prepared by digesting plasmid pLG-T7 with SmaI and ClaI. In the second step, plasmid pLS-lucPP is prepared from two DNA fragments: 1) a vector DNA of 9.9 kB prepared by digesting plasmid pLS-T7 with NotI and treating the resulting vector with alkaline phosphatase, and 2) a DNA fragment of 2.5 kB containing the luciferase indicator gene cassette prepared by digesting plasmid plucPP with NotI. Clones corresponding to pLS-lucPP, which contain the indicator gene cassette inserted into the viral vector with a transcriptional orientation opposite to that of the viral LTRs, are identified by restriction mapping.

Plasmid pCS-lucPP is prepared from two DNA fragments: 1) a vector DNA of 11.6 kB prepared by digesting plasmid pLS-lucPP with SmaI and ClaI, and 2) a DNA fragment of 1.3 containing the CMV IE promoter fused to the R5 region with an inserted T7 promoter, prepared by digesting plasmid pCG-T7 with SmaI and ClaI.

Resistance Test Vectors—Construction

Figure 2A:
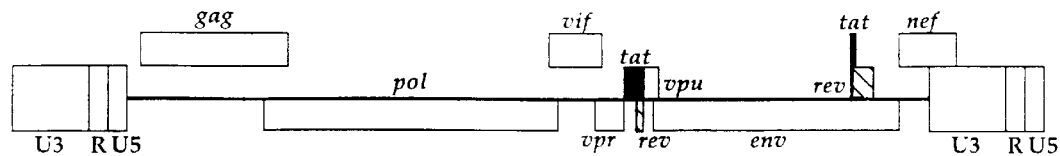
FIG. 2. A. Diagrammatic representation of the DNA genomic structure of HIV-1.
Figure 2B:
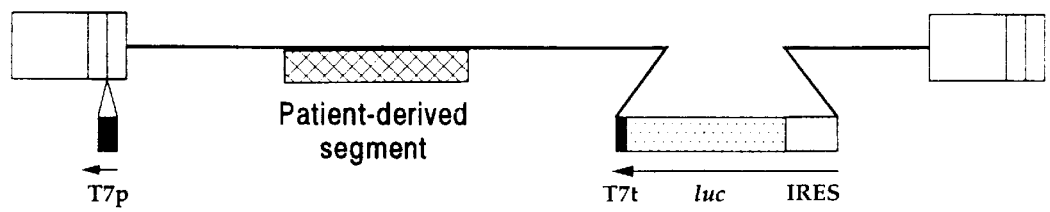
Figure 2C:
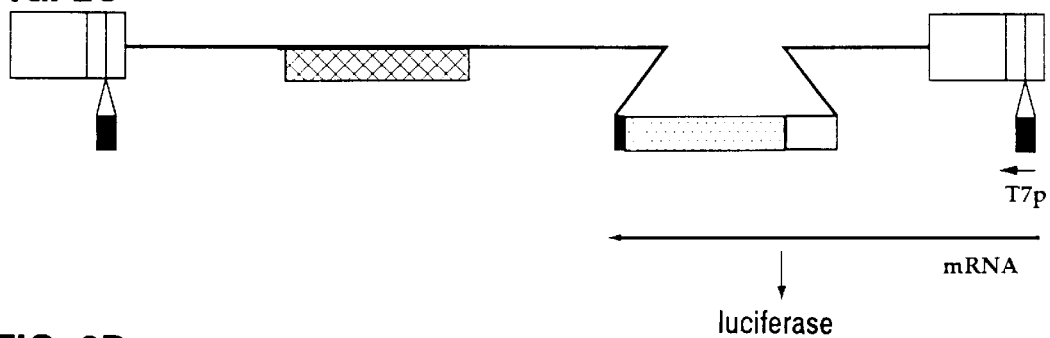
Figure 2D:
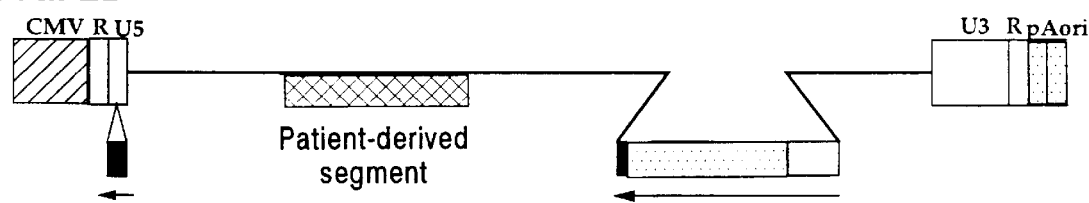
Figure 2E:
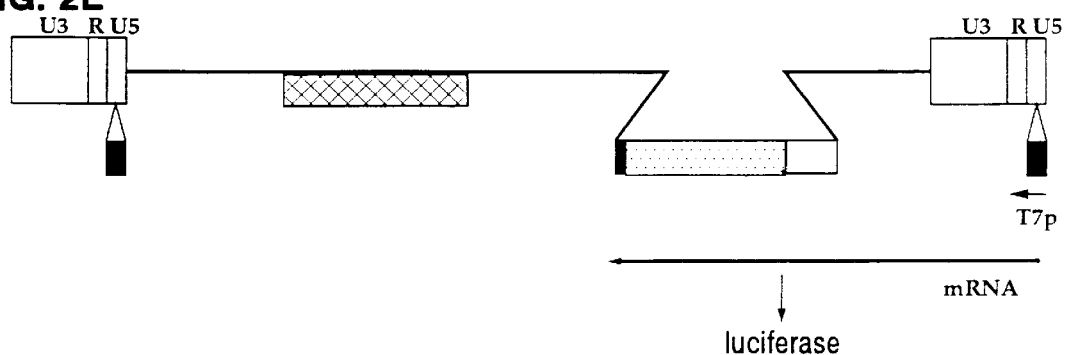

Resistance test vectors are prepared by 1) modifying the indicator gene viral vectors pLG-lucPP, pCG-lucPP, pLS-lucPP and pCS-lucPP by introducing unique restriction sites, called patient sequence acceptor sites, in or near the pol gene, 2) amplifying patient-derived segments corresponding to the HIV protease and reverse transcriptase coding regions by PCR using complementary DNA (cDNA) prepared from viral RNA or DNA present in the serum or cells of infected patients, and 3) inserting the amplified sequences precisely into indicator gene viral vectors at patient sequence acceptor sites (FIG. 2B). Two sets of patient sequence acceptor sites are introduced by site-directed mutagenesis into each of the four indicator gene viral vectors. The first set of patient sequence acceptor sites consist of a HpaI site and a SalI site which define an interval comprising the entire protease coding region and most of the reverse transcriptase coding region, resulting in plasmids pLG-lucPP-HS, pCG-lucPP-HS, pLS-lucPP-HS and pCS-lucPP-HS. The second set of patient sequence acceptor sites consist of a PvuI site and a BamHI site which define the same interval, resulting in plasmids pLG-lucPP-PB, pCG-lucPP-PB, pLS-lucPP-PB and pCS-lucPP-PB, respectively. Cognate pairs of resistance test vectors which define the same restriction site interval (eg., those derived from pLG-lucPP-HS and pLG-lucPP-PB) are used together in some resistance tests to improve the representation of those patient-derived segments that contain internal restriction sites identical to a given patient sequence acceptor site, and would thus be underrepresented in either resistance test vector alone.

Plasmid pLG-lucPP-HS is prepared by three consecutive steps of site-directed mutagenesis using plasmid pLG-lucPP as a template. The first two steps are for the purpose of introducing two new restriction sites, one of which (HpaI) is unique to, and one of which (SalI) is already is present once in each indicator gene viral vector. The third step is for the purpose of deleting the pre-existing SalI site in each vector to make the introduced SalI site unique. In step 1, a HpaI site is introduced immediately upstream of the mature coding region of the HIV protease at position 2243 using oligonucleotide 11 which contains the following sequences (5' to 3'): 1) an 18 nucleotide sequence complementary to positions 2249 to 2266 of HXB2, 2) a six nucleotide HpaI site, which leaves the gag protein sequence at this position unaltered and introduces a conservative amino acid change (Phe to Val) into the pol precursor sequence, and 3) an 18 nucleotide sequence complementary to positions 2225 to 2242 of HXB2. In step 2, a SalI site is introduced at the carboxy-terminal coding region of the HIV reverse transcriptase at position 4190 using oligonucleotide 12 which contains the following sequences (5' to 3'): 1) an 18 nucleotide sequence complementary to positions 4196 to 4213 of HXB2, 2) a six nucleotide SalI site which leaves the reverse transcriptase protein sequence at this position unaltered, and 3) an 18 nucleotide sequence complementary to positions 4172 to 4189 of HXB2. In step 3, the pre-existing SalI site within the vpr coding region at position 5785 of HXB2 is deleted using oligonucleotide 13 which contains the following sequences (5' to 3'): 1) an 18 nucleotide sequence complementary to positions 5791 to 5808 of HXB2, 2) the 6 nucleotide sequence GCCGAC which ablates the SalI site but leaves the vpr protein sequence at this position unaltered, 3) an 18 nucleotide sequence complementary to positions 5767 to 5784 of HXB2.

Plasmids pCG-lucPP-HS, pLS-lucPP-HS and pCS-lucPP-HS are derived from pLG-lucPP-HS as follows. Plasmid pCG-lucPP-HS is prepared from two DNA fragments: 1) a vector DNA of 12.9 kB prepared by digesting plasmid pLG-lucPP-HS with SmaI and ClaI, and 2) a DNA fragment of 1.3 kB prepared by digesting plasmid pCG-lucPP with SmaI and ClaI. Plasmid pLS-lucPP-HS is prepared from two DNA fragments: 1) a vector DNA of 11.1 kB prepared by digesting plasmid pLG-lucPP-HS with NdeI and XhoI, and 2) a DNA fragment of 1.3 kB prepared by digesting plasmid pLS-lucPP with NdeI and XhoI. Plasmid pCS-lucPP-HS is prepared from two DNA fragments: 1) a vector DNA of 11.6 kB prepared by digesting plasmid pLS-lucPP-HS with SmaI and ClaI, and 2) a DNA fragment of 1.3 kB prepared by digesting plasmid pCS-lucPP with SmaI and ClaI.

Plasmid pLG-lucPP-PB is prepared by four consecutive steps of site-directed mutagenesis using plasmid pLG-lucPP as a template. The first two steps are for the purpose of introducing two new restriction sites (PvuI and BamHI), each of which is already present once in each indicator gene viral vector. The third and fourth steps are for the purpose of deleting the pre-existing PvuI and BamHI sites in each vector to make the newly introduced sites unique. In step 1, a PvuI site is introduced immediately upstream of the mature coding region of the HIV protease at position 2221 using oligonucleotide 14 which contains the following sequences (5' to 3'): 1) an 18 nucleotide sequence complementary to positions 2227 to 2244 of HXB2, 2) a six nucleotide PvuI site, which leaves the gag and pol precursor protein sequences at this position unaltered, and 3) an 18 nucleotide sequence complementary to positions 2203 to 2220 of HXB2. In step 2, a BamHI site is introduced at the carboxy-terminal coding region of the HIV reverse transcriptase at position 4212 using oligonucleotide 15 which contains the following sequences (5' to 3'): 1) an 18 nucleotide sequence complementary to positions 4218 to 4235 of HXB2, 2) a six nucleotide BamHI site which leaves the reverse transcriptase protein sequence at this position unaltered, and 3) an 18 nucleotide sequence complementary to positions 4194 to 4211 of HXB2. In step 3, the pre-existing PvuI site within the b-lactamase coding region at position 2413 (coordinates references to GenBank, accession number X52331) is deleted using oligonucleotide 16 which contains the following sequences (5' to 3'): 1) an 18 nucleotide sequence complementary to positions 2395 to 2412 of pBluescript KS (+), 2) the 6 nucleotide sequence CAATCG which ablates the PvuI site but leaves the b-lactamase protein sequence at this position unaltered, and 3) an 18 nucleotide sequence complementary to positions 2419 to 2436 of pBluescript KS (+). In step 4, the pre-existing BamHI site within the HIV rev coding region at position 8474 of HXB2 is deleted using oligonucleotide 17 which contains the following sequences (5' to 3'): 1) an 18 nucleotide sequence complementary to positions 8480 to 8497 of HXB2, 2) the 6 nucleotide sequence GGATTC which ablates the BamHI site but leaves the HIV rev protein sequence at this position unaltered, and 3) an 18 nucleotide sequence complementary to positions 8456 to 8473 of HXB2.

Plasmids pCG-lucPP-PB, pLS-lucPP-PB and pCS-lucPP-PB are derived from pLG-lucPP-PB as follows. Plasmid pCG-lucPP-PB is prepared from two DNA fragments: 1) a vector DNA of 12.9 kB prepared by digesting plasmid pLG-lucPP-PB with SmaI and ClaI, and 2) a DNA fragment of 1.3 kB prepared by digesting plasmid pCG-lucPP with SmaI and ClaI. Plasmid pLS-lucPP-PB is prepared from three DNA fragments: 1) a vector DNA of 11.1 kB prepared by digesting plasmid pLG-lucPP-PB with NdeI and XhoI, 2) a DNA fragment of 0.5 kB prepared by digesting plasmid pLS-lucPP with NdeI and HindIII and 3) a DNA fragment of 0.8 kB prepared by digesting plasmid pLG-lucPP-PB with HindIII and XhoI. Plasmid pCS-lucPP-PB is prepared from two DNA fragments: 1) a vector DNA of 11.6 kB prepared by digesting plasmid pLS-lucPP-PB with SmaI and ClaI, and 2) a DNA fragment of 1.3 kB prepared by digesting plasmid pCS-lucPP with SmaI and ClaI.

Patient-derived segment(s) corresponding to the HIV protease and reverse transcriptase coding regions are amplified by the reverse transcription-polymerase chain reaction method (RT-PCR), using viral RNA isolated from the serum of HIV-infected patients. Two RT-PCR protocols are used as described. In the first method (Piatak et al. (1993) *Science* 259, 1749–1754), separate enzymes, Moloney murine leukemia virus reverse transcriptase (BRL, Bethesda, Md.) and Taq DNA polymerase (Roche Molecular Diagnostics, Ontario, Canada), are used for the preparation of cDNA and for the PCR reaction, respectively. In the second method (Mulder et al. (1994) *J. Clin. Microbiol.* 32, 292–300), a single enzyme, *Thermus thermophilus* (Tth) DNA polymerase, is used to carry both cDNA synthesis and the PCR reaction. Two primer pairs, consisting of oligonucleotides 18 and 19, and oligonucleotides 20 and 21, are employed for the amplification of patient-derived segments that can be inserted precisely into the indicator gene viral vectors containing the HpaI/SalI and PvuI/BamHI patient acceptor sites, respectively.

A first set of four resistance test vectors incorporating the first primer pair is constructed from the following two DNA preparations: 1) a vector DNA prepared from plasmid pLG-lucPP-HS, pCG-lucPP-HS, pLS-lucPP-HS or pCS-lucPP-HS, digested with HpaI and SalI, and 2) an amplified DNA product of 2.0 kB prepared by RT-PCR using viral RNA isolated from the serum of an HIV-infected individual as a template and oligonucleotides 18 and 19 as primers, followed by digestion with HpaI and SalT. A second set of four resistance test vectors incorporating the second primer pair are constructed from the following two DNA preparations: 1) a vector DNA prepared from plasmid pLG-lucPP-PB, pCG-lucPP-PB, pLS-lucPP-PB or pCS-lucPP-PB, digested with PvuI and BamHI, and 2) an amplified DNA product of 2.0 kB prepared by RT-PCR using viral RNA isolated from the serum of an HIV-infected individual as a template and oligonucleotides 18 and 19 as primers, followed by digestion with PvuI and BamHI. Oligonucleotides 18, 19, 20 and 21 incorporate HpaI, SalI, PvuI and BamHI restriction sites, respectively. To ensure that the plasmid DNA corresponding to each of the eight resulting resistance test vectors comprises a representative sample of the HIV viral quasi-species present in the serum of a given patient, at least one hundred independent E. coli transformants obtained in the construction of a given resistance test vector are used for the preparation of plasmid DNA.

To improve the representation of patient-derived segments, a third and fourth set of resistance test vectors are prepared using partially degenerate PCR primer pools, called oligonucleotides 22, 23, 24 and 25, which are based on the sequences of oligonucleotides 18, 19, 20 and 21, respectively. Each primer pool is synthesized in a manner that incorporates more than one nucleotide base (G, A, T or C) at the each of the 18 nucleotide positions located at the 3' end of the parent primer that display sequence variations among the different patient isolates cataloged in the Los Alamos HIV sequence database (Myers et al. (1993) Human Retroviruses and AIDS 1993, Los Alamos National Laboratory, Los Alamos, N.Mex.). The third set of four resistance test vectors is constructed using vectors prepared from plasmid pLG-lucPP-HS, pCG-lucPP-HS, pLS-lucPP-HS or pCS-lucPP-HS, with amplified patient sequences prepared with oligonucleotides 22 and 23; the fourth set of four resistance test vectors is constructed using vectors prepared from plasmid pLG-lucPP-PB, pCG-lucPP-PB, pLS-lucPP-PB or pCS-lucPP-PB, with amplified patient sequences prepared with oligonucleotides 24 and 25. Oligonucleotides 22, 23, 24 and 25 incorporate HpaI, SalI, PvuI and BamHI restriction sites, respectively.

Host Cells—Preparation

Packaging Host Cells and Resistance Test Vector Host Cells

Resistance test vectors are used to prepare resistance test vector host cells from packaging host cells expressing viral packaging proteins. The packaging proteins may be provided for by the expression of viral genes contained within the resistance test vector itself, a packaging expression vector(s), or both. Either transient or stable transfection of the packaging host cell may be employed to produce the packaging proteins. A packaging expression vector encoding an amphotrophic MLV env gene product enables production in a resistance test vector host cell of resistance test vector viral particles which can efficiently infect human target cells. Resistance test vectors derived from plasmids pLG-lucPP-HS, pLG-lucPP-PB, pCG-lucPP-HS and pCG-lucPP-PB encode all HIV genes with the exception of env, and are used to produce resistance test vector host cells. The pVL-env4070A packaging expression vector which encodes the amphotrophic MLV 4070A env gene product is used with the foregoing genomic-based resistance test vectors to enable production in the resistance test vector host cell of resistance test vector viral particles. Resistance test vectors derived from plasmids pLS-lucPP-HS, pLS-lucPP-PB, pCS-lucPP-HS and pCS-lucPP-PB encode the HIV gag-pol gene products only, and are used to prepare resistance test vector host cells. The pVL-env4070A which provides env, and either the pLTR-HIV3' or the pCMV-HIV3' packaging expression vectors, each of which provides the HIV vif, vpr, tat, rev, vpu and nef genes are used with the foregoing subgenomic based resistance test vectors to enable production in the resistance test vector host cells of resistance test vector viral particles.

Figure 3A:
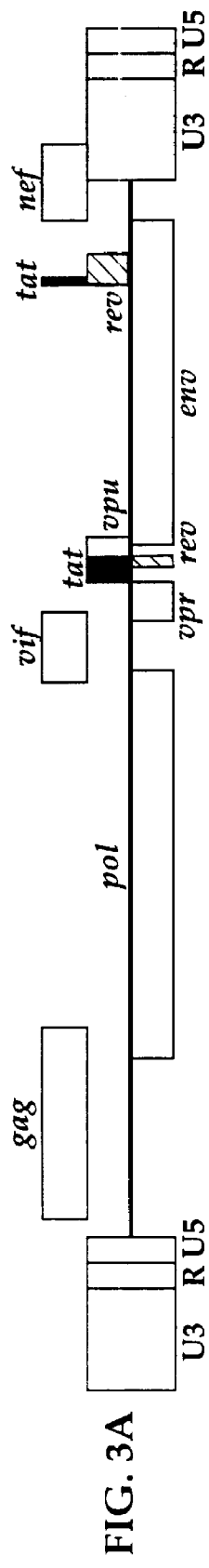
FIG. 3. A. Diagrammatic representation of the DNA genomic structure of HIV-1.
Figure 3B:
Figure 3C:

Plasmids pLTR-HIV3' and pCMV-HIV3' are each derived by removing most of the gag-pol coding region from the genomic viral vectors pLG and pCG, respectively. Plasmid pLTR-HIV3' (FIG. 3B) is prepared by site-directed mutagenesis using plasmid pLG as a template with oligonucleotide 26 which contains the following sequences (5' to 3'): 1) an 18 nucleotide sequence complementary to positions 4712 to 4729 of HXB2 within the pol gene, and 2) an 18 nucleotide sequence complementary to positions 925 to 942 of HXB2 within the gag gene. Plasmid pCMV-HIV3' (FIG. 3C) is prepared from two DNA fragments: 1) a vector fragment of 6.8 kB prepared by digesting plasmid pLTR-HIV3' with SmaI and ClaI, and 2) a DNA fragment of 1.3 kB prepared by digesting plasmid pCG with SmaI and ClaI.

Plasmid pVL-env4070A (FIG. 3D) is constructed from two DNA fragments: 1) a vector fragment of 4.3 kB prepared by digestion of the pVL-2 mammalian expression vector with NruI and BglII, and 2) a DNA fragment of 2.0 kB containing the complete coding region of the MLV4070A env gene product (nucleotides 37 to 2001, coordinates given in GenBank, accession number M33469, Ott et al. (1990) *J. Virol.* 64, 757–766) prepared by PCR using plasmid pCRIPamgag-2 (Danos and Mulligan (1988) *Proc. Natl. Acad. Sci.* 85, 6460) as a template with oligonucleotides 27 and 28 as primers, followed by digestion with NruI and BglII. Oligonucleotide 27 incorporates a unique NruI site followed by a consensus sequence for mammalian translation initiation (e.g., Kozak (1991) *J. Biol. Chem*, 266, 19867–19870), while oligonucleotide 28 incorporates a unique BglII site.

The mammalian expression vector pVL-2 contains the following elements in a 5' to 3' direction: the CMV IE promoter/enhancer, the CMV IE first exon splice donor, the human α1 globin second exon splice acceptor, a cloning site polylinker, the polyadenylation site of the SV40 T antigen gene, and the SV40 origin of replication. Plasmid pVL-2 is constructed in four steps as follows. In the first step, plasmid pVL is prepared by replacing the cloning site polylinker and phage T7 and T3 promoters of plasmid pBluescript II KS (+) with a cloning site polylinker containing BssHII, NotI, SmaI, HindIII, SphI, SmaI, EcoRI, NruI, ApaI, BglII, NheI, NotI, XhoI, and BssHII restriction sites. pVL is constructed from two DNA fragments: 1) a vector fragment of 3.0 kB prepared by cutting plasmid pBluescript II KS (+) with BssHII, and treating the resulting vector with alkaline phosphatase, and 2) a DNA fragment prepared by annealing overlapping oligonucleotides 29 and 30, extending with Klenow DNA polymerase and digesting with BssHII. Plasmids containing the HindIII to XhoI sites in a 5' to 3' order relative to the pBluescript II KS (+) plasmid map (GenBank accession number X52327) are identified by restriction mapping analysis. In the second step, an intermediate plasmid is prepared from plasmid pVL by inserting the CMV IE enhancer-promoter and first exon splice donor, and the human α1 globin second exon splice acceptor. This intermediate plasmid is prepared from three DNA fragments: 1) a vector fragment of 3.0 kB prepared by digesting plasmid pVL with HindIII and EcoRI, 2) a DNA fragment of 0.9 kB containing a CMV IE promoter-enhancer and first exon splice donor (nucleotides −674 to −19, coordinates referenced to Boshart et al. (1985) *Cell* 41, 521–530), prepared by PCR using the plasmid pCM5027 containing the PstI m-fragment from HCMV strain AD169 (Boshart et al., Ibid) as template with oligonucleotides 31 and 32 as primers, followed by digestion with HindIII and SphI, and 3) a DNA fragment of 0.1 kB containing the human α1 globin second exon splice acceptor (nucleotides 6808 to 6916, coordinates by reference to GenBank, accession number J00153) prepared by PCR using plasmid ppSVaHP (Treisman et al. (1983) *Proc. Natl. Acad. Sci.* 80, 7428–7432) as a template with oligonucleotides 33 and 34 as primers, followed by digestion with SphI and EcoRI. Oligonucleotides 31, 32, 33 and 34 incorporate HindIII, SphI, SphI and EcoRI restriction sites at their respective ends. In the third step, plasmid pVL-1 is prepared by inserting the SV40 T antigen polyadenylation site into this intermediate plasmid. Plasmid pVL-1 is prepared from two DNA fragments: 1) a vector fragment of 4.0 kB prepared by cutting the intermediate plasmid with BglII and NheI, and 2) a DNA fragment of 0.2 kB containing the SV40 T antigen polyadenylation site (nucleotides 2770 to 2533 of SV40, coordinates by reference to Reddy et al. (1978) *Science* 200, 494–502) prepared by PCR using plasmid pSV2 (Southern and Berg (1982) *J. Mol. Appl. Gen.* 1, 327–341) as template with oligonucleotides 35 and 36 as primers, followed by digestion with BglII and NheI. Oligonucleotides 35 and 36 incorporate unique BglII and NheI restriction sites at their respective ends. In the fourth step, plasmid pVL-2 is prepared by inserting the SV40 origin of replication into plasmid pVL-1. Plasmid pVL-2 is prepared from two DNA fragments: 1) a vector fragment of 4.2 kB prepared by digesting plasmid pVL-1 with NheI and XhoI, and 2) a DNA fragment of 0.2 kB containing the SV40 origin of replication (nucleotides 5725 to 5578 of SV40, Ibid) prepared by PCR using plasmid pSV2 as template with oligonucleotides 37 and 38 as primers, followed by digestion with NheI and SalI. Oligonucleotides 37 and 38 incorporate unique NheI and SalI restriction sites at their respective ends.

Target Host Cells

Target host cells used for resistance tests carried out with resistance test vectors derived from plasmids pLG-lucPP-HS, pLG-lucPP-PB, pCG-lucPP-HS, pCG-lucPP-PB, pLS-lucPP-HS, pLS-lucPP-PB, pCS-lucPP-HS or pCS-lucPP-PB are prepared from the human embryonic kidney cell line 293 and the Jurkat leukemic T cell line (American Type Culture Collection, Rockville, Md.). Each cell line is stably transfected with an expression vector encoding a variant phage T7 RNA polymerase. This variant contains an SV40 T antigen nuclear localization signal (NLS) fused in frame to the N-terminus of the T7 RNA polymerase, permitting its transport into, and function in, the cell nucleus (Lieber et al. (1989) *Nucleic Acids Res.* 17, 8485–8493). The nonfunctional indicator gene in the resistance test vector is converted into a functional indicator gene by reverse transcriptase upon infection of the target cells, resulting from the repositioning of the T7 promoter relative to the indicator gene coding region. Following the integration of the repaired indicator gene into the target cell chromosome by HIV integrase, the nuclear T7 RNA polymerase expressed by the target cell is capable of functionally transcribing the indicator gene.

Plasmid pVL-T7RNAP-NLS is used to direct the expression of a variant T7 RNA polymerase linked to an NLS, in human and other mammalian cells and cell lines. pVL-T7RNAP-NLS is prepared from three DNA fragments: 1) a vector fragment of 4.3 kB prepared by digestion of the plasmid pVL-2 with EcoRI and BglII, 2) a DNA fragment of 2.6 kB encoding T7 RNA polymerase amino acid residues 34 to 883 (nucleotides 267 to 2817, coordinates by reference to GenBank, accession number M38308, Grachev and Pletnev (1984) *Bioorg. Khim.* 10, 824–843) prepared by PCR using plasmid pT7-G1 (Deng et al. (1994) *Gene* 143, 245–249) as a template with oligonucleotides 39 and 40 as primers, followed by digestion with NruI and BglII, and 3) a synthetic DNA fragment encoding the first three amino acids of SV40 T antigen followed by amino acids 118 to 133 of the SV40 large T antigen containing the NLS (Lieber et al., Ibid), prepared by annealing the overlapping oligonucleotides 41 and 42, extending with Klenow DNA polymerase and digesting with EcoRI and NruI. oligonucleotides 39, 40, 41, 42 incorporate NruI, BglII, EcoRI and NruI restrictions site, respectively.

Plasmid pVL-Neo is employed as a selectable marker for the establishment of stable transfectants of human and other mammalian cells and cell lines by co-transfection. pVL-Neo directs the expression of neomycin phosphotransferase and confers resistance to the antibiotic G418. Plasmid pVL-Neo is prepared from two DNA fragments: 1) a vector fragment of 4.3 kB prepared by digesting plasmid pVL-2 with EcoRI and BglII, and 2) a DNA fragment of 0.8 kB containing the complete Neo coding region (nucleotides 1551 to 2345 of the Tn5 transposon sequence, coordinates given in GenBank accession number U00004, Beck et al. (1982) *Gene* 19, 327–336) prepared by PCR using plasmid pSV2neo (Southern and Berg (1982) *J. Mol. Appl. Gen.* 1, 327–341) as a template with oligonucleotides 43 and 44 as primers, followed by digestion with EcoRI and BglII. Oligonucleotide 43 incorporates a unique EcoRI site followed by a consensus sequence for mammalian translation initiation, while oligonucleotide 44 incorporates a unique BglII site. pVL-T7RNAP is introduced by stable transfection into 293 cells by the calcium phosphate coprecipitation method (Wigler et al. (1979) *Cell* 16, 777) and into Jurkat cells by electroporation (Irving et al. (1991) *Cell* 64, 891–901). 293 cells are maintained in DMEM medium (JRH Biosciences) supplemented with 1 g/L glucose, 10% donor calf serum (Tissue Culture Biologics). Jurkat cells are maintained in RPMI 1640 medium supplemented with 10% fetal bovine serum (Irvin Scientific), glutamine, penicillin and streptomycin. Transfection cocktails for 293 cells and Jurkat cells each contain a mixture of 10 micrograms of pVL-T7RNAP and the selectable marker pVL-Neo in a mass ratio of 10:1 to 20:1. Twenty-four to 48 hours following transfection, cells are replated in the same media containing the antibiotic G418 (GIBCO, Grand Island, N.Y.). Independent 293 cell clones resistant to G418 are picked directly from selection plates after two weeks and are expanded for analysis. Independent Jurkat cell clones resistant to G418 are obtained by limiting dilution after two to three weeks of drug selection and are expanded for analysis.

G418-resistant 293 and Jurkat cell clones are screened for their level of expression of T7 RNA polymerase by determining the level of steady-state T7 RNA polymerase-specific mRNA synthesized by the cells using the Northern blot hybridization method (Ausubel et al. (1987) Current Protocols in Molecular Biology, Wiley-Interscience). 293 and Jurkat cell clones expressing optimal levels of the T7 RNA polymerase are then identified by determining their ability to support T7 RNA polymerase-specific transcription in transient transfections with plasmid pEMCLucbgAn (Deng et al. (1991) Gene 109, 193–201) in which the transcription of the luciferase gene is directed by a T7 promoter. 293 and Jurkat clones supporting the highest levels of luciferase gene expression are chosen for further use; these are referred to as 293/T7RNAP-NLS cells and Jurkat/T7RNAP-NLS cells, respectively.

Drug Susceptibility and Resistance Tests

Resistance tests are carried out with resistance test vectors based on indicator gene viral vectors pLG-lucPP-HS, pLG-lucPP-PB, pCG-lucPP-HS, pCG-lucPP-PB, pLS-lucPP-HS, pLS-lucPP-PB, pCS-lucPP-HS or pCS-lucPP-PB, using either two types of host cell or one type of host cell. In the first type of resistance test, resistance test vector viral particles are produced by a first host cell (the resistance test vector host cell) that is prepared by transfecting a packaging host cell with the resistance test vector and packaging expression vector(s). The resistance test vector viral particles are then used to infect a second host cell (the target host cell) in which the expression of the indicator gene is measured. In the second type of resistance test, a single host cell type (the resistance test vector host cell) serves both purposes: some of the packaging host cells in a given culture are transfected and produce resistance test vector viral particles and some of the host cells in the same culture are the target of infection by the resistance test vector particles thus produced. Resistance tests employing a single host cell type are possible with resistance test vectors comprising a non-functional indicator gene with a permuted promoter: while such indicator genes are efficiently expressed upon infection of a permissive host cell, they are not efficiently expressed upon transfection of the same host cell type, and thus provide an opportunity to measure the effect of the anti-viral agent under evaluation. For similar reasons, resistance tests employing two cell types may be carried out by co-cultivating the two cell types as an alternative to infecting the second cell type with viral particles obtained from the supernatants of the first cell type.

Susceptibility and Resistance Test—Two Cell

Resistance test vector host cells are prepared by the cotransfection of a resistance test vector and the appropriate packaging expression vector(s) using either the 293 cell line, the tsa54 or tsa201 cell lines (Heinzel et al. (1988) J. Virol. 62, 3738), or the BOSC 23 cell line (Pear et al. (1993) Proc. Natl. Acad. Sci. 90, 8392) as packaging host cells. Resistance test vectors constructed by inserting patient-derived segment into pLG-lucPP-HS, pCG-lucPP-HS, pLG-lucPP-PB and pCG-lucPP-PB are cotransfected with the packaging expression vector pVL-env4070A, while resistance test vectors prepared by inserting patient-derived segments into pLS-lucPP-HS, pCS-lucPP-HS, pLS-lucPP-PB and pCS-lucPP-PB are cotransfected with the packaging expression vectors pVL-env4070A and either pLTR-HIV3' or pCMV-HIV3'. Jurkat/T7RNAP-NLS cells are employed as target host cells.

Packaging host cells are grown in DMEM media, 1 g/L glucose, 10% donor calf serum and passaged at a 1:10 dilution every three days. Cells are plated 48 hours prior to transfection at $1 \times 10^6$ cells per 10 cm plate. Cells are transfected by the calcium phosphate coprecipitation method using 5 to 10 mg each of the resistance test vector and the appropriate packaging expression vector(s) to produce resistance test vector host cells. Individual anti-viral agents, including the reverse transcriptase inhibitors AZT, ddI, ddC, d4T and 3TC, and the protease inhibitors saquinavir, ritonavir and indinavir, as well as combinations thereof, are added to individual plates of transfected cells at the time of their transfection, at an appropriate range of concentrations. Twenty-four to 48 hours after transfection, target host cells are infected by co-cultivation with resistance test vector host cells or with viral particles obtained from filtered supernatants of resistance test vector host cells. Each anti-viral agent, or combination thereof, is added to the target host cells at the time of infection to achieve the same final concentration of the given agent, or agents, present during the transfection.

For infection by co-cultivation, media is removed from a 10 cm plate of resistance test vector host cells prepared by transfection 24 to 48 hours earlier, and 0.5 to $1.0 \times 10^6$ Jurkat/T7RNAP-NLS target cells are added to the plate in Jurkat cell media containing the anti-viral agent at the appropriate concentration. Target cells are co-cultivated with the resistance test vector host cells for 24 hours, then removed and added to freshly prepared resistance test vector host cells for a second co-cultivation in Jurkat cell media containing the anti-viral agent(s) at the appropriate concentration. Twenty-four hours later, the target host cells are harvested from the second co-cultivation, collected by centrifugation, washed three times with ice-cold phosphate-buffered saline (PBS), and assayed for luciferase activity. For infection with filtered supernatants, media is removed from a 10 cm plate of resistance test vector host cells prepared by transfection 24 to 48 hours earlier. The media is filtered through a 0.45 mm filter at the time of harvest, frozen at −70° C., and thawed before transduction. Jurkat/T7RNAP-NLS cells (0.5 to $1.0 \times 10^6$) are added to 5 ml of an equal mixture of Jurkat cell media and the filtered supernatant, made up to 8 mg/ml of polybrene (Sigma, St. Louis, Mo.) and the appropriate concentration of the anti-viral agent(s). Twenty-four to 48 hours post-infection, the target host cells are collected by centrifugation, washed three times with ice-cold phosphate-buffered saline, and assayed for indicator gene expression. Target host cells infected by co-cultivation or with filtered viral supernatants are assayed for firefly luciferase activity as described (Ausubel et al. (1987) Current Protocols in Molecular Biology, Wiley-Interscience). The reduction in luciferase activity observed for target host cells infected with a given preparation of resistance test vector viral particles in the presence of a given anti-viral agent, or agents, as compared to a control run in the absence of the anti-viral agent, generally relates to the log of the concentration of the anti-viral agent as a sigmoidal curve.

This inhibition curve is used to calculate the apparent inhibitory concentration (IC) of that agent, or combination of agents, for the viral target product encoded by the patient-derived segments present in the resistance test vector.

Susceptibility and Resistance Test—One Cell

Resistance test vector host cells are prepared by the cotransfection of a resistance test vector and the appropriate packaging expression vector(s) using either 293/T7RNAP-NLS cells or Jurkat/T7RNAP-NLS cells as packaging host cells. Resistance test vectors constructed by inserting patient-derived segments into pLG-lucPP-HS, pCG-lucPP-HS, pLG-lucPP-PB and pCG-lucPP-PB are cotransfected with the packaging expression vector pVL-env4070A, while resistance test vectors prepared by inserting patient-derived segments into pLS-lucPP-HS, pCS-lucPP-HS, pLS-lucPP-PB and pCS-lucPP-PB are cotransfected with the packaging expression vectors pVL-env4070A and either pLTR-HIV3' or pCMV-HIV3'.

Cells are transfected using 5 to 10 mg each of the resistance test vector and the appropriate packaging expression vector(s) to produce resistance test vector host cells. 293/T7RNAP-NLS cells are transfected by the calcium phosphate coprecipitation method and Jurkat/T7RNAP-NLS cells are transfected by electroporation. Individual anti-viral agents, or combinations thereof, are added to individual plates of transfected cells at the time of their transfection, at an appropriate range of concentrations. Twenty-four to 72 hours after transfection, cells are collected by centrifugation, washed three times with ice-cold phosphate-buffered saline, and assayed for firefly luciferase activity as described. As transfected cells in the culture do not efficiently express the indicator gene, transfected cells in the culture, as well superinfected cells in the culture, can serve as target host cells for indicator gene expression. The reduction in luciferase activity observed for cells transfected in the presence of a given anti-viral agent, or agents as compared to a control run in the absence of the anti-viral agent(s), generally relates to the log of the concentration of the anti-viral agent as a sigmoidal curve. This inhibition curve is used to calculate the apparent inhibitory concentration (IC) of that agent, or combination of agents, for the viral target product encoded by the patient-derived segments present in the resistance test vector.

EXAMPLE 2

HIV Drug Susceptibility And Resistance Tests Using Resistance Test Vectors Comprising Patient-derived Segments And A Non-Functional Indicator Gene With A Permuted Coding Region Indicator Gene Viral Vector—Construction The genomic indicator gene viral vectors with patient sequence acceptor sites, pLG-lucPC-HS, pLG-lucPC-PB, pCG-lucPC-HS and pCG-lucPC-PB, and resistance test vectors derived therefrom, each contain the following elements in a 5' to 3' orientation (FIG. 4B): 1) an HIV-LTR U3 region (pLG-lucPC-HS and pLG-lucPC-PB) or a first CMV IE enhancer-promoter (pCG-lucPC-HS and pCG-lucPC-PB), 2) the HIV-LTR R and U5 regions, 3) the coding regions of the HIV gag-pol, vif, vpr, tat, rev, vpu, deleted env, and nef genes, 4) a first indicator gene cassette containing the 5' coding region of the luciferase gene, inserted into the deleted env gene, 5) a second indicator gene cassette containing the 3' coding region of the luciferase gene, inserted into a deleted 3' HIV-LTR U3 region, and 6) a 3' HIV-LTR R and U5 region. pLG-lucPC-HS and pCG-lucPC-HS contain unique HpaI and SalI patient sequence acceptor sites at nucleotides 2243 and 4190 of HXB2, respectively; pLG-lucPC-PB and pCG-lucPC-PB contain unique PvuI and BamHI patient sequence acceptor sites at nucleotides 2221 and 4212 of HXB2, respectively (see Example 1 for details). The first indicator gene cassette contains: 1) a second CMV enhancer-promoter, 2) the 5' coding region of the luciferase gene (amino acids 1 to 446), and 3) a CMV IE splice donor. The second indicator gene cassette contains: 1) an _-globin gene second exon splice acceptor, 2) the 3' coding region of the luciferase gene (amino acids 447 to 550), and 3) an SV40 polyadenylation site. The transcriptional orientation of the luciferase 5' and 3' coding regions are identical to one another, and opposite to that of the first CMV enhancer-promoter and viral LTRs. However, as the luciferase 5' and 3' coding regions are permuted in the resistance test vectors (ie., the 5' coding region is downstream of the 3' coding region), no mRNA is transcribed which can be spliced to generate a functional luciferase coding region. Following reverse transcription and strand transfer, the luciferase 3' coding region is copied from the 3' LTR to the 5' LTR, permitting the transcription of mRNA which can be spliced to generate a functional luciferase coding region (FIG. 4C).

The subgenomic indicator gene viral vectors with patient sequence acceptor sites, pLS-lucPC-HS, pLS-lucPC-PB, pCS-lucPC-HS and pCS-lucPC-PB, and resistance test vectors derived therefrom, each contain the following elements in a 5' to 3' orientation (FIG. 4B): 1) an HIV-LTR U3 region (pLS-lucPC-HS and pLS-lucPC-PB) or a first CMV IE enhancer-promoter (pCS-lucPC-HS and pCS-lucPC-PB), 2) the HIV-LTR R and U5 regions, 3) the coding region of the HIV gag-pol gene, 4) a first indicator gene cassette containing the 5' coding region of the luciferase gene, 5) an RRE element from the HIV env gene containing a viral packaging sequence, 6) a second indicator gene cassette containing the 3' coding region of the luciferase gene, inserted into a deleted 3' HIV-LTR U3 region, and 7) a 3' HIV-LTR R and U5 region. pLS-lucPC-HS and pCS-lucPC-HS contain unique HpaI and SalI patient sequence acceptor sites at nucleotides 2243 and 4190 of HXB2, respectively; pLS-lucPC-PB and pCS-lucPC-PB contain unique PvuI and BamHI patient sequence acceptor sites at nucleotides 2221 and 4212 of HXB2, respectively. The first indicator gene cassette contains: 1) a second CMV enhancer-promoter, 2) the 5' coding region of the luciferase gene (amino acids 1 to 446), and 3) a CMV IE splice donor. The second indicator gene cassette contains: 1) an $\alpha$-globin gene second exon splice acceptor, 2) the 3' coding region of the luciferase gene (amino acids 447 to 550), and 3) an SV40 polyadenylation site. As the luciferase 5' and 3' coding regions are permuted in the resistance test vectors, reverse transcription and strand transfer must occur to generate non-permuted luciferase 5' and 3' coding regions, permitting the transcription of mRNA which can be spliced to generate a functional luciferase coding region (FIG. 4C).

Plasmid pVL-luc5', which contains the first indicator gene cassette, is prepared in three steps. In the first two steps, the artificial intron contained in pVL-1 consisting of the CMV IE splice donor and $\alpha$-globin gene splice acceptor is subjected to site-directed mutagenesis to create restriction sites which upon digestion yield a DNA fragment whose 5' and 3' termini correspond precisely to the start and end of the artificial intron. In step one, site-directed mutagenesis is carried out with pVL-1 using oligonucleotide 45 which contains the following sequences (5' to 3'): 1) the 18 nucleotide sequence which precedes the CMV IE splice donor, 2) a TAC trinucleotide sequence corresponding to first half of the SnaBI restriction site, and 3) the 18 nucleotide sequence at the beginning of the artificial intron. As the sequence of the first three nucleotides of the intron is GTA, the resulting plasmid pVL-SnaBI contains a SnaBI restriction site which upon digestion releases the 5' sequence of the intron as a blunt DNA end. In step two, site-directed mutagenesis is carried out with pVL-SnaBI using oligonucleotide 46 which contains the following sequences (5' to 3'): 1) the 18 nucleotide sequence at the end of the artificial intron, 2) a CTG trinucleotide sequence corresponding to last half of the PvuII restriction site, and 3) the 18 nucleotide sequence following the _-globin splice acceptor. As the sequence of the last three nucleotides of the intron is CAG, the resulting plasmid pVL-SnaBI/PvuII contains a PvuII restriction site which upon digestion releases the 3' sequence of the intron as a blunt DNA end. In the third step, plasmid pVL-luc5' is prepared from two DNA fragments: 1) a vector DNA of 5.3 kB prepared by digesting plasmid pVL-luc with EcoRV and NheI, and treating the resulting vector with Klenow DNA polymerase and alkaline phosphatase, and 2) a DNA fragment of 0.1 kB containing the CMV IE splice donor, prepared by digesting plasmid pVL-SnaBI/PvuII with SnaBI and SmaI. Clones corresponding to pVL-luc5', which contain the CMV IE splice donor inserted in the correct orientation into the luciferase coding region, are identified by restriction mapping.

Plasmid pVL-luc3', which contains the second indicator gene cassette, is prepared in three steps. In step one, plasmid pBS-LTR, in which the 3' LTR of pBS-HXB2 is subcloned, is prepared from two DNA fragments: 1) a vector DNA of 3.0 kB prepared by digesting plasmid pBluescript II KS (+) with XhoI and XbaI, and 2) a DNA fragment of 0.8 kB containing the 3' LTR, prepared by digesting pBS-HXB2 with XhoI and XbaI. In step two, plasmid pBS-LTR-luc3', which contains the 3' coding region of luciferase followed by an SV40 polyadenylation site, inserted into the deleted 3' LTR, is prepared from two fragments: 1) a vector DNA of 3.5 kB prepared by digesting pBS-LTR with EcoRV, and treating the resulting vector with alkaline phosphatase, and 2) a DNA fragment of 0.5 kB containing the 3' luciferase coding region and SV40 polyA site, prepared by digesting plasmid pVL-luc with EcoRV and NheI, followed by treatment of the resulting fragment with Klenow DNA polymerase. Clones having the 3' luciferase coding region inserted in the correct orientation (ie., opposite to the direct of transcription in the 3' LTR) are identified by restriction mapping. In step three, plasmid pVL-luc3' is prepared from two DNA fragments: 1) a vector DNA of 4.0 kB prepared by digesting plasmid pBS-LTR-luc3' with EcoRV, followed by treatment of the resulting vector with alkaline phosphatase, and 2) a DNA fragment of 0.1 kB containing the α-globin gene second exon splice acceptor, prepared by digesting plasmid pVL-SnaBI/PvuII with PvuII and SmaI. Clones corresponding to pVL-luc3', which contain the α-globin second exon splice acceptor inserted in the correct orientation into the luciferase coding region, are identified by restriction mapping.

Plasmids pLG-lucPC-HS, pLG-lucPC-PB, pLS-lucPC-HS and pLS-lucPC-PB are prepared by the same three step procedure. In step one, plasmids pLG-lucDP-HS, pLG-lucDP-PB, pLS-lucDP-HS and pLS-lucDP-PB are prepared from two DNA fragments: 1) a vector DNA prepared by digesting plasmids pLG-lucPP-HS, pLG-lucPP-PB, pLS-lucPP-HS, pLS-lucPP-PB, respectively, with SmaI and ClaI, and 2) a DNA fragment of 0.8 kB prepared by digesting plasmid pLG with SmaI and ClaI. In step two, plasmids pLG-luc5' -HS, pLG-luc5' -PB, pLS-luc5' -HS and pLS-luc5' -PB are prepared from two DNA fragments: 1) a vector DNA prepared by digesting plasmids pLG-lucDP-HS, pLG-lucDP-PB, pLS-lucDP-HS and pLS-lucDP-PB, respectively, and treating the resulting vectors with alkaline phosphatase, and 2) a DNA fragment of 2.5 kB containing the first indicator gene cassette prepared by digesting pVL-luc5' with NotI. Clones which contain the first indicator gene cassette inserted into the viral vector with a transcriptional orientation opposite to that of the viral LTRs are identified by restriction mapping. In step three, plasmids pLG-lucPC-HS, pLG-lucPC-PB, pLS-lucPC-HS and pLS-lucPC-PB are prepared from two DNA fragments: 1) a vector DNA prepared by digesting plasmids pLG-luc5' -HS, pLG-luc5' -PB, pLS-luc5' -HS and pLS-luc5' -PB, respectively, with XhoI and XbaI, and 2) a DNA fragment of 1.1 kB containing the second indicator gene cassette, prepared by digesting plasmid pVL-luc3' with XhoI and XbaI. Plasmids pCG-lucPC-HS, pCG-lucPC-PB, pCS-lucPC-HS and pCS-lucPC-PB are each prepared from two DNA fragments: 1) a vector DNA prepared by digesting either plasmids pLG-lucPC-HS, pLG-lucPC-PB, pLS-lucPC-HS and pLS-lucPC-PB, respectively, with SmaI and ClaI, and 2) a DNA fragment of 1.3 kB prepared by digesting plasmid pCG with SmaI and ClaI.

Resistance Test Vector—Construction

Resistance test vectors containing a non-functional indicator gene with a permuted coding region were designed using the HIV genomic and subgenomic viral vectors comprising anti-viral target genes described in Example 1.

Resistance test vectors are prepared from plasmids pLG-lucPC-HS, pLG-lucPC-PB, pCG-lucPC-HS, pCG-lucPC-PB, pLS-lucPC-HS, pLSlucPC-PB, pCS-lucPC-HS and pCS-lucPC-PB (FIG. 4B), by the procedure described in Example 1. Resistance test vectors are constructed with vectors prepared from plasmids pLG-lucPC-HS, pCG-lucPC-HS, pLS-lucPC-HS or pCS-lucPC-HS using amplified patient sequences prepared with oligonucleotides 18 and 19, and with oligonucleotides 22 and 23. Resistance test vectors are constructed with vectors prepared from plasmids pLG-lucPC-PB, pCG-lucPC-PB, pLS-lucPC-PB or pCS-lucPC-PB using amplified patient sequences prepared with oligonucleotides 20 and 21, and with oligonucleotides 24 and 25.

Drug Susceptibility and Resistance Test

Resistance tests are carried out by the procedures described in Example 1 as follows. Resistance test vectors prepared from plasmids pLG-lucPC-HS, pLG-lucPC-PB, pCG-lucPC-HS and pCG-lucPC-PB lack a functional HIV env gene, and are used in conjunction with the packaging expression vector pVL-env4070A. Resistance test vectors prepared from plasmids pLS-lucPC-HS, pLS-lucPC-PB, pCS-lucPC-HS and pCS-lucPC-PB encode the HIV gag-pol gene products only, and are used in conjunction with pVL-env4070, and either the pLTR-HIV3' or pCMV-HIV3' packaging expression vectors. In resistance tests carried out using two host cell types, the 293 cell line, the tsa54 cell line, the tsa201 cell line, or the BOSC 23 cell line are employed as packaging host cells, and unmodified Jurkat cells are employed as target cells. As the non-functional indicator genes with permuted coding regions contained within these resistance test vectors are not efficiently expressed upon transfection of the packaging host cells, infection of target host cells is carried out either by co-cultivation with packaging host cells, or by using virus from the packaging host cell supernatant. For similar reasons, resistance tests carried out with these resistance test vectors may employ a single host cell type. Resistance tests using a single host cell type are carried out using either 293, tsa54, tsa201, BOSC 23 or Jurkat cells.

EXAMPLE 3

HIV Drug Susceptibility And Resistance Test Using Resistance Test Vectors Comprising Patient-derived Segment(s) And A Non-Functional Indicator Gene With An Inverted Intron Resistance test vectors containing a non-functional indicator gene with an inverted intron were designed using the HIV genomic and subgenomic viral vectors comprising anti-viral target genes described in Example 1.

Indicator Gene Viral Vectors—Inverted Intron

The genomic indicator gene viral vectors with patient sequence acceptor sites, pLG-lucII-HS, pLG-lucII-PB, pCG-lucII-HS and pCG-lucII-PB, and resistance test vectors derived therefrom, each contain the following elements in a 5' to 3' orientation (FIG. 5B): 1) an HIV-LTR U3 region (pLG-lucII-HS and pLG-lucII-PB) or a first CMV IE enhancer-promoter (pCG-lucII-HS and pCG-lucII-PB), 2) the HIV-LTR R and U5 regions, 3) the coding regions of the HIV gag-pol, vif, vpr, tat, rev, vpu, deleted env, and nef genes, 4) an indicator gene cassette inserted into the deleted env gene, and 5) a 3' HIV-LTR. pLG-lucII-HS and pCG-lucII-HS contain unique HpaI and SalI patient sequence acceptor sites at nucleotides 2243 and 4190 of HXB2, respectively; pLG-lucII-PB and pCG-lucII-PB contain unique PvuI and BamHI patient sequence acceptor sites at nucleotides 2221 and 4212 of HXB2, respectively (see Example 1 for details). The indicator gene cassette contains 1) a second CMV enhancer-promoter, 2) the coding region of the luciferase gene interrupted by an inverted artificial intron, and 3) an SV40 polyadenylation sequence. The overall transcriptional orientation of the indicator gene cassette is opposite to that of the first CMV enhancer-promoter and viral LTRs, while the orientation of the artificial intron is the same as the latter elements. Transcription of the indicator gene by the second CMV enhancer-promoter does not lead to the production of functional transcripts as the inverted intron cannot be spliced in this orientation. Transcription of the indicator gene by the 5' viral LTR or the first CMV IE enhancer-promoter, however, leads to the removal of the inverted intron by RNA splicing, although the indicator gene is still not functionally expressed as the resulting transcript has an antisense orientation. Following the reverse transcription of this transcript and integration of the resultant proviral DNA, the indicator gene can be functionally transcribed by the second CMV enhancer-promoter as the inverted intron has been previously removed (FIG. 5C).

The subgenomic indicator gene viral vectors with patient sequence acceptor sites, pLS-lucII-HS, pLS-lucII-PB, pCS-lucII-HS and pCS-lucII-PB, and resistance test vectors derived therefrom, each contain the following elements in a 5' to 3' orientation (FIG. 5B): 1) an HIV-LTR U3 region (pLS-lucII-HS and pLS-lucII-PB) or a first CMV IE enhancer-promoter (pCS-lucII-HS and pCS-lucII-PB), 2) the HIV-LTR R and U5 regions, 3) the coding region of the HIV gag-pol gene, 4) the indicator gene cassette, 5) an RRE element from the HIV env gene containing a viral packaging sequence, and 6) a 3' HIV-LTR. pLS-lucII-HS and pCS-lucII-HS contain unique HpaI and SalI patient sequence acceptor sites at nucleotides 2243 and 4190 of HXB2, respectively; pLS-lucII-PB and pCS-lucII-PB contain unique PvuI and BamHI patient sequence acceptor sites at nucleotides 2221 and 4212 of HXB2, respectively. The indicator gene cassette contains 1) a second CMV enhancer-promoter, 2) the coding region of the luciferase gene interrupted by an inverted artificial intron, and 3) an SV40 polyadenylation sequence. As is the case for the pLG-lucII and pCG-lucII genomic viral vectors, the indicator genes of pLS-lucII and pCS-lucII cannot be functionally transcribed until after the inverted intron is removed and reverse transcription and proviral integration occur (FIG. 5C).

Plasmid pVL-lucII, which contains the indicator gene cassette, in which the artificial intron from pVL-SnaBI/PvuII is inserted into the luciferase coding region in an inverted orientation, is prepared from two DNA fragments: 1) a vector fragment of 5.8 kB prepared by digesting pVL-luc with EcoRV and treating the resulting vector with alkaline phosphatase, and 2) a DNA fragment of 0.2 kB corresponding precisely to the artificial intron sequence prepared by digesting pVL-SnaBI/PvuII with SnaI and PvuII. Clones corresponding to pVL-lucII which contain the artificial intron inserted into the luciferase coding region in an inverted orientation are identified by restriction mapping.

Plasmids pLG-lucII-HS, pLG-lucII-PB, pLS-lucII-HS and pLS-lucII-PB are prepared from two DNA fragments: 1) a vector DNA prepared by digesting plasmids pLG-lucDP-HS, pLG-lucDP-PB, pLS-lucDP-HS and pLS-lucDP-PB, respectively, and treating the resulting vectors with alkaline phosphatase, and 2) a DNA fragment of 3.2 kB containing the luciferase indicator gene cassette prepared by digesting pVL-lucII with NotI. Clones which contain the correct plucII indicator gene cassette inserted into the viral vector with a transcriptional orientation opposite to that of the viral LTRs are identified by restriction mapping and are used for the preparation of resistance test vectors.

Plasmids pCG-lucII-HS, pCG-lucII-PB, pCS-lucII-HS and pCS-lucII-PB are each prepared from two DNA fragments: 1) a vector DNA prepared by digesting plasmids pLG-lucII-HS, pLG-lucII-PB, pLS-lucII-HS and pLS-lucII-PB, respectively, with SmaI and ClaI, and 2) a DNA fragment of 1.3 kB prepared by digesting plasmid pCG with SmaI and ClaI.

Resistance Test Vector—Construction

Resistance test vectors are prepared from plasmids pLG-lucII-HS, pLG-lucII-PB, pCG-lucII-HS, pCG-lucII-PB, pLS-lucII-HS, pLS-lucII-PB, pCS-lucII-HS and pCS-lucII-PB (FIG. 5B), by the procedure described in Example 1. Resistance test vectors are constructed with vectors prepared from plasmids pLG-lucII-HS, pCG-lucII-HS, pLS-lucII-HS or pCS-lucII-HS using amplified patient sequences prepared with oligonucleotides 18 and 19, and with oligonucleotides 22 and 23. Resistance test vectors are constructed with vectors prepared from plasmids pLG-lucII-PB, pCG-lucII-PB, pLS-lucII-PB or pCS-lucII-PB using amplified patient sequences prepared with oligonucleotides 20 and 21, and with oligonucleotides 24 and 25.

Drug Susceptibility and Resistance Test

Resistance tests are carried out by the procedures described in Example 1 as follows. Resistance test vectors prepared from plasmids pLG-lucII-HS, pLG-lucII-PB, pCG-lucII-HS and pCG-lucII-PB lack a functional HIV env gene, and are used in conjunction with the packaging expression vector pVL-env4070A. Resistance test vectors prepared from plasmids pLS-lucII-HS, pLS-lucII-PB, pCS-lucII-HS and pCS-lucII-PB encode the HIV gag-pol gene products only, and are used in conjunction with pVL-env4070A, and either the pLTR-HIV3' or pCMV-HIV3' packaging expression vectors. In resistance tests carried out using two host cell types, the 293 cell line, the tsa54 cell line, the tsa201 cell line, or the BOSC 23 cell line are employed as packaging host cells, and unmodified Jurkat cells are employed as target cells. As the non-functional indicator genes with inverted introns contained within these resistance test vectors are not efficiently expressed upon transfection of the packaging host cells, infection of target host cells is carried out either by co-cultivation with packaging host cells, or by using virus from the packaging host cell supernatant. For similar reasons, resistance tests carried out with these resistance test vectors may employ a single host cell type. Resistance tests using a single host cell type are carried out using either 293, tsa54, tsa201, BOSC 23 or Jurkat cells.

EXAMPLE 4

Non-Particle Based HIV Drug Susceptibility And Resistance Test Using Resistance Test Vectors Comprising Patient-derived Segment(s) And A Non-functional Indicator Gene.

Drug Susceptibility and Resistance Test

Non-particle based resistance tests are carried out using the resistance test vectors comprising non-functional indicator genes with either permuted promoters, permuted coding regions or inverted introns, described in Examples 1, 2 and 3. These non-particle based resistance tests are performed by transfection of a single host cell type with each resistance test vector in the absence of packaging expression vectors. Although the non-functional indicator genes contained within these resistance test vectors are not efficiently expressed upon transfection of the host cells, there is detectable indicator gene expression resulting from non-viral particle-based reverse transcription. Reverse transcription and strand transfer results in the conversion of the permuted, non-functional indicator gene to a non-permuted, functional indicator gene. As reverse transcription is completely dependent upon the expression of the pol gene contained within each resistance test vector, anti-viral agents may be tested for their ability to inhibit the pol gene products encoded by the patient-derived segments contained within the resistance test vectors. Non-particle based resistance tests are carried out by the general procedures described in Example 1 with the following modifications: 1) Resistance test vectors are transfected into the appropriate host cells, 2) anti-viral agents, or combinations thereof, are added at appropriate concentrations to individual cultures of transfected host cells immediately after transfection, 3) host cells are harvested 24 to 72 hours following transfection and assayed for luciferase activity. The reduction in luciferase activity observed for host cells transfected with a given resistance test vector in the presence of a given anti-viral agent, or agents, as compared to a control run in the absence of the anti-viral agent(s) is used to calculate the apparent inhibitory content (Ki) of that agent, or combination of agents, for the viral target gene product encoded by the patient-derived segments present in the resistance test vector.

Resistance Test Vector—Construction

For non-particle based resistance tests with resistance test vectors comprising a non-functional indicator gene with a permuted promoter, resistance test vectors are prepared as described in Example 1 using plasmids pLG-lucPP-HS, pLG-lucPP-PB, pCG-lucPP-HS, pCG-lucPP-PB, pLS-lucPP-HS, pLS-lucPP-PB, pCS-lucPP-HS or pCS-lucPP-PB. Each resistance test vector is transfected into host cells expressing a cytoplasmic T7 RNA polymerase (eg., 293/T7RNAP cells or Jurkat/T7RNAP cells). Such host cells are prepared by the stable transfection of 293 cells and Jurkat cells as described in Example 1, using plasmid pVL-T7RNAP, which directs the expression of a cytoplasmic phage T7 RNA polymerase in human and other mammalian cells and cell lines. pVL-T7RNAP is constructed from the following two DNA fragments: 1) a vector fragment of 4.3 kB prepared by digestion of the mammalian expression vector pVL-2 with EcoRI and BglII, and 2) a DNA fragment of 2.6 kB containing the complete coding region of the T7 RNA polymerase (nucleotides 166 to 2815, coordinates given in GenBank accession number M38308, Grachev and Pletnev (1984) *Bioorg. Khim.* 10, 824–843) prepared by PCR using plasmid pT7-G1 as a template with oligonucleotides 47 and 40 as primers, followed by digestion with EcoRI and BglII. Oligonucleotide 47 incorporates a unique EcoRI site followed by a consensus sequence for eukaryotic translation initiation (e.g., Kozak (1991) *J. Biol. Chem*, 266, 19867–19870), while oligonucleotide 40 incorporates a unique BglII site.

For non-particle based resistance tests with resistance test vectors comprising a non-functional indicator gene with a permuted coding region or inverted intron, resistance test vectors are prepared as described in Example 1 using plasmids pLG-lucPC-HS, pLG-lucPC-PB, pCG-lucPC-HS, pCG-lucPC-PB, pLS-lucPC-HS, pLS-lucPC-PB, pCS-lucPC-HS, pCS-lucPC-PB, pLG-lucII-HS, pLG-lucII-PB, pCG-lucII-HS, pCG-lucII-PB, pLS-lucII-HS, pLS-lucII-PB, pCS-lucII-HS or pCS-lucII-PB. Each resistance test vector is transfected into either 293, tsa54, tsa201, BOSC 23 or Jurkat cells.

EXAMPLE 5

HIV Drug Susceptibility And Resistance Test Using Resistance Test Vectors Comprising Patient-derived Segment(s) And A Functional Indicator Gene.

Indicator Gene Viral Vector—Functional Indicator Gene

The genomic indicator gene viral vectors with patient sequence acceptor sites, plasmids pLG-luc-HS-1, pLG-luc-HS-2, pLG-luc-PB-1, pLG-luc-PB-2, pCG-luc-HS-1, pCG-luc-HS-2, pCG-luc-PB-1 and pCG-luc-PB-2, and resistance test vectors derived therefrom, each contain the following elements in a 5' to 3' orientation (FIG. 6): 1) an HIV-LTR U3 region (pLG-luc-HS-1, pLG-luc-HS-2, pLG-luc-PB-1 and pLG-luc-PB-2) or a first CMV IE enhancer-promoter (pCG-luc-HS-1, pCG-luc-HS-2, pCG-luc-PB-1 and pCG-luc-PB-2), 2) the HIV-LTR R and U5 regions, 3) the coding regions of the HIV gag-pol, vif, vpr, tat, rev, vpu, deleted env, and nef genes, 4) an indicator gene cassette inserted into the deleted env gene, and 5) a 3' HIV-LTR. pLG-luc-HS-1, pLG-luc-HS-2, pCG-luc-HS-1 and pCG-luc-HS-2 contain unique HpaI and SalI patient sequence acceptor sites at nucleotides 2243 and 4190 of HXB2, respectively; pLG-luc-PB-1, pLG-luc-PB-2, pCG-luc-PB-1 and pCG-luc-PB-2 contain unique PvuI and BamHI patient sequence acceptor sites at nucleotides 2221 and 4212 of HXB2, respectively (see Example 1 for details). The indicator gene cassettes of each plasmid contain 1) a second CMV enhancer-promoter, 2) the coding region of the luciferase gene, and 3) an SV40 polyadenylation sequence. The indicator gene cassettes of pLG-luc-HS-1, pLG-luc-PB-1, pCG-luc-HS-1 and pCG-luc-PB-1 are inserted into the vector with a transcriptional orientation opposite to the viral LTRs or first CMV enhancer-promoter (FIG. 6B), while the indicator gene cassettes of pLG-luc-HS-2, pLG-luc-PB-2, pCG-luc-HS-2 and pCG-luc-PB-2 are inserted into the vector with the same orientation (FIG. 6C).

The subgenomic indicator gene viral vectors with patient sequence acceptor sites, plasmids pLS-luc-HS-1, pLS-luc-HS-2, pLS-luc-PB-1, pLS-luc-PB-2, pCS-luc-HS-1, pCS-luc-HS-2, pCS-luc-PB-1 and pCS-luc-PB-2, and resistance test vectors derived therefrom, each contain the following elements in a 5' to 3' orientation (FIG. 6): 1) an HIV-LTR U3 region (pLS-luc-HS-1, pLS-luc-HS-2, pLS-luc-PB-1 and pLS-luc-PB-2) or a first CMV IE enhancer-promoter (pCS-luc-HS-1, pCS-luc-HS-2, pCS-luc-PB-1 and pCS-luc-PB-2), 2) the HIV-LTR R and U5 regions, 3) the coding region of the HIV gag-pol gene, 4) the indicator gene cassette, 5) an RRE element from the HIV env gene containing a viral packaging sequence, and 6) a 3' HIV-LTR. pLS-luc-HS-1, pLS-luc-HS-2, pCS-luc-HS-1 and pCS-luc-HS-2 contain unique HpaI and SalI patient sequence acceptor sites at nucleotides 2243 and 4190 of HXB2, respectively; pLS-luc-PB-1, pLS-luc-PB-2, pCS-luc-PB-1 and pCS-luc-PB-2 contain unique PvuI and BamHI patient sequence acceptor sites at nucleotides 2221 and 4212 of HXB2, respectively. The indicator gene cassettes of each plasmid contain 1) a second CMV enhancer-promoter, 2) the complete coding region of the luciferase gene, and 3) an SV40 polyadenylation sequence. The indicator gene cassettes of pLS-luc-HS-1, pLS-luc-PB-1, pCS-luc-HS-1 and pCS-luc-PB-1 are inserted into the vector with a transcriptional orientation opposite to the viral LTRs or first CMV enhancer-promoter (FIG. 6B), while the indicator gene cassettes of pLS-luc-HS-2, pLS-luc-PB-2, pCS-luc-HS-2 and pCS-luc-PB-2 are inserted into the vector with the same orientation (FIG. 6C).

Plasmids pLG-luc-HS-1 and pLG-luc-HS-2, pLG-luc-PB-1 and pLG-luc-PB-2, pCG-luc-HS-1 and pCG-luc-HS-2, pCG-luc-PB-1 and pCG-luc-PB-2, pLS-luc-HS-1 and pLSluc-HS-2, pLS-luc-PB-1 and pLS-luc-PB-2, pCS-luc-HS-1 and pCS-luc-HS-2, pCS-luc-PB-1 and pCS-luc-PB-2 are each prepared from two DNA fragments: 1) a vector DNA prepared by digesting either pLG-lucII-HS, pLG-luII-PB, pCG-lucII-HS, pCG-lucII-PB, pLS-luc-HS, pLS-lucII-PB, pCS-lucII-HS and pCS-lucII-PB, respectively with NotI and treating the resulting vectors with alkaline phosphatase, and 2) a DNA fragment of 3.0 kB containing the luciferase indicator gene cassette prepared by digesting pVL-luc with NotI. Clones containing the indicator gene cassette inserted into a given viral vector in both transcriptional orientations relative to the viral LTRs are identified by restriction mapping (eg., pLG-luc-HS-1 and pLG-luc-HS-2).

Resistance Test Vector—Construction

Resistance test vectors containing a functional indicator gene were designed using the HIV genomic and subgenomic viral vectors comprising anti-viral target genes described in Example 1. Resistance test vectors are prepared from the above plasmids (FIG. 6) by the procedure described in Example 1. Resistance test vectors are constructed with vectors prepared from plasmids pLG-luc-HS-1, pLG-luc-HS-2, pCG-luc-HS-1, pCG-luc-HS-2, pLS-luc-HS-1, pLS-luc-HS-2, pCS-luc-HS-1 or pCS-luc-HS-1 using amplified patient sequences prepared with oligonucleotides 18 and 19, and with oligonucleotides 22 and 23. Resistance test vectors are constructed with vectors prepared from plasmids pLG-luc-PB-1, pLG-luc-PB-2, pCG-luc-PB-1, pCG-luc-PB-2, pLS-luc-PB-1, pLS-luc-PB-2, pCS-luc-PB-1 or pCS-luc-PB-1 using amplified patient sequences prepared with oligonucleotides 20 and 21, and with oligonucleotides 24 and 25.

Drug Susceptibility and Resistance Test

Resistance tests are carried out by the procedures described in Example 1 as follows. Resistance test vectors prepared from plasmids pLG-luc-HS-1, pLG-luc-HS-2, pLG-luc-PB-1, pLG-luc-PB-2, pCG-luc-HS-1, pCG-luc-HS-2, pCG-luc-PB-1 and pCG-luc-PB-2 lack a functional HIV env gene, and are used in conjunction with the packaging expression vector pVL-env4070A. Resistance test vectors prepared from plasmids pLS-luc-HS-1, pLS-luc-HS-2, pLS-luc-PB-1, pLS-luc-PB-2, pCS-luc-HS-1, pCS-luc-HS-2, pCS-luc-PB-1 and pCS-luc-PB-2 encode the HIV gag-pol gene products only, and are used in conjunction with pVL-env4070A, and either the pLTR-HIV3' or pCMV-HIV3' packaging expression vectors. Resistance tests are carried out with two host cell types, using the 293 cell line, the tsa54 cell line, the tsa201 cell line, or the BOSC 23 cell line as packaging host cells, and using unmodified Jurkat cells as target cells. The infection of target cells with these or other resistance test vectors containing functional indicator genes is carried out employing the procedure for infection with resistance test vector viral particles from the filtered supernatants obtained from resistance test vector indicator host cells, as described in Example 1. In contrast to resistance test vectors comprising non-functional indicator gene viral vectors with a permuted promoter or an inverted intron, those comprising a functional indicator genes are typically able to express their indicator genes in the transfected packaging host cells. Neither the co-cultivation procedure, nor the resistance test using a single cell type can therefore be readily adapted for the infection of target cells using resistance test vectors with functional indicator genes, as it would be difficult to distinguish between indicator gene expression in infected target host cells and the transfected packaging host cells.

All publications and patent applications cited in this specification are herein incorporated by reference in their entirety as if each individual publication or patent application were specifically and individually indicated to be incorporated by reference.

As will be apparent to those skilled in the art to which the invention pertains, the present invention may be embodied in forms other than those specifically disclosed above, for example to carry out the drug susceptibility and resistance test on other viruses, without departing from the spirit or essential characteristics of the invention. The particular embodiments of the invention described above, are, therefore to be considered as illustrative and not restrictive. The scope of the present invention is as set forth in the appended claims rather than being limited to the examples contained in the foregoing description.

EXAMPLE 6

HIV Drug Susceptibility And Resistance Test Using Resistance Test Vectors Comprising Patient-derived Segment(s) And A Functional Indicator Gene.

Indicator Gene Viral Vector—Construction

Figure 3D:
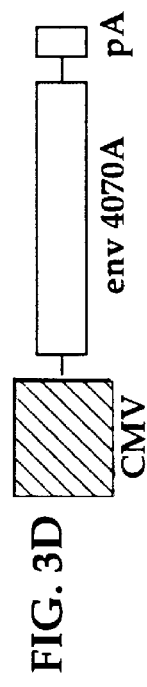

The genomic indicator gene viral vector, pCG-CXCN(F-lucP)2 containing a functional indicator gene was made using a genomic HIV viral vector pCG which has a deletion in the HIV env gene. The genomic indicator gene viral vector, pCG-CXCN(F-lucP)2 was used to generate resistance test vectors by the insertion of patient-derived sequences into the patient sequence acceptor sites. Infectious virus particles carrying the resistance test vector were produced using a packaging expression vector encoding the amphotrophic murine leukemia virus (A-MuLV) 4070A env gene product (FIG. 3D).

The genomic indicator gene viral vector PCG-CXCN(F-lucP)2 and resistance test vectors derived therefrom, each contain the following elements in a 5' to 3 orientation (FIG. 7B): 1) a CMV IE enhancer-promoter region, 2) HIV LTR R and U5 regions, 3) the coding regions of the HIV gag-pol, vif, vpr, tat, rev, vpu, deleted env, and nef genes, 4) a luciferase indicator gene cassette inserted into the deleted env gene, 5) 3' HIV LTR U3 and R regions, 6) the SV40 polyadenylation signal sequence region, and 7) the SV40 origin of replication region. The resistance test vector pCG-CXCN(F-lucP)2-AA contains unique ApaI and AgeI patient sequence acceptor sites.

The luciferase indicator gene cassette, CXCN(lucP), inserted in the deleted env gene contains each of the following elements in a 5' to 3' direction: 1) a CMV IE enhancer-promoter region, and 2) the coding region of the firefly (*Photinus pyralis*) luciferase gene inserted into a multiple cloning site region. The luciferase indicator gene cassette was inserted into the genomic viral vector pCG in the same transcriptional orientation as the first CMV IE and HIV-R-U5 promoter enhancer region.

Genomic Indicator Gene Viral Vector—PCG-CXCN(F-luc)2

The indicator gene viral vector pCG-CXCN(F-luc)2 was prepared from two DNA fragments: 1) an 11.1 kB vector fragment was prepared by digesting plasmid pCG (described below) with XmaI and treating the vector with alkaline phosphatase, and 2) a 2.5 kB fragment containing the luciferase indicator gene cassette prepared by digesting the expression vector pCXCN(lucP) (described below) with SgrAI. Plasmids containing the luciferase gene cassette inserted into the viral vector in the same transcriptional orientation as the viral transcription units were identified by restriction enzyme digestion.

Genomic HIV Viral Vector—pCG

The genomic viral vector, pCG, was derived from the HIV proviral plasmid, pNL4-3 (GenBank Accession No.

M19921, Adachi et. al. (1986) *J. Virol.* 59:284–291). In pCG, the HIV 5' LTR U3 region has been replaced with the CMV immediate-early (IE) enhancer-promoter region. The pCG vector contains unique ApaI and AgeI patient sequence acceptor sites. PCG also has a unique XmaI restriction site within the deleted env gene for insertion of an indicator gene cassette.

pCG was assembled from three component pieces. The first piece (plasmid p1.3) consisted of the CMV IE promoter enhancer region fused to the R region of the 5' HIV LTR, and the U5 and gag-pol regions. The second piece (plasmid p2) consisted of the 5' tat and 5' rev exons, the deleted env region containing a unique XmaI insertion site, the 3 tat and 3' rev exons and the 5' region of the nef gene. The third piece (plasmid 3A) consisted of the 3' region of the nef gene, the 3' LTR U3 and R regions, the SV40 polyadenylation signal sequence region and the SV40 origin of replication region.

Plasmid pCG was assembled in two steps. In the first step, an intermediate plasmid was prepared from two DNA fragments: 1) a 6.5 kB fragment containing the CMV IE enhancer-promoter region, which is fused to the HIV R-U5 sequence (at position 1 of R), and the gag and pol open reading frames of HIV and 2) a 3.6 kB fragment containing the env coding region bearing a 1.2 kB deletion into which was inserted an XmaI restriction site. The 6.5 kB fragment was prepared by digesting plasmid 1.3 (p1; described below) with EcoRI and PvuI. The 3.6 kB fragment was prepared by digesting plasmid p2 (described below) with EcoRI and PvuI. Intermediate plasmids with the correct structure were identified by restriction enzyme digestion. In the second step, plasmid pCG was assembled from two DNA fragments: 1) a 9.5 kB fragment containing the CMV IE enhancer-promoter fused to HIV R-U5 sequence and the gag, pol and deleted env coding regions and 2) a 2.6 kB fragment containing the nef coding region and the U3-R sequence of the HIV LTR followed by the SV40 polyadenylation signal region and the SV40 origin of replication region. The 9.5 kB fragment was prepared by digesting the intermediate plasmid (described above) with XhoI and PvuI. The 2.6 kB fragment was prepared by digesting plasmid p3A (described below) with XhoI and PvuI. Plasmids with the correct pCG structure were identified by restriction enzyme digestion.

Plasmid p1.3 containing the CMV IE enhancer-promoter, the 5' R and U5 regions of HIV and the gag and pol coding regions, was prepared in two steps. In the first step, an intermediate plasmid p1.2 was prepared from two DNA fragments: 1) a 2.4 kB vector fragment prepared by digesting plasmid pSP72 (Promega Corp.) with EcoRI and SstI, and 2) a 5.2 kB fragment containing the 3' portion of the HIV R sequence, followed by the U5 and gag and pol coding regions. The 5.2 kB fragment was prepared by digesting plasmid pNL4-3 (GenBank Accession No. M19921) with SstI and EcoRI. Plasmids with the correct structure were identified by restriction enzyme digestion. Plasmid p1.3 was prepared from two DNA fragments: 1) a 7.1 kB vector fragment containing the gag and pol coding regions, prepared by digesting plasmid p1.2, described above, with AatII and BssHII, and 2) a 1 kB fragment containing the CMV IE promoter-enhancer fused to the R region of HIV (at position 1 of R), prepared by digesting a PCR-generated fragment with BstXI and BssHII. This fragment was generated in two steps. In the first step, a 0.7 kB fragment was generated using plasmid pCMV-EBNA as the template, and oligonucleotides A1 (48) and p1SS-(49)) as primers. Oligonucleotide A1 (48) has the recognition sequence for the type II restriction enzyme BstXI that results in an AatII compatible end following digestion of the PCR product with BstXI. Oligonucleotide p1SS-(49) contains sequences complementary to positions −18 to −1 of the CMV IE enhancer-promoter (coordinates referenced to Boshart et al. [1985]), followed by sequences complementary to positions 1 to 33 of the pNL4-3 isolate of HIV. After gel isolation, this fragment was used as a double stranded primer, together with B2(50) to generate the 1 kB fragment, using plasmid p1.2 as the template. Plasmids with the correct structure were identified by restriction enzyme digestion and the DNA sequence of the PCR-generated region was confirmed by DNA sequencing.

Plasmid p2 contains the coding regions for the tat and rev proteins, a deleted env coding region containing an XmaI site for inserting the indicator gene expression cassette, and the 5' portion of the nef coding region. It was prepared from three DNA fragments: 1) a 2.9 kB vector fragment prepared by digesting pbluescript II KS+ (Stratagene) with EcoRI and XhoI, 2) a 0.6 kB fragment that contains the 5' tat and rev exons and the 5' portion of the env coding region prepared by digesting pNL4-3 with EcoRI and NdeI, and 3) a 1.3 kB fragment that contains the 3' portion of the env coding region and was adapted to have cohesive ends compatible with XhoI and NdeI generated cohesive ends. This fragment was prepared as follows: 1) oligonucleotides 2NM−(53) and 2BX+(54) were treated with T4 polynucleotide kinase (NEB) and then were annealed separately with 2NM+(55) and 2BX−(56), respectively; 2) the annealed oligonucleotides were ligated to a 1.2 kB 3' env fragment prepared by digesting pNL4-3 with MfeI and BsmBI. The annealed oligonucleotides 2NM+(55) and 2NM−(53) contain the following sequences (5' to 3'): 1) an NdeI compatible cohesive overhang, 2) an XmaI restriction site, flanked by Bson BI sties such that Bson BI and SuaI all cleave at the same position, 3) a 35 bp sequence identical to bases 7157 to 7191 of NL4-3 within the env gene, and 4) an MfeI-compatible cohesive end. The annealed oligonucleotides 2BX+(54) and 2BX−(56) contain the following sequences (5' to 3') 1) a BsmBI compatible cohesive end, 2) sequences identical to bases 8392 to 8433 of NL4-3, except for a single C to A base change at position 8396 to disrupt the BsmBI restriction site while not changing the encoded amino acid sequences, and 3) an XhoI compatible cohesive overhang. Plasmids containing the proper structure were identified by restriction digestion, and the DNA sequence of the synthetically-generated regions were verified by DNA sequencing.

Plasmid p3A contains the 3' portion of the nef coding region, the U3 and R sequences of HIV, and the polyadenylation signal and origin of replication regions of SV40. It was prepared from three DNA fragments: 1) a 2.3 kB vector fragment prepared by digesting plasmid pSP70 (Promega) with XhoI and BspMI, 2) a 0.8 kB fragment containing the 3' portion of nef, U3 and the 5' portion of R prepared by digesting plasmid pNL4-3 with XhoI and HindIII, and 3) a 420 bp fragment containing the 3' portion of R and the polyadenylation signal and origin of replication regions of SV40. The 420 bp fragment was prepared from 13 oligonucleotides 3.1–3.13, (57–70). All of the oligonucleotides, except p3.1 and p3.13, were treated with T4 Polynucleotide Kinase and ATP, and then all were annealed and ligated. The 420 bp ligation product was isolated by gel electrophoresis. The 420 bp fragment contains the following elements in a 5' to 3' orientation: 1) a Hind III compatible cohesive end; 2) sequences identical to bases 9152 to 9173 of pNL4-3; 3) an XbaI restriction site; 4) sequences identical to bases 2770 to 2533 of SV40 containing the T antigen polyadenylation site; 5) an SgrAI and an AscI restriction site; 6) sequences identical to bases 5725 to 5578 of SV40, containing the origin of replication; 7) AscI and BspMI restriction sites, and a cohesive end compatible with the BspMI cohesive end in pSP70 (Promega). Plasmids containing the proper elements were identified by restriction digestion, and the DNA sequence of the synthetically-generated region was confirmed by DNA sequencing.

Luciferase Indicator Gene Cassette—pCXCN(lucP)

The luciferase indicator gene cassette, pCXCN(lucP), contains the coding region of the firefly (Photinus pyralis) luciferase gene inserted into the mammalian expression vector pCXCN. pCXCN(lucP) was prepared from two DNA fragments: 1) a vector DNA of 3 kB prepared by digesting PCXCN with BglII and XbaI, and 2) a fragment of 1.6 kB containing the complete luciferase coding region prepared by digesting plasmid p4AlucPSgrAI(−) (described below) with BglII and XbaI.

The pCXCN expression vector contains the following sequence components in the 5' to 3' orientation: 1) the CMV IE enhancer-promoter; 2) multiple cloning sites consisting of the recognition sequences for restriction enzymes BglII, NheI, XhoI, EcoRI, MluI, KpnI, XbaI; 3) the SV40 origin of replication region. pCXCN was constructed from two DNA fragments: 1) a 1424 bp fragment generated by digesting plasmid pCXCS (described below) with XbaI and PvuI, 2) a 1610 bp fragment generated by digesting p3C (described below) with PvuI and XbaI. The pCXCS expression vector contains the following sequence components in the 5' to 3' orientation: 1) the CMV IE enhancer-promoter; 2) multiple cloning sites consisting of the recognition sequences for restriction enzymes BglII, NheI, XhoI, EcoRI, MluI, KpnI, XbaI; 3) the SV40 polyadenylation signal sequence region; 4) the SV40 origin of replication region. The expression vector pCXCS was constructed from three DNA fragments: 1) an 1840 bp fragment generated by digesting plasmid p3A (described above) with XbaI and PvuI, 2) a 1200 bp fragment generated by digesting plasmid p1.1 (described below) with PvuI and SstI, and 3) a 200 bp fragment generated by digesting plasmid p4C (described below) with SstI and XbaI. Plasmid p1.1 contains the CMV IE enhancer-promoter region inserted into the pSP72 (Promega) multiple cloning site region. p1A was assembled by ligating the following two fragments: 1) a 0.7 kB fragment that contains the CMV IE enhancer-promoter and is flanked by AatII and SstI overhangs, and 2) a 2.4 kB vector fragment prepared by digesting pSP72 with AatII and SstI. The 0.7 kB fragment was made as follows: oligonucleotide 1AH−(51) was kinased and annealed to the oligonucleotide 1AH+(52) to form an AatII to HindIII linker. The annealed oligonucleotide linker pair was then ligated to a 0.7 kB fragment generated by digesting pCMV-EBNA with HindIII and SstI. Plasmids with the correct structure were identified by restriction enzyme analysis. Plasmid p4C contains the CMV IE promoter-enhancer, but differs from plasmid 4A, described below, in that it does not contain the artificial intron A sequence. This plasmid was assembled using the following two fragments: 1) a 5.1 kB vector fragment, containing the 5' portion of the CMV IE promoter-enhancer, generated by digesting plasmid pCINeo (Promega) with SstI and NheI; 2) a synthetic 153 bp fragment with SstI and NheI compatible single stranded DNA overhangs, containing the 3' end of the CMV IE enhancer-promoter. The 153 bp fragment was constructed by assembling 5 synthetic oligonucleotides 4A1 (78), 4A2 (79), 4A4 (80), 4C1(88), and 4C2(89). All of the oligonucleotides except 4A1 and 4C2 were phosphorylated using T4 polynucleotide kinase in the presence of ATP and then were annealed and ligated. The ligation product corresponding to 153 bp was separated by gel electrophoresis and purified. Correct plasmids were identified by restriction enzyme digestion. Synthetic DNA sequences were confirmed by DNA sequencing.

Plasmid p4A-lucP-SgrAI(−) contains the complete coding sequence of luciferase that was mutated to eliminate an SgrAI site but not alter the encoded amino acid sequence of the luciferase protein. Plasmid p4A-lucP-SgrAI(−) was derived from p4A-lucP (described below) by site-directed mutagenesis, using single-stranded p4A-lucP DNA as template and oligonucleotide 75 as the mutagenic primer. Plasmids lacking the SgrAI site were identified by restriction digestion and the sequence confirmed by DNA sequencing.

Plasmid p4A-lucP was prepared from two DNA fragments: 1) a 5.4 kB vector fragment prepared by digesting plasmid p4A (described below) with BglII and XbaI; and 2) a 1.6 kB fragment containing the luciferase gene that was obtained by digesting plasmid p5B (described below) with BglII and XbaI.

Plasmid p4A contains the CMV IE promoter-enhancer linked to artificial intron A (CMV IE splice donor/α-globin splice acceptor). Plasmid p4A was assembled using the following two fragments: 1) a 5.1 kB vector fragment, containing the 5' end of the CMV IE promoter-enhancer, generated by digesting plasmid pCINeo (Promega) with SstI and NheI; 2) a synthetic 309 bp fragment with SstI and NheI single stranded DNA overhangs, containing the 3' end of the CMV IE enhancer-promoter and the artificial intron A sequence. The 309 bp fragment was constructed by assembling 10 synthetic oligonucleotide sequences 4A1–10 (78–87). All of the oligonucleotides except 4A1 and 4A10 were phosphorylated using T4 polynucleotide kinase in the presence of ATP and then were annealed and ligated. The ligation product corresponding to 309 bp was separated by gel electrophoresis and purified. Correct plasmids were identified by restriction enzyme digestion. Synthetic DNA sequences were confirmed by DNA sequencing.

Plasmid p5B was prepared from three DNA fragments: 1) a 2.4 kB vector fragment prepared by digesting pSP72 (Promega) with HindIII and XbaI; 2) a 1.6 kB fragment containing the complete firefly luciferase coding region prepared by digesting plasmid pGL3-control (Promega) with NcoI and XbaI; and 3) a synthetic DNA fragment of 19 bp having HindIII and NcoI cohesive ends prepared by treating oligonucleotide sequence G5'(−)(90) with T4 polynucleotide kinase and ATP and then annealing it with oligonucleotide sequence G5'(+)(91). Plasmids with the correct structure were identified by restriction enzyme digestion, and the sequence of the synthetic insert was confirmed by DNA sequencing.

Resistance Test Vectors—Construction

Figure 7A:
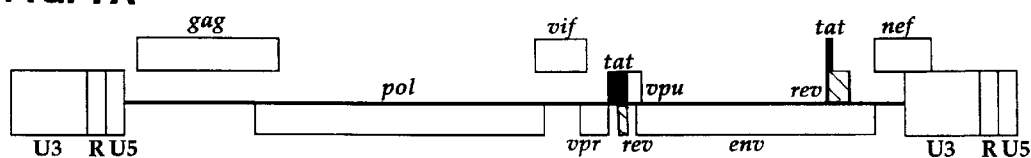
FIG. 7. A. Diagrammatic representation of the DNA genomic structure of HIV-1 is shown above (a) and (b).
Figure 7B:
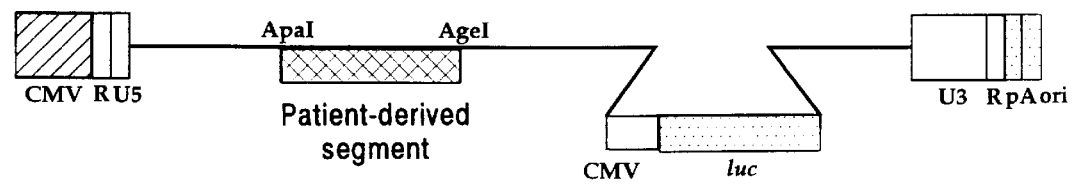
Figure 7C:
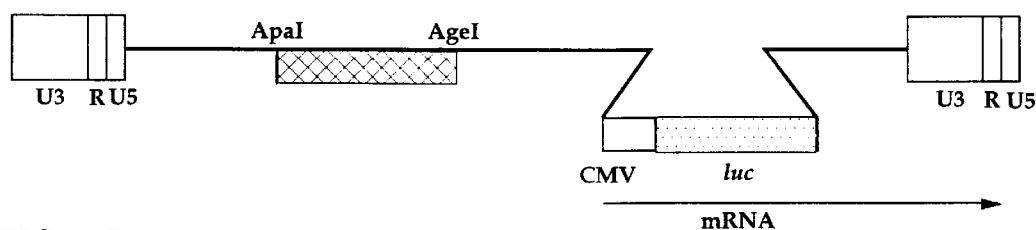

Resistance test vectors were prepared by 1) either modifying the indicator gene viral vector pCG-CXCN(F-lucP)2 by introducing unique patient sequence acceptor sites or by selecting unique patient sequence acceptor sites such as ApaI and AgeI, which define an interval comprising the entire protease coding region and most of the reverse transcriptase coding region; 2) amplifying "test" patient-derived segments, as described below, corresponding to the HIV protease (PR) and reverse transcriptase (RT) coding regions by RT-PCR using complementary DNA (cDNA) prepared from viral RNA obtained from the serum of infected patients, and 3) inserting the amplified sequences precisely into the indicator gene viral vector at the unique patient sequence acceptor sites (FIG. 7B).

In these experiments patient-derived segment(s) corresponding to the HIV protease and reverse transcriptase coding regions were "test" patient-derived segments in that they were reference strains of HIV-1 from the NIH AIDS Research and Reference Reagent Program and/or were mutants of wild type HIV-1 made by site directed mutagenesis amplified by the reverse transcription-polymerase chain reaction method (RT-PCR) using viral RNA isolated from viral particles present in the serum of HIV-infected individuals. Isolation of viral RNA was performed using standard procedures (e.g. RNAgents Total RNA Isolation System, Promega, Madison Wis. or RNAzol, Tel-Test, Friendswood, Tex.). The RT-PCR protocol was divided into two steps. A retroviral reverse transcriptase [e.g. Moloney MuLV reverse transcriptase (Roche Molecular Systems, Inc., Branchburg, N.J.), or avian myeloblastosis virus (AMV) reverse transcriptase, (Boehringer Mannheim, Indianapolis, Ind.)] was used to copy viral RNA into cDNA. The cDNA was then amplified using a thermostable DNA polymerase [e.g. Taq (Roche Molecular Systems, Inc., Branchburg, N.J.), Tth (Roche MolecularSystems, Inc., Branchburg, N.J.), PrimeZyme (isolated from Thermus brockianus, Biometra, Gottingen, Germany)] or a combination of thermostable polymerases as described for the performance of "long PCR" (Barnes, W. M., (1994) *Proc. Natl. Acad. Sci, USA* 91, 2216–2220) [e.g. Expand High Fidelity PCR System (Taq+Pwo), (Boehringer Mannheim. Indianapolis, Ind.) OR GeneAmp XL PCR kit (Tth+Vent), (Roche Molecular Systems, Inc., Branchburg, N.J.)].

The primers, ApaI primer (PDSApa) (76) and AgeI primer (PDSAge)(77) used to amplify the "test" patient-derived segments contained sequences resulting in ApaI and AgeI recognition sites being introduced into the 5' and 3' termini of the PCR product, respectively.

Resistance test vectors incorporating the "test" patient-derived segments were constructed from the following two DNA preparations: 1) a vector DNA prepared from the indicator gene viral vector pCG-CXCN(F-lucP)2, digested with ApaI and AgeI, and 2) an amplified DNA product of 1.5 kB prepared by RT-PCR using viral RNA as a template and oligonucleotides PDSApa (76) and PDSAge (77) as primers, followed by digestion with ApaI and AgeI. To ensure that the plasmid DNA corresponding to the resultant resistance test vector comprises a representative sample of the HIV viral quasi-species present in the serum of a given patient, many independent *E. coli* transformants obtained in the construction of a given resistance test vector were used for the preparation of plasmid DNA.

Host Cells

Packaging Host Cells and Resistance Test Vector Host Cells

A packaging expression vector encoding an amphotrophic MuLV 4070A env gene product enables production in a resistance test vector host cell of resistance test vector viral particles which can efficiently infect human target cells. Resistance test vectors derived from genomic indicator gene viral vectors encode all HIV genes with the exception of env, and were used to transfect a packaging host cell (once transfected the host cell is referred to as a resistance test vector host cell). The pCXAS packaging expression vector which encodes the amphotrophic MuLV 4070A env gene product is used with the resistance test vector to enable production in the resistance test vector host cell of resistance test vector viral particles.

Resistance test vectors were constructed by inserting an ApaI/AgeI "test" patient-derived segment into pCG-CXCN (F-lucP)2 and cotransfecting with the packaging expression vector pCXAS(4070A-env) (described below) into the 293 cell line, (Heinzel et al. (1988) *J. Virol.* 62, 3738), which was used as packaging host cells.

Envelope Gene Expression Vector—pCXAS(4070A-env)

The envelope protein of the amphotropic murine leukemia virus 4070A was expressed transiently in packaging host cells by transfection of the mammalian expression vector PCXAS (4070A-env). The parent expression vector PCXAS contains the following sequence components in the 5' to 3' orientation: 1) the CMV IE enhancer-promoter; 2) artificial intron A (CMV IE splice donor/α-globin splice acceptor); 3) multiple cloning sites consisting of the recognition sequences for restriction enzymes PvuII, BglII, NheI, XhoI, EcoRI, MluI, KpnI, XbaI; 4) the SV40 polyadenylation signal sequence region; 5) the SV40 origin of replication region. pCXAS was constructed from three DNA fragments: 1) an 1840 bp fragment generated by digesting plasmid p3A (described above) with XbaI and PvuI, 2) a 342 bp fragment generated by digesting plasmid 4A (described above) with SstI and XbaI, and 3) a 1200 bp fragment generated by digesting plasmid p1.1 (described above) with PvuI and SstI. Plasmid pCXAS(4070A-env) (FIG. 3D) was constructed from two DNA fragments: 1) a vector fragment of 3.3 kB prepared by digestion of the pCXAS mammalian expression vector with BglII and XbaI, and 2) a DNA fragment of 2.0 kB containing the complete coding region of the MuLV 4070A env gene product; GenBank Accession No. M33469; Ott et al. (1990) *J. Virol.* 64, 757–766) obtained by digestion of plasmid p7.3 (described below) with BglII and XbaI.

Plasmid p7.3 contains the A-MuLV envelope gene as a BglII to XbaI fragment and was constructed in 3 steps. In the first step, plasmid p7.1 which contains the 5' end of the 4070A envelope sequence was constructed using DNA fragments obtained from pSV-A-MLVenv (Landau N., et al., (1991) *J. Virol.* 65 162–169) and pBluescriptII KS+ (Stratagene, San Diego, Calif.). Plasmid p7.1 was constructed as follows: a 1 kB DNA fragment, obtained by digestion of pSV-A-MLV-env with XbaI and EcoRI, was digested with PflMI to generate a 610 bp PflMI/EcoRI fragment; oligonucleotide E5'(−)(92) was kinased and annealed to oligonucleotide E5(+)(93) to create a synthetic DNA fragment with an internal BglII recognition sequence and HindIII and PflMI overhangs at the 5' and 3' ends, respectively. The annealed oligonucleotides together with the 610 bp PflMI/EcoRI fragment were ligated to a 3 kB vector fragment that was obtained by digestion of pBluescriptII KS+ with HindIII and EcoRI. In the second step, a plasmid which is referred to as 7.2 and contains the middle and 3' regions of the 4070A env sequence was constructed using DNA fragments obtained from pSV-A-MLVenv (N. Landau, Ibid.), pLC/63 (Chattopadhyay S. K. (1981) *J. Virol.* 39 777–791, GenBank accession number M33469), and pBluescriptII KS+ (Stratagene, San Diego, Calif.). Plasmid p7.2 was constructed as follows: pSV-A-MLVenv was digested with EcoRI and ClaI to obtain a 1.3 kB fragment representing the middle region of the env sequence; pLC/63 was digested with ClaI and NheI to obtain a 170 bp fragment representing the 3' end of the env sequence; and the 1.3 kB EcoRI/ClaI fragment together with the 170 bp ClaI/NheI fragment were ligated to a 3 kB vector fragment obtained by digestion of pBluescriptII KS+ with EcoRI and SpeI (note: NheI and SpeI digestions create compatible overhangs). In the third step, plasmid 7.3 which contains the complete coding region of the 4070A env gene was assembled using DNA fragments obtained from plasmid 7.1 and plasmid 7.2. Plasmid 7.3 was constructed as follows: a 1.45 kB fragment containing the 3' region of the env sequence was prepared from plasmid 7.2 by digestion with EcoRI and XbaI; a 3.5 kB fragment containing the PBSKS+ vector sequences and the 5' region of the env gene was prepared by digestion of plasmid 7.1 with EcoRI and XbaI; and the two fragments were ligated together.

Target Host Cells

Resistance tests performed with resistance test vectors derived from genomic indicator gene viral vectors pCG-CXCN(F-lucP)2 were carried out using target host cells consisting of the human embryonic kidney cell line 293 (Cell Culture Facility, UC San Francisco, SF, Calif.) or the Jurkat leukemic T-cell line (Arthur Weiss, UC San Francisco, SF, Calif.).

Drug Susceptibility and Resistance Tests

Resistance tests were carried out with resistance test vectors based on the indicator gene viral vector pCG-CXCN (F-lucP)2 using two host cell types. Resistance test vector viral particles were produced by a first host cell (the resistance test vector host cell) that was prepared by transfecting a packaging host cell with the resistance test vector and the packaging expression vector. The resistance test vector viral particles were then used to infect a second host cell (the target host cell) in which the expression of the indicator gene is measured.

AZT Drug Susceptibility/Resistance Tests

The resistance test vectors pCG-CXCN(F-lucP)2-AA containing a functional luciferase gene cassette was constructed and host cells were transfected with the resistance test vector DNA. The resistant test vectors contained "test" patient-derived reverse transcriptase sequences that were either susceptible or resistant to the nucleoside reverse transcriptase inhibitor, AZT (Sigma). The resistance test vector viral particles produced by transfecting the resistance test vector DNA into host cells were used to infect target host cells grown either in the absence of AZT or in the presence of increasing concentrations of the drug (ranging from approximately 0.0001 $\mu$M to 1000 $\mu$M). The amount of luciferase activity produced in infected target host cells in the presence of drug was compared to the amount of luciferase produced in infected target host cells in the absence of drug. Drug resistance was measured as the amount of drug required to inhibit by 50% the luciferase activity detected in the absence of drug (inhibitory concentration 50%, $IC_{50}$). The $IC_{50}$ values were determined by plotting percent drug inhibition vs. $\log_{10}$ drug concentration.

Figure 8D:
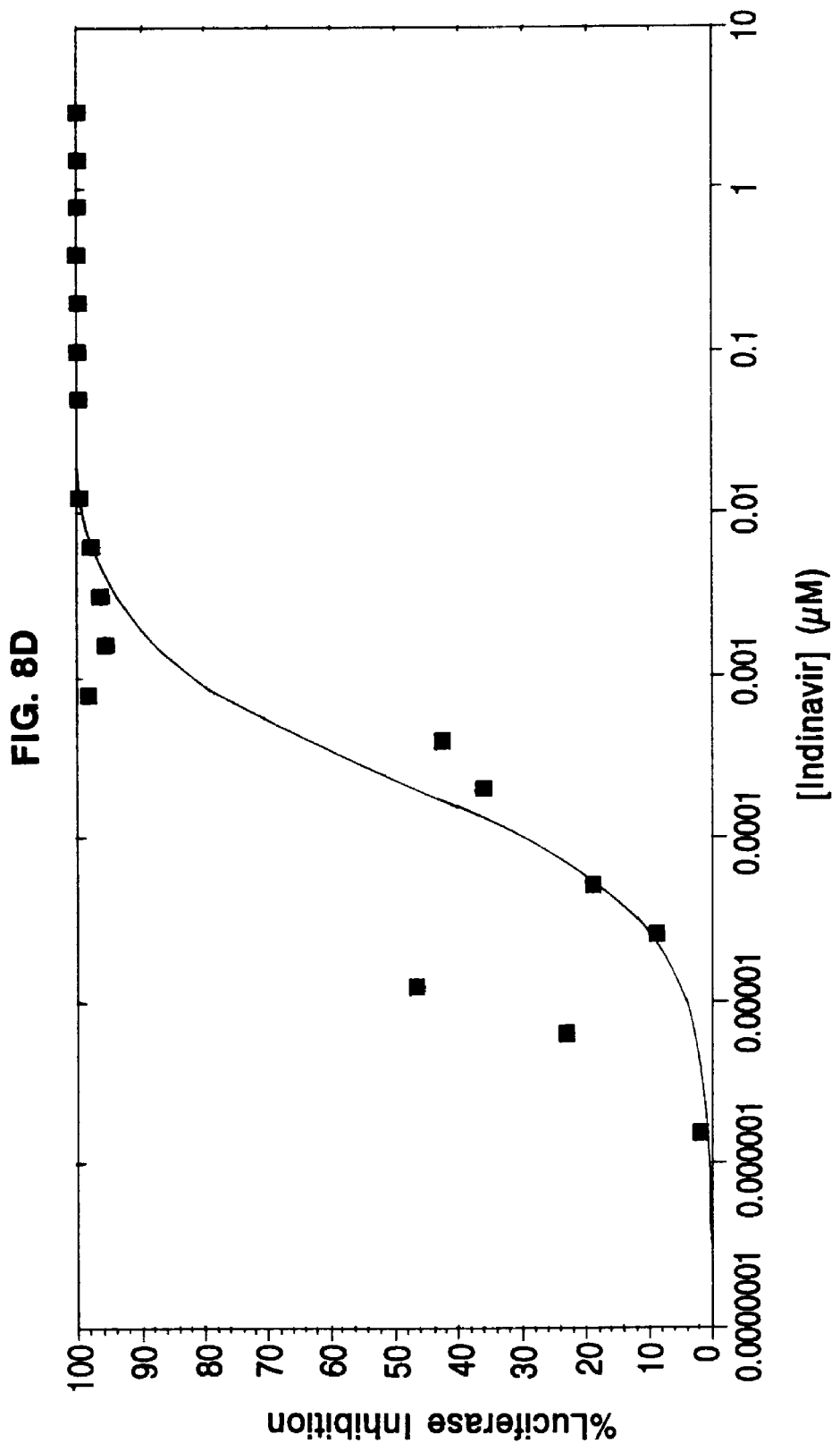
FIG. 8. A. Demonstration of drug susceptibility using the resistance test vectors, pCG-CXCN(F-lucP)2-AA and pCG-CXAT(F-lucP)2-AA. Data are presented as luciferase gene activity in target host cells as Relative Light Units (RLU) in the absence of AZT or in the presence of 5 mM AZT.

Host cells (293) were seeded in 10-cm-diameter dishes and were transfected several days after plating with resistance test vector plasmid DNA and the envelope expression vector pCXAS(4070A-env). Transfections were performed using a calcium-phosphate precipitation procedure. The cell culture media containing the DNA precipitate was replaced with fresh medium, from one to 24 hours, after transfection. Cell culture media containing resistance test vector viral particles was harvested one to four days after transfection and was passed through a 0.45-mm filter before being stored at −80° C. HIV capsid protein (p24) levels in the harvested cell culture media were determined by an EIA method as described by the manufacturer (SIAC; Frederick, Md.). Six to forty-eight hours before infection, target cells (293 and 293/T) were plated in cell culture media containing no AZT or serial two fold dilutions of AZT beginning at 100 $\mu$M and ending at 0.00005 $\mu$M. The AZT concentrations were maintained throughout the infection. Target host cells were inoculated with 90 $\mu$l of transfected resistance test vector host cell supernatant. Control infections were performed using cell culture media from mock transfections (no DNA) or transfections containing the resistance test vector plasmid DNA without the envelope expression plasmid DNA (pCXAS (4070A-env)). One to twenty-four hours after the inoculation, fresh medium was added to each well. Twelve to thirty-six hours later the media was completely replaced with fresh media. One to three or more days after infection the media was removed and cell lysis buffer (Promega) was added to each well. Cell lysates were diluted 100 fold in lysis buffer and each diluted cell lysate was assayed for luciferase activity (FIG. 8A). The inhibitory effect of AZT was determined using the following equation:

% luciferase inhibition=1−(RLUluc$_{[AZT]}$÷RLUluc)

where RLUluc$_{[AZT]}$ is the Relative Light Unit of luciferase activity in infected cells in the presence of AZT and RLUluc is the Relative Light Unit of luciferase activity in infected cells in the absence of AZT. $IC_{50}$ values were obtained from the sigmoidal curves that were generated from the data by plotting the percent inhibition of luciferase activity vs. the $\log_{10}$ drug concentration. The AZT inhibition curves are shown in (FIG. 8B).

Nevirapine Drug Susceptibility/Resistance Test

The resistant test vector, based on the indicator gene viral vector pCG-CXCN(F-lucP)2, contained the reverse transcriptase sequence derived from the biologically active proviral clone, pNL4-3, that is susceptible to the non-nucleoside reverse transcriptase inhibitor, nevirapine (BI-RG-587, Boehringer Ingleheim). Transfection of host packaging cells and infection of host target cells were performed as described for the AZT drug susceptibility/resistance tests as described above. Nevirapine susceptibility/resistance was evaluated using nevirapine concentrations ranging from 0.0001 $\mu$M to 100 $\mu$M. The nevirapine inhibition curve was determined as described above for AZT and is shown in FIG. 8C.

Indinavir Drug Susceptibility/Resistance Tests

The resistant test vector, based on the indicator gene viral vector pCG-CXCN(F-lucP)2, contained the protease sequence derived from the biologically active proviral clone, pNL4-3, that is susceptible to the protease inhibitor, indinavir (MK-639, Merck). Transfection of host packaging cells and infection of host target cells were performed as described for the AZT drug susceptibility/resistance test except that the protease inhibitor, indinavir, was present in the transfected packaging host cell cultures as well as the infected target host cell cultures, as described above. Indinavir susceptibility/resistance was evaluated using indinavir concentrations ranging from 1.5 pM to 3 $\mu$M. The indinavir inhibition curve was determined as described above for AZT and is shown in FIG. 8D.

EXAMPLE 7

HIV Drug Susceptibility and Resistance Test Using Resistance Test Vectors Comprising Patient-derived Segment(s), And A Functional Luciferase Indicator Gene Cassette.

Indicator Gene Viral Vector—Construction

Figure 7D:
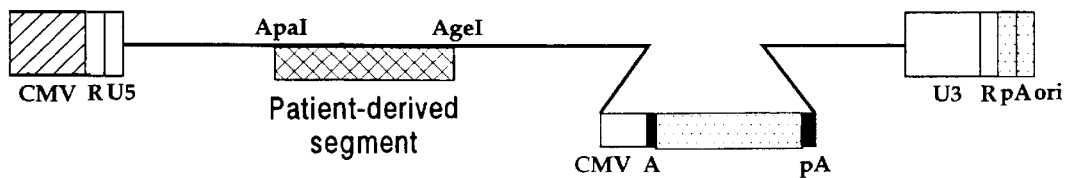
Figure 7E:
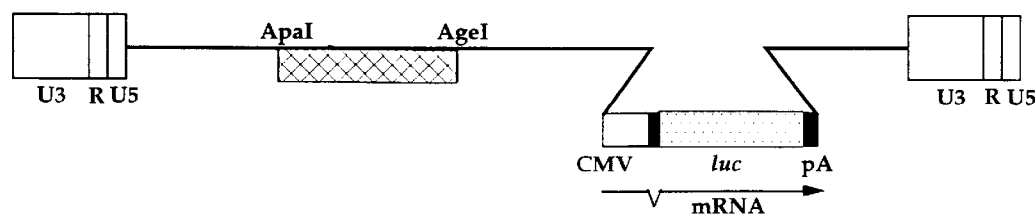

The genomic indicator gene viral vector pCG-CXAT(F-lucP)2 is identical to pCG-CXCN(F-lucP)2 with the exception of the luciferase indicator gene cassette. The resistance test vector based on the genomic indicator gene viral vector comprises patient sequence acceptor sites and a luciferase indicator gene cassette inserted into the deleted env gene cassette which contains the following elements in a 5' to 3' orientation (FIG. 7D): 1) a CMV IE enhancer-promoter region; 2) artificial intron A (CMV IE splice donor/α-globin splice acceptor); 3) the coding region of the firefly (*Photinus pyralis*) luciferase gene inserted into a multiple cloning site, and 4) the thymidine kinase gene polyadenylation signal region from Herpes Simplex Virus type 1 (HSV-1) (GenBank Accession No. M11414, Cole and Stacy (1985)

71

*Mol. Cell Biol.* 5, 2104–2113). The luciferase indicator gene cassette was inserted into the genomic viral vector pCG in the same transcriptional orientation as the first CMV IE promoter-enhancer region.

Genomic Indicator Gene Viral Vector

The indicator gene viral vector pCG-CXAT(F-lucP)2 was prepared from two DNA fragments: 1) a 11.1 kB vector fragment prepared by digesting plasmid pCG with XmaI and treating the vector with alkaline phosphatase, and 2) a 2.8 kB fragment containing the luciferase indicator gene cassette prepared by digesting the expression vector pCXAT(lucP) (described below) with SgrAI. Plasmids containing the luciferase gene cassette inserted into the viral vector in the same transcriptional orientation as the viral transcription units were identified by restriction enzyme digestion. Plasmids containing the luciferase gene cassette inserted into the viral vector in the reverse transcriptional orientation as the viral transcription units were identified by restriction enzyme digestion for use elsewhere (see e.g. Example 1).

Luciferase Indicator Gene Cassette—pCXAT(lucP)

The luciferase indicator gene cassette, pCXAT(lucP) contains the coding region of the firefly (*Photinus pyralis*) luciferase gene inserted into the expression vector pCXAT (described below). pCXAT(lucP) was constructed from a vector DNA of 3.3 kB prepared by digesting pCXAT with BglII and XbaI, and a fragment of 1.6 kB containing the complete luciferase coding region prepared by digesting p4AlucPSgrAI (−) (described in Example 6) with BglII and XbaI.

The pCXAT expression vector contains the following sequences in the 5' to 3' orientation: 1) the CMV IE enhancer-promoter; 2) artificial intron A (CMV IE splice donor/α-globin splice acceptor); 3) multiple cloning sites consisting of recognition sequences for restriction enzymes PvuII, BglII, NheI, XhoI, EcoRI, MluI, KpnI, and XbaI; 4) the thymidine kinase gene polyadenylation signal region from HSV-1, and 5) the SV40 origin of replication region. PCXAT was constructed from two DNA fragments: 1) a 1.6 kB fragment prepared by digesting plasmid PCXAS with XbaI and PvuI, and 2) a 1.7 kB fragment prepared by digesting plasmid p3B (described below) with PvuI and XbaI. Plasmid p3B contains the 3' portion of the nef coding region, the U3 and R sequences of HIV, the HSV-1 thymidine kinase gene polyadenylation signal region, and 5) the SV40 origin of replication region. It was constructed from two DNA fragments: 1) a 3.2 kB vector fragment prepared by digesting plasmid p3A with Xba I and SgrAI, and 2) a 140 bp synthetic fragment containing the thymidine kinase gene polyadenylation signal region from HSV-1. The 140 bp fragment was prepared from 5 oligonucleotides, TKT 1–TKT 5 (94–98). TKT 2, TKT 3, and TKT 4 were phosphorylated with T4 polynucleotide kinase and ATP, and then annealed and ligated, together with TKT 1 (94) and TKT 5 (98). The 140 bp ligation product was isolated by gel electrophoresis. The 140 bp fragment contains the following elements in a 5' to 3' orientation 1) an XbaI compatible cohesive end, 2) sequences identical to bases 24 to 150 of the HSV-1 thymidine kinase gene polyadenylation signal region, and 3) an SgrAI compatible cohesive end.

Resistance Test Vectors—Construction

Resistance test vectors were prepared as described in Example 6 except the genomic indicator gene viral vector pCG-CXAT(F-lucP)2 was used instead of pCG-CXCN(F-lucP)2. The packaging host cells, resistance test vector host cells and target host cells were also as described in Example 6. The AZT drug susceptibility was carried out at an AZT concentration of 5 μM as described in Example 6 and the results are shown in FIG. 8A.

72

EXAMPLE 8

Hepatitis Drug Susceptibility And Resistance Test Using Resistance Test Vectors Comprising Patient-Derived Segment(s) And A Non-Functional Indicator Gene Containing An Inverted Intron.

Indicator Gene Viral Vector—Construction

Indicator gene viral vectors containing a non-functional indicator gene with an inverted intron were designed using HBV subgenomic viral vectors comprising viral genes which are the target(s) of anti-viral drugs. The indicator gene viral vectors pCS-HBV(NF-IG)II-(PSAS−), are based on the subgenomic viral vector pCS-HBV. The indicator gene viral vector contains a non-functional indicator gene cassette containing an inverted intron and all of the cis-acting regulatory elements that are necessary for HBV DNA replication (i.e. DR1, 5' ε DR2, DR1*, 3' pA) but lacks the HBV gene sequences (i.e. C, P, S, X genes) that provide the trans-acting structural and enzymatic functions that are necessary for HBV DNA replication and virus particle formation (FIG. 9B). The C, P, S and X genes and patient sequence acceptor sites are contained within a packaging vector pPK-CPX (described below, FIG. 9D) and pPK-S (described below, FIG. 9E). In this embodiment the indicator gene viral vector pCS-HBV(NF-IG)II-(PSAS−) and the packaging vector pPK-CPX constitute a resistance test vector system. The non-functional indicator gene viral vector pCS-HBV(NF-IG)II-(PSAS−) contains the following elements in a 5' to 3' orientation: (1) the CMV IE enhancer promoter region, (2) the 5' region of the HBV genome and the DR1 and 5' copy of the encapsidation signal region (ε) (the pre-C ORF translation initiation codon is eliminated), (3) a non-functional indicator gene cassette in which the indicator gene ORF contains an inverted intron, (4) the region of the HBV genome containing DR2, DR1*, the 3' ε, and the 3' HBV polyadenylation (pA) signal region. The non-functional indicator gene expression cassette is comprised of some or all of the following elements arranged in the 5' to 3' orientation: (1) a transcriptional enhancer-promoter region, (2) an intron, (3) an indicator gene containing an inverted intron, (4) a transcriptional polyadenylation signal sequence (e.g. SV40) (HSV-1 thymidine kinase gene). The indicator gene expression cassette has a transcriptional orientation opposite to the HBV sequence elements (FIG. 9B). However, the intron within the indicator gene ORF has the same transcriptional orientation as the HBV sequence elements.

Figure 9A:
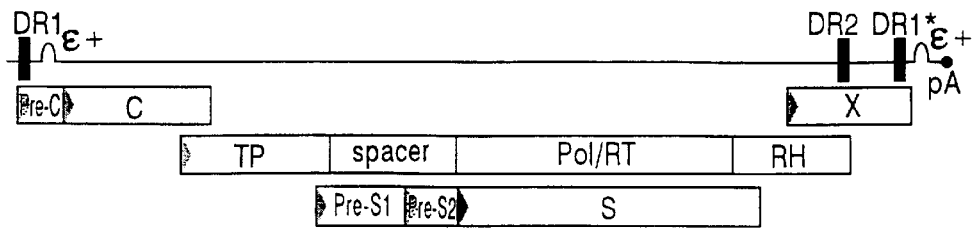
FIG. 9 A. Diagrammatic representation of the RNA pregenomic structure of HBV. Pregenomic RNA is shown as a solid line. Direct repeat sequences (DR) are shown as closed rectangles. The positions of the encapsidation signal sequence is shown (E). The C, P, S, and X genes are shown as open rectangles. The terminal protein (TP), spacer, DNA polymerase/reverse transcriptase (pol/RT), and RNase H regions of the P gene are indicated. Sites of C, P, S, and X translation initiation are indicated by shaded triangles.
Figure 9B:
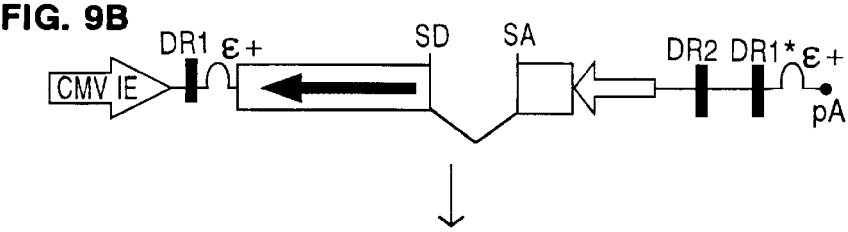
Figure 9C:
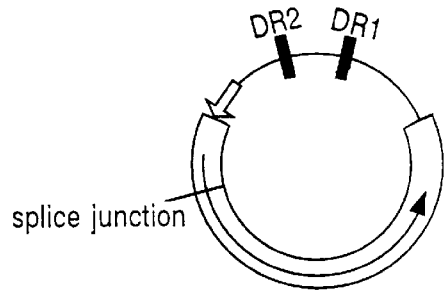
Figure 9D:
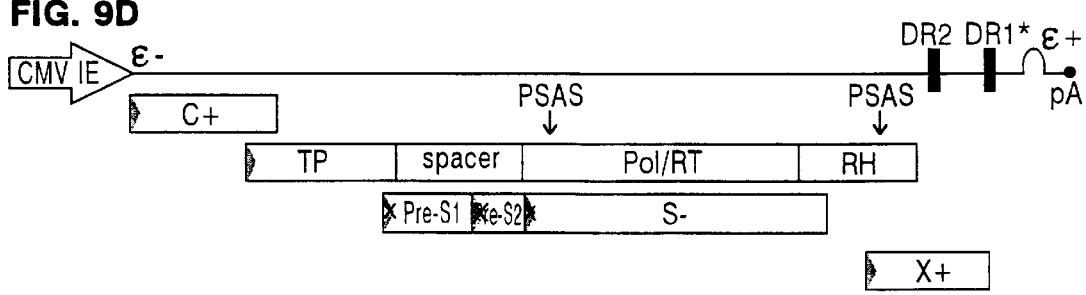

In a second embodiment, the non-functional indicator gene viral vector, pCS-HBV(NF-IG)II(PSAS+), contains a non-functional indicator gene cassette containing an inverted intron, all of the cis-acting regulatory elements that are necessary for HBV DNA replication, and some or all of the HBV gene sequences (i.e. C, P, S, X genes) that provide the trans-acting structural and enzymatic functions that are necessary for HBV DNA replication and virus particle formation (FIG. 9F). Resistance test vectors derived from the indicator gene viral vector pCS-HBV(NF-IG)II(PSAS+) contain patient sequence acceptor sites (PSAS) and are used in conjunction with the packaging vector, pPK-CSX (FIG. 9H). In this embodiment the indicator gene viral vector may also provide some or all of the packaging functions, such as P. The structural and enzymatic activities that are not provided by the indicator gene viral vector, but that are necessary for HBV DNA replication and virus particle formation, are provided using additional packaging vector(s) pPK-CSX (described below, FIG. 9H). In this embodiment, the non-functional indicator gene viral vector, pCS-HBV(NF-IG)II (PSAS+) contains the following elements in a 5' to 3' orientation: (1) the CMV IE enhancer-promoter region, (2) the 5' region of the HBV genome and the DR1 and 5' ε (the pre-C ORF translation initiation codon is eliminated), (3) an indicator gene cassette, containing an inverted intron, positioned within the region of the HBV genome which may contain some or all of the C, P, S, and X genes as well as a patient-derived P gene segment, (4) the region of the HBV genome containing DR2, DR1*, the 3' ε, and the 3' the HBV pA signal region. Within the non-functional indicator gene viral vector, pCS-HBV(NF-IG)II-(PSAS+) the indicator gene expression cassette has a transcriptional orientation opposite to the HBV sequence elements (FIG. 9F). However, the intron within the indicator gene ORF has the same transcriptional orientation as the HBV sequence elements.

In transfected cells the packaging vectors (FIGS. 9D, 9E and 9H) provide, in trans, the structural and enzymatic functions that are necessary for HBV DNA replication and virus particle formation, but that are not provided by the resistance test vector or the indicator gene viral vector. In the embodiment in which an indicator gene viral vector such as pCS-HBV(NF-IG)PP-(PSAS−) is co-transfected with a packaging vector, such as pPK-CPX, the combination of those vectors constitute a resistance test vector system, it is the packaging vector that contains patient sequence acceptor sites for insertion of the patient-derived P gene segment (described above). The packaging vector pPK-CPX contains the following elements in a 5' to 3' orientation: (1) the CMV IE enhancer-promoter region, (2) the region of the HBV genome spanning from the C ORF translation initiation codon to the 3' pA signal and including the C, P, S, and X genes. The C gene of the packaging vectors is modified such that it does not contain and/or express the pre-C ORF sequences and does not express the S proteins (described below).

In HBV, RNA that encodes C and/or P proteins is preferentially packaged, in cis, and consequently could interfere with the efficient packaging of the resistance test vector containing a non-functional indicator gene or a non-functional indicator gene viral vector RNA that does not encode C and P proteins. Two steps are taken to prevent the encapsidation of RNA produced from packaging vectors and to improve the encapsidation efficiency of the resistance test vector or non-functional indicator gene viral vector RNA. First, the RNA produced by packaging vectors does not contain the 5' encapsidation signal region (ϵ) (FIGS. 9D, 9E and 9H). Second, in cases where either the C gene and/or P gene packaging functions are provided by the resistance test vector or non-functional indicator gene viral vector, packaging vectors, such as pPK-S or pPK-CSK, that do not express the C and/or P gene products are used (FIGS. 9E and 9H).

Resistance Test Vectors—Construction

Resistance test vectors are prepared by 1) modifying the indicator gene viral vector pCS-HBV(NF-IG)II-(PSAS−) by introducing unique restriction sites, called patient sequence acceptor sites (PSAS) in the P gene region, 2) amplifying patient-derived segments corresponding to the HBV drug target, e.g. reverse transcriptase or DNA polymerase, by the amplification of viral DNA present in the serum or cells of infected patients, and 3) inserting the amplified sequences precisely into the indicator gene viral vectors at patient sequence acceptor sites (FIG. 9F). Alternatively, resistance test vector systems are prepared by 1) modifying the packaging vectors, pPK-CPX, by introducing patient sequence acceptor sites in the P gene, 2) amplifying patient-derived segments corresponding to the HBV drug target, e.g. reverse transcriptase or DNA polymerase, by amplification using viral DNA present in the serum or cells of infected patients, and 3) inserting the amplified sequences precisely into the packaging vectors at patient sequence acceptor sites (FIG. 9D). In one embodiment, the 5' PSAS is situated near the border of the spacer and RT domains of the P protein (immediately downstream of the S protein translation initiation site) and the 3' PSAS is situated near the C-terminal end of the RNase H domain of the P protein. Insertion of a patient-derived P gene segment into the patient sequence acceptor sites results in the formation of a chimeric P gene sequence in which the TP and spacer domains are encoded by the vector P gene sequence while the reverse transcriptase/polymerase and RNase H domains are encoded by the patient-derived segments (FIGS. 9D and 9F).

In HBV the entire S gene ORF overlaps the P gene ORF but is expressed using a different reading frame (Nassal, M. and Schaller, H. (1993) *Trends in Microbiology* 1, 221–228). Thus, HBV P gene sequences (reverse transcriptase and RNase H domains) obtained from patients also contain the corresponding patient S gene sequences. Expression of the patient-derived S gene region from the overlapping S gene ORF is prevented by eliminating the three S gene ORF (pre-S1, pre-S2, and S) translation initiation sites and/or introducing in-frame termination codons in the pCS-HBV (NF-IG)II-(PSAS+) or pPK-CPK vectors (FIGS. 9F and 9D). S gene expression is provided, in trans, using a separate packaging vector that provides well-characterized S gene products (FIGS. 9E and 9H). The modifications that eliminate S gene expression are performed without introducing changes to the overlapping amino acid sequences that are encoded by the terminal protein (TP) or spacer domains of the P gene.

Drug Susceptibility and Resistance Tests

Drug susceptibility and resistance tests are carried out with a resistance test vector based on indicator gene viral vectors pCS-HBV(NF-IG)II-(PSAS+) or with a resistance test vector system based on an indicator gene viral vector, pCS-HBV(NF-IG)II-(PSAS−) and a packaging vector, pPK-CPX, using either one type of host cell or two types of host cell. Co-transfection of packaging host cells either with a resistance test vector, such as pCS-HBV(NF-IG)II-(PSAS+) and a packaging vector, pPK-CSX, or with an indicator gene viral vector, such as pCS-HBV(NF-IG)II-(PSAS−) and packaging vector-containing patient-derived segment, such as pPK-CPX, (i.e. resistance test vector system) produces HBV viral particles containing an encapsidated indicator gene "pregenome" RNA, which as a result of splicing of the inverted intron, contains a functional indicator gene. (FIGS. 9B and 9C).

Replicate transfections are performed on a series of packaging host cell cultures maintained either in the absence of the anti-viral drug or in increasing concentrations of the anti-HBV drug (e.g., an HBV P protein reverse transcriptase or polymerase inhibitor). After maintaining the packaging host cells for up to several days in the presence or absence of the anti-HBV drug the level of drug susceptibility or resistance can be assessed either directly in the host packaging cell lysates, or in isolated HBV particles obtained by harvesting the host packaging cell culture media. Alternative approaches can be used to evaluate drug susceptibility and resistance in the cell lysates and the isolated HBV particles.

In one embodiment, referred to as the one cell assay, drug susceptibility or resistance is assessed by measuring indicator gene expression e.g. luciferase activity in the transfected packaging host cells in the presence or absence of anti-viral drug. A reduction in luciferase activity observed for cells transfected in the presence of a given anti-viral agent, or combination of agents as compared to a control run in the absence of the anti-viral agent(s), generally relates to the log of the concentration of the anti-viral agent as a sigmoidal curve.

In a second embodiment, referred to as the two cell assay, drug susceptibility or resistance is assessed by measuring indicator gene expression, e.g. luciferase activity, in the target host cells following infection or transfection with HBV particles or HBV particle DNA, respectively. HBV viral particles obtained from packaging host cells are used to infect the target host cells or DNA from those particles is used to transfect target host cells. At the time of infection or transfection the appropriate concentration of the anti-viral drug is added to the cell culture. Up to several days following the infection or transfection, the target host cells are lysed and indicator gene expression is measured. A reduction in indicator gene expression will be observed for cells transfected or infected in the presence of drugs which inhibit HBV replication, for example by inhibiting either the reverse transcriptase (−strand DNA) or the DNA polymerase (+strand DNA) activities of the HBV P protein as compared to a control run in the absence of drug.

In a third embodiment, referred to as the DNA structure indicator assay, drug susceptibility or resistance is assessed by measuring the level of HBV DNA replication that has occurred within the transfected packaging host cells or within the virus particles produced by the packaging host cells. In transfected host cells the HBV subgenomic viral vector is transcribed and the RNA transcript is packaged as "pregenomic" RNA. During virus maturation, the pregenomic RNA is converted to the relaxed circular form of the genomic DNA (rc-DNA) consisting of a complete minus strand and partial plus strand DNA copy. In a subsequent step, the rc-DNA is converted to a covalently closed circular DNA form (cccDNA). To measure HBV DNA replication, amplification primers are designed to amplify an HBV DNA structure that is formed by the splicing of pregenomic RNA and the conversion of this spliced RNA to the rc-DNA and cccDNA forms.

Formation of the correct amplification target structure within HBV particles requires successful completion of HBV DNA replication resulting in the formation of rc-DNA and cccDNA. Anti-viral drugs that inhibit HBV DNA replication (reverse transcription and DNA polymerase activities) will limit the formation of the DNA target sequence, which in turn, can be measured as a decrease in the amplified DNA product using a number of quantitative amplification assays. In one example (FIG. 10B), the binding site of the reverse primer (Pr) is separated into two components by an intron sequence that is inserted into an indicator gene ORF in the same transcriptional orientation as the HBV sequences. The primer binding site of the forward primer (Pf) is located within the region of the viral vector that is flanked by the DR2 and DR1* sequences. In the linear HBV vector the Pf and Pr primers direct DNA synthesis in opposite directions and are oriented outward with respect to each other. In this case, the Pr primer directs DNA synthesis in the upstream direction (toward the 5' copy of ε) and the Pf primer directs DNA synthesis in the downstream direction (toward the 3' ε). This arrangement of primers and template does not constitute a functional amplification unit in the linear indicator gene viral vector. Furthermore, the Pr binding site is not intact in the linear unspliced vector and thus Pr will not anneal to the target DNA. In contrast, the Pf and Pr primers assume an inward orientation with respect to each other in the relaxed circle form of HBV DNA found in mature virions and splicing of the RNA pregenome has assembled an intact Pr primer binding site. Both primers now direct DNA synthesis toward the single copy of DR1 within the plus strand copy of rc-DNA and in either plus or minus strand or cccDNA. This arrangement of primers and template constitutes a functional amplification unit (FIG. 10C).

In an alternative embodiment of the DNA sequence indicator assay (FIG. 10D) the 5' exonuclease activity of the amplification enzyme (e.g. Taq polymerase) is measured rather than the production of amplified DNA (C. Heid et al., 1996. *Genome Research* 6:986–994). The 5' exonuclease activity is measured by monitoring the nucleolytic cleavage of a fluorescently tagged oligonucleotide probe that is capable of binding to the amplified DNA template region flanked by the Pf and Pr binding sites. The performance of this assay is dependent on the close proximity of the 3' end of the upstream primer (Pf) to the 5' end of the oligonucleotide probe. When the Pf primer is extended it displaces the 5' end of the oligonucleotide probe such that the 5' exonuclease activity of the polymerase cleaves the oligonucleotide probe. The purpose of the intron is to distance the Pf binding site sufficiently far away from the 5' end of the exonuclease probe sequence to essentially eliminate detectable exonuclease digestion of the probe oligonucleotide in the unspliced target template. Removing the intron by splicing serves to position the 3' end of the Pf binding site immediately upstream of the probe 5' binding site. The latter rearrangement enables the quantitative detection of exonuclease activity of the amplified target template (FIG. 10E).

Drug Screening

Drug screening is carried out using an indicator gene viral vector containing a non-functional indicator gene cassette with an inverted intron and a packaging vector(s). In transfected packaging host cells, the indicator gene viral vector produces an encapsidation competent (ε+) RNA transcript containing the indicator gene. The packaging vector(s) provide, in trans, the structural and/or enzymatic viral functions that are not provided by the resistance test vector, but that are necessary for viral DNA replication and particle formation. Upon co-transfection of packaging host cells, the indicator gene viral vector and packaging vectors give rise to HBV viral particles containing an encapsidated indicator gene viral vector "pregenome" RNA, which as a result of splicing of the inverted intron, contains a functional indicator gene.

Drug screening is performed as follows: indicator gene viral vector and packaging vector DNA is used to transfect the packaging host cells. Replicate transfections are performed on a series of packaging host cell cultures maintained either in the absence or presence of potential anti-viral compounds (e.g., candidate HBV P protein reverse transcriptase or polymerase inhibitors). After maintaining the packaging host cells for up to several days in the presence or absence of the candidate anti-viral drugs the level of inhibition of DNA replication is assessed either directly in the packaging host cell lysates, or in isolated HBV particles obtained by harvesting the host packaging cell culture media. Either DNA detection or indicator gene activity methods, described above, can be used to evaluate potential anti-HBV drug candidates.

EXAMPLE 9

Hepatitis Drug Susceptibility And Resistance Test Using Resistance Test Vectors Comprising Patient-Derived Segment(s) And A Non-Functional Indicator Gene Containing A Permuted Promoter.

Indicator Gene Viral Vector—Construction

Indicator gene viral vectors containing a non-functional indicator gene with a permuted promoter were designed using an HBV subgenomic viral vector comprising viral genes which are the target(s) of anti-viral drugs. The indicator gene viral vectors, pCS-HBV(NF-IG)PP-(PSAS−), are based on the subgenomic viral vector pCS-HBV. The indicator gene viral vector, pCS-HBV(NF-IG)PP-(PSAS−), contains a non-functional indicator gene cassette with a permuted promoter and all of the cis-acting regulatory elements that are necessary for HBV DNA replication (i.e. DR1, 5' ε, DR2, DR1*, 3' pA) but lacks the HBV gene sequences (i.e. C, P, S, X genes) that provide the trans-acting structural and enzymatic functions that are necessary for HBV DNA replication and virus particle formation (FIG. 11B). The C, P and X and patient sequence acceptor sites are contained within a packaging vector pPK-CPX (described in Example 8, see FIG. 9D). The S gene is contained within a packaging vector pPK-S (described in Example 8, see FIG. 9E). In this embodiment, the indicator gene viral vector, pCS-HBV(NF-IG)PP-(PSAS−) and the packaging vector pPK-CPX constitute a resistance test vector system. The non-functional indicator gene viral vector, pCS-HBV(NF-IG)PP-(PSAS−), contains the following elements in a 5' to 3' orientation: (1) the CMV IE enhancer promoter region, (2) the 5' region of the HBV genome and the DR1 and 5' ε (the pre-C ORF translation initiation codon is eliminated), (3) a non-functional indicator gene cassette assembled such that the promoter region is positioned 3', i.e. downstream, of the indicator gene ORF, (4) the 3' region of the HBV genome containing DR2, DR1*, the 3' ε, and the 3' HBV pA signal region (the pre-C ORF translation initiation codon is eliminated). The non-functional indicator gene expression cassette is comprised of some or all of the following elements arranged in the 5' to 3' orientation: (1) an internal ribosome entry site (IRES), (2) an indicator gene, which may contain an inverted intron, and (3) a transcriptional polyadenylation signal sequence (e.g. HSV-1 thymidine kinase gene, SV40) (4) an enhancer-promoter region. Within the non-functional indicator gene viral vector, the indicator gene expression cassette has a transcriptional orientation either opposite to or the same as the HBV sequence elements. In cases where the indicator gene ORF contains an intron, the intron has the same transcriptional orientation as the HBV sequence elements.

In a second embodiment, the non-functional indicator gene viral vector contains a non-functional indicator gene cassette containing a permuted promoter region, all of the cis-acting regulatory elements that are necessary for HBV DNA replication, and some or all of the HBV gene sequences (i.e. C, P, S, X genes) that provide the trans-acting structural and enzymatic functions that are necessary for HBV DNA replication and virus particle formation, pCS-HBV(NF-IG)PP-(PSAS+) (FIG. 11D). Resistance test vectors derived from the indicator gene viral vector, pCS-HBV (NF-IG)PP-(PSAS+), contain patient sequence acceptor sites and are used in conjunction with the packaging vector pPK-CSK (FIG. 9H). In this embodiment the indicator gene viral vector may also provide some or all of the packaging functions. Furthermore, in this embodiment the structural and enzymatic activities that are not provided by the indicator gene viral vector, but that are necessary for HBV DNA replication and virus particle formation, are provided using additional packaging vectors. In this embodiment, the non-functional indicator gene viral vector, pCS-HBV(NF-IG)PP-(PSAS+), contains the following elements in a 5' to 3' orientation: (1) the CMV IE enhancer-promoter region, (2) the 5' region of the HBV genome and the DR1 and 5' ε (the pre-C ORF translation initiation codon is eliminated), (3) an enhancer-promoter region (permuted promoter), (4) the P gene containing patient-derived segment (5) the indicator gene ORF (6) an internal ribosome entry site (IRES), and (7) the 3' region of the HBV genome containing DR2, DR1*, the 3' ε, and the 3' HBV pA signal region (the pre-C ORF translation initiation codon is eliminated). Within the non-functional indicator gene viral vector, the indicator gene expression cassette has a transcriptional orientation either in the reverse or forward direction with respect to the HBV sequence elements. In cases where the indicator gene contains an inverted intron, the intron has a transcriptional orientation the same as to the HBV sequence elements.

Resistance Test Vector—Construction

Figure 9E:
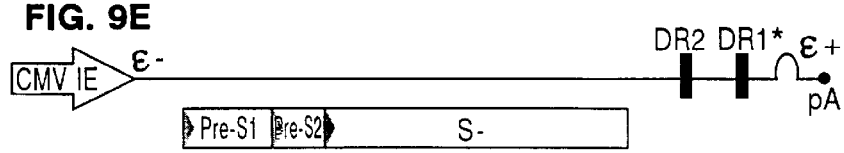

Resistance test vectors containing a non-functional indicator gene with a permuted promoter were designed using the HBV subgenomic viral vector comprising anti-viral target genes as described in Example 8. The indicator gene viral vector or the packaging vector is modified to include patient sequence acceptor sites (PSAS) for the insertion of P gene containing patient-derived segments (PDS) (described in Example 8, see FIGS. 9D and 9F). The expression of the patient-derived S gene is eliminated as described in Example 8 (see FIG. 9D). Uniform S gene expression is provided, in trans, using a separate packaging vector that provides well-characterized S gene products (FIG. 9E).

Drug Susceptibility and Resistance Test

Drug susceptibility and resistance tests are carried out with a resistance test vector based on indicator gene viral vectors, pCS-HBV(NF-IG)PP-(PSAS+), or with a resistance test vector system comprising an indicator gene viral vector, pCS-HBV(NF-IG)PP-(PSAS−) and a packaging vector, pPK-CPX, using either one type of host cell or two types of host cell. Upon co-transfection of packaging host cells, either with a resistance test vector and a packaging vector or with an indicator gene viral vector and packaging vectors (i.e. resistance test vector system) HBV viral particles are produced containing an encapsidated indicator gene "pre-genome" RNA containing a non-functional indicator gene. Within the transfected host cells, the non-functional indicator gene with the permuted promoter is converted to a functional indicator gene during the HBV DNA replication process (FIGS. 11B and 11C).

Drug susceptibility and resistance tests are performed as described in Example 8 (above). The resistance or susceptibility of patient-derived reverse transcriptase and/or DNA polymerase activities to various anti-viral drugs can be measured by measuring the levels of indicator gene expression in transfected or infected host cells. Alternatively, resistance or susceptibility can be measured by quantitating the amount of HBV DNA replication that has taken place. The latter can be performed using quantitative DNA amplification assays. In one example of this type of assay, (FIGS. 10F and 10G) the primer binding site of the reverse primer (Pr) is located in the region downstream of the 5' ε. The primer binding site of the forward primer (Pf) is located within the region flanked by the DR2 and DR1* sequences. In the linear HBV vector the Pf and Pr primers direct DNA synthesis in opposite directions. In this case, the Pr primer directs DNA synthesis in the upstream direction (toward the 5' ε) and the Pf primer directs DNA synthesis in the downstream direction (toward the 3' ε). This primer configuration does not constitute a functional amplification unit in the linear copy of the viral vector that is used for transfection. In contrast, the Pf and Pr primers assume an orientation toward each other in the rc-DNA form that is found in mature virions. Both primers now direct DNA synthesis toward the single copy of DR1 within the plus strand copy of rc-DNA. This arrangement of primers and template constitutes a functional amplification unit.

Drug Screening

Drug screening using an indicator gene viral vector that contains a non-functional indicator gene with a permuted promoter is performed essentially as described in Example 8 above.

EXAMPLE 10

Hepatitis Drug Susceptibility And Resistance Test Using Resistance Test Vectors Comprising Patient-derived Segments And A Non-Functional Indicator Gene Containing A Permuted Promoter And Translation Initiation Sites.

Indicator Gene Viral Vector

Indicator gene viral vectors containing a non-functional indicator gene with a permuted promoter and translation initiation site, pCS-HBV(NF-IG)PPTIS were designed using HBV subgenomic viral vector comprising viral genes which are the target(s) of anti-viral drugs. The indicator gene viral vectors pCS-HBV(NF-IG)PPTIS(PSAS−), are based on the subgenomic viral vector pCS-HBV. The indicator gene viral vector contains a non-functional indicator gene cassette with permuted promoter and translation initiation regions, and all of the cis-acting regulatory elements that are necessary for HBV DNA replication (i.e. DR1, 5' $\epsilon$, DR2, DR1*, 3' pA) but lacks the HBV gene sequences (i.e. C, P, S, X genes) that provide the trans-acting structural and enzymatic functions that are necessary for HBV DNA replication and virus particle formation (FIG. 12B). The C, P and X genes and patient sequence acceptor sites are contained within a packaging vector pPK-CPX (Example 8, FIG. 9D). The S gene is contained in the packaging vector, pPK-S, (Example 8, FIG. 9E). In this embodiment the indicator gene viral vector pCS-HBV(NF-IG)PPTIS (PSAS−) and the packaging vector pPK-CPX constitute a resistance test vector system. The non-functional indicator gene viral vector, pCS-HBV(NF-IG)PPTIS(PSAS−), contains the following elements in a 5' to 3' orientation: (1) the CMV IE enhancer-promoter region, (2) the 5' region of the HBV genome including the DR1 and 5' $\epsilon$ (the pre-C ORF translation initiation codon is eliminated), (3) an indicator gene ORF lacking a translation initiation site, (4) an enhancer-promoter region (permuted promoter) (5) the 3' region of the HBV genome containing DR2, a functional pre-C ORF translation initiation codon, DR1*, the 3' $\epsilon$, and the 3' HBV pA signal region. The non-functional indicator gene cassette is comprised of some or all of the following elements arranged in a 5' to 3' orientation: (1) an indicator gene ORF that does not contain an in-frame translation initiation site, (2) a transcriptional polyadenylation signal sequence (e.g. HSV-1 thymidine kinase gene, SV40), (3) an enhancer-promoter region. Within the non-functional indicator gene viral vector, pCS-HBV(NF-IG)PPTIS(PSAS−) the indicator gene expression cassette transcriptional orientation is the same as the HBV sequence elements. In cases where the indicator gene ORF contains an intron, the intron has a transcriptional orientation the same as the HBV sequence elements.

Figure 12D:
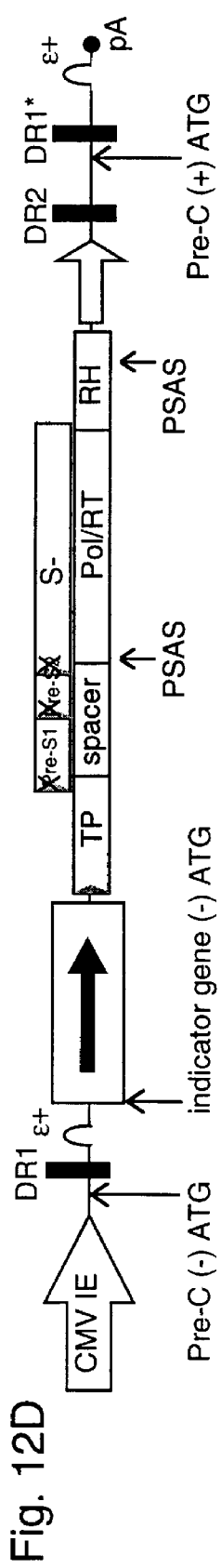
FIG. 12 A. Diagrammatic representation of the RNA pregenomic structure of HBV.
Figure 12E:
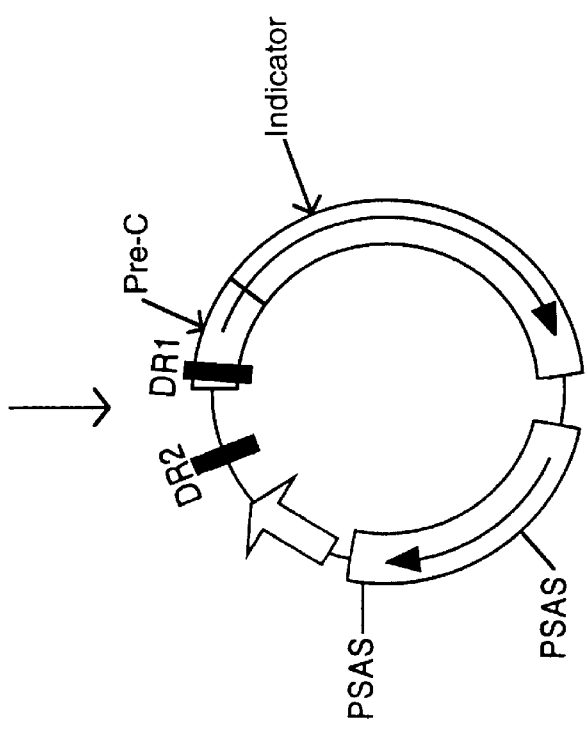

In a second embodiment, the non-functional indicator gene viral vector contains a non-functional indicator gene cassette containing a permuted promoter and translation initiation regions, all of the cis-acting regulatory elements that are necessary for HBV DNA replication, and some or all of the HBV gene sequences (i.e. C, P, S, X genes) that provide the trans-acting structural and enzymatic functions that are necessary for HBV DNA replication and virus particle formation, pCS-HBV(NF-IG)PPTIS(PSAS+) (FIG. 12D). The structural and enzymatic activities that are not provided by the indicator gene viral vector, but that are necessary for HBV DNA replication and virus particle formation, are provided using additional packaging vectors pPK-CSX (described in Example 8, see FIG. 9E). The C, S and X genes are contained within the packaging vector pPK-CSX (described in Example 8, see FIG. 9H). In this embodiment, the non-functional indicator gene viral vector, pCS-HBV(NF-IG)PPTIS(PSAS+), contains the following elements in a 5' to 3' orientation (FIG. 12D): (1) the CMV IE enhancer-promoter region, (2) the 5' region of the HBV genome including the DR1 and 5' $\epsilon$ (the pre-C ORF translation initiation codon is eliminated), (3) an indicator gene ORF lacking a translation initiation site, (4) the P gene containing patient-derived segment, (5) an enhancer-promoter region (permuted promoter) (6) the 3' region of the HBV genome containing DR2, pre-C ORF translation initiation codon, DR1*, the 3' $\epsilon$, and the 3' HBV pA signal region. Within the non-functional indicator gene viral vector, the indicator gene expression cassette has a transcriptional orientation the same as the HBV sequence elements. In cases where the indicator gene contains an inverted intron, the intron has a transcriptional orientation the same as the HBV sequence elements.

Resistance Test Vectors—Construction

Resistance test vectors containing a non-functional indicator gene with a permuted promoter were designed using the HBV subgenomic viral vector comprising anti-viral target genes as described in Example 8. The indicator gene viral vector or the packaging vector is modified to include patient sequence acceptor sites (PSAS) for the insertion of P gene containing patient-derived segments (PDS) (described in Example 8, see FIGS. 9D and 9F). The expression of the patient-derived S gene is eliminated as described in Example 8 (see FIG. 9D). Uniform S gene expression is provided, in trans, using a separate packaging vector that provides well-characterized S gene products (FIG. 9E).

Drug Susceptibility and Resistance Test

Drug susceptibility and resistance tests are carried out by the procedures described in Examples 8 and 9. Non-functional indicator gene is converted to functional indicator gene during HBV replication (FIGS. 12B and 12C).

Drug Screening

Drug screening using an indicator gene viral vector that contains a non-functional indicator gene with permuted promoter and translation initiation regions is performed essentially as described in Examples 8 and 9 (above).

EXAMPLE 11

Hepatitis Drug Susceptibility And Resistance Test Using Resistance Test Vectors Comprising Patient-derived Segments And A Non-Functional Indicator Gene With Permuted Coding Regions.

Indicator Gene Viral Vector—Constuction

Indicator gene viral vectors containing a non-functional indicator gene with permuted coding region were designed using HBV subgenomic viral vectors comprising viral genes which are the target(s) of anti-viral drugs. The indicator gene viral vectors pCS-HBV(NF-IG)PCR(PSAS−), are based on the subgenomic viral vector pCS-HBV. The indicator gene viral vector contains a non-functional indicator gene cassette with a permuted coding region, and all of the cis-acting regulatory elements that are necessary for HBV DNA replication (i.e. DR1, 5' $\epsilon$, DR2, DR1*, 3' pA) but lacks the HBV gene sequences (i.e. C, P, S, X genes) that provide the trans-acting structural and enzymatic functions that are necessary for HBV DNA replication and virus particle formation (FIG. 13B). The C, P and X genes and patient sequence acceptor sites are contained within a packaging vector, pPK-CPX and the S gene is provided by the packaging vector pPK-S (described in Example 8, see FIGS. 9D and 9E). In this embodiment the indicator gene viral vector pCS-HBV(NF-IG)PCR(PSAS−) and the packaging vector pPK-CPX constitute a resistance test vector system. The non-functional indicator gene viral vector, pCS-HBV(NF-IG)PCR(PSAS−), contains the following elements in a 5' to 3' orientation: (1) the CMV IE enhancer-promoter region, (2) the 5' region of the HBV genome including the DR1 and 5' ε (the pre-C ORF translation initiation codon is eliminated), (3) a non-functional indicator gene cassette assembled such that the promoter region and a 5' portion of the coding region are positioned 3', i.e. downstream, of the remaining 3' portion of the coding region, (4) the 3' region of the HBV genome containing DR2, DR1*, the 3' ε, and the 3' HBV pA signal region (the pre-C ORF translation initiation codon is eliminated). The non-functional indicator gene cassette is comprised of some or all of the following elements arranged in the 5' to 3' orientation: (1) the 3' region of an intron ending in a splice acceptor sequence (2) the 3' region of an indicator (reporter) ORF or selectable marker ORF, (3) a transcriptional polyadenylation signal sequence (e.g. HSV-1 thymidine kinase gene, SV40), (4) an enhancer-promoter region, (5) the 5' region of an indicator gene ORF, (6) the 5' region of an intron beginning in a splice donor sequence. Within the non-functional indicator gene viral vector, the indicator gene expression cassette has a transcriptional orientation either the same or opposite the HBV sequence elements. In cases where the indicator gene ORF contains an intron, the intron is oriented in the same orientation with respect to the HBV sequence elements.

Figures 13D, 13E:
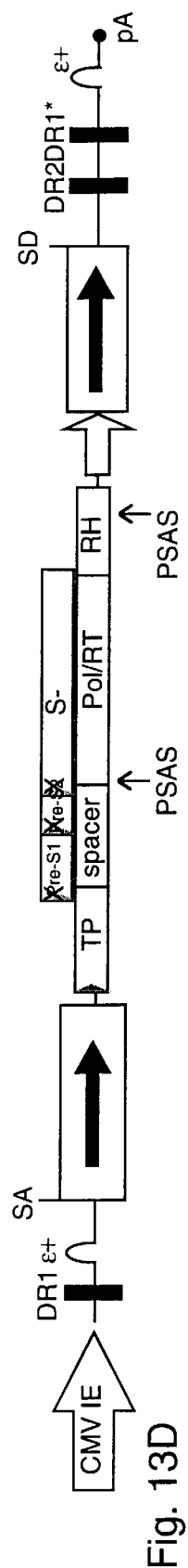
FIG. 13 A. Diagrammatic representation of the RNA pregenomic structure of HBV.

In a second embodiment, the non-functional indicator gene viral vector contains a non-functional indicator gene cassette containing a permuted coding region, all of the cis-acting regulatory elements that are necessary for HBV DNA replication, and some or all of the HBV gene sequences (i.e. C, P, S, X genes) that provide the trans-acting structural and enzymatic functions that are necessary for HBV DNA replication and virus particle formation pCS-HBV(NF-IG)PCR(PSAS+) (FIG. 13D). Resistance test vectors derived from the indicator gene viral vector pCS-HBV(NF-IG)PCR(PSAS+) contain patient sequence acceptor sites (PSAS) and are used in conjunction with the packaging vector pPK-CSK (described in Example 8, see FIG. 9H). In this embodiment the indicator gene viral vector may also provide some or all of the packaging functions. In this embodiment the structural and enzymatic activities that are not provided by the indicator gene viral vector, but that are necessary for HBV DNA replication and virus particle formation, are provided using additional packaging vectors. In this embodiment, the non-functional indicator gene viral vector contains the following elements in a 5' to 3' orientation: (1) the CMV IE enhancer promoter region, (2) the region of the HBV genome immediately downstream of the pre-C ORF translation initiation codon and the DR1 and 5' ε, (3) the indicator gene cassette containing a region of the HBV genome which may contain some or all of the C, P, S, and X genes, (4) the region of the HBV genome containing DR2, DR1*, the 3' ε, and the 3' HBV pA signal region (the pre-C ORF initiation codon has been eliminated). Within the non-functional indicator gene viral vector, pCS-HBV(NF-IG)PCR(PSAS+) the indicator gene expression cassette has a transcriptional orientation either the same or opposite to HBV sequence elements. In cases where the indicator gene contains an inverted intron, the intron is oriented in the same orientation with respect to the HBV sequence elements.

Resistance Test Vectors—Construction

Resistance test vectors containing a non-functional indicator gene with a permuted coding region were designed using the HBV subgenomic viral vector comprising anti-viral target genes as described in Example 8. The indicator gene viral vector or the packaging vector is modified to include patient sequence acceptor sites (PSAS) for the insertion of P gene containing patient-derived segments (PDS) (described in Example 8, see FIGS. 9D and 9F). The expression of the patient-derived S gene is eliminated as described in Example 8 (see FIG. 9D). Uniform S gene expression is provided, in trans, using a separate packaging vector that provides well-characterized S gene products (FIG. 9E).

Drug Susceptibility and Resistance Tests

Drug susceptibility and resistance tests are carried out by the procedures described in Examples 8 and 9. The non-functional indicator gene is converted to a functional indicator gene during HBV replication (FIGS. 13B and 13C).

Drug Screening

Drug screening using an indicator gene viral vector that contains a non-functional indicator gene with permuted promoter and translation initiation regions is performed essentially as described in Examples 8 and 9 (above).

EXAMPLE 12

Hepatitis Drug Susceptibility And Resistance Test Using Resistance Test Vector Comprising Patient-Derived Segment(s) And A Functional Indicator Gene.

Indicator Gene Viral Vector—Construction

Indicator gene viral vectors containing a functional indicator gene were designed using HBV subgenomic viral vectors comprising viral genes which are the target(s) of anti-viral drugs. The indicator gene viral vectors pCS-HBV (F-IG)(PSAS−), are based on the subgenomic viral vector pCS-HBV. The indicator gene viral vector, pCS-HBV(F-IG) (PSAS−), contains a functional indicator gene cassette and all of the cis-acting regulatory elements that are necessary for HBV DNA replication (i.e. DR1, 5' ε, DR2, DR1*, 3' pA) but lacks the HBV gene sequences (i.e. C, P, S, X genes) that provide the trans-acting structural and enzymatic functions that are necessary for HBV DNA replication and virus particle formation (FIG. 14B). The C, P and X genes and patient sequence acceptor sites are contained within a packaging vector pPK-CPX and the S gene is contained within the packaging vector, pPK-S, (described below see FIGS. 9D and 9E). In this embodiment the indicator gene viral vector pCS-HBV(F-IG)(PSAS−) and the packaging vector pPK-CPX constitute a resistance test vector system. The functional indicator gene viral vector pCS-HBV(F-IG) (PSAS-) contains the following elements in a 5' to 3' orientation: (1) the CMV IE enhancer-promoter region, (2) the 5' region of the HBV genome including the DR1 and 5' ε (the pre-C ORF translation initiation codon is eliminated), (3) a functional indicator gene cassette, (4) the 3' region of the HBV genome containing DR2, DR1*, the 3' ε, and the 3' HBV pA signal region (the pre-C ORF translation initiation codon is eliminated). The indicator gene expression cassette is comprised of some or all of the following elements arranged in the 5' to 3' orientation: (1) a transcriptional enhancer-promoter region, (2) an intron, (3) an indicator gene ORF or selectable marker gene ORF, (4) a transcriptional polyadenylation signal sequence (e.g. SV40) or unidirectional (HSV-1 thymidine kinase gene). The indicator gene expression cassette has a transcriptional orientation the same as or opposite to the HBV sequence elements.

Figure 14D:
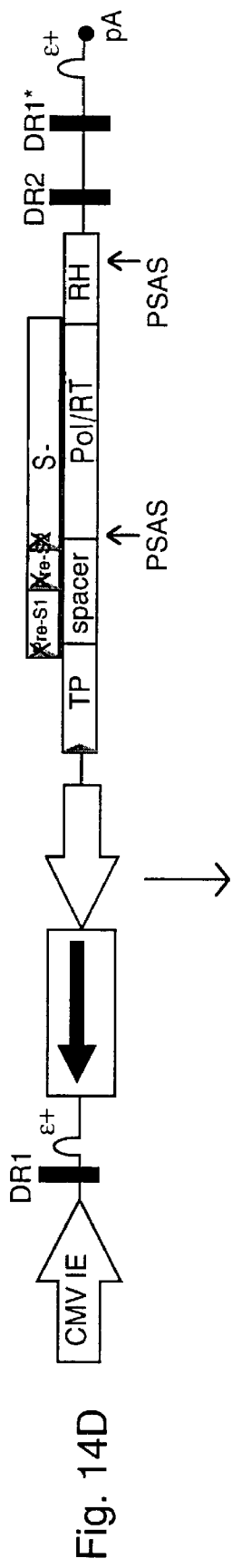
FIG. 14 A. Diagrammatic representation of the RNA pregenomic structure of HBV.

In a second embodiment, the indicator gene viral vector contains a functional indicator gene cassette, all of the cis-acting regulatory elements that are necessary for HBV DNA replication, and some or all of the HBV gene sequences (i.e. C, P, S, X genes) that provide the trans-acting structural and enzymatic functions that are necessary for HBV DNA replication and virus particle formation pCS-HBV(F-IG)(PSAS+) (FIG. 14D). Resistance test vectors derived from the indicator gene viral vector pCS-HBV(F-IG)(PSAS+) contain patient sequence acceptor sites (PSAS) and are used in conjunction with the packaging vector pPK-CSK. In this embodiment the indicator gene viral vector also provides some or all of the packaging functions. The structural and enzymatic activities that are not provided by the indicator gene viral vector, but that are necessary for HBV DNA replication and virus particle formation, are provided using additional packaging vectors pPK-CSX (described in Example 8, see FIG. 9H). In this embodiment, the functional indicator gene viral vector contains the following elements in a 5' to 3' orientation: (1) the CMV IE enhancer promoter region, (2) the region of the HBV genome immediately downstream of the pre-C ORF translation initiation codon and the DR1 and 5' ε, (3) a functional indicator gene cassette within the region of the HBV genome that contains some or all of the C, P, S, and X genes, (4) the region of the HBV genome containing DR2, DR1*, the 3' ε, and the 3' HBV pA signal region. Within the indicator gene viral vector, the indicator gene expression cassette has a transcriptional orientation either opposite to or the same as the HBV sequence elements.

Resistance Test Vector—Construction

Resistance test vectors containing a non-functional indicator gene with a permuted promoter were designed using the HBV subgenomic viral vector comprising anti-viral target genes as described in Example 8. The indicator gene viral vector or the packaging vector is modified to include patient sequence acceptor sites (PSAS) for the insertion of P gene containing patient-derived segments (PDS) (described in Example 8, see FIGS. 9D and 9F). The expression of the patient-derived S gene is eliminated as described in Example 8 (see FIG. 9D). Uniform S gene expression is provided, in trans, using a separate packaging vector that provides well-characterized S gene products (FIG. 9E).

Drug Susceptibility and Resistance Test

Drug susceptibility and resistance test are carried out with a resistance test vector based on a functional indicator gene viral vector, pCS-HBV(F-IG) (PSAS+) or with a resistance test vector system based on an indicator gene viral vector, pCS-HBV(F-IG)(PSAS−) and a packaging vector(s). In transfected packaging host cells, the indicator gene viral vector produces an encapsidation competent (ε+) RNA transcript containing a functional indicator gene cassette. The packaging vector(s) provide, in trans, the structural and/or enzymatic viral functions that are not provided by the functional indicator gene viral vector, but that are necessary for viral DNA replication and particle formation. Upon co-transfection of packaging host cells, the indicator gene viral vector and packaging vectors are capable of forming HBV particles containing an encapsidated indicator gene viral vector "pregenome" RNA containing a functional indicator gene cassette.

Figure 14E:
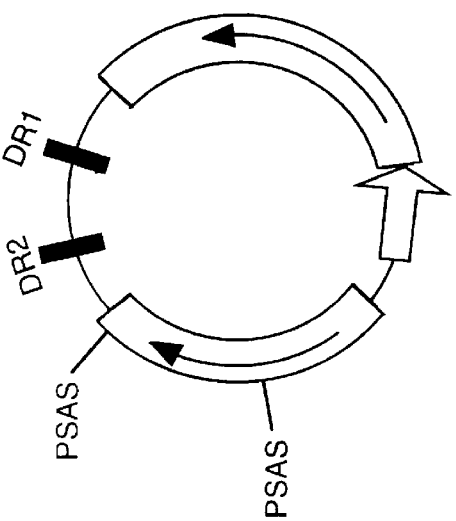

In this example, the indicator gene viral vector contains a functional indicator gene cassette and therefore can produce indicator gene activity in transfected cells in the absence of HBV DNA replication (FIG. 14). In the case of a functional indicator gene, the inhibition of HBV DNA replication by drugs can be evaluated by harvesting the virus particles produced in the packaging host cell and using the particles (or particle DNA) to infect (or transfect) a target host cell. Alternatively, DNA replication can be measured directly in virus particles isolated from packaging host cells by using the DNA as an indicator. A drug which inhibits HBV DNA replication will reduce the formation of virus particles containing the "mature" rc-DNA form of the functional indicator gene viral vector. Consequently, the functional indicator gene will not be efficiently transferred to the target host cells during infection/transfection and the amount of indicator gene viral vector cccDNA and indicator gene activity in these cells will be reduced. The detection of indicator gene expression in target host cells in a two cell assay is performed as described in Example 8. The detection of rc-DNA in virus particles is performed using DNA as an indicator as described in Example 9 and illustrated in FIGS. 10F and 10G.

Drug Screening

Drug screening using an indicator gene viral vector that contains a non-functional indicator gene with permuted promoter and translation initiation regions is performed essentially as described in Examples 8 and 9 (above).

| | Oligonucleotides |
|---|---|
| 1) | 5'-AGTGAATTAGCCCTTCCACCCGGGTCGAGCTTGGCGTAATCA-3' (42-mer) (SEQ ID NO: 1) |
| 2) | 5'-CTGTTGGGAAGGGCGATCTCTAGATGCTAGAGATTTTCCACA-3' (42-mer) (SEQ ID NO: 2) |
| 3) | 5'-CTCCTCCTCCAAGTCTGAGCGGCCGCCTTTAGCATCTGATGCAC-3' (44-mer) (SEQ ID NO: 3) |
| 4) | 5'-CTCCTCCTCCAAGTCTGAGCGGCCGCCATATGGTGTTTACTAA-3' mer) (SEQ ID NO: 4) |
| 5) | 5'-GGTCTAACCAGAGAGACCCGGTTCACTAAACGAGCT-3' (36-mer) (SEQ ID NO: 5) |
| 6) | 5'-GAATTCGCGGCCGCAATTCCGCCCCTCTCCCT-3' (32-mer) (SEQ ID NO: 6) |
| 7) | 5'-GTTAACGCGGCCGCGATATAGTTCCTCCTTTC-3' (32-mer) (SEQ ID NO: 7) |
| 8) | 5'-GAATTCTCGCGACCATGGAAGACGCCAAAAAC-3' (32-mer) (SEQ ID NO: 8) |
| 9) | 5'-GTTAACAGATCTCTCGAGTTACAATTTGGACTTTCC-3' (36-mer) (SEQ ID NO: 9) |
| 10) | 5'-AGACGGGCACACACTACTTAATACGACTCACTATAGGG TGAAGCACTCAAGGCAAG-3' (56-mer) (SEQ ID NO: 10) |
| 11) | 5'-AAGAGTGACCTGAGGGAAGTTAACGGATACAGTTCCTTGTCT-3' (42-mer) (SEQ ID NO: 11) |
| 12) | 5'-TCCAGCACTGACTAATTTGTCGACTTGTTCATTTCCTCCAAT-3' (42-mer) (SEQ ID NO: 12) |
| 13) | 5'-TAACGCCTATTCTGCTATGCCGACACCCAATTCTGAAAATGG-3' |

-continued

Oligonucleotides (42-mer) (SEQ ID NO: 13)
14) 5'-AAGGATACAGTTCCTTGTCGATCGGCTCCTGCTTCTGAGGGG-3'
   (42-mer) (SEQ ID NO: 14)
15) 5'-CTAAAAATAGTACTTTCCGGATCCCAGCACTGACTAATTTAT-3'
   (42-mer) (SEQ ID NO: 15)
16) 5'-TTAGCTCCTTCGGTCCTCCAATCGTTGTCAGAAGTAAGTTGG-3'
   (42-mer) (SEQ ID NO: 16)
17) 5'-GTCCCAGATAAGTGCCAAGGATTCGTTCACTAATCGAATGGA-3'
   (42-mer) (SEQ ID NO: 17)
18) 5'-GAATTCGTTAACTTCCCTCAGATCACTCTTTGG-3'
   (33-mer) (SEQ ID NO: 18)
19) 5'-GTTAACGTCGACTTGTTCATTTCCTCCAAT-3'
   (30-mer) (SEQ ID NO: 19)
20) 5'-GAATTCCGATCGACAAGGAACTGTATCCTTTAACTTCCC
   TCAGATCACTCTTTGG-3' (55-mer) (SEQ ID NO: 20)
21) 5'-GTTAACGGATCCCAGCACTGACTAATTTATCTACTTGTTC
   ATTTCCTCCAAT-3' (52-mer) (SEQ ID NO: 21)
22) 5'-GAATTCGTTAACTTCCCTCA(G/A)ATC(A/C)CTCTTTGG-3'
   (33-mer pool) (SEQ ID NO: 22)
23) 5'-GTTAACGTCGACTT(G/T)(T/C)TCATTTCCTCC(A/T)AT-3'
   (30-mer pool) (SEQ ID NO: 23)
24) 5'-GAATTCCGATCGACAAGGAACTGTATCCTTTAACTTCCC
   TCA(G/A)ATC(A/C)CTCTTTGG-3' (55-mer pool) (SEQ ID
   NO: 24)
25) 5'-GTTAACGGATCCCAGCACTGACTAATTTATCTACTT(G/T)
   (T/C)TCATTTCCTCC(A/T) AT-3'
   (52-mer pool) (SEQ ID NO: 25)
26) 5'-ATCTCTTACCTGTCCTATCTAACAGGCCAGGATTAA-3'
   (36-mer) (SEQ ID NO: 26)
27) 5'-GAATTCTCGCGACCACCATGGCGCGTTCAACGCTC-3'
   (35-mer) (SEQ ID NO: 27)
28) 5'-GTTAACAGATCTTCATGGCTCGTACTCTAT-3'
   (30-mer) (SEQ ID NO: 28)
29) 5'-GAATTCGCGCGCAAGCGGCCGCAACCCGGGAAAAGCTT
   AAGCATGCAACCCGGGAAGAATTCAATCGCGAAA-3'
   (72-mer) (SEQ ID NO: 29)
30) 5'-GTTAACGCGCGCTTCTCGAGTTGCGGCCGCTTGCTAGCTT
   AGATCTTTGGGCCCTTTCGCGATTGAATTCTT-3'
   (72-mer) (SEQ ID NO: 30)
31) 5'-GAATTCAAGCTTGGCCATTGCATACGTTGT-3'
   (30-mer) (SEQ ID NO: 31)
32) 5'-GTTAACGCATGCATAAGAAGCCAA-3'
   (24-mer) (SEQ ID NO: 32)
33) 5'-GAATTCGCATGCTCCCCTGCTCCGACCCGG-3'
   (30-mer) (SEQ ID NO: 33)
34) 5'-GTTAACGAATTCTCCTGCGGGGAGAAGCAG-3'
   (30-mer) (SEQ ID NO: 34)
35) 5'-GAATTCAGATCTGCCATACCACATTTGTAG-3'
   (30-mer) (SEQ ID NO: 35)
36) 5'-GTTAACGCTAGCTCCAGACATGATAAGATA-3'
   (30-mer) (SEQ ID NO: 36)
37) 5'-GAATTCGCTAGCATCCCGCCCCTAACTCCG-3'
   (30-mer) (SEQ ID NO: 37)
38) 5'-GTTAACGTCGACGCAAAAGCCTAGGCCTCC-3'
   (30-mer) (SEQ ID NO: 38)
39) 5'-GAATTCTCGCGAACAGTTGGCCCT-3'
   (24-mer) (SEQ ID NO: 39)
40) 5'-GTTAACAGATCTTTACGCGAACGCGAAGTC-3'
   (30-mer) (SEQ ID NO: 40)
41) 5'-GTTAACGAATTCTTGCAAAAAGCTTTGCAAGATGGATA
   AAGTTTTTAGAAACTCCAGTAGGACTCC-3'
   (66-mer) (SEQ ID NO: 41)
42) 5'-GAATTCTCGCGATCTAGACGTTCTACCTTTCTCTTCTT
   TTTTGGAGGAGTCCTACTGGAGTTT-3'
   (63-mer) (SEQ ID NO: 42)
43) 5'-GTTAACGAATTCCCACCATGATTGAACAAGATGGA-5'
   (35-mer) (SEQ ID NO: 43)
44) 5'-GAATTCAGATCTTCAGAAGAACTCGTCAAG-3'
   (30-mer) (SEQ ID NO: 44)
45) 5'-CCCCGTGCCAAGAGTGACTACGTAAGTACCGCCTATAGA-3'
   (39-mer) (SEQ ID NO: 45)
46) 5'-CTCTGCTTCTCCCCGCAGCTGGAGAATTCAATCGCGAAA-3'
   (39-mer) (SEQ ID NO: 46)
47) 5'-GTTAACGAATTCCCACCATGAACACGATTAACATC-5'
   (35-mer) (SEQ ID NO: 47)
48) 5'-CAGGATCCAGACGTCTGGCGGCCGCCGGTGAAGCTTGGCCCATTGCAT
   ACG-3'
   (51-mer) (SEQ ID NO: 48)

-continued

Oligonucleotides 49) 5'-CCAGGCTCAGATCTGGTCTAACCAGAGAGACCCGGTTCACTAAACGA
GCT-3'
(51-mer) (SEQ ID NO: 49)
50) 5'-CCCATCTCTCTCCTTCTAGC-3'
(20-mer) (SEQ ID NO: 50)
51) 5'-AGCTTCACCGGCGGCCGCGACGT-3'
(23-mer) (SEQ ID NO: 51)
52) 5'-CGCGGCCGCCGGTGA-3'
(15-mer) (SEQ ID NO: 52)
53) 5'-AATTGTCCCTCATATCGCCTCCTCCAGGTCTGAAGATCTCGTCTCCCCGGG
GAGACGCA-3'
(59-mer) (SEQ ID NO: 53)
54) 5'-AGAATGAGAAGAGCTGAGCCAGCAGCAGATGGGGTGGGAGCAGTATC-3'
(47-mer) (SEQ ID NO: 54)
55) 5'-TATGCQTCTCCCCGGGGAGACGAGATCTTCAGACCTGGAGGAGGCGATATG
AGGGAC-3'
(57-mer) (SEQ ID NO: 55)
56) 5'-TCGAGATACTGCTCCCACCCCATCTGCTGCTGGCTCAGCTCTTCTCA-3'
(47-mer) (SEQ ID NO: 56)
57) 5'-AGCTTGCCTTGAGTGCTTCAATCTAGAGCCATACCACATTTGTAGAGGTTT
TACTTGCTTTAAAAAACCT-3'
(70-mer) (SEQ ID NO: 57)
58) 5'-AACCTCTACAAATGTGGTATGGCTCTAGATTGAAGCACTCAAGGCA-3'
(46-mer) (SEQ ID NO: 58)
59) 5'-CCCACACCTCCCCCTGAACCTGAAACATAAAATGAATGCAATTGTTGTTAT
TAACTTGTTTATTGCAG-3'
(68-mer) (SEQ ID NO: 59)
60) 5'-ACAACAATTGCATTCATTTTATGTTTCAGGTTCAGGGGGAGGTGTGGGAGG
TTTTTTAAAGCAAGTAA-3'
(68-mer) (SEQ ID NO: 60)
61) 5'-CTTATAATGGTTACAAATAAAGCAATAGCATCACAAATTTCACAAATAAAG
CATTTTTTTCACTGCAT-3'
(68-mer) (SEQ ID NO: 61)
62) 5'-TATTTGTGAAATTTGTGATGCTATTGCTTTATTTGTAACCATTATAAGCTG
CAATAAACAAGTTAATA-3'
(68-mer) (SEQ ID NO: 62)
63) 5'-TATTTGTGAAATTTGTGATGCTATTGCTTTATTTGTAACCATTATAAGCTG
CAATAAACAAGTTAATA-3'
(68-mer) (SEQ ID NO: 63)
64) 5'-CCAGACATGATAAGATACATTGATGAGTTTGGACAAACCACAACTAGAATG
CAGTGAAAAAAATGCTT-3'
(68-mer) (SEQ ID NO: 64)
65) 5'-CCCTAACTCCGCCCAGTTCCGCCCATTCTCCQCCCCATGGCTGACTAATTT
TTTTTATTTATGCAGAGGCCGAGGCCGC-3'
(79-mer) (SEQ ID NO: 65)
66) 5'-TTAGTCAGCCATGGGGCGGAGAATGGGCGGAACTGGGCGGAGTTAGGGGCG
GGATGGCGCGCCGGTGT-3'
(68-mer) (SEQ ID NO: 66)
67) 5'-CTCGGCCTCTGAGCTATTCCAGAAGTAGTGAGGAGGCTTTTTTGGAGGCCT
AGGCTTTTGCGGCGCGCCACCTGCATTA-3'
(79-mer) (SEQ ID NO: 67)
68) 5'-GCCTCCTCACTACTTCTGGAATAGCTCAGAGGCCGAGGCGGCCTCGGCCTC
TGCATAAATAAAAAAAA-3'
(68-mer) (SEQ ID NO: 68)
69) 5'-TCATTAATGCAGGTGGCGCGCCGCAAAAGCCTAGGCCTCCAAAAAA-3'
(46-mer) (SEQ ID NO: 69)
70) 5'-CTAGAGGGGGAGGCTAACTGAAACACGGAAGGAGACAATACCGGAAGGAAC
CCGCGCTATGACGGCA-3'
(67-mer) (SEQ ID NO: 70)
71) 5'-ATAAAAAGACAGAATAAAACCCACGGGTGTTGGGTCGTTTGTTCATAAACC
CGGGCTTCGGTCCCA-3'
(66-mer) (SEQ ID NO: 71)
72) 5'-CTTCCGGTATTGTCTCCTTCCGTGTTTCAGTTAGCCTCCCCCT-3'
(43-mer) (SEQ ID NO: 72)
73) 5'-GTGGGTTTTATTCTGTCTTTTTATTGCCGTCATAGCGCGGGTTC-3'
(44-mer) (SEQ ID NO: 73)
74) 5'-CCGGTGGGACCGAAGCCCGGGTTTATGAACAAACGACCCAACACCC-3'
(46-mer) (SEQ ID NO: 74)
75) 5'-AACGGCGGCGGGAAGTTCTCCTGCGTCATCGTCGGGAAGA-3'
(40-mer) (SEQ ID NO: 75)
76) 5'-CATGTTGCAGGGCCCCTAGGAAAAAGGGCTGTTGGAAATGTG-3'
(42-mer) (SEQ TD NO: 76)
77) 5'-CACTCCATGTACCGGTTCTTTTAGAATYTCYCTG-3'
(34-mer) (SEQ ID NO: 77)
78) 5'-CGTTTAGTGAACCGTCAGATCGCCTGGAGACGCCATCCACGCTGTTTTGAC
CTCCATAGAAGACAC-3'
(66-mer) (SEQ ID NO: 78)
79) 5'-AACAGCGTGGATGGCGTCTCCAGGCGATCTGACGGTTCACTAAACGA -continued

| | Oligonucleotides |
|---|---|
| | GCT-3' |
| | (50-mer) (SEQ ID NO: 79) |
| 80) | 5'-CGGGACCGATCCAGCCTCCGCGGCCGGGAACGGTGCATTGGAACGCGGATT CCCCGTGCCAAGAGTTAC-3' |
| | (69-mer) (SEQ ID NO: 80) |
| 81) | 5'-TCCGCGTTCCAATGCACCGTTCCCGGCCGCGGAGGCTGGATCGGTCCCGGT GTCTTCTATGGAGGTCAA-3' |
| | (69-mer) (SEQ ID NO: 81) |
| 82) | 5'-GTAAGTACCGCCTATAGAGTCTATAGGCCCACCCCCTTGGCTTCTTATGCA TGCTCCCCTGCTCCG-3' |
| | (66-mer) (SEQ ID NO: 82) |
| 83) | 5'-AAGAAGCCAAGGGGGTGGGCCTATAGACTCTATAGGCGGTACTTACGTAAC TCTTGGCACGGGGAA-3' |
| | (66-mer) (SEQ ID NO: 83) |
| 84) | 5'-ATCCGGGCTCCTCGCCCGCCCGGACCCACAGGCCACCCTCAACCGTCCTGG CCCCGGACC-3' |
| | (60-mer) (SEQ ID NO: 84) |
| 85) | 5'-GAGGGTGGCCTGTGGGTCCGGGCGGGCGAGGAGCCCGGATCGGAGCAGGGG AGCATGCAT-3' |
| | (60-mer) (SEQ ID NO: 85) |
| 86) | 5'-CAAACCCCACCCCTCACTCTGCTTCTCCCCGCAGCTGAGATCTG-3' |
| | (44-mer) (SEQ ID NO: 86) |
| 87) | 5'-CTAGCAGATCTCAGCTGCGGGGAGAAGCAGAGTGAGGGGTGGGGTTTGGG TCCGGGGCCAGGACGGTT-3' |
| | (68-mer) (SEQ ID NO: 87) |
| 88) | 5'-CGGGACCGATCCAGCCTCCGCGGCCGGGAACGGTGCATTGGAACGCGGAT TCCCCGTGCCAAGAGTTACCTGAGATCT-3' |
| | (78-mer) (SEQ ID NO: 88) |
| 89) | 5'-CTAGCAGATCTCAGGTAACTCTTGGCACGGGGAA-3' |
| | (34-mer) (SEQ ID NO: 89) |
| 90) | 5'-CATGGTGGTAGATCTCACA-3' |
| | (19-mer) (SEQ ID NO: 90) |
| 91) | 5'-AGCTTGTGAGATCTACCAC-3' |
| | (16-mer) (SEQ ID NO: 91) |
| 92) | 5'-AGATCTCACACACA-3' |
| | (14-mer) (SEQ ID NO: 92) |
| 93) | 5'-AGCTTGTGTGTGAGATCTCCT-3' |
| | (21-mer) (SEQ ID NO: 93) |
| 94) | 5'-CTAGAGGGGGAGGCTAACTGAAACACGGAAGGAGACAATACCGGAAGGAAC CCGCGCTATGACGGCA-3' |
| | (67-mer) (SEQ ID NO: 94) |
| 95) | 5'-ATAAAAAGACAGAATAAAACCCACGGGTGTTGGGTCGTTTGTTCATAAACC CGGGCTTCGGTCCCA-3' |
| | (66-mer) (SEQ ID NO: 95) |
| 96) | 5'-CTTCCGGTATTGTCTCCTTCCGTGTTTCAGTTAGCCTCCCCCT-3' |
| | (43-mer) (SEQ ID NO: 96) |
| 97) | 5'-GTGGGTTTTATTCTGTCTTTTTATTGCCGTCATAGCGCGGGTTC-3' |
| | (44-mer) (SEQ ID NO: 97) |
| 98) | 5'-CCGGTGGGACCGAAGCCCGGGTTTATGAACAAACGACCCAACACCC-3' |
| | (46-mer) (SEQ ID NO: 98) |
| 99) | 5'-GAGGCCCCAAGGGGTTATGCTATCTAGAGGTACCACGCGTGAATTCTCGA GGCTAGCAGATCTCCATGGTATTATCGTGTTTTCAAAGGAAAACCACGTC CC-3' |
| | (103-mer) (SEQ ID NO: 99) |
| 100) | 5'-GCATAACCCCTTGGGGCCTCTAAACGGGTCTTGAGGGGTTTTTGCTCACC GGCGCGCCACCTGCATTA-3' |
| | (69-mer) (SEQ ID NO: 100) |
| 101) | 5'-CACGGGGACGTGGTTTTCCTTTGAAAAACACGATAATACCATGGAGATCT GCTAGCCTCGAGAATTCACGCGTGGTACCTCTAGATA-3' |
| | (87-mer) (SEQ ID NO: 101) |
| 102) | 5'-TCATTAATGCAGGTGGCGCGCCGGTGAGCAAAAAACCCCTCAAGACC CGTTTA-3' |
| | (53-mer) (SEQ ID NO: 102) |
| 103) | 5'-AATTACACCGGCGTCGCCCTATAGTGAGTCGTATTAGCGGCCGCGAC GT-3' |
| | (49-mer) (SEQ ID NO: 103) |
| 104) | 5'-CGCGGCCGCTAATACGACTCACTATAGGGCGACGCCGGTGT-3' |
| | (41-mer) (SEQ ID NO: 104) |
| 105) | 5'-GTCTGTTGTGTGACTCTGCCCTATAGTGAGTCGTATTACCCTTTTAGTCAG TGTGG-3' |
| | (56-mer) (SEQ ID NO: 105) |

SEQUENCE LISTING ( 1 ) GENERAL INFORMATION:

( i i i ) NUMBER OF SEQUENCES: 105

( 2 ) INFORMATION FOR SEQ ID NO:1:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

AGTGAATTAG CCCTTCCACC CGGGTCGAGC TTGGCGTAAT CA      42

( 2 ) INFORMATION FOR SEQ ID NO:2:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

CTGTTGGGAA GGGCGATCTC TAGATGCTAG AGATTTTCCA CA      42

( 2 ) INFORMATION FOR SEQ ID NO:3:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

CTCCTCCTCC AAGTCTGAGC GGCCGCCTTT AGCATCTGAT GCAC      44

( 2 ) INFORMATION FOR SEQ ID NO:4:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

CTCCTCCTCC AAGTCTGAGC GGCCGCCATA TGGTGTTTTA CTAA      44

( 2 ) INFORMATION FOR SEQ ID NO:5:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

GGTCTAACCA GAGAGACCCG GTTCACTAAA CGAGCT 36

(2) INFORMATION FOR SEQ ID NO:6:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

GAATTCGCGG CCGCAATTCC GCCCCTCTCC CT 32

(2) INFORMATION FOR SEQ ID NO:7:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

GTTAACGCGG CCGCGATATA GTTCCTCCTT TC 32

(2) INFORMATION FOR SEQ ID NO:8:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

GAATTCTCGC GACCATGGAA GACGCCAAAA AC 32

(2) INFORMATION FOR SEQ ID NO:9:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

GTTAACAGAT CTCTCGAGTT ACAATTTGGA CTTTCC 36

(2) INFORMATION FOR SEQ ID NO:10:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

AGACGGGCAC ACACTACTTA ATACGACTCA CTATAGGGTG AAGCACTCAA 50

GGCAAG 56

( 2 ) INFORMATION FOR SEQ ID NO:11:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

```
AAGAGTGACC TGAGGGAAGT TAACGGATAC AGTTCCTTGT CT                    42
```

( 2 ) INFORMATION FOR SEQ ID NO:12:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

```
TCCAGCACTG ACTAATTTGT CGACTTGTTC ATTTCCTCCA AT                    42
```

( 2 ) INFORMATION FOR SEQ ID NO:13:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

```
TAACGCCTAT TCTGCTATGC CGACACCCAA TTCTGAAAAT GG                    42
```

( 2 ) INFORMATION FOR SEQ ID NO:14:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

```
AAGGATACAG TTCCTTGTCG ATCGGCTCCT GCTTCTGAGG GG                    42
```

( 2 ) INFORMATION FOR SEQ ID NO:15:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

```
CTAAAAATAG TACTTTCCGG ATCCCAGCAC TGACTAATTT AT                    42
```

( 2 ) INFORMATION FOR SEQ ID NO:16:

( i ) SEQUENCE CHARACTERISTICS:
        ( A ) LENGTH: 42 base pairs
        ( B ) TYPE: nucleic acid ( C ) STRANDEDNESS: single
( D ) TOPOLOGY: linear ( i i ) MOLECULE TYPE: DNA (genomic)

( x i ) SEQUENCE DESCRIPTION: SEQ ID NO:16:

TTAGCTCCTT CGGTCCTCCA ATCGTTGTCA GAAGTAAGTT GG 42

( 2 ) INFORMATION FOR SEQ ID NO:17:

( i ) SEQUENCE CHARACTERISTICS:
( A ) LENGTH: 42 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:17:

GTCCCAGATA AGTGCCAAGG ATTCGTTCAC TAATCGAATG GA 42

( 2 ) INFORMATION FOR SEQ ID NO:18:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:18:

GAATTCGTTA ACTTCCCTCA GATCACTCTT TGG 33

( 2 ) INFORMATION FOR SEQ ID NO:19:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:19:

GTTAACGTCG ACTTGTTCAT TTCCTCCAAT 30

( 2 ) INFORMATION FOR SEQ ID NO:20:

( i ) SEQUENCE CHARACTERISTICS:
( A ) LENGTH: 55 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:20:

GAATTCCGAT CGACAAGGAA CTGTATCCTT TAACTTCCCT CAGATCACTC 50

TTTGG 55

( 2 ) INFORMATION FOR SEQ ID NO:21:

( i ) SEQUENCE CHARACTERISTICS:
( A ) LENGTH: 52 base pairs
( B ) TYPE: nucleic acid
( C ) STRANDEDNESS: single
( D ) TOPOLOGY: linear (  i  i  ) MOLECULE TYPE: DNA (genomic)

(  x  i  ) SEQUENCE DESCRIPTION: SEQ ID NO:21:

GTTAACGGAT CCCAGCACTG ACTAATTTAT CTACTTGTTC ATTTCCTCCA      50

AT      52

( 2 ) INFORMATION FOR SEQ ID NO:22:

(  i  ) SEQUENCE CHARACTERISTICS:
( A ) LENGTH: 33 base pairs
( B ) TYPE: nucleic acid
( C ) STRANDEDNESS: single
( D ) TOPOLOGY: linear (  i  i  ) MOLECULE TYPE: DNA (genomic)

(  x  i  ) SEQUENCE DESCRIPTION: SEQ ID NO:22:

GAATTCGTTA ACTTCCCTCA RATCMCTCTT TGG      33

( 2 ) INFORMATION FOR SEQ ID NO:23:

(  i  ) SEQUENCE CHARACTERISTICS:
( A ) LENGTH: 30 base pairs
( B ) TYPE: nucleic acid
( C ) STRANDEDNESS: single
( D ) TOPOLOGY: linear (  i  i  ) MOLECULE TYPE: DNA (genomic)

(  x  i  ) SEQUENCE DESCRIPTION: SEQ ID NO:23:

GTTAACGTCG ACTTKYTCAT TTCCTCCWAT      30

( 2 ) INFORMATION FOR SEQ ID NO:24:

(  i  ) SEQUENCE CHARACTERISTICS:
( A ) LENGTH: 55 base pairs
( B ) TYPE: nucleic acid
( C ) STRANDEDNESS: single
( D ) TOPOLOGY: linear (  i  i  ) MOLECULE TYPE: DNA (genomic)

(  x  i  ) SEQUENCE DESCRIPTION: SEQ ID NO:24:

GAATTCCGAT CGACAAGGAA CTGTATCCTT TAACTTCCCT CARATCMCTC      50

TTTGG      55

( 2 ) INFORMATION FOR SEQ ID NO:25:

(  i  ) SEQUENCE CHARACTERISTICS:
( A ) LENGTH: 52 base pairs
( B ) TYPE: nucleic acid
( C ) STRANDEDNESS: single
( D ) TOPOLOGY: linear (  i  i  ) MOLECULE TYPE: DNA (genomic)

(  x  i  ) SEQUENCE DESCRIPTION: SEQ ID NO:25:

GTTAACGGAT CCCAGCACTG ACTAATTTAT CTACTTKYTC ATTTCCTCCW      50

AT      52

( 2 ) INFORMATION FOR SEQ ID NO:26:

(  i  ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:26:

ATCTCTTACC TGTCCTATCT AACAGGCCAG GATTAA 36

( 2 ) INFORMATION FOR SEQ ID NO:27:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:27:

GAATTCTCGC GACCACCATG GCGCGTTCAA CGCTC 35

( 2 ) INFORMATION FOR SEQ ID NO:28:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:28:

GTTAACAGAT CTTCATGGCT CGTACTCTAT 30

( 2 ) INFORMATION FOR SEQ ID NO:29:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:29:

GAATTCGCGC GCAAGCGGCC GCAACCCGGG AAAAGCTTAA GCATGCAACC 50

CGGGAAGAAT TCAATCGCGA AA 72

( 2 ) INFORMATION FOR SEQ ID NO:30:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:30:

GTTAACGCGC GCTTCTCGAG TTGCGGCCGC TTGCTAGCTT AGATCTTTGG 50

GCCCTTTCGC GATTGAATTC TT 72

( 2 ) INFORMATION FOR SEQ ID NO:31:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:31:

GAATTCAAGC TTGGCCATTG CATACGTTGT 30

( 2 ) INFORMATION FOR SEQ ID NO:32:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:32:

GTTAACGCAT GCATAAGAAG CCAA 24

( 2 ) INFORMATION FOR SEQ ID NO:33:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:33:

GAATTCGCAT GCTCCCCTGC TCCGACCCGG 30

( 2 ) INFORMATION FOR SEQ ID NO:34:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:34:

GTTAACGAAT TCTCCTGCGG GGAGAAGCAG 30

( 2 ) INFORMATION FOR SEQ ID NO:35:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:35:

GAATTCAGAT CTGCCATACC ACATTTGTAG 30

( 2 ) INFORMATION FOR SEQ ID NO:36:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:36:

GTTAACGCTA GCTCCAGACA TGATAAGATA 30

( 2 ) INFORMATION FOR SEQ ID NO:37:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:37:

GAATTCGCTA GCATCCCGCC CCTAACTCCG        30

( 2 ) INFORMATION FOR SEQ ID NO:38:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:38:

GTTAACGTCG ACGCAAAAGC CTAGGCCTCC        30

( 2 ) INFORMATION FOR SEQ ID NO:39:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:39:

GAATTCTCGC GAACAGTTGG CCCT        24

( 2 ) INFORMATION FOR SEQ ID NO:40:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:40:

GTTAACAGAT CTTTACGCGA ACGCGAAGTC        30

( 2 ) INFORMATION FOR SEQ ID NO:41:

( i ) SEQUENCE CHARACTERISTICS:
        ( A ) LENGTH: 66 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:41:

GTTAACGAAT TCTTGCAAAA AGCTTTGCAA GATGGATAAA GTTTTAGAA        50

ACTCCAGTAG GACTCC        66

( 2 ) INFORMATION FOR SEQ ID NO:42:

( i ) SEQUENCE CHARACTERISTICS:
    ( A ) LENGTH: 63 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:42:

```
GAATTCTCGC GATCTAGACG TTCTACCTTT CTCTTCTTTT TTGGAGGAGT        50

CCTACTGGAG TTT                                                63
```

( 2 ) INFORMATION FOR SEQ ID NO:43:

( i ) SEQUENCE CHARACTERISTICS:
    ( A ) LENGTH: 35 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:43:

```
GTTAACGAAT TCCCACCATG ATTGAACAAG ATGGA                        35
```

( 2 ) INFORMATION FOR SEQ ID NO:44:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:44:

```
GAATTCAGAT CTTCAGAAGA ACTCGTCAAG                              30
```

( 2 ) INFORMATION FOR SEQ ID NO:45:

( i ) SEQUENCE CHARACTERISTICS:
    ( A ) LENGTH: 39 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:45:

```
CCCCGTGCCA AGAGTGACTA CGTAAGTACC GCCTATAGA                    39
```

( 2 ) INFORMATION FOR SEQ ID NO:46:

( i ) SEQUENCE CHARACTERISTICS:
    ( A ) LENGTH: 39 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:46:

```
CTCTGCTTCT CCCCGCAGCT GGAGAATTCA ATCGCGAAA                    39
```

( 2 ) INFORMATION FOR SEQ ID NO:47:

( i ) SEQUENCE CHARACTERISTICS:
    ( A ) LENGTH: 35 base pairs (B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:47:

GTTAACGAAT TCCCACCATG AACACGATTA ACATC                             35

(2) INFORMATION FOR SEQ ID NO:48:

(i) SEQUENCE CHARACTERISTICS:
   (A) LENGTH: 51 base pairs
   (B) TYPE: nucleic acid
   (C) STRANDEDNESS: single
   (D) TOPOLOGY: linear (i i) MOLECULE TYPE: DNA (genomic)

(x i) SEQUENCE DESCRIPTION: SEQ ID NO:48:

CAGGATCCAG ACGTCTGGCG GCCGCCGGTG AAGCTTGGCC CATTGCATAC             50

G                                                                  51

(2) INFORMATION FOR SEQ ID NO:49:

(i) SEQUENCE CHARACTERISTICS:
   (A) LENGTH: 50 base pairs
   (B) TYPE: nucleic acid
   (C) STRANDEDNESS: single
   (D) TOPOLOGY: linear (i i) MOLECULE TYPE: DNA (genomic)

(x i) SEQUENCE DESCRIPTION: SEQ ID NO:49:

CCAGGCTCAG ATCTGGTCTA ACCAGAGAGA CCCGGTTCAC TAAACGAGCT             50

(2) INFORMATION FOR SEQ ID NO:50:

(i) SEQUENCE CHARACTERISTICS:
   (A) LENGTH: 20 base pairs
   (B) TYPE: nucleic acid
   (C) STRANDEDNESS: single
   (D) TOPOLOGY: linear (i i) MOLECULE TYPE: DNA (genomic)

(x i) SEQUENCE DESCRIPTION: SEQ ID NO:50:

CCCATCTCTC TCCTTCTAGC                                              20

(2) INFORMATION FOR SEQ ID NO:51:

(i) SEQUENCE CHARACTERISTICS:
   (A) LENGTH: 23 base pairs
   (B) TYPE: nucleic acid
   (C) STRANDEDNESS: single
   (D) TOPOLOGY: linear (i i) MOLECULE TYPE: DNA (genomic)

(x i) SEQUENCE DESCRIPTION: SEQ ID NO:51:

AGCTTCACCG GCGGCCGCGA CGT                                          23

(2) INFORMATION FOR SEQ ID NO:52:

(i) SEQUENCE CHARACTERISTICS:
   (A) LENGTH: 15 base pairs
   (B) TYPE: nucleic acid
   (C) STRANDEDNESS: single
   (D) TOPOLOGY: linear ( i i ) MOLECULE TYPE: DNA (genomic)

( x i ) SEQUENCE DESCRIPTION: SEQ ID NO:52:

CGCGGCCGCC GGTGA     15

( 2 ) INFORMATION FOR SEQ ID NO:53:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:53:

AATTGTCCCT CATATCGCCT CCTCCAGGTC TGAAGATCTC GTCTCCCCGG     50

GGAGACGCA     59

( 2 ) INFORMATION FOR SEQ ID NO:54:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:54:

AGAATGAGAA GAGCTGAGCC AGCAGCAGAT GGGGTGGGAG CAGTATC     47

( 2 ) INFORMATION FOR SEQ ID NO:55:

( i ) SEQUENCE CHARACTERISTICS:
        ( A ) LENGTH: 57 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:55:

TATGCGTCTC CCCGGGGAGA CGAGATCTTC AGACCTGGAG GAGGCGATAT     50

GAGGGAC     57

( 2 ) INFORMATION FOR SEQ ID NO:56:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:56:

TCGAGATACT GCTCCCACCC CATCTGCTGC TGGCTCAGCT CTTCTCA     47

( 2 ) INFORMATION FOR SEQ ID NO:57:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear (  i  i  ) MOLECULE TYPE: DNA (genomic)

( x i ) SEQUENCE DESCRIPTION: SEQ ID NO:57:

```
AGCTTGCCTT GAGTGCTTCA ATCTAGAGCC ATACCACATT TGTAGAGGTT          50

TTACTTGCTT TAAAAAACCT                                            70
```

( 2 ) INFORMATION FOR SEQ ID NO:58:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:58:

```
AACCTCTACA AATGTGGTAT GGCTCTAGAT TGAAGCACTC AAGGCA               46
```

( 2 ) INFORMATION FOR SEQ ID NO:59:

( i ) SEQUENCE CHARACTERISTICS:
        ( A ) LENGTH: 68 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:59:

```
CCCACACCTC CCCCTGAACC TGAAACATAA AATGAATGCA ATTGTTGTTA          50

TTAACTTGTT TATTGCAG                                              68
```

( 2 ) INFORMATION FOR SEQ ID NO:60:

( i ) SEQUENCE CHARACTERISTICS:
        ( A ) LENGTH: 68 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:60:

```
ACAACAATTG CATTCATTTT ATGTTTCAGG TTCAGGGGGA GGTGTGGGAG          50

GTTTTTTAAA GCAAGTAA                                              68
```

( 2 ) INFORMATION FOR SEQ ID NO:61:

( i ) SEQUENCE CHARACTERISTICS:
        ( A ) LENGTH: 68 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:61:

```
CTTATAATGG TTACAAATAA AGCAATAGCA TCACAAATTT CACAAATAAA          50

GCATTTTTTT CACTGCAT                                              68
```

( 2 ) INFORMATION FOR SEQ ID NO:62:

( i ) SEQUENCE CHARACTERISTICS:
        ( A ) LENGTH: 68 base pairs
        ( B ) TYPE: nucleic acid (C) STRANDEDNESS: single
(D) TOPOLOGY: linear (ii) MOLECULE TYPE: DNA (genomic)

(xi) SEQUENCE DESCRIPTION: SEQ ID NO:62:

TATTTGTGAA ATTTGTGATG CTATTGCTTT ATTTGTAACC ATTATAAGCT            50

GCAATAAACA AGTTAATA                                              68

(2) INFORMATION FOR SEQ ID NO:63:

(i) SEQUENCE CHARACTERISTICS:
      (A) LENGTH: 68 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:63:

TATTTGTGAA ATTTGTGATG CTATTGCTTT ATTTGTAACC ATTATAAGCT            50

GCAATAAACA AGTTAATA                                              68

(2) INFORMATION FOR SEQ ID NO:64:

(i) SEQUENCE CHARACTERISTICS:
      (A) LENGTH: 68 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:64:

CCAGACATGA TAAGATACAT TGATGAGTTT GGACAAACCA CAACTAGAAT            50

GCAGTGAAAA AAATGCTT                                              68

(2) INFORMATION FOR SEQ ID NO:65:

(i) SEQUENCE CHARACTERISTICS:
      (A) LENGTH: 79 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:65:

CCCTAACTCC GCCCAGTTCC GCCCATTCTC CGCCCCATGG CTGACTAATT            50

TTTTTTATTT ATGCAGAGGC CGAGGCCGC                                  79

(2) INFORMATION FOR SEQ ID NO:66:

(i) SEQUENCE CHARACTERISTICS:
      (A) LENGTH: 68 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:66:

TTAGTCAGCC ATGGGGCGGA GAATGGGCGG AACTGGGCGG AGTTAGGGGC            50

GGGATGGCGC GCCGGTGT                                              68

(2) INFORMATION FOR SEQ ID NO:67:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:67:

```
CTCGGCCTCT GAGCTATTCC AGAAGTAGTG AGGAGGCTTT TTTGGAGGCC      50
TAGGCTTTTG CGGCGCGCCA CCTGCATTA                             79
```

(2) INFORMATION FOR SEQ ID NO:68:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:68:

```
GCCTCCTCAC TACTTCTGGA ATAGCTCAGA GGCCGAGGCG GCCTCGGCCT      50
CTGCATAAAT AAAAAAAA                                         68
```

(2) INFORMATION FOR SEQ ID NO:69:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:69:

```
TCATTAATGC AGGTGGCGCG CCGCAAAAGC CTAGGCCTCC AAAAAA          46
```

(2) INFORMATION FOR SEQ ID NO:70:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:70:

```
CTAGAGGGGG AGGCTAACTG AAACACGGAA GGAGACAATA CCGGAAGGAA      50
CCCGCGCTAT GACGGCA                                          67
```

(2) INFORMATION FOR SEQ ID NO:71:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:71:

```
ATAAAAGAC AGAATAAAAC CCACGGGTGT TGGGTCGTTT GTTCATAAAC       50
```

```
          CCGGGCTTCG GTCCCA                                                    66
```

( 2 ) INFORMATION FOR SEQ ID NO:72:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:72:

```
          CTTCCGGTAT TGTCTCCTTC CGTGTTTCAG TTAGCCTCCC CCT                      43
```

( 2 ) INFORMATION FOR SEQ ID NO:73:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:73:

```
          GTGGGTTTTA TTCTGTCTTT TTATTGCCGT CATAGCGCGG GTTC                     44
```

( 2 ) INFORMATION FOR SEQ ID NO:74:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:74:

```
          CCGGTGGGAC CGAAGCCCGG GTTTATGAAC AAACGACCCA ACACCC                   46
```

( 2 ) INFORMATION FOR SEQ ID NO:75:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:75:

```
          AACGGCGGCG GGAAGTTCTC CTGCGTCATC GTCGGGAAGA                          40
```

( 2 ) INFORMATION FOR SEQ ID NO:76:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:76:

```
          CATGTTGCAG GGCCCCTAGG AAAAAGGGCT GTTGGAAATG TG                       42
```

( 2 ) INFORMATION FOR SEQ ID NO:77:

( i ) SEQUENCE CHARACTERISTICS:
    ( A ) LENGTH: 34 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:77:

CACTCCATGT ACCGGTTCTT TTAGAATYTC YCTG 34

( 2 ) INFORMATION FOR SEQ ID NO:78:

( i ) SEQUENCE CHARACTERISTICS:
    ( A ) LENGTH: 66 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:78:

CGTTTAGTGA ACCGTCAGAT CGCCTGGAGA CGCCATCCAC GCTGTTTTGA 50

CCTCCATAGA AGACAC 66

( 2 ) INFORMATION FOR SEQ ID NO:79:

( i ) SEQUENCE CHARACTERISTICS:
    ( A ) LENGTH: 50 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:79:

AACAGCGTGG ATGGCGTCTC CAGGCGATCT GACGGTTCAC TAAACGAGCT 50

( 2 ) INFORMATION FOR SEQ ID NO:80:

( i ) SEQUENCE CHARACTERISTICS:
    ( A ) LENGTH: 69 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:80:

CGGGACCGAT CCAGCCTCCG CGGCCGGGAA CGGTGCATTG GAACGCGGAT 50

TCCCCGTGCC AAGAGTTAC 69

( 2 ) INFORMATION FOR SEQ ID NO:81:

( i ) SEQUENCE CHARACTERISTICS:
    ( A ) LENGTH: 69 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:81:

TCCGCGTTCC AATGCACCGT TCCCGGCCGC GGAGGCTGGA TCGGTCCCGG 50

TGTCTTCTAT GGAGGTCAA 69

( 2 ) INFORMATION FOR SEQ ID NO:82:

( i ) SEQUENCE CHARACTERISTICS:
   ( A ) LENGTH: 66 base pairs
   ( B ) TYPE: nucleic acid
   ( C ) STRANDEDNESS: single
   ( D ) TOPOLOGY: linear ( i i ) MOLECULE TYPE: DNA (genomic)

( x i ) SEQUENCE DESCRIPTION: SEQ ID NO:82:

| | | | | | |
|---|---|---|---|---|---|
| GTAAGTACCG | CCTATAGAGT | CTATAGGCCC | ACCCCCTTGG | CTTCTTATGC | 50 |
| ATGCTCCCCT | GCTCCG | | | | 66 |

( 2 ) INFORMATION FOR SEQ ID NO:83:

( i ) SEQUENCE CHARACTERISTICS:
      ( A ) LENGTH: 66 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:83:

| | | | | | |
|---|---|---|---|---|---|
| AAGAAGCCAA | GGGGGTGGGC | CTATAGACTC | TATAGGCGGT | ACTTACGTAA | 50 |
| CTCTTGGCAC | GGGGAA | | | | 66 |

( 2 ) INFORMATION FOR SEQ ID NO:84:

( i ) SEQUENCE CHARACTERISTICS:
      ( A ) LENGTH: 60 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:84:

| | | | | | |
|---|---|---|---|---|---|
| ATCCGGGCTC | CTCGCCCGCC | CGGACCCACA | GGCCACCCTC | AACCGTCCTG | 50 |
| GCCCCGGACC | | | | | 60 |

( 2 ) INFORMATION FOR SEQ ID NO:85:

( i ) SEQUENCE CHARACTERISTICS:
      ( A ) LENGTH: 60 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:85:

| | | | | | |
|---|---|---|---|---|---|
| GAGGGTGGCC | TGTGGGTCCG | GGCGGGCGAG | GAGCCCGGAT | CGGAGCAGGG | 50 |
| GAGCATGCAT | | | | | 60 |

( 2 ) INFORMATION FOR SEQ ID NO:86:

( i ) SEQUENCE CHARACTERISTICS:
      ( A ) LENGTH: 44 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:86:

| | | | | |
|---|---|---|---|---|
| CAAACCCCAC | CCCTCACTCT | GCTTCTCCCC | GCAGCTGAGA | TCTG | 44 |

( 2 ) INFORMATION FOR SEQ ID NO:87:

( i ) SEQUENCE CHARACTERISTICS:
        ( A ) LENGTH: 68 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:87:

```
CTAGCAGATC  TCAGCTGCGG  GGAGAAGCAG  AGTGAGGGGT  GGGGTTTGGG        50

TCCGGGGCCA  GGACGGTT                                              68
```

( 2 ) INFORMATION FOR SEQ ID NO:88:

( i ) SEQUENCE CHARACTERISTICS:
        ( A ) LENGTH: 78 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:88:

```
CGGGACCGAT  CCAGCCTCCG  CGGCCGGGAA  CGGTGCATTG  GAACGCGGAT        50

TCCCCGTGCC  AAGAGTTACC  TGAGATCT                                  78
```

( 2 ) INFORMATION FOR SEQ ID NO:89:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:89:

```
CTAGCAGATC  TCAGGTAACT  CTTGGCACGG  GGAA                          34
```

( 2 ) INFORMATION FOR SEQ ID NO:90:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:90:

```
CATGGTGGTA  GATCTCACA                                             19
```

( 2 ) INFORMATION FOR SEQ ID NO:91:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:91:

```
AGCTTGTGAG  ATCTACCAC                                             19
```

(2) INFORMATION FOR SEQ ID NO:92:

(i) SEQUENCE CHARACTERISTICS:
  (A) LENGTH: 14 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:92:

AGATCTCACA CACA    14

(2) INFORMATION FOR SEQ ID NO:93:

(i) SEQUENCE CHARACTERISTICS:
  (A) LENGTH: 21 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:93:

AGCTTGTGTG TGAGATCTCC T    21

(2) INFORMATION FOR SEQ ID NO:94:

(i) SEQUENCE CHARACTERISTICS:
  (A) LENGTH: 67 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:94:

CTAGAGGGGG AGGCTAACTG AAACACGGAA GGAGACAATA CCGGAAGGAA    50

CCCGCGCTAT GACGGCA    67

(2) INFORMATION FOR SEQ ID NO:95:

(i) SEQUENCE CHARACTERISTICS:
  (A) LENGTH: 66 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:95:

ATAAAAAGAC AGAATAAAAC CCACGGGTGT TGGGTCGTTT GTTCATAAAC    50

CCGGGCTTCG GTCCCA    66

(2) INFORMATION FOR SEQ ID NO:96:

(i) SEQUENCE CHARACTERISTICS:
  (A) LENGTH: 43 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:96:

CTTCCGGTAT TGTCTCCTTC CGTGTTTCAG TTAGCCTCCC CCT    43

( 2 ) INFORMATION FOR SEQ ID NO:97:

( i ) SEQUENCE CHARACTERISTICS:
    ( A ) LENGTH: 44 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:97:

```
GTGGGTTTTA TTCTGTCTTT TTATTGCCGT CATAGCGCGG GTTC                44
```

( 2 ) INFORMATION FOR SEQ ID NO:98:

( i ) SEQUENCE CHARACTERISTICS:
    ( A ) LENGTH: 46 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:98:

```
CCGGTGGGAC CGAAGCCCGG GTTTATGAAC AAACGACCCA ACACCC             46
```

( 2 ) INFORMATION FOR SEQ ID NO:99:

( i ) SEQUENCE CHARACTERISTICS:
    ( A ) LENGTH: 103 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:99:

```
GAGGCCCCAA GGGGTTATGC TATCTAGAGG TACCACGCGT GAATTCTCGA          50
GGCTAGCAGA TCTCCATGGT ATTATCGTGT TTTTCAAAGG AAAACCACGT         100
CCC                                                            103
```

( 2 ) INFORMATION FOR SEQ ID NO:100:

( i ) SEQUENCE CHARACTERISTICS:
    ( A ) LENGTH: 69 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:100:

```
GCATAACCCC TTGGGGCCTC TAAACGGGTC TTGAGGGGTT TTTTGCTCAC          50
CGGCGCGCCA CCTGCATTA                                            69
```

( 2 ) INFORMATION FOR SEQ ID NO:101:

( i ) SEQUENCE CHARACTERISTICS:
    ( A ) LENGTH: 87 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:101:

```
CACGGGGACG TGGTTTTCCT TTGAAAAACA CGATAATACC ATGGAGATCT          50
```

```
           GCTAGCCTCG  AGAATTCACG  CGTGGTACG  CGTGGTACCT  CTAGATA                                    8 7
```

( 2 ) INFORMATION FOR SEQ ID NO:102:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:102:

```
           TCATTAATGC  AGGTGGCGCG  CCGGTGAGCA  AAAAACCCCT  CAAGACCCGT                                5 0
           TTA                                                                                       5 3
```

( 2 ) INFORMATION FOR SEQ ID NO:103:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:103:

```
           AATTACACCG  GCGTCGCCCT  ATAGTGAGTC  GTATTAGCGG  CCGCGACGT                                 4 9
```

( 2 ) INFORMATION FOR SEQ ID NO:104:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:104:

```
           CGCGGCCGCT  AATACGACTC  ACTATAGGGC  GACGCCGGTG  T                                         4 1
```

( 2 ) INFORMATION FOR SEQ ID NO:105:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:105:

```
           GTCTGTTGTG  TGACTCTGCC  CTATAGTGAG  TCGTATTACC  CTTTTAGTCA                                5 0
           GTGTGG                                                                                    5 6
```

What is claimed is:

1. A method for determining susceptibility for an anti-HIV drug comprising:

(a) introducing a resistance test vector comprising a patient-derived segment and an indicator gene into a host cell;

(b) culturing the host cell from (a);

(c) measuring expression of the indicator gene in a target host cell, wherein the expression of the indicator gene is dependent upon the patient-derived segment; and (d) comparing the expression of the indicator gene from (c) with the expression of the indicator gene measured when steps (a)–(c) are carried out in the absence of the anti-HIV drug, wherein a test concentration of the anti-HIV drug is present at steps (a)–(c); at steps (b)–(c); or at step (c).

2. The method of claim 1, wherein the resistance test vector comprises DNA of a genomic viral vector.

3. The method of claim 1, wherein the resistance test vector comprises DNA of a subgenomic viral vector.

4. A method for determining anti-HIV drug resistance in a patient comprising:
   (a) developing a standard curve of drug susceptibility for an anti-HIV drug;
   (b) determining anti-HIV drug susceptibility in the patient according to the method of claim 1; and
   (c) comparing the anti-HIV drug susceptibility in step (b) with the standard curve determined in step (a), wherein a decrease in anti-HIV susceptibility indicates development of anti-HIV drug resistance in the patient.

5. The method of claim 1, wherein the resistance test vector comprises DNA of HIV.

6. The method of claim 5, wherein the resistance test vector comprises DNA encoding vif, vpr, tat, rev, vpu, and nef.

7. The method of claim 1, wherein the patient-derived segment comprises a functional viral sequence.

8. The method of claim 1, wherein the patient-derived segment encodes one protein that is the target of an anti-HIV drug.

9. The method of claim 1, wherein the patient-derived segment encodes two or more proteins that are the targets of one or more anti-HIV drugs.

10. A method for determining anti-HIV drug resistance in a patient comprising:
   (a) determining anti-HIV drug susceptibility in the patient at a first time according to the method of claim 1, wherein the patient-derived segment is obtained from the patient at about said time;
   (b) determining anti-HIV drug susceptibility of the same patient at a later time; and
   (c) comparing the anti-HIV drug susceptibilities determined in step (a) and (b), wherein a decrease in anti-HIV drug susceptibility at the later time compared to the first time indicates development or progression of anti-HIV drug resistance in the patient.

11. The method of claim 1, wherein the patient-derived segment comprises an HIV gene.

12. The method of claim 11, wherein the patient-derived segment comprises an HIV gag-pol gene.

13. The method of claim 1, wherein the indicator gene is a functional indicator gene and the host cell is a resistance test vector host cell, including the additional step of infecting the target host cell with resistance test vector viral particles using filtered supernatants from said resistance test vector host cells.

14. The method of claim 1, wherein the indicator gene is a non-functional indicator gene.

15. The method of claim 14, wherein the host cell is a packaging host cell/resistance test vector host cell.

16. The method of claim 15, wherein the culturing is by co-cultivation.

17. The method of claim 15, wherein the target host cell is infected with resistance test vector viral particles using filtered supernatants from said packaging host cell/resistance test vector host cells.

18. The method of claim 1, wherein the indicator gene is a luciferase gene.

19. The method of claim 1, wherein the indicator gene is an *E. coli* lacZ gene.

20. The method of claim 15, wherein the packaging host cell/resistance test vector host cell is a human cell.

21. The method of claim 15, wherein the packaging host cell/resistance test vector host cell is a human embryonic kidney cell.

22. The method of claim 15, wherein the packaging host cell/resistance test vector host cell is a 293 cell.

23. The method of claim 1, wherein the target host cell is a human T cell.

24. The method of claim 1, wherein the target host cell is a human T cell leukemia cell line.

25. The method of claim 1, wherein the target host cell is a Jurkat cell line.

26. The method of claim 1, wherein the target host cell is a H9 cell line.

27. The method of claim 1, wherein the target host cell is a CEM cell line.

28. The method of claim 1, wherein the target host cell is a human embryonic kidney cell.

29. The method of claim 1, wherein the target host cell is a 293 cell.

30. A resistance test vector comprising an HIV patient-derived segment and an indicator gene, wherein the expression of the indicator gene is dependent upon the patient-derived segment.

31. The resistance test vector of claim 30, wherein the patient-derived segment encodes one protein that is the target of an anti-HIV drug.

32. The resistance test vector of claim 30, wherein the patient-derived segment encodes two or more proteins that are the targets of one or more anti-HIV drugs.

33. The resistance test vector of claim 30, wherein the patient-derived segment comprises an HIV gene.

34. The resistance test vector of claim 30, wherein the patient-derived segment comprises DNA of HIV.

35. The resistance test vector of claim 34, wherein the patient-derived segment comprises DNA encoding vif, vpr tat, rev, vpu, and nef.

36. The resistance test vector of claim 33, wherein the patient-derived segment comprises an HIV gag-pol gene.

37. The resistance test vector of claim 30, wherein the indicator gene is a functional indicator gene.

38. The resistance test vector of claim 30, wherein the indicator gene is a non-functional indicator gene.

39. The resistance test vector of claim 30, wherein the indicator gene is a luciferase gene.

40. A packaging host cell transfected with a resistance test vector of claim 30.

41. The packaging host cell of claim 40 that is a mammalian host cell.

42. The packaging host cell of claim 40 that is a human host cell.

43. The packaging host cell of claim 40 that is a human embryonic kidney cell.

44. The packaging host cell of claim 40 that is 293 cells.

45. The resistance test vector of claim 30 comprising an indicator gene viral vector and a packaging vector said indicator gene viral vector comprising an indicator gene and said packaging vector comprising a patient-derived segment.

46. A method for determining susceptibility for an anti-HIV drug comprising:
   (a) introducing a resistance test vector comprising a patient-derived segment and a nonfunctional indicator gene into a host cell;
   (b) culturing the host cell from (a);
   (c) measuring expression of the indicator gene in a target host cell, wherein the expression of the indicator gene is dependent upon the patient-derived segment; and
   (d) comparing the expression of the indicator gene from (c) with the expression of the indicator gene measured when steps (a)–(c) are carried out in the absence of the anti-HIV drug,
   wherein a test concentration of the anti-HIV drug is present at steps (a)–(c); at steps (b)–(c); or at step (c).

47. The method of claim 46, wherein the resistance test vector comprises DNA of a genomic viral vector.

48. The method of claim 46, wherein the resistance test vector comprises DNA of a subgenomic viral vector.

49. The method of claim 46, wherein the resistance test vector comprises DNA of HIV.

50. The method of claim 49, wherein the resistance test vector comprises DNA encoding vif, vpr, tat, rev, vpu, and nef.

51. The method of claim 46, wherein the patient-derived segment encodes one protein that is the target of an anti-HIV drug.

52. The method of claim 46, wherein the patient-derived segment encodes two or more proteins that are the targets of one or more anti-HIV drugs.

53. The method of claim 46, wherein the patient-derived segment comprises an HIV gene.

54. The method of claim 53, wherein the patient-derived segment comprises an HIV gag-pol gene.

55. The method of claim 46, wherein the indicator gene is a luciferase gene.

56. The method of claim 46, wherein the host cell is a packaging host cell.

57. The method of claim 46, wherein the packaging host cell is a human cell.

58. The method of claim 46, wherein the packaging host cell is a human embryonic kidney cell.

59. The method of claim 46, wherein the packaging host cell is a 293 cell.

60. The method of claim 46, wherein the nonfunctional indicator gene comprises a permuted promoter.

61. The method of claim 46, wherein the nonfunctional indicator gene comprises a permuted coding region.

62. The method of claim 46, wherein the nonfunctional indicator gene comprises an inverted intron.

63. The method of claim 46, wherein the host cell and target host cell are the same cell.

64. The method of claim 46, wherein the target host cell is a human cell.

65. The method of claim 46, wherein the target host cell is a human T cell.

66. The method of claim 46, wherein the target host cell is a human embryonic kidney cell.

67. The method of claim 46, wherein the target host cell is a 293 cell.

68. The method of claim 46, wherein the target host cell is infected with resistance test vector viral particles using filtered supernatants from said packaging host cell/resistance test vector host cell.

69. The method of claim 46, wherein said culturing is by co-cultivation.

70. A method for determining anti-HIV drug resistance in a patient comprising:
   (a) developing a standard curve of drug susceptibility for an anti-HIV drug;
   (b) determining anti-HIV drug susceptibility in the patient according to the method of claim 46; and
   (c) comparing the anti-HIV drug susceptibility in step (b) with the standard curve determined in step (a), wherein a decrease in anti-HIV susceptibility indicates development of anti-HIV drug resistance in the patient.

71. A method for determining anti-HIV drug resistance in a patient comprising:
   (a) determining anti-HIV drug susceptibility in the patient at a first time according to the method of claim 46, wherein the patient-derived segment is obtained from the patient at about said time;
   (b) determining anti-HIV drug susceptibility of the same patient at a later time; and
   (c) comparing the anti-HIV drug susceptibilities determined in steps (a) and (b), wherein a decrease in anti-HIV drug susceptibility at the later time compared to the first time indicates development or progression of anti-HIV drug resistance in the patient.

72. A method for evaluating the biological effectiveness of a candidate anti-HIV drug compound comprising:
   (a) introducing a resistance test vector comprising a patient-derived segment and an indicator gene into a host cell;
   (b) culturing the host cell from step (a);
   (c) measuring expression of the indicator gene in a target host cell, wherein the expression of the indicator gene is dependent upon the patient-derived segment; and
   (d) comparing the expression of the indicator gene from step (c) with the expression of the indicator gene measured when steps (a)–(c) are carried out in the absence of the candidate anti-HIV drug compound,
   wherein a test concentration of the candidate anti-HIV drug compound is present at steps (a)–(c); at steps (b)–(c); or at step (c).

73. The method of claim 72, wherein the resistance test vector comprises DNA of HIV.

74. The method of claim 72, wherein the resistance test vector comprises DNA encoding HIV gag-pol.

75. The method of claim 72, wherein the patient-derived segment encodes one protein that is the target of an anti-HIV drug.

76. The method of claim 72, wherein the patient-derived segment encodes two or more proteins that are the targets of one or more anti-HIV drugs.

77. The method of claim 72, wherein the patient-derived segment comprises an HIV gene.

78. A method for determining susceptibility for an anti-HIV drug comprising:
   (a) introducing a resistance test vector comprising a patient-derived segment and an indicator into a host cell;
   (b) culturing the host cell from (a);
   (c) measuring the indicator in a target host cell, wherein a change in the indicator is dependent upon the patient-derived segment; and
   (d) comparing the measurement of the indicator from (c) with the measurement of the indicator when steps (a)–(c) are carried out in the absence of the anti-HIV drug,
   wherein a test concentration of the anti-HIV drug is present at steps (a)–(c); at steps (b)–(c); or at step (c).

79. The method of claim 78, wherein the indicator comprises a DNA structure.

80. The method of claim 78, wherein the indicator comprises a RNA structure.

81. A method for evaluating the biological effectiveness of a candidate anti-HIV drug compound comprising:
   (a) introducing a resistance test vector comprising a patient-derived segment and an indicator into a host cell;

(b) culturing the host cell from step (a);

(c) measuring the indicator in a target host cell, wherein a change in the indicator is dependent upon the patient-derived segment; and (d) comparing the measurement of the indicator from step (c) with the measurement of the indicator measured when steps (a)–(c) are carried out in the absence of the candidate anti-HIV drug compound, wherein a test concentration of the candidate anti-HIV drug compound is present at steps (a)–(c); at steps (b)–(c); or at step (c).

82. The method of claim 81, wherein the indicator comprises a DNA structure.

83. The method of claim 82, wherein the indicator comprises a RNA structure.

* * * * *

UNITED STATES PATENT AND TRADEMARK OFFICE
CERTIFICATE OF CORRECTION

PATENT NO. : 5,837,464　　　　　　　　　　　　　　　　　　　　　Page 1 of 1
DATED      : November 17, 1998
INVENTOR(S) : Daniel Capon It is certified that error appears in the above-identified patent and that said Letters Patent is hereby corrected as shown below:

<u>Title page,</u>
Between Items [22] and Item [51] add the text:
-- Related U.S. Application Data
[60] Provisional Application No. 60/010,715, filed Jan. 29, 1996 --

Signed and Sealed this

First Day of June, 2004

JON W. DUDAS
*Acting Director of the United States Patent and Trademark Office*